United States Patent
Payne et al.

(10) Patent No.: US 11,566,052 B2
(45) Date of Patent: Jan. 31, 2023

(54) CRISPR-ASSOCIATED (CAS) PROTEINS WITH REDUCED IMMUNOGENICITY

(71) Applicant: LONZA LTD, Visp (CH)

(72) Inventors: Thomas Payne, Cambridge (GB); Jesús Zurdo, Cambridge (GB); Noel Hillier Smith, Cambridge (GB)

(73) Assignee: LONZA LTD., Visp (CH)

(*) Notice: Subject to any disclaimer, the term of this patent is extended or adjusted under 35 U.S.C. 154(b) by 561 days.

(21) Appl. No.: 15/775,294

(22) PCT Filed: Nov. 11, 2016

(86) PCT No.: PCT/EP2016/077487
§ 371 (c)(1),
(2) Date: May 10, 2018

(87) PCT Pub. No.: WO2017/081288
PCT Pub. Date: May 18, 2017

(65) Prior Publication Data
US 2018/0319850 A1 Nov. 8, 2018

Related U.S. Application Data

(60) Provisional application No. 62/253,961, filed on Nov. 11, 2015.

(51) Int. Cl.
| | |
|---|---|
| *C07K 14/00* | (2006.01) |
| *C07K 14/315* | (2006.01) |
| *C12N 9/22* | (2006.01) |
| *C12N 15/86* | (2006.01) |
| *C12N 15/90* | (2006.01) |
| *G01N 33/68* | (2006.01) |
| *C12N 15/10* | (2006.01) |

(52) U.S. Cl.
CPC .............. *C07K 14/315* (2013.01); *C12N 9/22* (2013.01); *C12N 15/86* (2013.01); *C12N 15/907* (2013.01); *G01N 33/6878* (2013.01); *C12N 15/102* (2013.01); *C12N 2310/20* (2017.05); *C12N 2710/10045* (2013.01)

(58) Field of Classification Search
CPC ........ C07K 14/315; C12N 9/22; C12N 15/86; C12N 15/907; C12N 2310/20; C12N 15/102; C12N 2710/10045; G01N 33/6878
See application file for complete search history.

(56) References Cited

U.S. PATENT DOCUMENTS 7,702,465 B2   4/2010 Lasters et al.

FOREIGN PATENT DOCUMENTS

| EP | 1516275 B1 | 3/2007 |
|---|---|---|
| WO | 2014/204725 A1 | 12/2014 |
| WO | 2017/081288 A1 | 5/2017 |

OTHER PUBLICATIONS

Tangri et al: "Rationally engineered therapeutic proteins with reduced immunogenicity", The Journal of Immunology, The American Association of Immunologists, US, vol. 174, No. 6, Mar. 15, 2005 (Mar. 15, 2005), pp. 3187-3196). (Year: 2005).*
Chew et al (Nat Methods Oct. 2016; vol. 13, No. 10: pp. 868-874). (Year: 2016).*
Nishimasu et al in "Crystal Structure of Cas9 in Complex with Guide RNAand Target DNA", (Cell, Cell Press, US, vol. 156, No. 5, Feb. 13, 2014, pp. 935-949; IDS reference). (Year: 2014).*
Chew et al Supplemental (Nat Methods Oct. 2016; vol. 13, No. 10: pp. 868-874) . (Year: 2016).*
Nishimasu et al in "Crystal Structure of Cas9 in Complex with Guide RNA and Target DNA", (Cell, Cell Press, US, vol. 156, No. 5, Feb. 13, 2014, pp. 935-949). (Year: 2014).*
Chew et al (Nat Methods Oct. 2016; vol. 13, No. 10: pp. 868-874; and corresponding attached "Supplemental"). (Year: 2016).*
Tangri et al: "Rationally engineered therapeutic proteins with reduced immunogenicity", The Journal of Immunology, The American Association of Immunologists, US, vol. 174, No. 6, (Mar. 15, 2005), pp. 3187-3196). (Year: 2005).*
Chew et al (Nat Methods published Sep. 5, 2016, vol. 13, No. 10: "Supplemental Table 2"). (Year: 2016).*
Wang et al (Human Gene Therapy 2015; vol. 26, No. 7: pp. 432-442; published online Jun. 17, 2015). (Year: 2015).*
Agustín-Pavón et al., "Synthetic biology and therapeutic strategies for the degenerating brain," Bioessays 36(10):979-990 (2014).
Altschul et al., "Basic Local Alignment Search Tool," J. Mol. Biol. 215:403-10 (1990).
Altschul et al., "Gapped BLAST and PSI-BLAST: a new generation of protein database search programs," Nucleic Acids Res. 25(17):3389-3402 (1997).
Atchley et al., "Solving the protein sequence metric problem," Proc. Natl. Acad. Sc. U.S.A. 102:6395-6400 (2005).
Barrangou et al., "CRISPR-Cas systems: prokaryotes upgrade to adaptive immunity," Mol. Cell. 54(2):234-44 (2014).
Berdoz et al., "Constitutive and induced expression of the individual HLA-DR beta and alpha chain loci in different cell types," J. Immunol. 139(4):1336-41 (1987).
Castelli et al., "HLA-DP4, the most frequent HLA II molecule, defines new supertype of peptide-binding specifity," J. Immunol. 169(12):6928-34 (2002).
Chew et al., "A multifunctional AAV-CRISPR-Cas9 and its host response," HHS Public Access Author Manuscript 13(10):868-874 (2016).
Chylinski et al., "Classification and evolution of type II CRISPR-Cas systems," Nucleic Acids Research 42(10):6091-105 (2014).

(Continued)

*Primary Examiner* — Catherine S Hibbert
(74) *Attorney, Agent, or Firm* — Medler, Ferro, Woodhouse & Mills PLLC

(57) ABSTRACT

The invention relates to methods of reducing the immunogenicity of CRISPR-associated (Cas) proteins and the modified Cas proteins produced therefrom. In addition, the invention relates to methods for cell and gene therapy, including any and all genetic modifications and alterations of gene expression (and/or genetic elements) made in-vivo or ex-vivo using Cas proteins with reduced immunogenicity.

7 Claims, 118 Drawing Sheets

Specification includes a Sequence Listing.

(56) References Cited

OTHER PUBLICATIONS

Cong et al., "Multiplex genome engineering using CRISPR/Cas systems," Science 339(6121):81923 (2013).
Cox et al., "Therapeutic genome editing: prospects and challenges," Nature Medicine 21(2):121-31 (2015).
Esvelt et al., "Orthogonal Cas9 proteins for RNA-guided gene regulation and editing," Nature Methods 10(11):1116-21 (2013).
Fu et al., "Improving CRISPR-Cas nucleases using truncated guide RNAs," Nature Biotechnology 32(3):279-84 (2014).
Gagnon et al., "Efficient mutagenesis by Cas9 protein-mediated oligonucleotide insertion and large-scale assessment of single-guide RNAs," PLOS One9(8):e106396 (2014).
Gansbacher and Zier, "Regulation of HLA-DR, DP, and DQ expression in activated T cells," Cell Immunol. 117(1):22-34 (1988).
Grantham et al., "Amino acid difference formula to help explain protein evolution," Science 185:862-864 (1974).
Jinek et al., "A programmable dual-RNA-guided DNA endonuclease in adaptive bacterial immunity," Science 337(6096):816-21 (2012).
Karl E. Griswold et al., "Design and engineering of deimmunized biotherapeutics," Current Opinion in Structural Biology, Elsevier Ltd., GB 39:79-88 (2016).
Karlin and Altschul, "Methods for assessing the statistical significance of molecular sequence features by using generic scoring schemes," Proc. Natl. Acad. Sci. USA 87:2264-68 (1990).
Karlin and Altschul, "Applications and statistics for multiple high-scoring segments in molecular sequences," Proc. Natl. Acad. Sci. USA 90:5873-77 (1993).
Karplus et al., "Accuracy of protein flexibility predictions," Naturwissenschaften 72:212-213 (1985).
Kirschmann et al., "Naturally processed peptides from rheumatoid arthritis associated and non-associated HLA-DR alleles," J. Immunol. 155(12):5565-62 (1995).
Kleinstiver et al., "Engineered CRISPR-Cas9 nucleases with altered PAM specificities," Nature 523(7561):481-485 (2015).
Kolaskar et al., "A semi-empirical method for prediction of antigenic determinants on protein antigens," FEBS Lett. 276:172-174 (1990).
Laupeze et al., "Differential expression of major histocompatibility complex class Ia, Ib, and II molecules on monocytes-derived dendritic and macrophagic cells," Hum. Immunol. 60(7):591-7 (1999).
Mali et al., "Cas9 as a versatile tool for engineering biology," Nature Methods 10:957-63 (2013).
Mali et al., "RNA-guided human genome engineering via Cas9," Science 339(6121):823-26 (2013).
Maus et al., "Adoptive immunotherapy for cancer or viruses," Annual Rev. Immunol. 32:129-225 (2014).
Nishimasu et al., "Crystal structure of Cas9 in complex with guide RNA and target DNA," Cell 156(5):935-49 (2014).
Parker et al., "New hydrophilicity scale derived from high-performance liquid chromatography peptide retention data: correlation of predicted surface residues with antigenicity and x-ray-derived accessible sites," Biochemistry 25:5425-5432 (1986).
Penna et al., "Cutting edge: selective usage of chemokine receptors by plasmacytoid dendritic cells." J. Immunol. 167:1862-1866 (2001).
Ponnuswamy et al., "Hydrophobic packing and spatial arrangement of amino acid residues in globular proteins." Biochim. Biophys. Acta. 623:301-316 (1980).
Ran et al., "In vivo genome editing using *Staphylococcus aureus* Cas9," Nature 520(7546):186-91 (2015).
Rohn et al., "Upregulation of the CLIP self peptide on mature dendritic cells antagonizes T helper type 1 polarization," Nature Immunol. 5:909-918 (2004).
Sander and Joung, "CRISPR-Cas systems for editing, regulating and targeting genomes," Nature Biotechnology 32(4):347-55 (2014).
Shabnam et al., "Rationally engineered therapeutic proteins with reduced immunogenicity," The Journal of Immunology, The American Association of Immunologists, US. 174(6):3187-3196 (2005).
Sorek et al., "CRISPR—a widespread system that provides acquired resistance against phages in bacteria and archaea," Nat. Rev. Microbiol. 6(3)181-6 (2008).
Stunz et al., "HLA-DRB1 and -DRB4 genes are differentially regulated at the transcriptional level," J. Immunol. 143(9):3081-6 (1989).
Vader et al., "The HLA-DQ2 gene dose effect in celiac disease is directly related to the magnitude and breadth of gluten-specific T cell responses," PNAS 100(21):12390-5 (2003).
Verreck et al., "Natural peptides isolated from Gly86/Val86-containing variants of HLA-DR1, -DR11,-DR13 and -DR52," Immunogenetics 43(6):392-7 (1996).
Wang et al., "Adenovirus-Mediated Somatic Genome Editing of Pten by CRISPR/Cas9 in Mouse Liver in Spite of Cas9-Specific Immune Responses," Human Therapy 26(7):432-442 (2015).
Zetsche et al., "Cpf1 is a Single RNA-Guide Endonuclease of a Class 2 CRISPR-Cas System," Cell 163:759-771 (2015).
International Preliminary Report on Patentability issued in PCT application No. PCT/EP2016/077487, dated Apr. 18, 2017.
International Search Report issued in PCT application No. PCT/EP2016/077487, dated Apr. 18, 2017.
Written Opinion of the International Searching Authority issued in PCT application No. PCT/EP2016/077487, dated Apr. 18, 2017.

\* cited by examiner

FIG. 1

| Pos | Peptide | SEQ ID NO. | Length | Allele: A*01 | A*02 | A*02 | A*02 | A*02 | A*03 | A*11 | A*23 | A*24 | A*26 | A*29 | A*30 | A*31 | A*33 | A*68 | A*68 | B*07 | B*08 | B*15 | B*18 | B*27 | B*35 | B*40 | B*44 | B*51 | B*53 | B*57 | B*58 |
|---|---|---|---|---|---|---|---|---|---|---|---|---|---|---|---|---|---|---|---|---|---|---|---|---|---|---|---|---|---|---|---|
| 1 | mdkkysigl | 10 | 9 | | | | | | | | | | | | | | | | | | | M | | | | | | | | | |
| 1 | mdkkysigld | 11 | 10 | | M | | | | M | | | | | M | M | M | M M | M | | | M | | | | | | | | | | |
| 2 | dkkysigld | 12 | 9 | | | | | | | | | | | | | | M | | | | | | | | | | | | | | |
| 2 | dkkysigldi | 13 | 10 | | | | | | | | | | | M | | | | | | | | | | | | | | | | | |
| 3 | kkysigldi | 14 | 9 | | | | | | | | M | | | | | | | | | | | | | M | | | | | | | |
| 3 | kkysigldig | 15 | 10 | | | | | | | | | | | | | | | | | | | | | | | | | | | | |
| 4 | kysigldig | 16 | 9 | | | | | | | | | | | | | | | | | | | | | | | | | | | | |
| 4 | kysigldigt | 17 | 10 | | | | | | | | M | M | M | M | | | | M | M | | | | | | | | | M | | | |
| 5 | ysigldigt | 18 | 9 | | | M | M | M | | | | | | | | | | | | | | | | | | | | | | | |
| 5 | ysigldigtn | 19 | 10 | | | S | S | S | | | | | | | | | | | | | | | | | | | | | | | |
| 6 | sigldigtn | 20 | 9 | | | | | | | | | | | | | | | | | | | | | | | | | | | | |
| 6 | sigldigtns | 21 | 10 | | S | M S | | | | | M | M | M | M | M | | | M | | | | | | | | | | | | | |
| 7 | igldigtns | 22 | 9 | | | | | | | | | | | | | | | | | | | | | | | | | | | | |
| 7 | igldigtnsv | 23 | 10 | | | | | | | | | M | | | | | | | M | | | | | | | | | | | | |
| 8 | gldigtnsv | 24 | 9 | | | | | | | | M | | | | | | | | | | | | | | | | | | | | |
| 8 | gldigtnsvg | 25 | 10 | | | | | | | | M | M | M S | M | M | | | M | M | | | | | | M | | | M | M | | |
| 9 | ldigtnsvg | 26 | 9 | | | | | | | | M | M | M | | | | | M | | | | | | | | | | | | | |
| 9 | ldigtnsvgw | 27 | 10 | | | | | | | | M | M | M | | | | | | | | | M | | | | | | | | | M |
| 10 | digtnsvgw | 28 | 9 | | | | | | | | | | | | | | | | | | | | | | | | | | | | |

| | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|
| 26 | kvpskkfkv | 9 | | | | | | | | | | | | | | | | | | | | | | | | | | | | | | | M | | |
| 26 | kvpskkfkvl | 10 | | | | | | | | | | | | | | | | | | | | | M | | | | | | | | | | | M | M |
| 27 | vpskkfkvl | 9 | | | | | | | | | | | | | | | | | | | | M | | | | | | | | | | | S | S | | |
| 27 | vpskkfkvlg | 10 | | | | | | | | | | | | | | | | | | | | M | | | | | | | | | | | | | | |
| 28 | pskkfkvlg | 9 | | | | | | | | | | | | | | | | | | | | | | | | | | | | | | | | | | |
| 28 | pskkfkvlgn | 10 | | | | | | | | | | | | | | | | | | | | | | | | | | | | | | | | | | |
| 29 | skkfkvlgn | 9 | | | | | | | | | | | | | | | | | | | | | | | | | | | | | | | | | | |
| 29 | skkfkvlgnt | 10 | | | | | | | | | | | | | | | | | | | | | | | | | | | | | | | | | | |
| 30 | kkfkvlgnt | 9 | | | | | | | | | | | | | | | M | | | | | | | | | | | | | M | | | | | | |
| 30 | kkfkvlgntd | 10 | | | | | | | | | | | | | | | M | M | | | | | | | | | | | | | | | | | | |
| 31 | kfkvlgntd | 9 | | | | | | | | | | | | | | | | | | | | | | | | | | | | | | | | | | |
| 31 | kfkvlgntdr | 10 | | | | | | | | | | | | | | M | S | | | | | | | | | | | | | | | | | | | |
| 32 | fkvlgntdr | 9 | | | | | | | | | | | | | | | M | | | | | | | | | | | | | | | | | | | |
| 32 | fkvlgntdrh | 10 | | | | | | | | | | | | | | | | M | | | | | | | | | | | | | | | | | | |
| 33 | kvlgntdrh | 9 | | | | | | | | | | | | | | | | | | | | | | | | | | | | | | | | | | |
| 33 | kvlgntdrhs | 10 | | | | | | | | | | | | | | | M | | | | | | | | | | | | | | | | | | | |
| 34 | vlgntdrhs | 9 | | | | | | | | | | | | | | | | | | | | | | | | | | | | | | | | | | |
| 34 | vlgntdrhsi | 10 | | | | | | | | | | | M | | | S | M | | | | | S | | | | | | | | | | | | | | |
| 35 | lgntdrhsi | 9 | | | | | | | | | | | | | | | | M S | | | | M M | | | | | | | | | | | | | | |
| 35 | lgntdrhsik | 10 | | | | | | | | | | | | | | | | | | | | M | | | M | | | | | | | | | | | |
| 36 | gntdrhsik | 9 | | | | | | | | | | | | | | | | | | | | | | | | | | | | | | | | | | |
| 36 | gntdrhsikk | 10 | | | | | | | | | | | | | | | | | | | | | | | | M | | | | M | | | | | | |
| 37 | ntdrhsikk | 9 | | | | | | | | | | | | | | | | | | | | M | | | | | | | | | | | | | | |
| 37 | ntdrhsikkn | 10 | | | | | | | | | | | | | | | | | | | | | | | | | | | | | | | | | | |
| 38 | tdrhsikkn | 9 | | | | | | | | | | | | | | | | | | | | | | | | | | | | M | | | | | | |
| 38 | tdrhsikknl | 10 | | | | | | | | | | | | | | | | | | | | | | | | | | | | | | | | M | | |
| 39 | drhsikknl | 9 | | | | | | | | | | | | | | | | | | | | | | | | | | | | | | | | | | |
| 39 | drhsikknli | 10 | | | | | | | | | | | | | | | | | | | | | | | | | | | | | | | | M | | |
| 40 | rhsikknli | 9 | | | | | | | | | | | | | | | | | | | | | | | | | | | | | | | | | | |
| 40 | rhsikknlig | 10 | | | | | | | | | | | | | | | | | | | | | | | | | | | | | | | | | | |
| 41 | hsikknlig | 9 | | | | | | | | | | | | | | | | | | | | | | | | | | | | | | | | | | |

| | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|
| 72 | ytrknricy | 10 | M | | | | | | | | | | | | | | | | | | | | | | | | | | | | | | | | | | | |
| 73 | trknricy | 9 | | | | | | | | | | | | | | | | | | | | | | | | | | | | | | | | | | | | |
| 73 | trknricyl | 10 | | | | | | | | | | | | | | | | | | | | | | | | | | | | | | | | | | | | |
| 74 | rknricyl | 9 | | | | | | | | | | | | | | | | | | | | | | | | | | | | | | | | | | | | |
| 74 | rknricylq | 10 | | | | | | | | | | | | | | | | | | | | | | | | | | | | | | | | | | | | |
| 75 | knricylq | 9 | | | | | | | | | | | | | | | | | | | | | | | | | | | | | | | | | | | | |
| 75 | knricylqe | 10 | | | | | | | | | | | | | | | | | | | | | | | | | | | | | | | | | | | | |
| 76 | nricylqe | 9 | | | | | M | | | | | | | | | | | | | | | | | | | | | | | | | | | | | | | |
| 76 | nricylqei | 10 | | | | | M S | | | | | | | | | | | | | | | | | | | | | | | | | | | | | | | |
| 77 | ricylqei | 9 | | | | | M S | | | | | | | | | | | | | | | | | | | | | | | | | | | | | | | |
| 77 | ricylqeif | 10 | | | | | M | | | | M | | | | | | | | | | | | | | | | | | | | | | | | | | | |
| 78 | icylqeif | 9 | | | | | | | | | M | | | | | | | | | | | | | | | | | | | | | | | | | | | |
| 78 | icylqeifs | 10 | | | | | | M | S | M | | M | | | | | | | | | | | | | | | | | | | | | | | | | | |
| 79 | cylqeifs | 9 | | | | | | M | M | | | M | | | | | | | | | | | | | | | | | | | | | | | | | | |
| 79 | cylqeifsn | 10 | | | | | | S | | M | | M S | | | | | | | | | | | | | | | | | | | | | | | | | | |
| 80 | ylqeifsn | 9 | | | | | | | S | | M | M | | | | | | | | | | | | | | | | | | | | | | | | | | |
| 80 | ylqeifsne | 10 | | | | | M | S | M | | M | M S | M | | | | | | | | | | | | | | | | | | | | | | | | | |
| 81 | lqeifsne | 9 | | | | | | | M | | | M S | | | | | | | | | | | | | | | | | | | | | | | | | | |
| 81 | lqeifsnem | 10 | | | | | | | | | | M | M | S | | | | | | | | | | | | | | | | | | | | | | | | |
| 82 | qeifsnem | 9 | | | | | | | | | | | M | | | | | | | | | | | | | | | | | | | | | | | | | |
| 82 | qeifsnema | 10 | | | | | | | | | | M | M | M | S | | | | | | | | | | | | | | | | | | | | | | | |
| 83 | eifsnema | 9 | | | | | | | M | | | | S | M | | M | | | | | | | | | | | | | | | | | | | | | | |
| 83 | eifsnemak | 10 | | | | | M | | S | | | | | M | | M | | M | | | | | | | | | | | | | | | | | | | | |
| 84 | ifsnemak | 9 | | | | | | | | | | | | | | M | | | | | | | | | | | | | | | | | | | | | | |
| 84 | ifsnemakv | 10 | | | | | | | | | | | | | | M | M | | | M | | | | | | | | | | | | | | | | | | |
| 85 | fsnemakv | 9 | | | | | | | | | | | | | | | M | | | | | | | | | | | | | | | | | | | | | |
| 85 | fsnemakvd | 10 | | | | | | | | | | | | | | | | | M | | | | | | | | | | | | | | | | | | | |
| 86 | snemakvd | 9 | | | | | | | | | | | | | | | | | | | | | | | | | | | | | | | | | | | | |
| 86 | snemakvdd | 10 | | | | | | | | | | | | | | | | | | | M | M | | | | | | | | | | | | | | | | |
| 87 | nemakvdd | 9 | | | | | | | | | | | | | | | | | | | M M | M | | | | | | | | | | | | | | | | |
| 87 | nemakvdds | 10 | | | | | | | | | | | | | | | | | | | M M | M | | | | | | | | | | | | | | | | |

| # | seq | len | | | | | | | | | | | | | | | | | | | | | | | | | |
|---|---|---|---|---|---|---|---|---|---|---|---|---|---|---|---|---|---|---|---|---|---|---|---|---|---|---|---|
| 103 | esflveedkk | 10 | | | | | | | | | | | | | | | | | | | | | | | | | M | |
| 104 | sflveedkk | 9 | | | | | | | | | | | | | | | | | | | | | | | | | | |
| 104 | sflveedkkh | 10 | | | | | | | | | | | | | M | | | | | | | | | | | | | |
| 105 | flveedkkh | 9 | | | | | | | | | | | | | | | | | | | | | | | | | | |
| 105 | flveedkkhe | 10 | | | | | | | | | | | | | | | | | | | | | | | | | | |
| 106 | lveedkkhe | 9 | | | | | | | | | | | | | | | | | | | | | | | | | | |
| 106 | lveedkkher | 10 | | | | | | | | | | | | | | | M | | | | | | | M | | | | |
| 107 | veedkkher | 9 | | | | | | | | | | | | | | | M | | | | | | | | | | | |
| 107 | veedkkherh | 10 | | | | | | | | | | | | | | | M | S | | | | | | | | | | |
| 108 | eedkkherh | 9 | | | | | | | | | | | | | | | | M | | | | | | | | | | |
| 108 | eedkkherhp | 10 | | | | | | | | | | | | | | M | S | M | | | | | | | | | | |
| 109 | edkkherhp | 9 | | | | | | | | | | | | | | | | S | | | | | | | | | | |
| 109 | edkkherhpi | 10 | | | | | | | | | | | | | | | | M | S | M | | | | | | | | |
| 110 | dkkherhpi | 9 | | | | | | | | | | | | | | | | | S | M | | | | | | | | |
| 110 | dkkherhpif | 10 | | | | | | | | | | | | | | | | | M | | | | | | | | | |
| 111 | kkherhpif | 9 | | | | | | | | | | | | | | | | | | | | | | | | | | |
| 111 | kkherhpifg | 10 | | | | | | | | | | | | | | | | | M | | | | | | | | | |
| 112 | kherhpifg | 9 | | | | | | | | | | | | | | | | | | | | | | | | | | |
| 112 | kherhpifgn | 10 | | | | | | | | | | | | | | | | | | | | | | | | | | |
| 113 | herhpifgn | 9 | | | | | | | | | | | | | | | | | M | | | | | | | | | |
| 113 | herhpifgni | 10 | | | | | | | | M | | | | | | M | S | M | | S | | | | | | | | M |
| 114 | erhpifgni | 9 | | | | | | | | | | | | | | M | | S | | | | | | | | | | | |
| 114 | erhpifgniv | 10 | | | | | | | | | | | | | | M | | M | | | | | | | | | M | |
| 115 | rhpifgniv | 9 | | | | | | | | | | | | | | | | S | | | | | | | | | | |
| 115 | rhpifgnivd | 10 | | | | | | | | | | | | | | M | | M | | | | | | | | | M | |
| 116 | hpifgnivd | 9 | | | | | | | | | | | | | | | | | | | | | | | | | | |
| 116 | hpifgnivde | 10 | | | | | | | | | | | | | | | S | M | | | | | | | | | M | |
| 117 | pifgnivde | 9 | | | | | | | | | | | | | S | | S | | | | | | | | | | | |
| 117 | pifgnivdev | 10 | | | | | | | | | | | | | M | S | M | M | | | | | | | | | M | |
| 118 | ifgnivdev | 9 | | | | | | | | | | | | | | | S | M | | | | | | | | | | |
| 118 | ifgnivdeva | 10 | | | | | | | | | | | | | M | | M | | | | | | | | | | M | |

FIG. 1 (Continued)

| # | sequence | len | | | | | | | | | | | | | | | | | | | | | | | | | |
|---|---|---|---|---|---|---|---|---|---|---|---|---|---|---|---|---|---|---|---|---|---|---|---|---|---|---|---|
| 119 | fgnivdeva | 9 | | | | | | | | | | | | | | | | | | | | | | | | | |
| 119 | fgnivdevay | 10 | | | | | M | | | | | | | | | | | | | | | | | | | | |
| 120 | gnivdevay | 9 | | | | | | | | | | | | | | | | | | | | | | | | | |
| 120 | gnivdevayh | 10 | | | M | | | | | | | | | | | | | | | | | | | | | | |
| 121 | nivdevayh | 9 | | | M | | | | | | | | | | | | | | | | | | | | | | |
| 121 | nivdevayhe | 10 | | | | | | | | | | | | | | | | | | | | | | | | | |
| 122 | ivdevayhe | 9 | | | | | | | | | M | | | | | | | | | | | | | | | | |
| 122 | ivdevayhek | 10 | | | | | | S | | | | | | | | | | | | | | | | | | | |
| 123 | vdevayhek | 9 | | | | | | | | | | | | | | | | | | | | | | | | | |
| 123 | vdevayheky | 10 | | | | | | | | | | | M M | | | | | | | | | | | | | | |
| 124 | devayheky | 9 | | | | | | | | | | | | | | | | | | | | | | | | | |
| 124 | devayhekyp | 10 | | | | | | | | | | | M | | M M | M | | | | M | | | | | | | |
| 125 | evayhekyp | 9 | | | | | | | | | | | | | M | | M | | M | | M | | | | | | |
| 125 | evayhekypt | 10 | | | | | | | | | | | M | | M M | M S | S | | S S | | M S | | M | | | |

FIG. 2A

| Pos | Peptide | SEQ ID NO: | Allele: | DRB1*01 | DRB1*01 | DRB1*03 | DRB1*03 | DRB1*03 | DRB1*04 | DRB1*04 | DRB1*04 | DRB1*04 | DRB1*04 | DRB1*04 | DRB1*04 | DRB1*04 | DRB1*07 | DRB1*08 | DRB1*08 | DRB1*08 | DRB1*08 | DRB1*09 | DRB1*10 | DRB1*11 | DRB1*11 | DRB1*11 | DRB1*11 | DRB1*12 | DRB1*12 | DRB1*13 | DRB1*13 |
|---|---|---|---|---|---|---|---|---|---|---|---|---|---|---|---|---|---|---|---|---|---|---|---|---|---|---|---|---|---|---|---|
| 1 | mdkkysigld | 11 | | | | | | | | | | | | | | | | | | | | | | | | | | M | M | | |
| 2 | dkkysigldi | 13 | | | | | | | | | | | | | | | | | | | | | | | | | | | | | |
| 3 | kkysigldig | 15 | | | | | | | | | | | | | | | M | | | | | M | | | | | | | | | |
| 4 | kysigldigt | 17 | | | | | | | | | | | | | | | | | | | | | | | | | | | | | |
| 5 | ysigldigtn | 19 | | | | | | | | | | | | | | | | | | | | | | | | | | | | | |
| 6 | sigldigtns | 21 | | | | | | | | | | | | | | | | | | | | | | | | | | | | | |
| 7 | igldigtnsv | 23 | | | | | | | | | | | | | | | | | | | | | | | | S | | | | | M |
| 8 | gldigtnsvg | 25 | | M | | | | | | M | M | | | | | | | | | | | | | | | M | | | | M | |
| 9 | ldigtnsvgw | 27 | | | | | | | | | | | | | | | | | | | | | | | | | | | | | |
| 10 | digtnsvgwa | 29 | | | | | | | | | | | M | | | | | | | | | | | | | | | | | | |
| 11 | igtnsvgwav | 31 | | | | | | | | | | | | | | | | | | | | | | | | | | | | | |
| 12 | gtnsvgwavi | 33 | | | | | | | | | | | | | | | | | | | | | | | | | | | | | |
| 13 | tnsvgwavit | 35 | | | | | | | | | | | | | | | | | M | | | | | | | | | | | | |
| 14 | nsvgwavitd | 37 | | | | | | | | | | | | | | | | | | | | | | | | | | | | | |
| 15 | svgwavitde | 39 | | | | | | | | | | | | | | | | | | | | | | | | | | | | | |
| 16 | vgwavitdey | 41 | | | | | | | | | | | | | | | | | | | | | | | | | | | | | |
| 17 | gwavitdeyk | 43 | | | | | | | | | | | | | | | | | | | | | | | | | | | | | |

FIG. 2A (Continued)

| # | seq | | | | | | | | | | | | | | | | | | | | | | | |
|---|---|---|---|---|---|---|---|---|---|---|---|---|---|---|---|---|---|---|---|---|---|---|---|---|
| 18 | wavitdeykv | 45 | | | | | | | | | | | | | | | | | | | | | | |
| 19 | avitdeykvp | 47 | | | | | | | | | | | | | | | | | | | | | | |
| 20 | vitdeykvps | 49 | | | | | | | | | | | | | | | | | | | | | | |
| 21 | itdeykvpsk | 51 | | | | | | | | | | | | | | | | | | | | | | |
| 22 | tdeykvpskk | 53 | | | | | | | | | | | | | | | | | | | | | | |
| 23 | deykvpskkf | 55 | | | | | | | | | | | | | | | | | | | | | | |
| 24 | eykvpskkfk | 57 | | | | | | | | | | | | | | | | | | | | | | |
| 25 | ykvpskkfkv | 59 | | | | | | | | | | | | | | | | | M | M | | | | |
| 26 | kvpskkfkvl | 61 | | | | | | | | M | | | | | | | | | | | | | | |
| 27 | vpskkfkvlg | 63 | | | | | | | | | | | | | | | M | M | | | | | | |
| 28 | pskkfkvlgn | 65 | | | | | | | | | | | | | | | | | | | | | | |
| 29 | skfkfkvlgnt | 67 | | | | | | | | | | | | | | | | | | | | | | |
| 30 | kkfkvlgntd | 69 | | | | | | | | | | | M | | | | M | | | | | | | |
| 31 | kfkvlgntdr | 71 | | | | | | | | | M | M | | | | | | | | | | | | |
| 32 | fkvlgntdrh | 73 | | | | M | S | M | | | | | | | | | M | | | | | | | |
| 33 | kvlgntdrhs | 75 | | | | | | | | | | | | | | | | | | | | | | |
| 34 | vlgntdrhsi | 77 | | | | | | | | | | | | | M | | | | | | | | | |
| 35 | lgntdrhsik | 79 | | | | | | | | | | | | | | | | | | | | | | |
| 36 | gntdrhsikk | 81 | | | | | | | | | | | | | | | | | | | | | | |
| 37 | ntdrhsikkn | 83 | | | | | | | | | | | | | | | | | | | | | | |
| 38 | tdrhsikknl | 85 | | | | | | | | | | M | M | | | | | | | | | | | |
| 39 | drhsikknli | 87 | | | | | | | | | | | | | | | | | | | | | | |
| 40 | rhsikknlig | 89 | | | | | | | | | | | | | | | | | | | | M | M | |
| 41 | hsikknliga | 91 | | | | | | | | | | | | | | | | | | | M | M | | |
| 42 | sikknligal | 93 | | S | S | | | | | | | | | | | | | | | | | | | |
| 43 | ikknligall | 95 | | M | M | | | | | | | | | | | | | | | | | | | |
| 44 | kknligallf | 97 | | | | | | | | | | | | | M | | | | | | M | M | | |
| 45 | knligallfd | 99 | | | | | | | | M | | | | | | | | | | | | | | |
| 46 | nligallfds | 101 | | | | | | | | | | | | | | | | | | | | | | |
| 47 | ligallfdsg | 103 | | | | | | | | | | | | | | | | | | | | | | |
| 48 | igallfdsge | 105 | | | | | | | | | | | | | | | | | | | | | | |
| 49 | gallfdsget | 107 | | | | | | | | | | | | | | | | | | | | | | |
| 50 | allfdsgeta | 109 | | | | | | | | | | | | | | | | | | | | | | |

FIG. 2A (Continued)

| | | | | | | | | | | | | | | | | | | | | | | | | | | |
|---|---|---|---|---|---|---|---|---|---|---|---|---|---|---|---|---|---|---|---|---|---|---|---|---|---|---|
| 51 | lifdsgetae | 111 | M | M | | | | | | | | | | | | | | | | | | | | | | |
| 52 | lfdsgetaea | 113 | | | | | | | | | | | | | | | | | | | | | | | | |
| 53 | fdsgetaeat | 115 | | | M | M | | | | | | | | | | | | | | | | | | | | |
| 54 | dsgetaeatr | 117 | | | | M | | | | | | | | | | | | | | | | | | | | |
| 55 | sgetaeatrl | 119 | | | | | | | | | | | | | | | | | | | | | | | | |
| 56 | getaeatrlk | 121 | | | | | | | | | | | | | | | | | | | | | | | | |
| 57 | etaeatrlkr | 123 | | | | | | M | M | | | | | | | | | | | | | | | | | |
| 58 | taeatrlkrt | 125 | | | | | | | M | | | | | | | | | | | | | | | | | |
| 59 | aeatrlkrta | 127 | | | | | | | | | | | | | | | | | | | | | | | | |
| 60 | eatrlkrtar | 129 | | | | | | | | | | | M | | | | M | | | M | M | | M | | | |
| 61 | atrlkrtarr | 131 | | | | | | | | | | | | | | | M | S | | M | S | M | | | | |
| 62 | trlkrtarrr | 133 | | | | | | | | | | M | | | | | M | M | S | | M | | | | | |
| 63 | rlkrtarrry | 135 | | | | | | | | | | | | | | | | | | | | | | | | |
| 64 | lkrtarrryt | 137 | M | | | | | | | | M | | | | | | | | | | | | | | | |
| 65 | krtarrrytr | 139 | | M | M | | | | | | M | S | | | | | | | | | | | | | | |
| 66 | rtarrrytrr | 141 | | | M | | | | | | M | M | | | | | | | | | | | | | | |
| 67 | tarrrytrrk | 143 | | | | | | | | | | M | | | | | | | | | | | | | | |
| 68 | arrrytrrkn | 145 | | | | | | | | | | | | | | | | | | | | | | | | |
| 69 | rrrytrrknr | 147 | | | | | | | | | | | | S | | | | | S | | | | | | | |
| 70 | rrytrrknri | 149 | | | | | | | | | | M | | | | | M | M | | | | | | | | |
| 71 | rytrrknric | 151 | | | | | | | M | | | | | | | | | | | | | | | | | |
| 72 | ytrrknricy | 153 | | | | | | S | | | | | | | | | | | | | M | | | | | |
| 73 | trrknricyl | 155 | | | | | | | | | | | | | | | | | | | | | | | | |
| 74 | rrknricylg | 157 | | | | | | | | | | | | | | | | | | | | | | | | |
| 75 | rknricylgq | 159 | | | | | M | | | | | | | | | | | | | | | | | | | |
| 76 | knricylgqe | 161 | | | | | | | | | | | | | | | | | | | | | | | | |
| 77 | nricylgqei | 163 | | | | | | | | | | | | | | | | | | | | | | | | |
| 78 | ricylgqeif | 165 | | | | | M | | M | | | | | | | | | | | | | | | | | |
| 79 | icylgqeifs | 167 | | | | | | | | | | | | | | | | | | | | | | | | |
| 80 | cylgqeifsn | 169 | | | | | | | | | | | | | | | | | | | | | | | | |
| 81 | ylgqeifsne | 171 | | | | | | | | | | | | | | | | | | | | | | | | |
| 82 | lgqeifsnem | 173 | M | M | | | | | | | | | | | | | | | | | | | | | | |
| 83 | gqeifsnema | 175 | | | | | | | | | M | | | | | | | | | | | | | | | |

FIG. 2A (Continued)

| | | |
|---|---|---|
| 84 | eifsnemakv | 177 |
| 85 | ifsnemakvd | 179 |
| 86 | fsnemakvdd | 181 |
| 87 | snemakvdds | 183 |
| 88 | nemakvddsf | 185 |
| 89 | emakvddsff | 187 |
| 90 | makvddsffh | 189 |
| 91 | akvddsffhr | 191 |
| 92 | kvddsffhrl | 193 |
| 93 | vddsffhrle | 195 |
| 94 | ddsffhrlee | 197 |
| 95 | dsffhrlees | 199 |
| 96 | sffhrleesf | 201 |
| 97 | ffhrleesfl | 203 |
| 98 | fhrleesflv | 205 |
| 99 | hrleesflve | 207 |
| 100 | rleesflvee | 209 |
| 101 | leesflveed | 211 |
| 102 | eesflveedk | 213 |
| 103 | esflveedkk | 215 |
| 104 | sflveedkkh | 217 |
| 105 | flveedkkhe | 219 |
| 106 | lveedkkher | 221 |
| 107 | veedkkherh | 223 |
| 108 | eedkkherhp | 225 |
| 109 | edkkherhpi | 227 |
| 110 | dkkherhpif | 229 |
| 111 | kkherhpifg | 231 |
| 112 | kherhpifgn | 233 |
| 113 | herhpifgni | 235 |
| 114 | erhpifgniv | 237 |
| 115 | rhpifgnivd | 239 |
| 116 | hpifgnivde | 241 |

FIG. 2A (Continued)

| | | | | | | | | | | | | | | | | | | | | | | | |
|---|---|---|---|---|---|---|---|---|---|---|---|---|---|---|---|---|---|---|---|---|---|---|---|
| 117 | pifgnivdev | 243 | | | | | | | | | | | | | | | | | | | | | |
| 118 | ifgnivdeva | 245 | | | | | | | | | | | | | | | | | | | | | |
| 119 | fgnivdevay | 247 | | | | | | | | | | | | | | | | | | | | | |
| 120 | gnivdevayh | 249 | | | | | | | | | | | | | | | | | | | | | |
| 121 | nivdevayhe | 251 | | | | M | | | | | | | | | | | | | | | | | |
| 122 | ivdevayhek | 253 | | | | | | | | | | | | | | | | | | | | | |
| 123 | vdevayheky | 255 | | | | | | | | | | | | | | | | | | | | | |
| 124 | devayhekyp | 257 | | | | | | | | | | | | | | | | | | | | | |
| 125 | evayhekypt | 259 | | | | | | | | | | | | | | | | | | | | | |

FIG. 2B

| Pos | Peptide | SEQ ID NO: | Allele: DRB1*13 | DRB1*13 | DRB1*13 | DRB1*14 | DRB1*14 | DRB1*14 | DRB1*14 | DRB1*14 | DRB1*15 | DRB1*15 | DRB1*15 | DRB1*15 | DRB1*16 | DRB1*16 | DRB3*01 | DRB3*02 | DRB3*02 | DRB3*03 | DRB4*01 | DRB5*01 | DRB5*01 | DRB5*02 | DQA1*01 | DQA1*01 | DQA1*01 | DQA1*01 | DQA1*01 | DQA1*01 | DQA1*01 | DQA1*01 | DQA1*01 |
|---|---|---|---|---|---|---|---|---|---|---|---|---|---|---|---|---|---|---|---|---|---|---|---|---|---|---|---|---|---|---|---|---|
| 1 | mdkkysigld | 11 | | | | | | | | | | | | | | | | | | | | | | | | | | | | | | | |
| 2 | dkkysigldi | 13 | | | | | | | | | | | | | | | | | | M | | | | | | | | | | | | | |
| 3 | kkysigldig | 15 | | | | | | | | | | | | | | | | | | | M | | | | | | | | | | | | |
| 4 | kysigldigt | 17 | | | | | | | | | | | | | | | | | | | | | | | | | | | | | | | |
| 5 | ysigldigtn | 19 | | | | | | | | | | | | | | | M | | | | | | | | | | | | | | | | |
| 6 | sigldigtns | 21 | | S | | | | | | | | | | | | | | | | | | | | | | | | | | | | | |
| 7 | igldigtnsv | 23 | | | | | | | | | | | | | | | | | | | | | | | | | | | | | | | |
| 8 | gldigtnsvg | 25 | | | | | | | | | | | | | | | | | | | | | | | | | | | | | | | |
| 9 | ldigtnsvgw | 27 | | | | | | | | | | | | | | | | | | | | | | | | | | | | | | | |
| 10 | digtnsvgwa | 29 | | | | | | | | | | | | | | | | | | | | | | | | | | | | | | | |
| 11 | igtnsvgwav | 31 | | | | | | | | | | | | | | | | | | | | | | | | | | | | M | S | S | |
| 12 | gtnsvgwavi | 33 | | | | | | | | | | | | | | | | | | | | | | | | | | | | | | | |
| 13 | tnsvgwavit | 35 | | | | | | | | | | | | | | | | | | | | | | | | | | | | | | | |

FIG. 2B (Continued)

| | | | | | | | | | | | | | | | | | | | | | | | | | |
|---|---|---|---|---|---|---|---|---|---|---|---|---|---|---|---|---|---|---|---|---|---|---|---|---|---|
| 14 | nsvgwavitd | 37 | | | | | | | | | | | | | | | | | | | | | | | |
| 15 | svgwavitde | 39 | | | | | | | | | | | | | | | | | | | | | | M | |
| 16 | vgwavitdey | 41 | | | | | | | | | | | | | | | | | | | | | | | |
| 17 | gwavitdeyk | 43 | | | | | | | | | | | | | | | | | | | | | | | |
| 18 | wavitdeyky | 45 | | | | | | | | | | | | M | | | | | | | | | | | |
| 19 | avitdeykvp | 47 | | | | | | | | | | | | | | | | | | | | | | | |
| 20 | vitdeykvps | 49 | | | | | | | | | | | | | | | | | | | | | | | |
| 21 | itdeykvpsk | 51 | | | | | | | | | | M | | | | | | | | | | | | | |
| 22 | tdeykvpskk | 53 | | | | | | | | | | | | | | | | | | | | | | | |
| 23 | deykvpskkf | 55 | | | | | | | | | | | | S | | | | | | | | | | | |
| 24 | eykvpskkfk | 57 | | | | | | | | | | | | | | | | | | | | | | | |
| 25 | ykvpskkfkv | 59 | | | | | | | | | | | | S | | | | | | | | | | | |
| 26 | kvpskkfkvl | 61 | M | | | | | | | | | | | | | | | | | | | | | | |
| 27 | vpskkfkvlg | 63 | | | | | | | | | | | | | | | | | | | | | | | |
| 28 | pskkfkvlgn | 65 | | | | | | | | | | | | | | | | | | | | | | | |
| 29 | skkfkvlgnt | 67 | | | M | | | | | | | | | | | | | | | | | | | | |
| 30 | kkfkvlgntd | 69 | | M | M | | | | | | | | | | | | | | | | | | | | |
| 31 | kfkvlgntdr | 71 | | | | | | | | | | | | | | | | | | | | | | | |
| 32 | fkvlgntdrh | 73 | | M | | | | | | | | | | | | | | | | | | | | | |
| 33 | kvlgntdrhs | 75 | | | | | | | | M | | | | | | | | | | | | | | | |
| 34 | vlgntdrhsi | 77 | M | | | | | | M M | | | | | | | | | | | | | | | | |
| 35 | lgntdrhsik | 79 | | | | | | | | | | | | | | | | | | | | | | | |
| 36 | gntdrhsikk | 81 | | | | | | | | | | | | | | | | | | | | | | | |
| 37 | ntdrhsikkn | 83 | | | | | | | | | | | | | | | | | | | | | | | |
| 38 | tdrhsikknl | 85 | | | | | | | | | | | | | | | | | | | | | | | |
| 39 | drhsikknli | 87 | | | | | | | | | | | | | | | | | | | | | | | |
| 40 | rhsikknlig | 89 | | | | | | | M | | | | | | | | | | M | | | | | | |
| 41 | hsikknliga | 91 | | | | | | | | | | | | | | | | | | | | | | | |
| 42 | sikknligal | 93 | | | | | | | | | | | | | | | | | | | | | | | |
| 43 | ikknligall | 95 | | | | | | | | | M M | | | | | | | | | | | | | | |
| 44 | kknligallf | 97 | | | | | | | | | M | | | | | | | | | | | | | | |
| 45 | knligallfd | 99 | | | | | | | | | S | | | | | | | M | | | | | | | |
| 46 | nligallfds | 101 | | | | | | | | | | | | | | | | | | | | | | | |

FIG. 2B (Continued)

| | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| 47 | ligallfdsg | 103 | | | | | | | | | | | | | | | | | | | | | | | | | | | | | |
| 48 | igallfdsge | 105 | | | | | | | | | | | | | | | | | | | | | | | | | | | | | |
| 49 | gallfdsget | 107 | | | | | | | | | | | | | | | | | | | | | | | | | | | | | |
| 50 | allfdsgeta | 109 | | | | | | | | | | | | | | | | | | | | | | | | | | | | | |
| 51 | llfdsgetae | 111 | | | | | | | | | | | | | | | | | | | | | | | | | | | | | |
| 52 | lfdsgetaea | 113 | | | | | | | | | | | | | | | | | | | | | | | | | | | | | |
| 53 | fdsgetaeat | 115 | | | | | | | | | | | | | | | | | | | | | | | | | | | | | |
| 54 | dsgetaeatr | 117 | | | | | | | | | | | | | | | | | | | | | | | | | | | | | |
| 55 | sgetaeatrl | 119 | | | | | | | | | | | | | | | | | | | | | | | | | | | | | |
| 56 | getaeatrlk | 121 | | | | | | | | | | | | | | | | | | | | | | | | | | | | | |
| 57 | etaeatrlkr | 123 | | | | | | | | | | | | | | | | | | | | | | | | | | | | | |
| 58 | taeatrlkrt | 125 | | | | | | | | | | | | | | | | | | | | | | | | | | | | | |
| 59 | aeatrlkrta | 127 | | | | | | | | | | | | | | | | | | | | | | | | | | | | | |
| 60 | eatrlkrtar | 129 | | | | | | | | | | | | M | | | | | | | | | | | | | | | | | |
| 61 | atrlkrtarr | 131 | | | | | | | S | | | | | M | S | | | | | | | | | | | | | | | | |
| 62 | trlkrtarrr | 133 | | | | | | | M | | | | | M | M | | | | | | | | | | | | | | | | |
| 63 | rlkrtarrry | 135 | | | | | | | S | S | | | | M | S | | | | | | | | | | | | | | | | |
| 64 | lkrtarrryt | 137 | S | | | M | | M | M | M | | | | M | M | | | | | | | | | | | | | | | | |
| 65 | krtarrrytr | 139 | M | | | M | | S | S | M | | | | M | M | | | | | | | | | | | | | | | | |
| 66 | rtarrrytrr | 141 | | | | M | | M | M | M | | | | M | S | | | | | | | | | | | | | | | | |
| 67 | tarrrytrrk | 143 | | | | M | | S | S | M | | | | M | M | | | | | | | | | | | | | | | | |
| 68 | arrrytrrkn | 145 | | | | M | | M | M | M | | | | M | M | | | | | | | | | | | | | | | | |
| 69 | rrrytrrknr | 147 | | | | M | | S | S | M | | | | M | M | | | | | | | | | | | | | | | | |
| 70 | rrytrrknri | 149 | | | | M | | | | | | | | | M | M | | | | | | | | | | | | | | | |
| 71 | rytrrknric | 151 | | | | | | | | | | | | | M | | | | | | | | | | | | | | | | |
| 72 | ytrrknricy | 153 | | | M | | | | | | | | | | M | | | | | | | | | | | | | | | | |
| 73 | trrknricyl | 155 | | | | | | | | | | | | | | | M | | | | | | | | | | | | | | | |
| 74 | rrknricylq | 157 | | | | | | | | | | | | | M | | | | | | | | | | | | | | | | |
| 75 | rknricylqe | 159 | | | | | | | | | | | | | M | | | | | | | | | | | | | | | | |
| 76 | knricylqei | 161 | | | | | | | | | | | | | | | | | | | | | | | | | | | | | M |
| 77 | nricylqeif | 163 | | | | | | | | | | | | | | | | | | | | | | | | | | | | | |
| 78 | ricylqeifs | 165 | | | | | | | | | | | | | | | | | | | | | | | | | | | | | |
| 79 | icylqeifsn | 167 | | | | | | | | | | | | | | | | | | | | | | | | | | | | | |

FIG. 2B (Continued)

| | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| 80 | cylqeifsne | 169 | | | | | | | | | | | | | | | | | | | | | | | | | | | | |
| 81 | ylqeifsnem | 171 | | | | | | | | | | | | | | | | | | | | | | | | | | | | |
| 82 | lqeifsnema | 173 | | | | | | | M | | | | | | | | | | | | | | | | | | | | | |
| 83 | qeifsnemak | 175 | | | | | | | | | | | | | | | | | | | | | | | | | M | | | | |
| 84 | eifsnemakv | 177 | | | | | | | | | | | | | | | | | | | | | | | | | M M | | | | |
| 85 | ifsnemakvd | 179 | | | | | | | | | | | | | | | | | | | | | | | | | M M | | | M | |
| 86 | fsnemakvdd | 181 | | | | | | | | | | | | | | | | | | | | | | | | | | | | | |
| 87 | snemakvdds | 183 | | | | | | | | | | | | | | | | | | | | | | | | | | | | | |
| 88 | nemakvddsf | 185 | | | | | | | | | | | | | | | | | | | | | | | | | | | | | |
| 89 | emakvddsff | 187 | | | | | | | | | | | | | | | | | | | | | | | | | | | | | |
| 90 | makvddsffh | 189 | | | | | | | | | | | | | | | | | | | | | | | | | | | | | |
| 91 | akvddsffhr | 191 | | | M | | | | | | | | | | | | | | | | | | | | | | | | | | |
| 92 | kvddsffhrl | 193 | | | | | | | | | | | | | | | | | | | | | | | | | | | | | |
| 93 | vddsffhrle | 195 | | | | | | | | | | | | | | | | | | | | | | | | | | | | | |
| 94 | ddsffhrlee | 197 | | | | | | | | | | | | | | | | | | | | | | | | | | | | | |
| 95 | dsffhrlees | 199 | | | M | | | | | | | | | | | | | | | | | | | | | | | | | | |
| 96 | sffhrleesf | 201 | | M | | | | | | | | | | | | | | | M | | | | | | | | | | | | |
| 97 | ffhrleesfl | 203 | | S | | | | | | | | | | | | | | M S S | | | | | | | | | | | | | |
| 98 | fhrleesflv | 205 | | M | M M M | | | | | | | | | | | | | | | | | | | | | | | | | | |
| 99 | hrleesflve | 207 | | | M | | | | | | | | | | | | | | | | | | | | | | | | | | |
| 100 | rleesflvee | 209 | | | M | | | | | | | | | | | | | | | | | | | | | | | | | | |
| 101 | leesflveed | 211 | | | M | | | | | | | | | | | | | | | | | | | | | | | | | | |
| 102 | eesflveedk | 213 | | | | | | | | | | | | | | | | | | | | | | | | | | | | | |
| 103 | esflveedkk | 215 | | | | | | | | | | | | | | | | | | | | | | | | | | | | | |
| 104 | sflveedkkh | 217 | | | | | | | | | | | | | | | | | | | | | | | | | | | | | |
| 105 | flveedkkhe | 219 | | | | | | | | | | | | | | | | | | | | | | | | | | | | | |
| 106 | lveedkkher | 221 | | | | | | | M | | | | | | | | | | | | | | | | | | | | | | |
| 107 | veedkkherh | 223 | | | | | | | | | | | | | | | | | | | | | | | | | | | | | |
| 108 | eedkkherhp | 225 | | | | | | | | | | | | | | | | | | | | | | | | | | | | | |
| 109 | edkkherhpi | 227 | | | | | | | | | | | | | | | | | | | | | | | | | | | | | |
| 110 | dkkherhpif | 229 | | | | | | | | | | | | | | | | | M | | | | | | | | | | | | |
| 111 | kkherhpifg | 231 | | | | | | | | | | | | | | | | | | | | | | | | | | | | | |
| 112 | kherhpifgn | 233 | | | | | | | | | | | | | | | | | | | | | | | | | | | | | |

FIG. 2B (Continued)

| | | | | | | | | | | | | | | | | | | | | | | | | | | | |
|---|---|---|---|---|---|---|---|---|---|---|---|---|---|---|---|---|---|---|---|---|---|---|---|---|---|---|---|
| 113 | herhpifgni | 235 | | | | | | | | | | | | | | | | | | | | | | | | | |
| 114 | erhpifgniv | 237 | | | | | | | | | | | | | | | | | | | | | | | | | |
| 115 | rhpifgnivd | 239 | | | | | | | | | | | | | | | | | | | | | | | | | |
| 116 | hpifgnivde | 241 | | | | | | | | | | | | | | | | | | | | | | | | | |
| 117 | pifgnivdev | 243 | | | | | | | | | | | | | | | | | | | | | | | | | |
| 118 | ifgnivdeva | 245 | | | | | | | | | | | | | | | M | M | M | | | | | | | | | |
| 119 | fgnivdevay | 247 | | | | | | | | | | | | | | | | M | M | M | | | | | | | | |
| 120 | gnivdevayh | 249 | | | | | | | | | | | | | | | | | | M | | | | | | | | |
| 121 | nivdevayhe | 251 | | | | | | | | | | | | | | | | | M | M | | | | | | | | |
| 122 | ivdevayhek | 253 | | | | | | | | | | | | | | | | | | M | M | | | | | | | |
| 123 | vdevayheky | 255 | | | | | | | | | | | | | | | | | | | M | M | | | | | | |
| 124 | devayhekyp | 257 | | | | | | | | | | | | | | | | | | | | M | M | | | | | |
| 125 | evayhekypt | 259 | | | | | | | | | | | | | | | | | | | | | M | M | | | | |

FIG. 2C

| Pos | Peptide | SEQ ID NO: | DQA1*01DQB1*06 | DQA1*01DQB1*06 | DQA1*01DQB1*06 | DQA1*02DQB1*02 | DQA1*03DQB1*03 | DQA1*03DQB1*03 | DQA1*03DQB1*03 | DQA1*03DQB1*04 | DQA1*03DQB1*04 | DQA1*04DQB1*03 | DQA1*04DQB1*04 | DQA1*05DQB1*02 | DQA1*05DQB1*03 | DQA1*06DQB1*03 | DPA1*01DPB1*02 | DPA1*01DPB1*03 | DPA1*01DPB1*04 | DPA1*01DPB1*04 | DPA1*02DPB1*01 | DPA1*02DPB1*05 | DPA1*02DPB1*09 | DPA1*02DPB1*09 | DPA1*02DPB1*17 | DPA1*02DPB1*01 | DPA1*02DPB1*05 | DPA1*03DPB1*04 |
|---|---|---|---|---|---|---|---|---|---|---|---|---|---|---|---|---|---|---|---|---|---|---|---|---|---|---|---|---|
| 1 | mdkkysigld | 11 | | | | | | | | | | | | | | | | | | | | | | | | | | |
| 2 | dkkysigldi | 13 | | | | | | M | | | | | | | | | | | | | | | | | | | | |
| 3 | kkysigldig | 15 | | | | | | | | | | | | | | | | | | | | | M | M | M | | | |
| 4 | kysigldigt | 17 | | | | | | | | | | | | | | | | | | | | | | | | | | |
| 5 | ysigldigtn | 19 | | | | | | | | | | | | | | | | | | | | | | | | | | |
| 6 | sigldigtns | 21 | | | | | | | | | | M | | | M | M | | | | | | | | | | | | |
| 7 | igldigtnsv | 23 | | | | | | | | | | | | | | | | | | | | | | | | | | |
| 8 | gldigtnsvg | 25 | | | | | | | | | | | | | | | | | | | | | | | | | | |
| 9 | ldigtnsvgw | 27 | | | | | | | M | | | | | | | | | | | | | | | | | | | |
| 10 | digtnsvgwa | 29 | | | | | | | | | | | | | | | | | | | | | | | | | | |

FIG. 2C (Continued)

| | | | | | | | | | | | | | | | | | | | | | | | |
|---|---|---|---|---|---|---|---|---|---|---|---|---|---|---|---|---|---|---|---|---|---|---|---|
| 11 | igthsvgwav | 31 | M | S | M | | | | | | | | | | | | | | | | | | |
| 12 | gtnsvgwavi | 33 | | | | | | | | | | | | | | | | | | | | | |
| 13 | tnsvgwavit | 35 | | | | | | | | | | | | | | | | | | | | | |
| 14 | nsvgwavitd | 37 | M | | M | | | | | | | | | | | | | | | | | | |
| 15 | svgwavitde | 39 | | | | M | M | | | | | | | | | | | | | | | | |
| 16 | vgwavitdey | 41 | | | M | M | S | | | | | | | | | | | | | | | | |
| 17 | gwavitdeyk | 43 | | | | | M | M | | | | | | | | | | | | | | | |
| 18 | wavitdeyk v | 45 | | | | | M | M | M | | | | | | | | | | | | | | |
| 19 | avitdeykvp | 47 | | | | | | M | M | M | | | | | | | | | | | | | |
| 20 | vitdeykvps | 49 | | | | | | | M | M | M | | | | | | | | | | | | |
| 21 | itdeykvpsk | 51 | | | | | | | | | M | | | | | | | | | | | | |
| 22 | tdeykvpskk | 53 | | | | | | | | M | M | | | | | | | | | | | | |
| 23 | deykvpskkf | 55 | | | | | | | | M | M | | | | | | | | | | | | |
| 24 | eykvpskkfk | 57 | | | | | | | | | | | | | | | | | | | | | |
| 25 | ykvpskkfkv | 59 | | | | | | | | | | | | | | | | | | | | | |
| 26 | kvpskkfkvl | 61 | | | | | | | | | | | | | | | | | | | | | |
| 27 | vpskkfkvlg | 63 | | | | | | | | | | | | | | | | | | | | | |
| 28 | pskkfkvlgn | 65 | | | | | | | | | | | | | | | | | | | | | |
| 29 | skkfkvlgnt | 67 | | | | | | | | | | | | | | | | | | | | | |
| 30 | kkfkvlgntd | 69 | | | M | M | | | | | | | | | | | | | | | | | |
| 31 | kfkvlgntdr | 71 | | | | | | | | | | | | | | | | | | | | | |
| 32 | fkvlgntdrh | 73 | | | | | | | | | | | | | | | | | | | | | |
| 33 | kvlgntdrhs | 75 | | | | | | | | | | | | | | | | | | | | | |
| 34 | vlgntdrhsi | 77 | M | M | | | | | | | | | | | | | | | | | | | |
| 35 | lgntdrhsik | 79 | | | | | | | | | | | | | | | | | | | | | |
| 36 | gntdrhsikk | 81 | | | | | | | | | | | | | | | | | | | | | |
| 37 | ntdrhsikkn | 83 | | | | | | | | | | | | | | | | | | | | | |
| 38 | tdrhsikknl | 85 | | | | | | | | | | | | | | | | | | | | | |
| 39 | drhsikknli | 87 | | | | | | | | | | | | | | | | | | | | | |
| 40 | rhsikknlig | 89 | | | | | | | | | | | | | | | | | | | | | |
| 41 | hsikknliga | 91 | | | | | | | | | | | | | M | | | | | | | | |
| 42 | sikknligal | 93 | | | | | | | | | | | | | | | | | | | M | | |
| 43 | ikknligall | 95 | | | | | | | | | | | | | | | | | M | | M | M | M |

FIG. 2C (Continued)

| # | Sequence | No. |
|---|---|---|
| 44 | kknligallf | 97 |
| 45 | knligallfd | 99 |
| 46 | nligallfds | 101 |
| 47 | ligallfdsg | 103 |
| 48 | igallfdsge | 105 |
| 49 | gallfdsget | 107 |
| 50 | allfdsgeta | 109 |
| 51 | llfdsgetae | 111 |
| 52 | lfdsgetaea | 113 |
| 53 | fdsgetaeat | 115 |
| 54 | dsgetaeatr | 117 |
| 55 | sgetaeatrl | 119 |
| 56 | getaeatrlk | 121 |
| 57 | etaeatrlkr | 123 |
| 58 | taeatrlkrt | 125 |
| 59 | aeatrlkrta | 127 |
| 60 | eatrlkrtar | 129 |
| 61 | atrlkrtarr | 131 |
| 62 | trlkrtarrr | 133 |
| 63 | rlkrtarrry | 135 |
| 64 | lkrtarrryt | 137 |
| 65 | krtarrrytr | 139 |
| 66 | rtarrrytrr | 141 |
| 67 | tarrrytrrk | 143 |
| 68 | arrrytrrkn | 145 |
| 69 | rrrytrrknr | 147 |
| 70 | rrytrrknri | 149 |
| 71 | rytrrknric | 151 |
| 72 | ytrrknricy | 153 |
| 73 | trrknricyl | 155 |
| 74 | rrknricylq | 157 |
| 75 | rknricylqe | 159 |
| 76 | knricylqei | 161 |

FIG. 2C (Continued)

| | | | | | | | | | | | | | | | | | | | | | | | | | | |
|---|---|---|---|---|---|---|---|---|---|---|---|---|---|---|---|---|---|---|---|---|---|---|---|---|---|---|
| 77 | nricylqeif | 163 | | | | | | | | | | | | | | M | | M | | | | | M | | | |
| 78 | ricylqeifs | 165 | | | M | | | | | | | | | | M | M | | | | | | | | | | |
| 79 | icylqeifsn | 167 | | | | | | | | | | | | | | M | M | | | | | | M | | | |
| 80 | cylqeifsne | 169 | | | | | | | | | | | | | | | | M | | M | | | | | | |
| 81 | ylqeifsnem | 171 | | | M | M | | | | | | | M | | M | | M | M | | | | | | | | |
| 82 | lqeifsnema | 173 | | M | | | | | | | | | | | | | | | | | | | | | | |
| 83 | qeifsnemak | 175 | M | | | | | | | | | | | | M | | | | | | | | | | | |
| 84 | eifsnemakv | 177 | M | M | | | | | | | | | | | | | | | | | | | | | | |
| 85 | ifsnemakvd | 179 | | | | | | | | M | | | | | | | | | | | | | | | | |
| 86 | fsnemakvdd | 181 | | M | | | | | | | | | | | | | | | | | | | | | | |
| 87 | snemakvdds | 183 | | | | | | | | | | | | | | | | | | | | | | | | |
| 88 | nemakvddsf | 185 | | | | | | | M | | | | M | | | | | | | | | | | | | |
| 89 | emakvddsff | 187 | | | | | | | | | | | | | | | | | | | | | | | | |
| 90 | makvddsffh | 189 | | | | | | | | | M | | | | | | | | | | | | | | | |
| 91 | akvddsffhr | 191 | | | | | | | | | | | | | M | | | | | | | | | | | |
| 92 | kvddsffhrl | 193 | | | | | | | | | | | | | M | M | | | | | | | | | | |
| 93 | vddsffhrle | 195 | | | | | | | | | | | | M | M | | | | | | | | | | | |
| 94 | ddsffhrlee | 197 | | | | | | | | | | | | | | | | | | | | | | | | |
| 95 | dsffhrlees | 199 | | | | | M | | | | | | | | | | | | | | | | | | | |
| 96 | sffhrleesf | 201 | | M | | | M | | | M S | M M | | | | | | | | | | | | | | | |
| 97 | ffhrleesfl | 203 | | | | | | M | | | | | | | | | | | | | | | | | | |
| 98 | fhrleesflv | 205 | | | | | | | | | M S | | | | | | | | | | | | | | | |
| 99 | hrleesflve | 207 | | | | | | | | | | | | | | | | | | | | | | | | |
| 100 | rleesflvee | 209 | | | | | | | | M | | | | M | M | | | | | | | | | | | |
| 101 | leesflveed | 211 | | | | | | | | | M | | | | | | | M | | | | | | | | |
| 102 | eesflveedk | 213 | | | | | | | | | | | | | | | | | | | | | | | | |
| 103 | esflveedkk | 215 | | | | | | | | | | | | | | | | | | | | | | | | |
| 104 | sflveedkkh | 217 | | | | | | | | | | | | | | | | | | | | | | | | |
| 105 | flveedkkhe | 219 | | | | | | | | | | | | | | | | | | | | | | | | |
| 106 | lveedkkher | 221 | | | | | | | | | | | | | | | | | | | | | | | | |
| 107 | veedkkherh | 223 | | | | | | | | | | | | | | | | | | | | | | | | |
| 108 | eedkkherhp | 225 | | | | | | | | | | | | | | | | | | | | | | | | |
| 109 | edkkherhpi | 227 | | | | | | | | | | | | | | | | | | | | | | | | |

FIG. 2C (Continued)

| | | | | | | | | | | | | | | | | | | | | | | |
|---|---|---|---|---|---|---|---|---|---|---|---|---|---|---|---|---|---|---|---|---|---|---|
| 110 | dkkherhpif | 229 | | | | | | | | | | | | | | | | | | | | |
| 111 | kkherhpifg | 231 | | | | | | | | | | | | | | | | | | | | |
| 112 | kherhpifgn | 233 | | | | | | | | | | | | | | | | | | | | |
| 113 | herhpifgni | 235 | | | | | | | | | | | | | | | | | | | | |
| 114 | erhpifgniv | 237 | | | | | | | | | | | | | | | | | | | | |
| 115 | rhpifgnivd | 239 | | | | | | | | | | | | | | | | | | | | |
| 116 | hpifgnivde | 241 | | | | | | | | | | | | M | | | | | | | | | |
| 117 | pifgnivdev | 243 | | | | | | | | M | M | | | | | | | | | | | | |
| 118 | ifgnivdeva | 245 | | M | | | | | M | M | | | | | | | | | | | | | |
| 119 | fgnivdevay | 247 | | | | | | | | | | M | M | | | | | | | | | | |
| 120 | gnivdevayh | 249 | | | | | | | | | | | | M | M | | | | | | | | |
| 121 | nivdevayhe | 251 | | | | | | | | | | | | | | M | | | | | | | |
| 122 | ivdevayhek | 253 | | | | | | | | | | | | | | | M | | | | | | |
| 123 | vdevayheky | 255 | | | | | | | | | | | | | | | | | M | | | | |
| 124 | devayhekyp | 257 | | | | | | | | | | | | | | | | | | M | S | M | |
| 125 | evayhekypt | 259 | | | | | | | | | | | | | | | | | | | | | M |

FIG. 3

| Pos | Peptide | SEQ ID NO: | Len | A*01 | A*02 | A*02 | A*02 | A*02 | A*03 | A*11 | A*23 | A*24 | A*26 | A*29 | A*30 | A*31 | A*33 | A*68 | A*68 | B*07 | B*08 | B*15 | B*18 | B*27 | B*35 | B*40 | B*44 | B*51 | B*53 | B*57 | B*58 |
|---|---|---|---|---|---|---|---|---|---|---|---|---|---|---|---|---|---|---|---|---|---|---|---|---|---|---|---|---|---|---|---|
| 1026 | eqeigkata | 260 | 9 | | | | | | | | | | | | | | M | | | | | | | | | | | | | | |
| 1026 | eqeigkatak | 261 | 10 | | | | | M | | M | | | | | | | | | | | | | | | | | | | | | |
| 1027 | qeigkatak | 262 | 9 | | | | | | | | | | | S | M | | | M | M | | | M | M | | | S | M | | | | |
| 1027 | qeigkataky | 263 | 10 | | | | | | | | | M | S | M | | | | S | M | | | | | | | M | | | | | |
| 1028 | eigkataky | 264 | 9 | | | | | | | | M | M | | M | M | M | | M | M | | | | | | | | | | | | |
| 1028 | eigkatakyf | 265 | 10 | | | | | | | | M | | | | | | | M | | | | M | | | | | | | | | |
| 1029 | igkatakyf | 266 | 9 | | | | | | M | M | S | | | S | S | S | | | | | | | | | | | | | | | |
| 1029 | igkatakyff | 267 | 10 | | | | M | M | | S | M | M | | M | M | S | | M | | | | | | M | | | | | | | |
| 1030 | gkatakyff | 268 | 9 | | | | M | M | | | | | | | M | M | | M | | | | | | M | | | | | | | |
| 1030 | gkatakyffy | 269 | 10 | M | | | | | | | | | | | | | | | | | | | | | | | | | | | |
| 1031 | katakyffy | 270 | 9 | | | | M | M | M | | | | | | | S | M | | | | | | | | M | M | M | | | | |
| 1031 | katakyffys | 271 | 10 | | | M | M | | M | S | M | | | | M | M | M | | | | | | | | | | | | | | |
| 1032 | atakyffys | 272 | 9 | | | | | | | | M | | | | | S | M | | | | | | | | | | | | | | |
| 1032 | atakyffysn | 273 | 10 | | | | M | M | M | | | | | | | M | M | M | S | | | | | | | | | | | M | M |
| 1033 | takyffysn | 274 | 9 | | | | M | M | | | S | S | | | M | M | M | M | | | | | | | | | | | M | M | M |
| 1033 | takyffysni | 275 | 10 | | | | M | M | | | M | M | | | | | | | | | | | | | | | | | M | M | M |
| 1034 | akyffysni | 276 | 9 | | | M | | | M | | M | S | | | M | M | M | | | | | | | M | | | | | | | |
| 1034 | akyffysnim | 277 | 10 | | M | | | | | M | S | M | | | S | M | | | | | | | | M | | | | | | | |
| 1035 | kyffysnim | 278 | 9 | | | | | | | | S | M | | | | | M | | | | | | | | | | | | | | |
| 1035 | kyffysnimn | 279 | 10 | | M | | | | | | | | | | | | | | | | | | | | | | | | | | |
| 1036 | yffysnimn | 280 | 9 | | | | | | | | | | | | | | M | | | | | | | | | | | | | | |

FIG. 3 (Continued)

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| 1036 | yffysnimmf | 281 | 10 | | | S | M | M | S | | | | | | S | M | | | | | | | | | | | M | | | |
| 1037 | ffysnimmf | 282 | 9 | | S | S | M | M | S | | S | S | | | S | M | | | | | | M | | | | | M | M | | |
| 1038 | ffysnimmff | 283 | 10 | S | S | M | S | M | | S | S | | | M | S | | | | | S | S | | | | | S | M | | | |
| 1038 | fysnimmff | 284 | 9 | S | S | S | S | S | S | M | M | | S | S | M | | | | | | | | | | | | | | | |
| 1039 | fysnimmffk | 285 | 10 | S | M | S | S | S | M | S | | M | S | S | | | | | | | | | | | | | | | | |
| 1039 | ysnimmffk | 286 | 9 | M | S | M | M | S | M | | | S | M | | | M | | | | | | | | | | | M | M | | |
| 1040 | ysnimmffkt | 287 | 10 | | S | M | M | M | | | | | M | | | | | | | | | | | | | | | | | | |
| 1040 | snimmffkt | 288 | 9 | | | | | | | | | | | | | | | | | | | | | | | | | | | | |
| 1040 | snimmffkte | 289 | 10 | | | | | S | M | M | | M | S | | M | | | | | | | | | | | | | | | | |
| 1041 | nimmffkte | 290 | 9 | | | | | | | | | | | | | | | | | | | | | | | | | | | | |
| 1041 | nimmffktei | 291 | 10 | M | S | M | | M | | | S | S | | | | | | | | | | | | | | | | | | | |
| 1042 | immffktei | 292 | 9 | M | | | M | S | | | | M | | | | | | | | | | | | | | | | | | | |
| 1042 | immffkteit | 293 | 10 | | | | M | | | | | | | | | | | | | | | | | | | | | | | | |
| 1043 | mnffkteit | 294 | 9 | | | | | | | | | | | | | | | | | | | | | | | | | | | | |
| 1043 | mnffkteitl | 295 | 10 | M | S | M | S | | | | M | M | | | | M | M | | | | | | | | | | | | | | |
| 1044 | nffkteitl | 296 | 9 | M | | M | | | | | M | | | S | | M | M | | | | | | | | | | | | | | |
| 1044 | nffkteitla | 297 | 10 | M | | | | M | | | | | | M | | | | | | | | | | | | | | | | | |
| 1045 | ffkteitla | 298 | 9 | M | | S | M | M | | | | | | | | | | | | | | | | | | | | | | | |
| 1045 | ffkteitlan | 299 | 10 | | | | | | | | | | | | | M | | | | | | | | | | | | | | | |
| 1046 | fkteitlan | 300 | 9 | | | | | | | | | | | M | | | | | | | | | | | | | | | | | |
| 1046 | fkteitlang | 301 | 10 | | | | | | | | | | | | | M | | | | | | | | | | | | | M | | |
| 1047 | kteitlang | 302 | 9 | | | | | | | | | | | | | | | | | | | | | | | | | | | | |
| 1047 | kteitlange | 303 | 10 | | | | | M | | | M | M | | | | | | M | | | | | | | | | | | | | |
| 1048 | teitlange | 304 | 9 | | | | | | | | S | | | | | | | | | | | | | | | | | | | | |
| 1048 | teitlangei | 305 | 10 | | | | | M | M | M | S | | | | | | | | | | | | | | | M | | | | | |
| 1049 | eitlangei | 306 | 9 | | | | | S | | | | | | | | | | | | | | | | | | | | | | | |
| 1049 | eitlangeir | 307 | 10 | | | | | M | M | S | M | M | | | | | | | S | M | | | | | | | | | | | |
| 1050 | itlangeir | 308 | 9 | | | | | | | M | S | | | | | | | M | | | | | | | | | | | | | |
| 1050 | itlangeirk | 309 | 10 | | | | | M | S | S | M | | | | | | | | | | | | | | | | | | | | |
| 1051 | tlangeirk | 310 | 9 | | | | | | | | S | | | | | | | | | | | | | | | | | | | | |
| 1051 | tlangeirkr | 311 | 10 | | | | | | M | | | | | | | | | | | | | | | | | | | | | | |
| 1052 | langeirkr | 312 | 9 | | | | | | | | | | | | | | | | | | | | | | | | | | | | |
| 1052 | langeirkrp | 313 | 10 | | | | | | M | | | | | | | | | | | | | | | | | | | | | | |

FIG. 3 (Continued)

| | | | | | | | | | | | | | | |
|---|---|---|---|---|---|---|---|---|---|---|---|---|---|---|
| 1053 | angeirkrp | 314 | 9 | | | | | | | | | | | |
| 1053 | angeirkrpl | 315 | 10 | | | | | | | | | | M | |
| 1054 | ngeirkrpl | 316 | 9 | | | | | | | | | | | |
| 1054 | ngeirkrpli | 317 | 10 | | | | | | | | | | | M |
| 1055 | geirkrpli | 318 | 9 | | | | | | | | | | M | S |
| 1055 | geirkrplie | 319 | 10 | | | | | | | | | | | |
| 1056 | eirkrplie | 320 | 9 | | | | | | | | | M | | |
| 1056 | eirkrpliet | 321 | 10 | | | | | | | | | M | | |
| 1057 | irkrpliet | 322 | 9 | | | | | | | | | | | |
| 1057 | irkrplietn | 323 | 10 | | | | | | | | | | | |
| 1058 | rkrplietn | 324 | 9 | | | | | | | | | | | |
| 1058 | rkrplietng | 325 | 10 | | | | | | | | | | | |
| 1059 | krplietng | 326 | 9 | | | | | | | | | | | |
| 1059 | krplietnge | 327 | 10 | | | | | | | M | | | | |
| 1060 | rplietnge | 328 | 9 | | | | | | | | | | | |
| 1060 | rplietnget | 329 | 10 | | | | | | | | | | | |
| 1061 | plietnget | 330 | 9 | | | | | | | | | | | |
| 1061 | plietngetg | 331 | 10 | | | | | | | | | | | |
| 1062 | lietngetg | 332 | 9 | M | | | | | | | | | | |
| 1062 | lietngetge | 333 | 10 | | | | | | | | | | | |
| 1063 | ietngetge | 334 | 9 | | | | | | | | | | | |
| 1063 | ietngetgei | 335 | 10 | | | | | | | | | | | |
| 1064 | etngetgei | 336 | 9 | | | | | | M | S | | | | |
| 1064 | etngetgeiv | 337 | 10 | | | | | | S | M | | | | |
| 1065 | tngetgeiv | 338 | 9 | | | | | | | | | | | |
| 1065 | tngetgeivw | 339 | 10 | | | M | M | | | | M | M | | |
| 1066 | ngetgeivw | 340 | 9 | | | | | | | | | | | |
| 1066 | ngetgeivwd | 341 | 10 | | | M | M | | | | | | | |
| 1067 | getgeivwd | 342 | 9 | | | | | S | | | S | | | |
| 1067 | getgeivwdk | 343 | 10 | | | | | S S | M | S S | | M | | S |
| 1068 | etgeivwdk | 344 | 9 | | | | | | | | | | | S |
| 1068 | etgeivwdkg | 345 | 10 | | | | | S S | | S S | | | | |
| 1069 | tgeivwdkg | 346 | 9 | | | | | | | | | | | |

FIG. 3 (Continued)

| | | | | | | | | | | | | | | | | | | | | | | |
|---|---|---|---|---|---|---|---|---|---|---|---|---|---|---|---|---|---|---|---|---|---|---|
| 1069 | tgeivwdkgr | 347 | 10 | | | | | | | | | | | | | | | | | | | |
| 1070 | geivwdkgr | 348 | 9 | | | | | | | | | | | | | | | | | | | |
| 1070 | geivwdkgrd | 349 | 10 | | | | | | | | | | | | | | | | | | | |
| 1071 | eivwdkgrd | 350 | 9 | | | | | | | | | | | | | | | | | | | |
| 1071 | eivwdkgrdf | 351 | 10 | | | | | | | | M | | | | | | | | | | | |
| 1072 | ivwdkgrdf | 352 | 9 | | | | | | | S | S | | | M | | | | | M | | | | |
| 1072 | ivwdkgrdfa | 353 | 10 | | | | | | | | M | M | | | | | | | | | | | |
| 1073 | vwdkgrdfa | 354 | 9 | | | | | | | | M | | | | | | | | | | | | |
| 1073 | vwdkgrdfat | 355 | 10 | | | | | | | M | | | | | | | | | | | | | |
| 1074 | wdkgrdfat | 356 | 9 | | | | | | | | | | | | | | S | | | | | | |
| 1074 | wdkgrdfatv | 357 | 10 | | M | S | | | | M | | | | S | M | | M | | | | | | |
| 1075 | dkgrdfatv | 358 | 9 | | | | | | | | | S | M | | | | | | | | | | | |
| 1075 | dkgrdfatvr | 359 | 10 | | | | | | | | | M | S | | | | | | | | | | | |
| 1076 | kgrdfatvr | 360 | 9 | | | | | M | | M | M | | | | | | | | | | | | | |
| 1076 | kgrdfatvrk | 361 | 10 | | | | | | | | M | | | | M | | | | | | | M | M | |
| 1077 | grdfatvrk | 362 | 9 | | | | | | | | M | | | | M | M | | | | | | | | |
| 1077 | grdfatvrkv | 363 | 10 | | | | | | M | | | | S | | | | | | | | | | | |
| 1078 | rdfatvrkv | 364 | 9 | | | | | | | | | M | | S | M | | | | | | M | | | |
| 1078 | rdfatvrkvl | 365 | 10 | | | | | | | | M | M | | | M | M | | | | | | | | |
| 1079 | dfatvrkvl | 366 | 9 | | | | | | | | M | | | | | M | | | | | | | | |
| 1079 | dfatvrkvls | 367 | 10 | | | | | | | | M | | | | S | M | | | | | | | | |
| 1080 | fatvrkvls | 368 | 9 | M | | | | | | | M | | | | M | M | | | | | | | | |
| 1080 | fatvrkvlsm | 369 | 10 | | | | | | M | | M | M | | | | S | M | | | | | | | |
| 1081 | atvrkvlsm | 370 | 9 | | | | | | | | M | S | | | M | S | M | | | | | M | | |
| 1081 | atvrkvlsmp | 371 | 10 | | | | | | | | M | M | | | | M | | | | | | M | | |
| 1082 | tvrkvlsmp | 372 | 9 | | | | | | | | | S | | | | | | | | | | | | |
| 1082 | tvrkvlsmpq | 373 | 10 | | | | | M | | | M | M | | | | M | | | | | | | | |
| 1083 | vrkvlsmpq | 374 | 9 | | | | | | | | | | | | | | | | | | | | | |
| 1083 | vrkvlsmpqv | 375 | 10 | M | | | | | | | | M | | | | | | | | | | | | |
| 1084 | rkvlsmpqv | 376 | 9 | | | | | | | | M | | | | | | | | | | | | | |
| 1084 | rkvlsmpqvn | 377 | 10 | | | | | | | | | M | | | | | | | | | | | | |
| 1085 | kvlsmpqvn | 378 | 9 | | | | | | | | | | | | | | | | | | | | | |
| 1085 | kvlsmpqvni | 379 | 10 | | | | | | | | M | | | | | | | | | | | | | |

FIG. 3 (Continued)

| | | | | | | | | | | | | | | | | | | |
|---|---|---|---|---|---|---|---|---|---|---|---|---|---|---|---|---|---|---|
| 1086 | vlsmpqvni | 9 | | | | | | | M | | | | | | | | | |
| 1086 | vlsmpqvniv | 10 | | | | | | | S | | | | | | | | M | M |
| 1087 | lsmpqvniv | 9 | M | S | | | | | | | | | | | | | M | M |
| 1087 | lsmpqvnivk | 10 | S | M | S | | | | | | | | | | | | M | M | |
| 1088 | smpqvnivk | 9 | M | S | | | | | | | | | | | | | M | | |
| 1088 | smpqvnivkk | 10 | S | M | | | M | S | | | | | | | | M | | | |
| 1089 | mpqvnivkk | 9 | M | | | | M | M | | | | | | | S | | | | |
| 1089 | mpqvnivkkk | 10 | | | | | M | | | | | | | | | | | | |
| 1090 | pqvnivkkt | 9 | | | | | | | | | | | | | | | | | |
| 1090 | pqvnivkkte | 10 | | | | | | | | | M | | | | | | | | |
| 1091 | qvnivkkte | 9 | | | | | | | M | | | | | | | | | | |
| 1091 | qvnivkktev | 10 | | | | | | | M | | | | | | | | | | |
| 1092 | vnivkktev | 9 | | | | | | | | | | | | | | | | | |
| 1092 | vnivkktevq | 10 | | | | | | | | | | | | | | | | | |
| 1093 | nivkktevq | 9 | | | | | | | | | | | | | | | | | |
| 1093 | nivkktevqt | 10 | | | | | | | | | | | | | | | | | |
| 1094 | ivkktevqt | 9 | | | | | | | | | | | M | | | | | | |
| 1094 | ivkktevqtg | 10 | | | | | | | | | | | | | | | | | |
| 1095 | vkktevqtg | 9 | | | | | | | | | | | | | | | | | |
| 1095 | vkktevqtgg | 10 | | | | | | | | | | | | | | | | | |
| 1096 | kktevqtgg | 9 | | | | | | | | | S | | | | | | | | |
| 1096 | kktevqtggf | 10 | | | | | | | | M | M | | | | | M | | | |
| 1097 | ktevqtggf | 9 | | | | | | | M | | | | | | | | | | |
| 1097 | ktevqtggfs | 10 | | | | | | | | | | | | | | | | | |
| 1098 | tevqtggfs | 9 | | | | | | | | | | | | | | | | | |
| 1098 | tevqtggfsk | 10 | | | | | M | S | | | | | | | M | | | | |
| 1099 | evqtggfsk | 9 | | | | | | S | | | | | | | M | | | | |
| 1099 | evqtggfske | 10 | | | | | | | M | | | | | | | | | | |
| 1100 | vqtggfske | 9 | | | | | | | | | | | M | | | | | | |
| 1100 | vqtggfskes | 10 | | | | | | | M | | | | | | | | | | |
| 1101 | qtggfskes | 9 | | | | | | | S | | | | | | | | | | |
| 1101 | qtggfskesi | 10 | | | | | | | | | | | | | | | | | |
| 1102 | tggfskesi | 9 | | | | | | | M | | | | | | | | | | |

FIG. 3 (Continued)

| # | seq | len | | | | | | | | | | | | | | | | | | | | |
|---|---|---|---|---|---|---|---|---|---|---|---|---|---|---|---|---|---|---|---|---|---|---|
| 1102 | tggfskesil | 10 | | | | | | | | | | | | | | | | | | | | M |
| 1103 | ggfskesil | 9 | | | | | | | | | | | | | | | | | | | | |
| 1103 | ggfskesilp | 10 | | | | | | | | | | | | | | | | | | | | |
| 1104 | gfskesilp | 9 | | | | | | | | | | | | | | | | | | | | |
| 1104 | gfskesilpk | 10 | | | | | | | | | | | | | | | | | | | | |
| 1105 | fskesilpk | 9 | | | | | | M | | | | | | | | | | | | | | |
| 1105 | fskesilpkr | 10 | | | | | | | | | | | | | | | | | | | | |
| 1106 | skesilpkr | 9 | | | | | | | | | | | | | M | | | | | | | |
| 1106 | skesilpkrn | 10 | | | | | | | S | | | | | | | | | | | | | |
| 1107 | kesilpkrn | 9 | | | | | | | M S | | | | | | | | | | | | | |
| 1107 | kesilpkrns | 10 | | | | | | | M | | | M | | | | | | | | | | |
| 1108 | esilpkrns | 9 | | | | | | | | | | M S | | | | | | | | | | |
| 1108 | esilpkrnsd | 10 | | | | | | | | | | M | | | | | | | | | | |
| 1109 | silpkrnsd | 9 | | | | | | | | | | | | | | | | | | | | |
| 1109 | silpkrnsdk | 10 | | | | | | | | | | | | | M | | | | | | | |
| 1110 | ilpkrnsdk | 9 | | | | | | S | | | | | | | M S | | | | | | | |
| 1110 | ilpkrnsdkl | 10 | | | | | | | | | | | | | M | | | | | | | |
| 1111 | lpkrnsdkl | 9 | | | | | | | | | | | | | | | M | | | | | |
| 1111 | lpkrnsdkli | 10 | | | | | | | | | | | | | | | | | | | | |
| 1112 | pkrnsdkli | 9 | | | | | | | | | | | | | | | | | | | | |
| 1112 | pkrnsdklia | 10 | | | | | | | | | M M | | | | | | | | | | | |
| 1113 | krnsdklia | 9 | | | | | | | | | M | | | | | | | | | | | |
| 1113 | krnsdkliar | 10 | | | | | | | | | | | | | | | | | | | | |
| 1114 | rnsdkliar | 9 | | | | | | | | | | | | | | | M | | | | | |
| 1114 | rnsdkliark | 10 | | | | | | | | | | | | | | | M | | | | | |
| 1115 | nsdkliark | 9 | | | | | | | | | | | | | | | | | | | | |
| 1115 | nsdkliarkk | 10 | | | | | | | | | | | | | | | M S | | | | | |
| 1116 | sdkliarkk | 9 | | | | | | | | | | | | | | | M | | | | | |
| 1116 | sdkliarkkd | 10 | | | | | | | | | | | | | | | | | | | | |
| 1117 | dkliarkkd | 9 | | | | | | | | | | | | | M | | | | | | | |
| 1117 | dkliarkkdw | 10 | | | | | | | | | | | | | | M | | | | | | |
| 1118 | kliarkkdw | 9 | | | | | | | | | | | | M | | | | | | | S | |
| 1118 | kliarkkdwd | 10 | | | | | | | | | | | | | | | M | | | | | |

FIG. 3 (Continued)

| | | | | | | | | | | | | | | | | | | | | | | | |
|---|---|---|---|---|---|---|---|---|---|---|---|---|---|---|---|---|---|---|---|---|---|---|---|
| 1119 | liarkkdwd | 9 | | | | | | | | | | | | | | | | | | | | | M | M |
| 1119 | liarkkdwdp | 10 | | | | | | | | | | | | | | | | | | | M | S | | |
| 1120 | iarkkdwdp | 9 | | | | | | | M | | | | | | | | | | | | | | M | S |
| 1120 | iarkkdwdpk | 10 | | | | | | | | | | | | | | | | | | M | | | | |
| 1121 | arkkdwdpk | 9 | | | | | | | | | | | | | | | | | | | | | | |
| 1121 | arkkdwdpkk | 10 | | | | | | | | | M | | | | | | | | | | | | | |
| 1122 | rkkdwdpkk | 9 | | | | | M | | | | S | | | | | | | | | | | | | |
| 1122 | rkkdwdpkky | 10 | | | | | S | | | | M | | | | | | | | | | | | | |
| 1123 | kkdwdpkky | 9 | | | | | | | | | | | | | | | | | | | | | | |
| 1123 | kkdwdpkkyg | 10 | | | | | | | M | S | | | | | | | | | | | | | | |
| 1124 | kdwdpkkyg | 9 | | | | | | | M | M | | | | | | | | | | | | | | |
| 1124 | kdwdpkkygg | 10 | | | | | | M | | | | | | | | | | | | | | | | |
| 1125 | dwdpkkygg | 9 | | | | | | | | | | | | | | | | | | | | | | |
| 1125 | dwdpkkyggf | 10 | | | | | | M | M | | | | | | | | | | | | | | | |
| 1126 | wdpkkyggf | 9 | | | | | | | | | | | | | | | | | | | | | | |
| 1126 | wdpkkyggfd | 10 | | | | | | | | | | | | M | | | | | | | | | | |
| 1127 | dpkkyggfd | 9 | | | | | S | | M | | | | | | | | | | | | | | | |
| 1127 | dpkkyggfds | 10 | | | | | S | | M | | | M | | | | | | | | | | | | |
| 1128 | pkkyggfds | 9 | | | | | M | | | | | | | | | | | | | | | | | |
| 1128 | pkkyggfdsp | 10 | | | | | | | | | | | | | | | | | | | | | | |
| 1129 | kkyggfdsp | 9 | | | | | | | | | | | | | | | | | | | | | | |
| 1129 | kkyggfdspt | 10 | | | | | | | | | | | M | | | M | | | | | | | | |
| 1130 | kyggfdspt | 9 | | | | | | | | | | | | | | S | | | | | | | | |
| 1130 | kyggfdsptv | 10 | | | | | | | | | | | | | | M | | | | | | | | |
| 1131 | yggfdsptv | 9 | | | | | | | | | | | | | | | | | | | | | | |
| 1131 | yggfdsptva | 10 | | | | | | | M | | | | | | | | M | | | | | | | |
| 1132 | ggfdsptva | 9 | | | | | | | S | | | | | | | | | | | | | | | |
| 1132 | ggfdsptvay | 10 | | | | | | | M | | | | | S | | | | | | | | | | |
| 1133 | gfdsptvay | 9 | | | S | | | | S | | | | | S | | | | | M | | | | | |
| 1133 | gfdsptvays | 10 | | | | | | | M | | | | S | M | | | | | | | | | | |
| 1134 | fdsptvays | 9 | | | | | | | S | | | | | | | | | | | | | M | | |
| 1134 | fdsptvaysv | 10 | | | | | | | | | M | S | | | | | | | | | | | | |
| 1135 | dsptvaysv | 9 | | | | | | | | | | M | | | | | | | | | | | | |

FIG. 3 (Continued)

| | | | |
|---|---|---|---|
| 1135 | dsptvaysvl | 479 | 10 |
| 1136 | sptvaysvl | 480 | 9 |
| 1136 | sptvaysvlv | 481 | 10 |
| 1137 | ptvaysvlv | 482 | 9 |
| 1137 | ptvaysvlvv | 483 | 10 |
| 1138 | tvaysvlvv | 484 | 9 |
| 1138 | tvaysvlvva | 485 | 10 |
| 1139 | vaysvlvva | 486 | 9 |
| 1139 | vaysvlvvak | 487 | 10 |
| 1140 | aysvlvvak | 488 | 9 |
| 1140 | aysvlvvakv | 489 | 10 |
| 1141 | ysvlvvakv | 490 | 9 |
| 1141 | ysvlvvakve | 491 | 10 |
| 1142 | svlvvakve | 492 | 9 |
| 1142 | svlvvakvek | 493 | 10 |
| 1143 | vlvvakvek | 494 | 9 |
| 1143 | vlvvakvekg | 495 | 10 |
| 1144 | lvvakvekg | 496 | 9 |
| 1144 | lvvakvekgk | 497 | 10 |
| 1145 | vvakvekgk | 498 | 9 |
| 1145 | vvakvekgks | 499 | 10 |
| 1146 | vakvekgks | 500 | 9 |
| 1146 | vakvekgksk | 501 | 10 |
| 1147 | akvekgksk | 502 | 9 |
| 1147 | akvekgkskk | 503 | 10 |
| 1148 | kvekgkskk | 504 | 9 |
| 1148 | kvekgkskkl | 505 | 10 |
| 1149 | vekgkskkl | 506 | 9 |
| 1149 | vekgkskklk | 507 | 10 |
| 1150 | ekgkskklk | 508 | 9 |
| 1150 | ekgkskklks | 509 | 10 |

FIG. 4A

| Pos | Peptide | SEQ ID NO: | DRB1*01 | DRB1*01 | DRB1*03 | DRB1*03 | DRB1*03 | DRB1*04 | DRB1*04 | DRB1*04 | DRB1*04 | DRB1*04 | DRB1*04 | DRB1*04 | DRB1*07 | DRB1*08 | DRB1*08 | DRB1*08 | DRB1*09 | DRB1*10 | DRB1*11 | DRB1*11 | DRB1*11 | DRB1*11 | DRB1*12 | DRB1*12 | DRB1*13 | DRB1*13 |
|---|---|---|---|---|---|---|---|---|---|---|---|---|---|---|---|---|---|---|---|---|---|---|---|---|---|---|---|---|
| 1026 | egeigkatak | 261 | | | | | | | | | | | | | | | | | | | | | | | | | | |
| 1027 | qeigkataky | 263 | | | | | | | | | | | | | | | | | | | | | | | | | | |
| 1028 | eigkatakyf | 265 | | M | | | | | | | | | | | M | | | | | | | | | | | | M | M |
| 1029 | igkatakyff | 267 | M | M | | | | | | | | | | | | | | | | | | | | | | | | |
| 1030 | gkatakyffy | 269 | | | | | | | | | | | | | | | | | | | | | | | | | | |
| 1031 | katakyffys | 271 | | | | | | | | | | | | | | | | | | | | | | | | | | |
| 1032 | atakyffysn | 273 | | | | | | | | | | | | | | | | | | | | | | | | | | |
| 1033 | takyffysni | 275 | | | | | | | | | | | | | | | | | | | | | | | | | | |
| 1034 | akyffysnim | 277 | | | | | | | | | | | | | | | | | | | | | | | | | | |
| 1035 | kyffysnimn | 279 | S | M | | S | | M | S | S | M | | | | S | | | M | S | S | S | M | | | M | M | | |
| 1036 | yffysnimnf | 281 | | M | | | M | | | | | | | | | | | | | | | M | | M | M | | | |
| 1037 | ffysnimnff | 283 | | | | | | | | | | M | | | | | | | | | | | | | | M | | |
| 1038 | fysnimnffk | 285 | | | | | | | | | M | M | | | | | | | | | | | | | | | | |
| 1039 | ysnimnffkt | 287 | | | | | | | | | | | | | | | | | | | | | | | | | | |
| 1040 | snimnffkte | 289 | | | | | | | | | | | | | | | | | | | | | | | M | | | |
| 1041 | nimnffktei | 291 | | | | | | | | | | | | | | | | | | | | M | | M | | | | |
| 1042 | imnffkteit | 293 | | | | | | | | | | | | | | | | | | | | | | | M | | | |

FIG. 4A (Continued)

| # | Sequence |
|---|---|
| 1043 | mnffkteitl |
| 1044 | nffkteitla |
| 1045 | ffkteitlan |
| 1046 | fkteitlang |
| 1047 | kteitlange |
| 1048 | teitlangei |
| 1049 | eitlangeir |
| 1050 | itlangeirk |
| 1051 | tlangeirkr |
| 1052 | langeirkrp |
| 1053 | angeirkrpl |
| 1054 | ngeirkrpli |
| 1055 | geirkrplie |
| 1056 | eirkrpliet |
| 1057 | irkrplietn |
| 1058 | rkrplietng |
| 1059 | krplietnge |
| 1060 | rplietnget |
| 1061 | plietngetg |
| 1062 | lietngetge |
| 1063 | ietngetgei |
| 1064 | etngetgeiv |
| 1065 | tngetgeivw |
| 1066 | ngetgeivwd |
| 1067 | getgeivwdk |
| 1068 | etgeivwdkg |
| 1069 | tgeivwdkgr |
| 1070 | geivwdkgrd |
| 1071 | eivwdkgrdf |
| 1072 | ivwdkgrdfa |
| 1073 | vwdkgrdfat |
| 1074 | wdkgrdfatv |
| 1075 | dkgrdfatvr |

FIG. 4A (Continued)

| | | | | | | | | | | | | | | | | | | | | | | | | | |
|---|---|---|---|---|---|---|---|---|---|---|---|---|---|---|---|---|---|---|---|---|---|---|---|---|---|
| 1076 | kgrdfatvrk | 361 | | | | | | | | | | | | | | | | | | | | | | | |
| 1077 | grdfatvrkv | 363 | | | | | | | | | | | | | | | | | | | | | | | |
| 1078 | rdfatvrkvl | 365 | | | | | | | | | | | | | | | | | | | | | | | |
| 1079 | dfatvrkvls | 367 | | | | | | | | | | | | | | | | | | | | | | | |
| 1080 | fatvrkvlsm | 369 | | | M | | | | | M | M | | | | | | | | | | | | | | |
| 1081 | atvrkvlsmp | 371 | | | | | | | | M | M | | | | | | | | | | | | | | |
| 1082 | tvrkvlsmpq | 373 | | | | | | | | | | | | | | | | | | | | | | | |
| 1083 | vrkvlsmpqv | 375 | | | M | | | M | | M | | | | | M | | M | M | M | | | | | | |
| 1084 | rkvlsmpqvn | 377 | | | | | S | M | | | M | | | | S | M | S | M | | | | | | | |
| 1085 | kvlsmpqvni | 379 | | | M | | M | | | | M | | | | M | | | | | | | | | | |
| 1086 | vlsmpqvniv | 381 | | | | | M | | | | | | | | M | | | M | | | | | | | |
| 1087 | lsmpqvnivk | 383 | | | | | | | | | | | | | | M | | M | | | | | | | |
| 1088 | smpqvnivkk | 385 | | | | | | | | | | | | | | | | | | | | | | | |
| 1089 | mpqvnivkkt | 387 | | | | | | | | | | | | | | | | | | | | | | | |
| 1090 | pqvnivkkte | 389 | | | | | | | | | | | | | | | | | | | | | | | |
| 1091 | qvnivkktev | 391 | | | | | | | | | | | | | | | | | | | | | | | |
| 1092 | vnivkktevq | 393 | | | | | | | | | | | | | | | | | | | | | | | |
| 1093 | nivkktevqt | 395 | | | | | | | | | | | | | M | | | | | | | | | | |
| 1094 | ivkktevqtg | 397 | | | | | | | | | | | | | | | | | | | | | | | |
| 1095 | vkktevqtgg | 399 | | | | | | | | | | | | | | | | | | | | | | | |
| 1096 | kktevqtggf | 401 | | | | | | | | | | | | | | | | | | | | | | | |
| 1097 | ktevqtggfs | 403 | | | | | | | | | | | | | | | | | | | | | | | |
| 1098 | tevqtggfsk | 405 | | | | | | | | | | | | | | | | | | | | | | | |
| 1099 | evqtggfske | 407 | | | | | | | | | | | | | | | | | | | | | | | |
| 1100 | vqtggfskes | 409 | | | | | | | | | | | | | | | | | | | | | | | |
| 1101 | qtggfskesi | 411 | | | | | | | | | | | | | | | | | | | | | | | |
| 1102 | tggfskesil | 413 | | | | | | | | | | | | | | | | | | | | | | | |
| 1103 | ggfskesilp | 415 | | | | | | | | | | | | | | | | | | | | | | | |
| 1104 | gfskesilpk | 417 | | | | | | | | | | | | | | | | | | | | | | | |
| 1105 | fskesilpkr | 419 | | | | | | | | | | | | | | | | | | | | | | | |
| 1106 | skesilpkrn | 421 | | | | | | | | | | | | | | | | | | | | | | | |
| 1107 | kesilpkrns | 423 | | | | | | | | | | | | | | | | | | | | | | | |
| 1108 | esilpkrnsd | 425 | | | | | | | | | | | | | | | | | | | | | | | |

FIG. 4A (Continued)

| # | seq | idx | | | | | | | | | | | | | | | | | | | | | |
|---|---|---|---|---|---|---|---|---|---|---|---|---|---|---|---|---|---|---|---|---|---|---|---|
| 1109 | silpkrnsdk | 427 | | | | | | | | | | | | | | | | | | | | | M |
| 1110 | ilpkrnsdkl | 429 | | | | | | | | | | | | | | | | | | | | M | |
| 1111 | lpkrnsdkli | 431 | | | | | | | | | | | | | | | | | | | | | |
| 1112 | pkrnsdklia | 433 | | | | | | | | | | | | | | | | | | | | | |
| 1113 | krnsdkliar | 435 | | | | | | | | | M | | | | | | S | | | | | |
| 1114 | rnsdkliark | 437 | | | | | | | | | | | | | | | | | | | | | |
| 1115 | nsdkliarkk | 439 | | | | | | | | | | | | | | | | | | | | | |
| 1116 | sdkliarkkd | 441 | | | | | | | | | | | | | | | | | | | | | |
| 1117 | dkliarkkdw | 443 | | | | | | | | | | | | | | | | | | | | | |
| 1118 | kliarkkdwd | 445 | | | | | | | | | | | | | | | | | | | | | |
| 1119 | liarkkdwdp | 447 | | | | | M | | | | | | | | M | | | | | | | | |
| 1120 | iarkkdwdpk | 449 | | | | | | | S M | | | | | | | | | | | | | | |
| 1121 | arkkdwdpkk | 451 | | | | | | | | | | | | | | | | | | | | | |
| 1122 | rkkdwdpkky | 453 | | | | | | | | | | | | | | | | | | | | | |
| 1123 | kkdwdpkkyg | 455 | | | | | | | | | | | | | | | | | | | | | |
| 1124 | kdwdpkkygg | 457 | | | | | | | | | | | | | | | | | | | | | |
| 1125 | dwdpkkyggf | 459 | | | | | | | | | | | | | | | | | | | | | |
| 1126 | wdpkkyggfd | 461 | | | | | | | | | | | | | | | | | | | | | |
| 1127 | dpkkyggfds | 463 | | | | | | | | | | | | | | | | | | | | | |
| 1128 | pkkyggfdsp | 465 | | | | | | | | | | | | | | | | | | | | | |
| 1129 | kkyggfdspt | 467 | | | | | | | | | M | | | | | | | | | | | | |
| 1130 | kyggfdsptv | 469 | | | | | | | | | | | | | | | | | | | | | |
| 1131 | yggfdsptva | 471 | | | | | | | | | | | | | | | | | | | | | |
| 1132 | ggfdsptvay | 473 | | | | | M | | | | | | | | | | | | | | | | |
| 1133 | gfdsptvays | 475 | | | | | | | | | | | | | | | | | | | | | |
| 1134 | fdsptvaysv | 477 | | | | | | | | | | | | | | | | | | | | | |
| 1135 | dsptvaysvl | 479 | | | | | | | | | | | | | | | | | | | | | |
| 1136 | sptvaysvlv | 481 | | | M | | | | | | | | | | | | | | | | | | |
| 1137 | ptvaysvlvv | 483 | | M | | | | | | | | | | | | | | | | | | | | |
| 1138 | tvaysvlvva | 485 | M | | | | | | | | | | | | | | | | | | | | | |
| 1139 | vaysvlvvak | 487 | M | | | | | | | | | | | | | | | | | | M M | | | |
| 1140 | aysvlvvakv | 489 | | | | | | M M | | | | | | | | | | | | | | | |
| 1141 | ysvlvvakve | 491 | S | | M | | M M | | | | | | | | | | | | | | M | | |

FIG. 4A (Continued)

| | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| 1142 | svlvvakvek | 493 | | | | | | | | | | | | | | | | | | | | | | | | | | | | | | | |
| 1143 | vlvvakvekg | 495 | | | | | | | | | | | | | | | | | | | | | | | | | | | | | | | |
| 1144 | lvvakvekgk | 497 | | M | M | | | | | | | | | | | | | | | | | | | | | | | | | | | | |
| 1145 | vvakvekgks | 499 | | | | | | | | | | | | | | | | | | | | | | | | | | | | | | | |
| 1146 | vakvekgksk | 501 | | | | | | | | | | | | | M | | | | | | | | | | | | | | | | | | | |
| 1147 | akvekgkskk | 503 | | | | | | | | | | | | | | | M | | | | | | | | | | | | | | | | | |
| 1148 | kvekgkskkl | 505 | | | M | | | | | | | | | | | | | | M | | | | | | | | | | | | | | | |
| 1149 | vekgkskklk | 507 | | | | | | | | | | | | | | | | | | | | M | | | | | M | M | | | | | | |
| 1150 | ekgkskklks | 509 | | | | | | | | | | | | | | | | | | | | | | | | | | | M | | M | M | M | |

FIG. 4B

| Pos | Peptide | SEQ ID NO: | Allele: DRB1*13 | DRB1*13 | DRB1*13 | DRB1*14 | DRB1*14 | DRB1*14 | DRB1*14 | DRB1*14 | DRB1*15 | DRB1*15 | DRB1*15 | DRB1*15 | DRB1*15 | DRB1*16 | DRB1*16 | DRB3*01 | DRB3*02 | DRB3*02 | DRB3*03 | DRB4*01 | DRB5*01 | DRB5*01 | DRB5*02 | DQA1*01DQB1 | DQA1*01DQB1*05 | DQA1*01DQB1*05 | DQA1*01DQB1*05 | DQA1*01DQB1*05 | DQA1*01DQB1*06 | DQA1*01DQB1*06 | DQA1*01DQB1*06 |
|---|---|---|---|---|---|---|---|---|---|---|---|---|---|---|---|---|---|---|---|---|---|---|---|---|---|---|---|---|---|---|---|---|
| 1026 | eqeigkatak | 261 | | | | | | | | | | | | | | | | | | | | | | | | | | | | | | | |
| 1027 | qeigkataky | 263 | | | | | | | | | | | | | | | | | | | | | | | | | | | | | | | |
| 1028 | eigkatakyf | 265 | | | | | | | | M | M | | M | M | M | M | M | | | | M | | | | | | | | | | | | |
| 1029 | igkatakyff | 267 | | | | | | | | M | | | | | | M | M | | | | | | | | | | | | | | | | |
| 1030 | gkatakyffy | 269 | | | | | | | | | | | | | | | | | | | | | | | | | | | | | | | |
| 1031 | katakyffys | 271 | | | | | | | | | | | | | | | | | | | | | | | | | | | | | | | |
| 1032 | atakyffysn | 273 | | | | | | | | | M | M | M | | M | | | | | M | M | | | | | | | | | | | | |
| 1033 | takyffysni | 275 | | | | | | | | | S | S | S | S | S | S | S | | | | | | | | | | | | | | | | |
| 1034 | akyffysnim | 277 | | | | | | | | | S | M | M | M | M | M | M | | | | M | | | | | | | | | | | | |
| 1035 | kyffysnimn | 279 | S | M | | M | M | | M | M | | | | | | | | M | M | M | | | M | M | | M | M | M | | M | | | M |
| 1036 | yffysnimnf | 281 | M | | M | S | M | | | M | | | | | | | | M | | S | S | | M | M | M | M | | | | | | | |
| 1037 | ffysnimnff | 283 | | | | M | S | | | | | | | | | | | | | | M | | M | | | | | | | | | | |
| 1038 | fysnimnffk | 285 | | | | M | | | | | | | | | | | | M | | | M | | M | | M | | | | | | | | |

FIG. 4B (Continued)

| | | | | | | | | | | | | | | | | | | | | | |
|---|---|---|---|---|---|---|---|---|---|---|---|---|---|---|---|---|---|---|---|---|---|
| 1039 | ysnimffkt | 287 | | | | | | | | | | | | | | | | | | | |
| 1040 | snimffkte | 289 | | | | | | | | | | | | | | | | | | M | |
| 1041 | nimffktei | 291 | | | | | | | | | | | | | | | | | | | |
| 1042 | imnffktei t | 293 | | | M | | | | | | | | | | | | | | | | |
| 1043 | mnffkteitl | 295 | | | M | | | | | | | | | | | | | | | | |
| 1044 | nffkteitla | 297 | | | | | | | | | | | | | | | | | | | |
| 1045 | ffkteitlan | 299 | | | | | | | | | | | | | | | | | | | |
| 1046 | fkteitlang | 301 | | | | | | | | M | | | | | | | | | | | |
| 1047 | kteitlange | 303 | | | | | | | | | | | | | | | | | | | |
| 1048 | teitlangei | 305 | | | | | | | | | | M | | | | | | | | | |
| 1049 | eitlangeir | 307 | | | | | | | S | | | | | | | | | | | | |
| 1050 | itlangeirk | 309 | | | | | | | | | M | S | | | | | | | | | |
| 1051 | tlangeirkr | 311 | | | | | | | | | | | | | | | | | | | |
| 1052 | langeirkrp | 313 | | | | | | | | | | | | | | | | | | | |
| 1053 | angeirkrpl | 315 | | | | | | | | | | | | | | | | | | | |
| 1054 | ngeirkrpli | 317 | | | | | | | | | | | | | | | | | | | |
| 1055 | geirkrplie | 319 | | | | | | | | | | | | | | | | | | | |
| 1056 | eirkrpliet | 321 | | | | | | | | | | | | | | | | | | | |
| 1057 | irkrplietn | 323 | | | | | | | | | | | | | | | | | | | |
| 1058 | rkrplietng | 325 | | | | | | | | | | | | | | | | | | | |
| 1059 | krplietnge | 327 | | | | | | | | | | | | | | | | | | | |
| 1060 | rplietnget | 329 | | | | | | | | | | | | | | | | | | | |
| 1061 | plietngetg | 331 | | | | | | | | | | | | | | | | | | | |
| 1062 | lietngetge | 333 | | | | | | | | | | | | | | | | | | | |
| 1063 | ietngetgei | 335 | | | | | | | | | | | | | | | | | | | |
| 1064 | etngetgeiv | 337 | | | | | | | | | | | | | | | | | | | |
| 1065 | tngetgeivw | 339 | | | | | | | | | | | | | | | | | | | |
| 1066 | ngetgeivwd | 341 | | | | | | | | | | | | | | | | | | | |
| 1067 | getgeivwdk | 343 | | | | | | | | | | | | | | | | | | | |
| 1068 | etgeivwdkg | 345 | | | | | | | | | | | | | | | | | | | |
| 1069 | tgeivwdkgr | 347 | | | | | | | | | | | | | | | | | | | |
| 1070 | geivwdkgrd | 349 | | M | | | | | | | | | | | | | | | | | |
| 1071 | eivwdkgrdf | 351 | M | | | | | | | | | | | | | | | | | | |

FIG. 4B (Continued)

| | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|
| 1072 | ivwdkgrdfa | 353 | | | | | | | | | | | | | | | | | | | | | | | | | | | | | | | | M | | |
| 1073 | vwdkgrdfat | 355 | | | | | | | | | | | | | | | | | | | | | | | | | | | | | | | | | | |
| 1074 | wdkgrdfatv | 357 | | | | | | | | | | | | | | | | | | | | | | | | | | | | | | | | | | |
| 1075 | dkgrdfatvr | 359 | | | | | | | | | | | | | | | | | | | | | | | | | | | | | | | | | | |
| 1076 | kgrdfatvrk | 361 | | | | | | | | | | | | | | | | | | | | | | | | | | | | | | | | | | |
| 1077 | grdfatvrkv | 363 | | | | | | | | | | | | | | | | | | | | | | | | | | | | | | | | | | |
| 1078 | rdfatvrkvl | 365 | | | | | | | | | | | | | | | | | | | | | | | | | | | | | | | | | | |
| 1079 | dfatvrkvls | 367 | | | S | | | | | | | | | | | | | | | | | | | | | | | | | | | | | | | |
| 1080 | fatvrkvlsm | 369 | M | | | | M | | | | | | | | | | | | | | | | | | | | | | | | | | | | | |
| 1081 | atvrkvlsmp | 371 | | | | M | M | | | | | | | | | | | | | | | | | | | | | | | | | | | | | |
| 1082 | tvrkvlsmpq | 373 | | M | | M | M | | | | | | | | | | | | | | | | | | | | | | | | | | | | | |
| 1083 | vrkvlsmpqv | 375 | | M | | | M | | | | | | | | | | | | | | | | | | | | | | | | | | | | | |
| 1084 | rkvlsmpqvn | 377 | M | | | | | | | | | | | | | | | | | | | | | M | | | | | | | | | | | | | |
| 1085 | kvlsmpqvni | 379 | | M | | | | | | | | | | | | | | | | | | | | | | | | | | | | | | | | | |
| 1086 | vlsmpqvniv | 381 | | | | | | | | | | | | | | | | | | | | | | M | | | | | | | | | | | | | |
| 1087 | lsmpqvnivk | 383 | | | | | | | | | | | | | | | | | | | | | | | | | | | | | | | | | | | |
| 1088 | smpqvnivkk | 385 | | | | | | | | | | | | | | | | | | | | | | S | | | | | | | | | | | | | |
| 1089 | mpqvnivkkt | 387 | | | | | | | | | | | | | | | | | | | | | | | | | | | | | | | | | | | |
| 1090 | pqvnivkkte | 389 | | | | | | | | | | | | | | | | | | | | | | | | | | | | | | | | | | | |
| 1091 | qvnivkktev | 391 | M | | | M | | | | | | | | | | | | | | | | | | | | | | | | | | | | | | | |
| 1092 | vnivkktevq | 393 | M | | | M | M | | | | | | | | | | | | | | | | | | | | | | | | | | | | | | |
| 1093 | nivkktevqt | 395 | | | | | M | | | | | | | | | | | | | | | | | | | | | | | | | | | | | | |
| 1094 | ivkktevqtg | 397 | | | | | | | | | | | | | | | | | | | | | | | | | | | | | | | | | | | |
| 1095 | vkktevqtgg | 399 | | | | | | | | | | | | | | | | | | | | | | | | | | | | | | | | | | | |
| 1096 | kktevqtggf | 401 | | | | | | | | | | | | | | | | | | | | | | | | | | | | | | | | | | | |
| 1097 | ktevqtggfs | 403 | | | | | | | | | | | | | | | | | | | | | | | | | | | | | | | | | | | |
| 1098 | tevqtggfsk | 405 | | | | | | | | | | | | | | | | | | | | | | | | | | | | | | | | | | | |
| 1099 | evqtggfske | 407 | | | | | | | | | | | | | | | | | | | | | | | | | | | | | | | | | | | |
| 1100 | vqtggfskes | 409 | | | | | | | | | | | | | | | | | | | | | | | | | | | | | | | | | | | |
| 1101 | qtggfskesi | 411 | | | | | | | | | | | | | | | | | | | | | | | | | | | | | | | | | | | |
| 1102 | tggfskesil | 413 | | | | | | | | | | | | | | | | | | | | | | | | | | | | | | | | | | | |
| 1103 | ggfskesilp | 415 | | | | | | | | | | | | | | | | | | | | | | | | | | | | | | | | | | | |
| 1104 | gfskesilpk | 417 | | | | | | | | | | | | | | | | | | | | | | | | | | | | | | | | | | | |

FIG. 4B (Continued)

| | | | | | | | | | | | | | | |
|---|---|---|---|---|---|---|---|---|---|---|---|---|---|---|
| 1105 | fskesilpkr | 419 | | | | | | | | | | | | |
| 1106 | skesilpkrn | 421 | | | | | | | | | | | | S M |
| 1107 | kesilpkrns | 423 | | | | | | | | | | | | |
| 1108 | esilpkrnsd | 425 | M | | | | | | | | | | | |
| 1109 | silpkrnsdk | 427 | | | | | | | | | | | | |
| 1110 | ilpkrnsdkl | 429 | | M | | | | | | | | | | M |
| 1111 | lpkrnsdkli | 431 | | | | | | | | | | | | |
| 1112 | pkrnsdklia | 433 | | | | | | | | | | | | |
| 1113 | krnsdkliar | 435 | | M | | | | | | | | | | |
| 1114 | rnsdkliark | 437 | | | S M | | | | | | | | | |
| 1115 | nsdkliarkk | 439 | | | | | | | | | | | | |
| 1116 | sdkliarkkd | 441 | | | | | | | | | | | | |
| 1117 | dkliarkkdw | 443 | | | | | | | | | | | | |
| 1118 | kliarkkdwd | 445 | | | | | | | | | | | | |
| 1119 | liarkkdwdp | 447 | M | | M | | | | | | | | | |
| 1120 | iarkkdwdpk | 449 | | | M | | | | | | | | | |
| 1121 | arkkdwdpkk | 451 | | | | | | | | | | | | |
| 1122 | rkkdwdpkky | 453 | | | | | | | | | | | | |
| 1123 | kkdwdpkkyg | 455 | | | | | | | | | | | | |
| 1124 | kdwdpkkygg | 457 | | | | | | | | | | | | |
| 1125 | dwdpkkyggf | 459 | | | | | | | | | | | | |
| 1126 | wdpkkyggfd | 461 | | | | | | | | | | | | |
| 1127 | dpkkyggfds | 463 | | | | | | | | | | | | |
| 1128 | pkkyggfdsp | 465 | | | | | | | | | | | | |
| 1129 | kkyggfdspt | 467 | | | | | | | | | | | | |
| 1130 | kyggfdsptv | 469 | | | | | | | | | M | | | |
| 1131 | yggfdsptva | 471 | | | | | | | | | | S | | |
| 1132 | ggfdsptvay | 473 | | | | | | | | | | | | |
| 1133 | gfdsptvays | 475 | | | | | | | | | M | | | |
| 1134 | fdsptvaysv | 477 | | | | | | | | | | | M | |
| 1135 | dsptvaysvi | 479 | | | | | | | | | | | | |
| 1136 | sptvaysvlv | 481 | | | | | | | | | M | M | M | M |
| 1137 | ptvaysvlvv | 483 | | | | | | | | | | | M | |

FIG. 4B (Continued)

| | | | | | | | | | | | | | | | | | | | | | |
|---|---|---|---|---|---|---|---|---|---|---|---|---|---|---|---|---|---|---|---|---|---|
| 1138 | tvaysvlvva | 485 | | | | | | | | | | | | | | | | | | | |
| 1139 | vaysvlvvak | 487 | | | | | | | | | | | | | | | | | | | |
| 1140 | aysvlvvakv | 489 | | | | | | | | | | | | | | | | | | | |
| 1141 | ysvlvvakve | 491 | M | | | | | | | | | | | | | | | | | | |
| 1142 | svlvvakvek | 493 | | | M | | | | | | | | | | | | | | | | |
| 1143 | vlvvakvekg | 495 | | | | | M | | | | | | | | | | | | | | |
| 1144 | lvvakvekgk | 497 | | | | | | M | | | | | | | | | | | | | |
| 1145 | vvakvekgks | 499 | | | | | | | M | | | | | | | | | | | | |
| 1146 | vakvekgksk | 501 | | | | | | | | M | | | | | | | | | | | |
| 1147 | akvekgkskk | 503 | | | | | | | | | M | | | | | | | | | | |
| 1148 | kvekgkskkl | 505 | | | | | | | | | | M | | | | | | | | | |
| 1149 | vekgkskklk | 507 | | | | | | | | | | | M | | | | | | | | |
| 1150 | ekgkskklks | 509 | | | M | | | | | | | | | M | M | M | M | S | M | S | M | M |

FIG. 4C

| Pos | Peptide | SEQ ID NO: | Allele: | DQA1*01DQB1*06 | DQA1*01DQB1*06 | DQA1*01DQB1*06 | DQA1*02DQB1*02 | DQA1*03DQB1*03 | DQA1*03DQB1*03 | DQA1*03DQB1*03 | DQA1*03DQB1*04 | DQA1*03DQB1*04 | DQA1*04DQB1*03 | DQA1*04DQB1*04 | DQA1*05DQB1*02 | DQA1*05DQB1*03 | DQA1*06DQB1*03 | DPA1*01DPB1*02 | DPA1*01DPB1*03 | DPA1*01DPB1*04 | DPA1*01DPB1*04 | DPA1*02DPB1*01 | DPA1*02DPB1*05 | DPA1*02DPB1*09 | DPA1*02DPB1*09 | DPA1*02DPB1*17 | DPA1*02DPB1*01 | DPA1*02DPB1*05 | DPA1*03DPB1*04 |
|---|---|---|---|---|---|---|---|---|---|---|---|---|---|---|---|---|---|---|---|---|---|---|---|---|---|---|---|---|---|
| 1026 | eqeigkatak | 261 | | | | | | | | | | | | | | | | | | | | | | | | | | | |
| 1027 | qeigkataky | 263 | | | | | | | | | | | | | | | | | | | | | | | | | | | |
| 1028 | eigkatakyf | 265 | | | | | | | | | | | | | | | | | | | | | | | | | | | |
| 1029 | igkatakyff | 267 | | | | | | | | | | | | | M | | | | | | | | | | | | | | |
| 1030 | gkatakyffy | 269 | | | | | | | | | | | | | | | | | | | | | | | | | | | |
| 1031 | katakyffys | 271 | | | | | | | | | | | | | | | | M | | | M | M | | | | | | | |
| 1032 | atakyffysn | 273 | | | | | | | | | | | | | | | | M | M | | | M | M | M | | M | M | |
| 1033 | takyffysni | 275 | | | | | | | | | | | | | | | | | | M | M | | | | | | | | |
| 1034 | akyffysnim | 277 | | | | | | | | | | | | | | | | | | S | | | | | | | | | M |

FIG. 4C (Continued)

| # | seq | idx |
|---|---|---|
| 1035 | kyffysnimn | 279 |
| 1036 | yffysnimnf | 281 |
| 1037 | ffysnimnff | 283 |
| 1038 | fysnimnffk | 285 |
| 1039 | ysnimnffkt | 287 |
| 1040 | snimnffkte | 289 |
| 1041 | nimnffktei | 291 |
| 1042 | imnffkteit | 293 |
| 1043 | mnffkteitl | 295 |
| 1044 | nffkteitla | 297 |
| 1045 | ffkteitlan | 299 |
| 1046 | fkteitlang | 301 |
| 1047 | kteitlange | 303 |
| 1048 | teitlangei | 305 |
| 1049 | eitlangeir | 307 |
| 1050 | itlangeirk | 309 |
| 1051 | tlangeirkr | 311 |
| 1052 | langeirkrp | 313 |
| 1053 | angeirkrpl | 315 |
| 1054 | ngeirkrpli | 317 |
| 1055 | geirkrplie | 319 |
| 1056 | eirkrpliet | 321 |
| 1057 | irkrplietn | 323 |
| 1058 | rkrplietng | 325 |
| 1059 | krplietnge | 327 |
| 1060 | rplietnget | 329 |
| 1061 | plietngetg | 331 |
| 1062 | lietngetge | 333 |
| 1063 | ietngetgei | 335 |
| 1064 | etngetgeiv | 337 |
| 1065 | tngetgeiv | 339 |
| 1066 | ngetgeivwd | 341 |
| 1067 | getgeivwdk | 343 |

FIG. 4C (Continued)

| | | | | | | | | | | | | | | | | |
|---|---|---|---|---|---|---|---|---|---|---|---|---|---|---|---|---|
| 1068 | etgeivwdkg | 345 | | | | | | | | | | | | | | |
| 1069 | tgeivwdkgr | 347 | | | | | | | | | | | | | | |
| 1070 | geivwdkgrd | 349 | | | | | | | | | | | | | | |
| 1071 | eivwdkgrdf | 351 | | | M | | | | | | | | | | | |
| 1072 | ivwdkgrdfa | 353 | | | M | | | | | | | | | | | |
| 1073 | vwdkgrdfat | 355 | | | | | | | | | | | | | | |
| 1074 | wdkgrdfatv | 357 | | | | M | | | | | | | | | | |
| 1075 | dkgrdfatvr | 359 | | | | | | | | | | | | | | |
| 1076 | kgrdfatvrk | 361 | | | | | | | | | | | | | | |
| 1077 | grdfatvrkv | 363 | | M | | | | | | | | | | | | |
| 1078 | rdfatvrkvl | 365 | | | | | M | | | | | M | | | | |
| 1079 | dfatvrkvls | 367 | | | | | | | | | | | | | | |
| 1080 | fatvrkvlsm | 369 | | | | | M | M | | | | M | | | M | |
| 1081 | atvrkvlsmp | 371 | | | | | | | | | | M | | | | |
| 1082 | tvrkvlsmpq | 373 | | | | | | | | | | | | | | |
| 1083 | vrkvlsmpqv | 375 | | | | | | M | | | | | | | | |
| 1084 | rkvlsmpqvn | 377 | | | | | | M | M | | | M | | | | |
| 1085 | kvlsmpqvni | 379 | | | | | | M | M | | | | | | | |
| 1086 | vlsmpqvniv | 381 | | | | | | | M | | | M | S | M | M | |
| 1087 | lsmpqvnivk | 383 | | | | | | | | | | M | M | | | |
| 1088 | smpqvnivkk | 385 | | | | | | | | | | | | | | |
| 1089 | mpqvnivkkt | 387 | | | | | | | | | | M | S | M | | |
| 1090 | pqvnivkkte | 389 | | | | | | | | M | | | | | | |
| 1091 | qvnivkktev | 391 | | | | | | | | | | M | M | | M | |
| 1092 | vnivkktevq | 393 | | | | | | | | | | | | M | | M |
| 1093 | nivkktevqt | 395 | | | | | | | | | | | | | S | M |
| 1094 | ivkktevqtg | 397 | | | | | | | | | | | | | | |
| 1095 | vkktevqtgg | 399 | | | | | | | | | | | | | | |
| 1096 | kktevqtggf | 401 | | | | | | | | | | | | | | |
| 1097 | ktevqtggfs | 403 | | | | | | | | | | | | | | |
| 1098 | tevqtggfsk | 405 | | | | | | | | | | | | | | |
| 1099 | evqtggfske | 407 | | | | | | | | | | | | | | |
| 1100 | vqtggfskes | 409 | | | | | | | | | | | | | | |

FIG. 4C (Continued)

| | | | | | | | | | |
|---|---|---|---|---|---|---|---|---|---|
| 1101 | qtggfskesi | 411 | | | | | M | | |
| 1102 | tggfskesil | 413 | | | | M | | | |
| 1103 | ggfskesilp | 415 | | | | | | | |
| 1104 | gfskesilpk | 417 | | | | | | | |
| 1105 | fskesilpkr | 419 | | | | | | | |
| 1106 | skesilpkrn | 421 | | | | | | | |
| 1107 | kesilpkrns | 423 | | | | | | | |
| 1108 | esilpkrnsd | 425 | | | | | | | |
| 1109 | silpkrnsdk | 427 | | | | | | | |
| 1110 | ilpkrnsdkl | 429 | | | | | | | |
| 1111 | lpkrnsdkli | 431 | | | | | | | |
| 1112 | pkrnsdklia | 433 | | | | | | | |
| 1113 | krnsdkliar | 435 | | | | | | | |
| 1114 | rnsdkliark | 437 | | | | | | | |
| 1115 | nsdkliarkk | 439 | | | | | | | |
| 1116 | sdkliarkkd | 441 | | | | | | | |
| 1117 | dkliarkkdw | 443 | | | | | | | |
| 1118 | kliarkkdwd | 445 | | | | | | | |
| 1119 | liarkkdwdp | 447 | | | | | | | |
| 1120 | iarkkdwdpk | 449 | | | | | | | |
| 1121 | arkkdwdpkk | 451 | | | | | | | |
| 1122 | rkkdwdpkky | 453 | | | | | | | |
| 1123 | kkdwdpkkyg | 455 | | | | | | | |
| 1124 | kdwdpkkygg | 457 | | | | | | | |
| 1125 | dwdpkkyggf | 459 | | | | | | | |
| 1126 | wdpkkyggfd | 461 | | | | | | | |
| 1127 | dpkkyggfds | 463 | | | | | | | |
| 1128 | pkkyggfdsp | 465 | | | | | | | |
| 1129 | kkyggfdspt | 467 | | | | | | M | |
| 1130 | kyggfdsptv | 469 | | | | | | | |
| 1131 | yggfdsptva | 471 | | | | | | | |
| 1132 | ggfdsptvay | 473 | | | | | | | |
| 1133 | gfdsptvays | 475 | | | | | | | |

FIG. 4C (Continued)

| # | seq | | | | | | | | | | | | | | | | | | | | | | | |
|---|---|---|---|---|---|---|---|---|---|---|---|---|---|---|---|---|---|---|---|---|---|---|---|---|
| 1134 | fdsptvaysv | | | | | | | | | | | | | | | | | | | | | | | |
| 1135 | dsptvaysvl | | | | | | | | | | | | | | | | | | | | | | | |
| 1136 | sptvaysvlv | | | | | | | | | | | | | | | | | | | | | | | |
| 1137 | ptvaysvlvv | | | | | M | | | | | | | | | | | | | | | | | | |
| 1138 | tvaysvlvva | | | M | | M | | | S | | | | | | | | | | | | | | | | |
| 1139 | vaysvlvvak | | | M | S | M | | M | M | | | | | | M | | | | | | | | | | |
| 1140 | aysvlvvakv | | | | | | M | | | | | | | | | | | | | | | | | | |
| 1141 | ysvlvvakve | | | | | | | | M | | M | | | | | | | | | | | | | | |
| 1142 | svlvvakvek | | | | | | | M | M | | M | | M | | M | | | | | | | | | | |
| 1143 | vlvvakvekg | | | | | | | | M | | S | | S | | M | | | | | | | | | | |
| 1144 | lvvakvekgk | | | | | | | M | M | | M | | M | M | M | | M | | | | | | | | |
| 1145 | vvakvekgks | | | | | | | | | | M | | M | M | M | M | M | | | | | | | | |
| 1146 | vakvekgksk | | | | | | | | | | | | | M | | M | M | M | | | | | | | |
| 1147 | akvekgkskk | | | | | | | | | | | | | | | | M | M | M | | | | | | |
| 1148 | kvekgkskkl | | | | | | | | | | | | | | | | | | M | | | | | | |
| 1149 | vekgkskklk | | | | | | | | | | | | | | | | | M | M | | | | | | |
| 1150 | ekgkskklks | | | | | | | | | | | | | | | | | | M | M | | | | | |

FIG. 5A

| Pos | Residue | r_start | r_end | A | C | D | E | F | G | H | I | K | L | M | N | P | Q | R | S | T | V | W | Y |
|---|---|---|---|---|---|---|---|---|---|---|---|---|---|---|---|---|---|---|---|---|---|---|---|
| 1026 | e | 1018 | 1034 | 0 | 1 | 0 | 0 | 2 | -1 | 1 | 2 | 0 | 2 | 2 | 1 | 0 | 0 | 0 | 2 | 0 | 1 | 1 | 2 |
| 1027 | q | 1019 | 1035 | 0 | -1 | -1 | -1 | 0 | -1 | -1 | 0 | 0 | 0 | 0 | 0 | 0 | 0 | 0 | -1 | 0 | -1 | 0 | 0 |
| 1028 | e | 1020 | 1036 | -2 | -2 | -2 | 0 | 0 | -1 | -2 | -1 | -1 | 1 | -1 | -3 | -2 | -2 | -1 | -1 | -1 | 0 | 0 | 0 |
| 1029 | i | 1021 | 1037 | -2 | -2 | -2 | -2 | 0 | -2 | -3 | 0 | -2 | -2 | -1 | -3 | -2 | -3 | -1 | -1 | -1 | 0 | -1 | 0 |
| 1030 | g | 1022 | 1038 | -1 | -1 | 0 | -1 | -1 | 0 | 0 | 0 | -1 | 1 | 1 | -1 | -1 | -1 | -1 | -1 | -1 | 1 | 2 | 2 |
| 1031 | k | 1023 | 1039 | 2 | 1 | 0 | 1 | 1 | 0 | 0 | 2 | 0 | 2 | 2 | 0 | 1 | 0 | 0 | 1 | 1 | 2 | 2 | 2 |
| 1032 | a | 1024 | 1040 | 0 | 0 | 0 | -1 | 1 | 0 | 0 | 0 | -1 | 0 | 0 | 0 | -2 | -1 | -2 | -1 | -1 | 1 | 1 | 1 |
| 1033 | t | 1025 | 1041 | -3 | -2 | -2 | -2 | 1 | -3 | 0 | 0 | -3 | -1 | 1 | -2 | -3 | -1 | -3 | -2 | 0 | -2 | 0 | 0 |
| 1034 | a | 1026 | 1042 | 0 | -3 | -2 | -2 | 1 | -2 | -1 | 0 | -3 | -1 | -2 | -3 | -4 | -2 | -1 | -1 | -2 | -2 | 2 | 0 |
| 1035 | k | 1027 | 1043 | 1 | 0 | 0 | -1 | 3 | -1 | -1 | 1 | 0 | 0 | 0 | -2 | 0 | -1 | 1 | 1 | 0 | 0 | 3 | 1 |
| 1036 | y | 1028 | 1044 | -1 | -2 | -3 | -3 | -1 | -3 | -3 | -2 | -2 | -1 | -2 | -3 | -1 | -3 | 0 | -2 | -3 | -2 | -1 | 0 |
| 1037 | f | 1029 | 1045 | 0 | -1 | 0 | 0 | 0 | 0 | 1 | 0 | -1 | 0 | 0 | -2 | 0 | -1 | 0 | -1 | -1 | 0 | 0 | 1 |
| 1038 | f | 1030 | 1046 | -2 | -2 | -2 | -2 | 0 | -2 | 0 | -1 | -2 | -1 | -1 | -2 | -2 | -2 | -1 | -2 | -2 | -2 | -1 | 0 |
| 1039 | y | 1031 | 1047 | -1 | -1 | -1 | -1 | 0 | -1 | -1 | 1 | -2 | 0 | -2 | -2 | -1 | -2 | -1 | -1 | -3 | -2 | -1 | 0 |
| 1040 | s | 1032 | 1048 | 0 | 0 | 1 | 1 | 0 | 1 | 1 | -1 | 2 | 0 | 0 | 0 | 0 | -1 | -1 | 0 | -1 | 0 | 0 | 0 |
| 1041 | n | 1033 | 1049 | 1 | -1 | -1 | 1 | -1 | -1 | 2 | 0 | 1 | 2 | 0 | 0 | 1 | -1 | 1 | 0 | 1 | 0 | 1 | 2 |
| 1042 | i | 1034 | 1050 | 1 | -1 | -1 | 1 | 0 | -2 | 0 | -1 | -1 | -1 | 0 | -1 | 0 | -1 | 1 | 0 | 0 | 0 | 0 | 0 |
| 1043 | m | 1035 | 1051 | -2 | -2 | -2 | -1 | -1 | -2 | -2 | -1 | -1 | 2 | 2 | -2 | -1 | -2 | -1 | -2 | -1 | -1 | 0 | 0 |
| 1044 | n | 1036 | 1052 | 2 | 0 | 0 | 0 | 2 | -1 | 0 | 0 | 0 | -1 | -1 | 0 | 0 | -1 | -1 | 1 | -1 | 0 | 2 | 2 |
| 1045 | f | 1037 | 1053 | 0 | -2 | -2 | -1 | 0 | -1 | -1 | -2 | -1 | -1 | -1 | -2 | -1 | -2 | -1 | -2 | -1 | -2 | 0 | 1 |
| 1046 | f | 1038 | 1054 | -2 | -2 | 1 | 1 | 2 | -2 | 2 | 0 | -2 | 1 | 2 | -2 | -2 | 0 | -1 | -2 | -2 | -1 | -1 | -1 |
| 1047 | k | 1039 | 1055 | 2 | 1 | 1 | 1 | 2 | 2 | 0 | 1 | 0 | 0 | 0 | 0 | 1 | -1 | 0 | 2 | 1 | 2 | 2 | 2 |
| 1048 | t | 1040 | 1056 | 1 | -1 | -1 | -1 | 2 | 0 | 0 | 1 | 1 | 1 | 0 | 0 | -1 | 0 | 1 | -1 | 0 | 1 | 2 | 2 |
| 1049 | e | 1041 | 1057 | 0 | -1 | -1 | 0 | 1 | -1 | 0 | 0 | -1 | 1 | 0 | -1 | 0 | -2 | -1 | -1 | 0 | 0 | 1 | 1 |

FIG. 5A (Continued)

| | | | | | | | | | | | | | | | | | | | | | |
|---|---|---|---|---|---|---|---|---|---|---|---|---|---|---|---|---|---|---|---|---|---|
| 1050 | i | 1042 | -3 | -2 | -2 | -1 | 0 | -3 | -2 | 0 | -2 | -1 | -1 | -3 | -1 | -2 | -1 | -1 | 0 | -1 |
| 1051 | t | 1043 | 0 | -1 | -3 | -2 | -1 | -2 | -1 | -1 | -3 | -2 | -1 | -1 | -2 | 0 | 0 | -1 | 0 | 0 |
| 1052 | l | 1044 | 0 | -1 | 0 | 1 | 0 | 0 | 0 | 0 | 1 | 0 | 1 | -3 | 1 | 0 | 0 | 0 | 0 | 1 |
| 1053 | a | 1045 | 0 | -2 | -3 | -3 | 0 | -2 | -1 | -1 | -2 | -1 | 0 | -1 | -2 | -1 | 0 | -1 | 0 | 1 |
| 1054 | n | 1046 | 0 | -1 | -1 | -2 | 1 | -2 | 1 | 1 | 0 | 1 | 1 | 0 | 1 | -1 | 0 | 0 | 1 | 1 |
| 1055 | g | 1047 | 1 | -1 | 0 | 0 | 1 | 0 | 0 | 2 | 0 | -1 | 2 | 1 | 1 | 1 | 0 | 1 | 2 | 1 |
| 1056 | e | 1048 | 0 | 1 | -1 | 0 | 3 | 0 | 1 | 0 | 1 | 2 | 2 | 3 | 3 | 0 | 1 | 1 | 2 | 4 |
| 1057 | i | 1049 | -1 | -2 | -2 | 0 | -1 | -1 | 0 | 1 | -1 | 0 | -1 | -1 | -2 | -1 | 0 | 0 | 3 | 0 |
| 1058 | r | 1050 | 0 | -1 | -1 | 0 | 0 | -1 | -1 | 0 | 0 | -1 | -1 | -1 | 0 | 0 | -1 | 1 | 0 | 2 |
| 1059 | k | 1051 | 0 | 0 | 0 | 0 | 2 | 0 | 1 | 1 | 0 | 2 | 0 | 0 | 1 | 1 | 1 | 0 | 1 | 2 |
| 1060 | r | 1052 | 1 | 1 | 1 | 1 | 2 | 1 | 0 | 2 | 1 | 2 | 1 | 0 | 3 | -1 | 1 | -1 | 3 | 3 |
| 1061 | p | 1053 | 2 | 1 | 0 | 0 | 2 | 0 | 0 | 0 | 0 | 1 | 0 | -1 | 3 | 1 | -1 | 1 | 3 | 2 |
| 1062 | l | 1054 | 2 | -1 | -1 | -1 | 0 | 0 | 2 | 1 | -1 | 0 | -1 | 0 | 1 | -1 | 1 | 0 | 1 | 0 |
| 1063 | i | 1055 | 0 | 1 | 0 | 0 | 0 | 0 | 1 | 0 | 0 | 1 | 0 | 0 | 0 | 1 | -1 | -1 | 0 | 1 |
| 1064 | e | 1056 | 2 | 1 | 0 | -1 | 1 | 1 | 0 | 0 | 1 | 0 | 0 | 0 | 0 | 0 | 0 | 0 | 0 | -1 |
| 1065 | t | 1057 | 0 | 0 | 0 | 1 | 0 | 0 | -1 | 0 | 0 | -1 | 0 | 0 | 0 | 0 | 0 | -1 | -1 | 0 |
| 1066 | n | 1058 | 0 | 0 | 0 | -1 | 0 | 0 | 0 | -1 | 0 | -1 | -1 | -1 | 0 | 0 | -1 | -1 | 0 | 1 |
| 1067 | g | 1059 | 1 | -2 | -1 | -2 | -2 | 0 | -1 | -1 | 0 | -1 | 0 | -2 | -2 | -2 | 0 | -2 | 0 | -1 |
| 1068 | e | 1060 | -1 | -1 | -1 | 0 | 0 | -1 | 0 | 0 | -1 | -2 | 0 | 0 | -1 | -1 | -1 | -1 | 0 | -1 |
| 1069 | t | 1061 | -1 | -1 | -1 | 0 | 1 | -1 | 0 | 0 | 0 | 0 | -1 | -3 | -2 | 0 | 0 | 0 | 0 | 0 |
| 1070 | g | 1062 | -1 | -1 | 0 | 0 | 0 | 0 | 0 | -2 | -1 | -1 | -1 | -1 | 0 | -1 | -1 | -1 | 0 | -1 |
| 1071 | e | 1063 | -1 | -2 | -1 | -2 | -2 | -1 | 0 | 0 | 0 | 0 | -1 | -1 | -1 | -1 | -1 | 0 | -1 | -1 |
| 1072 | i | 1064 | -1 | -3 | -2 | -1 | -3 | -3 | -1 | -2 | -4 | 0 | 0 | -2 | -2 | -3 | -2 | -1 | 0 | 0 |
| 1073 | v | 1065 | 0 | -4 | -3 | -3 | -1 | -1 | -3 | -1 | -4 | -2 | -1 | -1 | -1 | -3 | -3 | -1 | 0 | -2 |
| 1074 | w | 1066 | -3 | 0 | 0 | 0 | -4 | -4 | -4 | -3 | -3 | -3 | -2 | -1 | -3 | -2 | 0 | -3 | 1 | -1 |
| 1075 | d | 1067 | -1 | 0 | 0 | -1 | -2 | -1 | -2 | 0 | 0 | -1 | -1 | -3 | -4 | -3 | 0 | -1 | 1 | 1 |
| 1076 | k | 1068 | 2 | 1 | 0 | 1 | 2 | 2 | 2 | 0 | 0 | 0 | 1 | 0 | 1 | 0 | 0 | 2 | 2 | 1 |
| 1077 | g | 1069 | 1 | 0 | -1 | 0 | 0 | 0 | 0 | 2 | 1 | 1 | 0 | -1 | 1 | 0 | 0 | -1 | 2 | 2 |

FIG. 5A (Continued)

| | | | | | | | | | | | | | | | | | | | | | | | |
|---|---|---|---|---|---|---|---|---|---|---|---|---|---|---|---|---|---|---|---|---|---|---|---|
| 1078 | r | 1070 | -2 | -2 | -2 | 1 | -1 | -1 | -1 | -2 | 0 | 0 | -1 | 0 | -1 | 0 | -1 | 0 | -1 | 0 | 0 | -1 | 0 |
| 1079 | d | 1071 | -1 | -2 | -2 | 0 | -1 | -2 | -2 | 0 | 0 | -1 | 2 | -1 | -1 | 0 | 0 | -1 | -1 | -1 | 0 | 1 | -1 |
| 1080 | f | 1072 | 0 | -2 | -2 | -3 | 0 | -2 | -2 | 0 | -2 | -1 | -2 | 0 | -1 | 0 | -2 | 0 | 0 | 0 | -1 | 0 | 0 |
| 1081 | a | 1073 | 0 | 0 | -3 | -1 | -1 | 0 | 0 | -1 | -2 | -1 | -1 | -1 | -2 | -1 | -2 | 0 | 0 | 0 | 0 | 0 | 0 |
| 1082 | t | 1074 | -1 | 1 | 0 | -1 | 0 | -1 | -1 | -1 | 0 | -1 | 0 | 0 | -1 | 1 | -1 | -1 | -1 | -2 | 0 | 0 | 0 |
| 1083 | v | 1075 | 0 | -1 | -1 | 0 | 1 | 1 | 1 | -1 | 0 | 0 | 0 | 0 | 0 | -1 | 0 | 2 | -1 | 0 | 0 | 1 | 1 |
| 1084 | r | 1076 | 0 | 1 | -1 | -2 | -3 | 0 | -2 | -1 | 0 | 0 | 1 | -3 | -2 | 0 | 1 | 0 | 0 | 0 | 1 | 0 | 1 |
| 1085 | k | 1077 | 1 | 0 | 0 | 1 | 2 | 0 | 0 | 2 | 0 | 0 | 1 | 0 | 0 | 1 | 0 | 0 | 2 | 0 | 0 | 2 | 3 |
| 1086 | v | 1078 | -1 | -2 | -1 | -3 | 1 | -1 | -1 | -1 | 1 | -1 | 0 | 0 | -3 | 0 | -2 | 0 | -3 | 0 | 0 | -2 | 1 |
| 1087 | l | 1079 | -1 | -1 | -2 | -2 | 0 | -3 | -3 | -2 | -2 | -1 | -1 | 0 | -1 | -1 | -1 | -1 | 0 | 0 | 0 | 0 | 0 |
| 1088 | s | 1080 | -1 | -2 | -3 | -3 | 0 | -2 | -3 | -2 | 0 | 0 | -3 | 1 | -3 | 0 | -3 | 0 | -2 | 0 | 0 | -1 | 0 |
| 1089 | m | 1081 | 0 | -3 | -1 | -1 | -2 | -1 | -3 | -2 | 1 | 0 | -2 | -1 | -1 | 0 | -1 | 1 | -1 | -1 | -1 | 0 | 0 |
| 1090 | p | 1082 | 0 | 0 | 0 | 0 | -2 | 0 | -3 | 0 | 0 | 0 | 0 | 0 | 0 | -1 | 0 | -1 | 1 | 1 | 1 | 1 | 0 |
| 1091 | q | 1083 | 0 | 0 | -1 | -1 | -1 | 1 | 0 | 0 | 1 | 0 | 1 | 1 | 1 | 1 | 1 | 1 | 0 | 1 | 0 | 0 | 0 |
| 1092 | v | 1084 | 0 | -1 | -1 | -1 | 0 | 2 | 0 | 1 | 0 | -1 | 0 | -1 | 1 | -1 | 0 | -1 | 0 | 0 | 1 | 0 | 1 |
| 1093 | n | 1085 | 0 | 0 | -2 | 0 | 1 | 1 | 0 | -1 | 2 | 0 | 0 | 0 | 0 | 0 | 0 | 0 | 0 | 0 | 0 | 1 | 1 |
| 1094 | i | 1086 | -2 | 1 | -2 | -2 | 0 | 0 | -2 | 0 | -1 | -1 | -1 | -2 | -2 | -1 | -2 | 0 | 0 | 0 | -1 | 0 | 0 |
| 1095 | v | 1087 | 0 | -1 | 0 | 0 | 0 | 0 | 0 | -1 | 0 | 0 | 0 | -1 | -1 | 0 | -1 | 0 | 0 | 0 | 0 | 0 | 0 |
| 1096 | k | 1088 | -1 | 0 | -1 | -1 | 1 | -1 | -1 | 0 | 0 | 0 | 0 | -1 | 0 | 0 | 0 | 0 | 0 | -1 | -1 | 0 | 1 |
| 1097 | k | 1089 | 0 | 0 | 0 | 0 | 0 | 0 | 0 | -1 | 0 | 0 | 1 | 0 | -1 | 0 | -1 | 1 | 0 | 0 | -1 | 1 | 1 |
| 1098 | t | 1090 | -1 | -1 | 0 | -1 | 1 | 0 | 0 | -1 | 0 | 0 | 1 | 0 | 0 | 1 | 0 | 0 | 0 | 0 | 0 | 0 | 0 |
| 1099 | e | 1091 | 0 | 0 | 0 | 0 | 0 | 0 | 1 | 1 | 0 | -1 | 0 | 0 | 0 | 0 | 0 | 0 | 1 | 0 | -1 | 0 | 0 |
| 1100 | v | 1092 | 0 | -1 | 0 | -1 | 1 | -1 | 0 | 0 | 0 | 0 | 0 | 0 | 0 | -1 | 0 | 0 | 0 | -1 | 0 | -1 | -1 |
| 1101 | q | 1093 | 0 | 0 | 0 | 1 | -1 | 0 | 0 | 1 | -1 | 0 | 0 | 0 | 0 | 0 | 0 | -1 | 0 | 0 | 0 | 0 | 1 |
| 1102 | t | 1094 | 0 | -1 | -1 | 0 | 0 | 1 | 0 | 0 | -1 | 0 | 0 | 0 | -1 | 0 | -1 | 0 | 0 | 0 | -1 | 0 | 1 |
| 1103 | g | 1095 | 0 | -1 | 0 | -1 | 1 | 0 | 0 | -1 | 0 | -1 | 0 | -1 | 0 | 0 | 0 | -1 | 0 | 0 | 0 | 1 | 1 |
| 1104 | g | 1096 | 1 | -1 | -1 | 0 | 0 | 1 | -1 | 0 | 0 | 0 | 0 | 0 | 0 | 0 | 0 | 0 | 0 | 0 | 1 | 0 | 1 |
| 1105 | f | 1097 | -1 | -1 | -1 | -2 | -1 | 0 | -1 | -3 | 0 | -1 | -1 | 0 | -1 | -2 | -2 | 0 | 0 | -2 | 0 | 0 | 0 |

FIG. 5A (Continued)

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| 1106 | s | 1098 | 1114 | 0 | -1 | 0 | 1 | 0 | 0 | 1 | 0 | 0 | 1 | -1 | 1 | 1 | 0 | 0 | 2 | 0 | 0 | 0 | 0 | 1 | 0 | 1 | 1 |
| 1107 | k | 1099 | 1115 | 0 | -1 | -1 | -1 | 0 | -1 | 0 | 1 | 0 | -1 | -1 | -1 | 1 | 0 | 0 | 0 | -1 | 0 | 0 | 0 | 1 | 1 | 1 | 0 |
| 1108 | e | 1100 | 1116 | 1 | 0 | 0 | 3 | 0 | -1 | 1 | 1 | 0 | 0 | 0 | 0 | 0 | 0 | 0 | 2 | 0 | 0 | 0 | 0 | 1 | 3 | 3 | 3 |
| 1109 | s | 1101 | 1117 | 0 | 0 | 0 | 3 | 0 | 1 | 1 | 1 | 1 | 1 | 1 | 1 | 0 | 0 | 1 | 2 | 0 | 1 | 0 | 1 | 1 | 0 | 0 | 1 |
| 1110 | i | 1102 | 1118 | 0 | 0 | 0 | 0 | 0 | 1 | 1 | 1 | 0 | 1 | 0 | 0 | 0 | 0 | 0 | 2 | 0 | 1 | 0 | 0 | 0 | 1 | 0 | 0 |
| 1111 | l | 1103 | 1119 | 1 | 0 | -1 | 0 | -1 | 0 | 0 | 0 | 0 | 1 | 0 | 0 | 0 | 0 | 0 | 2 | 0 | 0 | 0 | 0 | 0 | 0 | 0 | 1 |
| 1112 | p | 1104 | 1120 | 2 | 0 | 0 | 0 | 0 | 1 | 1 | 1 | 1 | 1 | 1 | 1 | 1 | 1 | 2 | 1 | 1 | 0 | 2 | 0 | 0 | 1 | 1 | 3 |
| 1113 | k | 1105 | 1121 | 1 | 0 | -1 | 2 | 0 | 0 | 1 | 1 | 1 | -1 | -1 | -1 | 0 | -1 | 1 | 0 | 0 | 1 | 1 | 1 | -1 | 1 | 1 | 1 |
| 1114 | r | 1106 | 1122 | 0 | 0 | 0 | 1 | -1 | 1 | 0 | 0 | 0 | 0 | -1 | -1 | -1 | 0 | 0 | 0 | 0 | 0 | -1 | -1 | -1 | -1 | -1 | -1 |
| 1115 | n | 1107 | 1123 | 2 | 1 | 0 | 0 | 0 | 0 | 2 | 2 | 2 | 1 | 1 | 1 | 1 | 0 | 3 | 0 | 2 | 2 | 2 | 2 | 2 | 2 | 2 | 4 |
| 1116 | s | 1108 | 1124 | 0 | 0 | 0 | 3 | 1 | 1 | 4 | 1 | 0 | 0 | 0 | 0 | 0 | 1 | 2 | 3 | 0 | 1 | 1 | 1 | 1 | 1 | 0 | 1 |
| 1117 | d | 1109 | 1125 | 4 | 2 | 0 | 1 | 0 | 3 | 3 | 4 | 4 | 3 | 3 | 3 | 3 | 4 | 3 | 1 | 3 | 4 | 4 | 4 | 4 | 4 | 3 | 4 |
| 1118 | k | 1110 | 1126 | 1 | 1 | 0 | 4 | 0 | 1 | 0 | 1 | 2 | 1 | 1 | 1 | 1 | 1 | 1 | 0 | 1 | 2 | 1 | 1 | 1 | 1 | 1 | 1 |
| 1119 | l | 1111 | 1127 | 0 | 0 | 1 | 0 | -1 | 0 | 1 | 0 | 0 | -1 | -1 | -1 | -1 | 1 | -1 | 0 | 0 | 0 | 0 | 1 | 1 | 1 | 0 | 4 |
| 1120 | i | 1112 | 1128 | 0 | 0 | 0 | 2 | 0 | 0 | 0 | 1 | 1 | 0 | 0 | 0 | 0 | 0 | 0 | -1 | 0 | 0 | 0 | 1 | 0 | 0 | -1 | 1 |
| 1121 | a | 1113 | 1129 | -1 | -1 | -1 | 1 | -1 | 0 | 1 | 0 | 0 | -1 | -1 | -2 | -2 | -1 | 0 | 0 | 0 | 0 | 0 | 0 | -1 | 0 | 0 | 1 |
| 1122 | r | 1114 | 1130 | 1 | -1 | 0 | 2 | 0 | 0 | 1 | 1 | 0 | 0 | -1 | 0 | 0 | 1 | 0 | 1 | 0 | 0 | 0 | 0 | 1 | 0 | 1 | 1 |
| 1123 | k | 1115 | 1131 | 1 | 0 | -1 | 1 | -1 | 1 | 1 | 1 | 2 | 1 | 0 | 0 | 0 | 0 | 1 | 0 | 1 | 2 | 1 | 1 | 1 | 1 | 1 | 1 |
| 1124 | k | 1116 | 1132 | 1 | -1 | 0 | 0 | 0 | 0 | 1 | 0 | 0 | -1 | -1 | 0 | 0 | 0 | -1 | 0 | -1 | 1 | 1 | 1 | 0 | 1 | 0 | 1 |
| 1125 | d | 1117 | 1133 | 1 | 1 | -1 | 3 | -1 | 0 | 0 | 3 | 2 | 2 | 0 | 1 | 0 | 1 | 2 | -1 | 1 | 0 | 1 | 1 | 1 | 1 | 1 | 1 |
| 1126 | w | 1118 | 1134 | 0 | 1 | 0 | 4 | 0 | 1 | 3 | 2 | 2 | 0 | -1 | 0 | 0 | 0 | 0 | 0 | 0 | 0 | 1 | 1 | 1 | 0 | 0 | 0 |
| 1127 | d | 1119 | 1135 | 2 | 1 | -1 | 1 | -1 | 1 | 2 | 3 | 0 | 1 | 1 | 1 | 1 | 3 | 3 | -1 | 2 | 3 | 1 | 1 | 2 | 2 | 4 | 4 |
| 1128 | p | 1120 | 1136 | 3 | 1 | 0 | 4 | 0 | 1 | 2 | 0 | 0 | 0 | 0 | 0 | 0 | 2 | 2 | 1 | 0 | 2 | 0 | -1 | 0 | 0 | 4 | 4 |
| 1129 | k | 1121 | 1137 | 2 | 1 | 1 | 1 | 0 | 0 | 3 | 0 | 2 | 1 | 1 | 1 | 1 | 0 | 0 | 0 | 1 | 0 | 1 | 1 | 1 | 0 | 2 | 2 |
| 1130 | k | 1122 | 1138 | 1 | 1 | 0 | 4 | 0 | 1 | 1 | 2 | 1 | -1 | 0 | 1 | 1 | 1 | 2 | 0 | 1 | 2 | 1 | 1 | 1 | 0 | 3 | 3 |
| 1131 | y | 1123 | 1139 | -1 | -1 | 0 | 1 | 0 | -1 | 1 | 1 | 1 | -1 | 1 | -1 | -1 | -1 | 1 | -1 | -1 | 0 | -1 | -1 | 0 | -1 | 1 | 1 |
| 1132 | g | 1124 | 1140 | 0 | 0 | 1 | 1 | 1 | 0 | 2 | 1 | 1 | 0 | 1 | 1 | 1 | 0 | 1 | 0 | 2 | 1 | 0 | 0 | 1 | 0 | 2 | 2 |
| 1133 | g | 1125 | 1141 | 1 | 1 | 0 | 2 | 0 | 0 | 0 | 1 | 2 | 1 | 0 | 0 | 0 | 1 | 0 | 1 | 0 | 1 | 1 | 1 | 1 | 1 | 1 | 1 |

FIG. 5A (Continued)

| | | | | | | | | | | | | | | | | | | | | |
|---|---|---|---|---|---|---|---|---|---|---|---|---|---|---|---|---|---|---|---|---|
| 1134 | f | 1126 | 1142 | 1 | 0 | -1 | 0 | 0 | 0 | 1 | 0 | 0 | 0 | -1 | 0 | 0 | 0 | 0 | 0 | 0 | 0 |
| 1135 | d | 1127 | 1143 | 0 | 1 | 0 | -1 | 0 | 3 | 1 | 1 | 2 | 2 | 0 | 0 | 1 | 0 | 1 | 2 | 2 | 3 |
| 1136 | s | 1128 | 1144 | 0 | -2 | -1 | 0 | -2 | 1 | -1 | 0 | 0 | 0 | -1 | -2 | -3 | 0 | 0 | 0 | 0 | 0 |
| 1137 | p | 1129 | 1145 | -1 | -1 | -2 | -1 | -2 | -1 | -1 | -2 | 0 | 0 | -2 | -1 | -2 | -1 | -2 | -1 | -1 | -1 |
| 1138 | t | 1130 | 1146 | -1 | -2 | -2 | -2 | -2 | -1 | -2 | -2 | -2 | -1 | -2 | -2 | -3 | -2 | 0 | -1 | -1 | 0 |
| 1139 | v | 1131 | 1147 | -2 | -3 | -3 | -3 | -1 | -2 | 0 | -4 | -2 | 0 | -3 | -4 | -4 | -2 | -2 | 0 | 0 | 0 |
| 1140 | a | 1132 | 1148 | 0 | -2 | -4 | -4 | 0 | -1 | -3 | -4 | -3 | -2 | -4 | -3 | -6 | -2 | -1 | -4 | -1 | 0 |
| 1141 | y | 1133 | 1149 | -2 | -3 | -3 | -3 | -3 | 0 | -2 | -5 | -4 | -1 | -4 | -5 | -2 | -2 | -2 | -1 | -2 | 0 |
| 1142 | s | 1134 | 1150 | 0 | -3 | -4 | -3 | -4 | 0 | -2 | -3 | -3 | -1 | -4 | -3 | -2 | 0 | -2 | -1 | 0 | 0 |
| 1143 | v | 1135 | 1151 | -1 | -2 | -3 | -3 | -3 | -1 | -3 | -2 | -3 | -1 | -4 | -3 | -3 | -2 | -3 | 0 | -1 | -1 |
| 1144 | l | 1136 | 1152 | -1 | -3 | -2 | -2 | -2 | 0 | -2 | -2 | -3 | -1 | -3 | -2 | -2 | -1 | -1 | -1 | 0 | 1 |
| 1145 | v | 1137 | 1153 | 0 | -1 | -3 | -2 | -3 | 1 | -2 | -2 | -2 | -2 | -2 | -1 | -1 | -2 | 0 | 0 | 1 | -1 |
| 1146 | v | 1138 | 1154 | -1 | -3 | -1 | -2 | -1 | 0 | -2 | -1 | -1 | -2 | -1 | -2 | -3 | -2 | -2 | 0 | 0 | 1 |
| 1147 | a | 1139 | 1155 | 0 | 1 | -1 | -1 | 0 | 1 | -1 | 1 | 0 | 1 | -1 | 0 | -1 | 1 | -1 | -2 | 1 | 1 |
| 1148 | k | 1140 | 1156 | 0 | -1 | 0 | 0 | 0 | 1 | 1 | 0 | 0 | 1 | -1 | 1 | 0 | 0 | 0 | -1 | 1 | -1 |
| 1149 | v | 1141 | 1157 | -1 | -1 | -1 | -1 | -1 | 1 | 0 | -1 | -1 | 2 | -1 | 0 | -2 | 0 | 2 | 0 | 0 | 0 |
| 1150 | e | 1142 | 1158 | 1 | 1 | 1 | 0 | 3 | 1 | 2 | 2 | 3 | 2 | 1 | 4 | 1 | 2 | 1 | 2 | 2 | 3 |

FIG. 5B

A score: 3934.5 (Global)

| Pos | Residue | r_start | r_end | A | C | D | E | F | G | H | I | K | L | M | N | P | Q | R | S | T | V | W | Y |
|---|---|---|---|---|---|---|---|---|---|---|---|---|---|---|---|---|---|---|---|---|---|---|---|
| 1026 | e | 1018 | 1034 | -14.9 | 3.7 | -28.3 | 13.9 | 98.0 | 1.8 | -15.9 | 46.1 | 0.0 | 47.3 | 93.8 | 28.9 | -16.4 | 24.0 | 6.0 | 38.4 | 29.3 | 46.2 | 77.3 | 85.2 |
| 1027 | q | 1019 | 1035 | 0.0 | -7.2 | -16.6 | -25.2 | 12.0 | 7.0 | 2.4 | 1.4 | -25.4 | 0.1 | 9.7 | -2.5 | -27.5 | -2.5 | -19.7 | 3.0 | 0.1 | 2.2 | 36.5 | 15.9 |
| 1028 | e | 1020 | 1036 | 0.0 | -5.0 | -21.6 | 33.0 | 74.2 | -34.8 | -17.9 | 19.4 | -25.4 | 17.3 | 68.1 | -21.6 | -34.5 | -18.0 | -25.4 | -32.2 | 0.0 | -4.6 | 34.9 | 27.1 |
| 1029 | i | 1021 | 1037 | 0.0 | -2.1 | 3.4 | 16.1 | 34.6 | 22.9 | 4.9 | 21.1 | -2.3 | 45.3 | 25.7 | -2.1 | -32.5 | -4.4 | -2.3 | 2.5 | 29.1 | 37.3 | 29.6 | 27.0 |
| 1030 | g | 1022 | 1038 | 9.4 | -3.6 | 8.6 | 0.0 | 18.5 | 0.0 | 7.8 | 12.0 | 5.5 | -2.3 | 12.0 | 2.3 | 0.0 | -2.3 | 0.0 | 3.9 | 10.4 | 9.4 | 15.3 | 10.1 |
| 1031 | k | 1023 | 1039 | -1.3 | -3.6 | -3.6 | -3.6 | 6.2 | -1.3 | -3.6 | 0.0 | 0.3 | -2.3 | -2.3 | -3.6 | -3.6 | -3.6 | 2.6 | -1.3 | 10.4 | 10.4 | 6.2 | 10.1 |
| 1032 | a | 1024 | 1040 | -1.3 | 1.3 | -1.0 | 0.0 | 16.3 | 6.9 | 1.3 | 2.6 | 31.4 | 18.6 | 2.6 | -3.6 | 4.9 | 1.3 | 3.4 | 6.2 | 25.5 | 52.3 | 7.5 | 10.1 |
| 1033 | t | 1025 | 1041 | 0.0 | -1.3 | -1.3 | -1.3 | 24.2 | -1.3 | 8.5 | -1.3 | 8.5 | -1.3 | 8.5 | 0.0 | -1.3 | 0.0 | 13.2 | 21.6 | 3.6 | -1.3 | 44.8 | 21.9 |
| 1034 | a | 1026 | 1042 | 0.0 | 4.9 | 0.0 | 0.0 | 49.8 | -1.3 | 14.7 | 44.1 | 1.0 | 19.9 | 22.2 | 2.3 | 4.9 | 0.0 | 1.0 | 22.2 | 12.4 | 35.3 | 37.6 | 40.0 |
| 1035 | k | 1027 | 1043 | 3.9 | 3.7 | -28.3 | 13.9 | 98.0 | 1.8 | -15.9 | 46.1 | 0.0 | 47.3 | 93.8 | 28.9 | -16.4 | 24.0 | 6.0 | 38.4 | 29.3 | 46.2 | 77.3 | 85.2 |

| | | | | 1103 | 1104 | 1105 | 1106 | 1107 | 1108 | 1109 | 1110 | 1111 | 1112 | 1113 | 1114 | 1115 | 1116 | 1117 |
|---|---|---|---|---|---|---|---|---|---|---|---|---|---|---|---|---|---|---|
| 1095 | v | 1087 | 0.0 | 8.8 | 17.6 | 2.6 | 30.1 | 4.9 | 0.0 | 2.6 | 20.2 | 22.9 | -1.6 | -2.3 | -22.9 | 10.1 |
| 1096 | k | 1088 | 0.0 | 4.9 | 25.2 | 30.1 | 25.2 | 2.3 | 0.0 | 0.0 | 26.8 | 1.3 | 2.3 | -2.3 | -22.9 | -12.4 |
| 1097 | k | 1089 | -22.9 | 3.9 | 1.1 | 22.9 | 21.2 | -20.3 | 25.2 | 8.1 | -22.9 | 24.2 | 0.0 | -2.3 | -22.9 | -12.4 |
| 1098 | t | 1090 | 0.0 | 4.9 | 3.9 | -20.7 | -31.7 | -22.9 | 1.6 | 7.8 | -17.4 | 0.0 | 0.0 | 3.9 | -22.9 | -12.4 |
| 1099 | e | 1091 | 3.9 | 9.6 | 32.4 | 1.6 | 0.0 | 2.3 | -2.3 | 3.9 | -17.9 | -1.3 | 0.0 | -1.6 | -22.9 | -12.4 |
| 1100 | v | 1092 | 2.6 | -4.9 | -25.2 | 24.6 | 0.0 | 0.0 | -22.9 | -22.9 | 22.9 | -1.3 | -2.3 | -2.3 | -22.9 | -12.4 |
| 1101 | q | 1093 | 4.7 | 4.9 | -20.3 | -45.8 | 15.6 | 0.0 | -3.2 | -20.3 | 26.8 | 13.2 | -2.3 | 0.0 | -22.9 | -12.4 |
| 1102 | t | 1094 | 3.9 | -1.0 | 13.0 | -20.3 | -27.8 | 0.0 | -2.3 | 0.0 | 22.9 | 8.5 | 0.0 | -2.3 | -22.9 | -10.1 |
| 1103 | g | 1095 | 4.7 | -0.2 | 0.0 | -19.0 | 3.4 | -22.9 | -2.3 | 0.0 | -13.5 | 26.8 | 10.6 | 0.0 | 0.0 | -10.5 |
| 1104 | g | 1096 | 0.0 | -4.9 | -2.0 | -38.2 | -31.4 | 6.2 | -2.3 | 0.0 | 2.6 | 26.8 | -1.3 | 0.0 | -2.3 | 0.0 | -10.1 |
| 1105 | f | 1097 | 0.0 | -4.9 | 26.8 | -38.2 | -18.0 | 4.9 | -2.3 | 0.0 | 8.1 | 26.8 | 5.8 | 0.0 | 0.0 | -22.9 | -12.4 |
| 1106 | s | 1098 | 0.0 | -0.2 | -20.3 | -27.8 | 0.0 | -2.3 | 0.0 | 0.0 | 26.8 | 1.3 | -2.3 | -2.3 | -22.9 | -12.4 |
| 1107 | k | 1099 | -2.3 | -4.9 | -29.1 | 22.9 | -56.9 | 0.0 | -2.3 | 2.6 | 22.9 | 26.8 | 2.3 | -2.3 | 0.0 | -12.4 |
| 1108 | e | 1100 | 0.0 | -4.9 | -29.1 | 34.0 | 7.8 | -22.9 | -2.3 | 0.0 | 0.0 | 26.8 | 1.3 | 0.0 | -22.9 | -12.4 |
| 1109 | s | 1101 | 8.6 | 1.6 | -18.5 | -16.4 | 14.8 | -2.3 | 9.8 | -13.5 | 20.3 | 17.1 | -2.3 | 6.5 | -19.0 | -7.7 |
| | | | 0.0 | -1.0 | -11.7 | 0.0 | 24.6 | 0.0 | -2.3 | 0.0 | 0.0 | -22.9 | -1.3 | 0.0 | -2.3 | -22.9 | -12.4 |
| | | | 5.5 | -4.9 | -16.6 | 3.9 | 34.0 | 0.0 | 0.0 | 0.0 | -20.3 | 5.5 | -1.3 | 0.0 | -2.3 | -22.9 | -12.4 |
| | | | 6.2 | 5.2 | -13.8 | 20.3 | -27.8 | 0.0 | -2.3 | 0.0 | 1.8 | 0.0 | -1.3 | 0.0 | -2.3 | -22.9 | 0.0 |
| | | | 2.6 | 19.7 | 22.1 | 20.6 | 25.2 | 0.0 | 1.8 | 0.0 | 17.9 | 26.8 | -1.3 | 0.0 | -2.3 | 0.0 | -12.4 |
| | | | 2.6 | 9.9 | 19.5 | 26.8 | -25.2 | 2.3 | 1.6 | 2.3 | 17.9 | 26.8 | 8.5 | 3.9 | -2.3 | 2.6 | 7.5 |

| Critical epitope count: 891 (all allotypes) | | | | | | | | | | | | | | | | | | | | | | | | |
|---|---|---|---|---|---|---|---|---|---|---|---|---|---|---|---|---|---|---|---|---|---|---|---|---|
| Pos | Residue | r_start | r_end | A | C | D | E | F | G | H | I | K | L | M | N | P | Q | R | S | T | V | W | Y |
| 1026 | e | 1017 | 1035 | 1 | 1 | 0 | 0 | 4 | 1 | 2 | 3 | 2 | 3 | 4 | 2 | 2 | 1 | 4 | 0 | 1 | 4 | 4 | 5 |
| 1027 | q | 1018 | 1036 | 1 | 1 | 0 | -2 | 3 | 1 | 2 | 1 | 0 | 1 | 2 | 0 | 1 | 0 | 1 | 2 | 1 | 2 | 2 | 3 |
| 1028 | e | 1019 | 1037 | 3 | 2 | -1 | 0 | 3 | 2 | 2 | 3 | 2 | 1 | 3 | 3 | 1 | 3 | 3 | 4 | 3 | 2 | 3 | 3 |
| 1029 | i | 1020 | 1038 | -1 | -3 | -4 | 0 | 2 | -3 | -1 | 0 | -2 | -1 | -1 | -2 | -3 | -3 | -1 | 0 | -1 | 0 | 1 | 1 |
| 1030 | g | 1021 | 1039 | 0 | -1 | 2 | 0 | 2 | 0 | 1 | 2 | 1 | 2 | 0 | 1 | -2 | 0 | 2 | 1 | 0 | 2 | 1 | 1 |
| 1031 | k | 1022 | 1040 | 1 | 0 | 1 | 1 | 2 | -1 | 2 | 2 | 0 | 2 | 2 | 1 | 1 | 0 | 1 | 2 | 2 | 1 | 2 | 2 |
| 1032 | a | 1023 | 1041 | 0 | -2 | -2 | -2 | 0 | -1 | 2 | 1 | -1 | 0 | 0 | -1 | 0 | 0 | 0 | -1 | -1 | 0 | 1 | 1 |
| 1033 | t | 1024 | 1042 | -2 | -1 | -2 | -3 | 1 | -3 | 0 | -1 | -2 | 0 | 0 | -1 | -3 | -2 | -1 | 0 | 0 | -1 | 0 | 0 |
| 1034 | a | 1025 | 1043 | 0 | -2 | -1 | -2 | 2 | -2 | 0 | 1 | 0 | 2 | 2 | 0 | 0 | 0 | 0 | 0 | -1 | 2 | 2 | 2 |
| 1035 | k | 1026 | 1044 | 0 | -1 | -5 | -6 | 0 | -5 | -4 | -1 | -2 | 0 | 0 | -5 | 0 | 0 | 1 | 0 | 0 | 0 | 0 | 0 |
| 1036 | y | 1027 | 1045 | -3 | -2 | -4 | -5 | 0 | -3 | -3 | -1 | -2 | -2 | -1 | -2 | -2 | -3 | -1 | -3 | -2 | -1 | 0 | 0 |
| 1037 | f | 1028 | 1046 | -3 | -2 | -4 | -4 | 0 | -4 | -2 | -3 | -4 | -1 | -3 | -3 | -4 | -4 | -2 | -2 | -1 | 0 | -1 | -1 |
| 1038 | f | 1029 | 1047 | -4 | -4 | -4 | -3 | 0 | -3 | 0 | 0 | -3 | 0 | -3 | -3 | -4 | -3 | -1 | -4 | -3 | -3 | -2 | -2 |
| 1039 | y | 1030 | 1048 | -2 | -3 | -1 | 1 | 1 | 0 | -1 | 1 | -2 | 1 | -1 | 0 | 0 | 0 | 0 | -3 | -3 | -1 | 1 | 0 |
| 1040 | s | 1031 | 1049 | 0 | -1 | -1 | 0 | 0 | -1 | 0 | 0 | -3 | 0 | 1 | 0 | 0 | 0 | 0 | 0 | -2 | 0 | 1 | 1 |
| 1041 | n | 1032 | 1050 | 0 | 0 | -1 | 0 | 0 | -2 | 0 | 0 | 0 | 0 | 0 | -3 | -2 | -3 | -1 | 1 | 1 | 1 | 1 | 0 |
| 1042 | i | 1033 | 1051 | -2 | -3 | -2 | -2 | 1 | -1 | -3 | 0 | -2 | -1 | 0 | -1 | -1 | -1 | 0 | -3 | -3 | 0 | -1 | 0 |
| 1043 | m | 1034 | 1052 | 0 | -2 | -3 | -2 | 0 | -2 | -2 | 0 | 0 | 0 | 0 | -2 | -2 | -2 | -1 | -1 | -1 | 0 | 0 | 0 |
| 1044 | n | 1035 | 1053 | -1 | -1 | -1 | 0 | 0 | -1 | 0 | 0 | 0 | -1 | 0 | 0 | -1 | -1 | 0 | -1 | 0 | 0 | 0 | 0 |
| 1045 | i | 1036 | 1054 | -2 | -2 | -3 | -2 | 0 | -2 | -3 | 0 | -2 | 0 | 0 | -2 | -2 | -2 | -1 | -2 | -2 | 0 | 0 | 0 |
| 1046 | f | 1037 | 1055 | -1 | -2 | -3 | -2 | 2 | -2 | -2 | 0 | 0 | 0 | 0 | -2 | -4 | -2 | -2 | -2 | -2 | -1 | -1 | -1 |
| 1047 | k | 1038 | 1056 | 1 | 0 | -1 | 0 | 2 | -1 | 2 | 1 | 0 | 1 | 1 | 1 | 0 | 1 | 0 | 2 | 1 | 0 | 1 | 2 |

FIG. 6A (Continued)

| | | | | | | | | | | | | | | | | | | | | | | | | | |
|---|---|---|---|---|---|---|---|---|---|---|---|---|---|---|---|---|---|---|---|---|---|---|---|---|---|
| 1048 | t | 1039 | 0 | -1 | -2 | 0 | 0 | 0 | -1 | 0 | 0 | 0 | -1 | 0 | -2 | 0 | -1 | -2 | -1 | 0 | 0 | -1 | 1 | 1 |
| 1049 | e | 1040 | 1 | 0 | -1 | 0 | 2 | 1 | 1 | 1 | -1 | 1 | 2 | 1 | -1 | 1 | -2 | -1 | 1 | 1 | 1 | 1 | 1 | 1 |
| 1050 | i | 1041 | -1 | 0 | -1 | -1 | 0 | 0 | -2 | 0 | 0 | 0 | 0 | -2 | -2 | 0 | -2 | -2 | 0 | 0 | -1 | -1 | -1 | -1 | -1 |
| 1051 | t | 1042 | -1 | -1 | 0 | 0 | 1 | 0 | 0 | 0 | 0 | 0 | 0 | -1 | -1 | -1 | 0 | 0 | -1 | 0 | 0 | 0 | 0 | 0 | 0 |
| 1052 | l | 1043 | 0 | 0 | -2 | 1 | 0 | 0 | 1 | 0 | -1 | -1 | -1 | 0 | 0 | -1 | -1 | 0 | -1 | 0 | 0 | 1 | 1 | 0 | 0 |
| 1053 | a | 1044 | 0 | -1 | -1 | 0 | 1 | 0 | 2 | 1 | 2 | 0 | 1 | 1 | 0 | -1 | 0 | -1 | 0 | 1 | 0 | 1 | 1 | 1 | 0 |
| 1054 | n | 1045 | 2 | 1 | 1 | 0 | 2 | 3 | 0 | 2 | 2 | 1 | 2 | 2 | 1 | 1 | 1 | 1 | 1 | -1 | 2 | 2 | 1 | 2 | 2 |
| 1055 | g | 1046 | 1 | 0 | -1 | -1 | 1 | 2 | 1 | 1 | 3 | 0 | 1 | 0 | 0 | -1 | 1 | 0 | 1 | 2 | 1 | -1 | -1 | 2 | 1 | 3 |
| 1056 | e | 1047 | 0 | -1 | 0 | 0 | 3 | 1 | 1 | 0 | 1 | 1 | 3 | 2 | 1 | -1 | 0 | 0 | -1 | 1 | -1 | 1 | 2 | 1 | 2 | 3 |
| 1057 | i | 1048 | -1 | -2 | -1 | -1 | 0 | 3 | 0 | 1 | 0 | 0 | 0 | -1 | 1 | -1 | -1 | -2 | -1 | 1 | 0 | 0 | 0 | 2 | 0 |
| 1058 | r | 1049 | 0 | -3 | 0 | 0 | 1 | 0 | 0 | 0 | -1 | 0 | 0 | -2 | 0 | -2 | 0 | 0 | -1 | 1 | 0 | -1 | -1 | 0 | -1 |
| 1059 | k | 1050 | 0 | 0 | -2 | -3 | 4 | 3 | -3 | 0 | 0 | 3 | 0 | 0 | 0 | -2 | -3 | 1 | 0 | -1 | 3 | 3 | 2 | 3 | 3 |
| 1060 | r | 1051 | -3 | -3 | 0 | 0 | 0 | 1 | 1 | 2 | 1 | 2 | 0 | 2 | 2 | 0 | 0 | 0 | 3 | 0 | 0 | 0 | 0 | 0 | 0 |
| 1061 | p | 1052 | 2 | 0 | 2 | 3 | 0 | -3 | 2 | 0 | 0 | 0 | -3 | -1 | -1 | -3 | 0 | -3 | 0 | 3 | 1 | -1 | -1 | -1 | -1 |
| 1062 | l | 1053 | -1 | -1 | -1 | 0 | -1 | 1 | -1 | 0 | 2 | -2 | 0 | 0 | 0 | 0 | 0 | 0 | 2 | 0 | -1 | 0 | 0 | 0 | 3 |
| 1063 | i | 1054 | 0 | 0 | -2 | -1 | 0 | 2 | -1 | 0 | 1 | 0 | 1 | 1 | 1 | 2 | 1 | 1 | 1 | 3 | 2 | 0 | 0 | 1 | 0 |
| 1064 | e | 1055 | 1 | 1 | 0 | 1 | 1 | 0 | 0 | 2 | 2 | 0 | 0 | 0 | 0 | 0 | 0 | 0 | 0 | 0 | 0 | 1 | 1 | 0 | 2 |
| 1065 | t | 1056 | 1 | 0 | 1 | 0 | 2 | 1 | 1 | 0 | 0 | 1 | 1 | 1 | 0 | 0 | 1 | 1 | 1 | 3 | 1 | 0 | 0 | 2 | 0 |
| 1066 | n | 1057 | 1 | 0 | 0 | 1 | 1 | 2 | 0 | 2 | 2 | 1 | 0 | 2 | 0 | 1 | 1 | -1 | 1 | 2 | 0 | 2 | 1 | 1 | 0 |
| 1067 | g | 1058 | -1 | -1 | -2 | 0 | 0 | 1 | 0 | 0 | -1 | 0 | 1 | 1 | 1 | -2 | -1 | -2 | 0 | 0 | 0 | -1 | 2 | 1 | 1 |
| 1068 | e | 1059 | 1 | -1 | 1 | 0 | 1 | 1 | 2 | 1 | 0 | 1 | 0 | 1 | 0 | 0 | 0 | 0 | 0 | 1 | 2 | -1 | 0 | 4 | 3 |
| 1069 | t | 1060 | -1 | -1 | 0 | 0 | 0 | 0 | 0 | 0 | 0 | 0 | 0 | 1 | -2 | 0 | -2 | 0 | -1 | 0 | -1 | 0 | 2 | 2 | 0 |
| 1070 | g | 1061 | -1 | -1 | -2 | 0 | 1 | 1 | 0 | 2 | 0 | 1 | 1 | 2 | 0 | -2 | 0 | -1 | -1 | 1 | 0 | 0 | 1 | 1 | 1 |
| 1071 | e | 1062 | 0 | -1 | 0 | 0 | 1 | 0 | 1 | 0 | 1 | 1 | 1 | 0 | 0 | -1 | -1 | 0 | -2 | 1 | 1 | 1 | 0 | 0 | 0 |
| 1072 | i | 1063 | -1 | -1 | 1 | -2 | 0 | 0 | -2 | 0 | 1 | 0 | 0 | 1 | -1 | -2 | -2 | -2 | 0 | 0 | 1 | 0 | 1 | 0 | 1 |
| 1073 | v | 1064 | -1 | 0 | 0 | -1 | 0 | 1 | 0 | 2 | 1 | 1 | 1 | 1 | 0 | -1 | -2 | -1 | -2 | 0 | -1 | -1 | -1 | 1 | 0 |
| 1074 | w | 1065 | -1 | 1 | 1 | -2 | 1 | 3 | 0 | 2 | 0 | 1 | 2 | 1 | -1 | 0 | 0 | 0 | 0 | 1 | 1 | -1 | -1 | 4 | 2 |
| 1075 | d | 1066 | -1 | 1 | 1 | -1 | 0 | 1 | 1 | 0 | 0 | 1 | 1 | 1 | 0 | -1 | 0 | -1 | -1 | 0 | 0 | 1 | 1 | 2 | 1 |
| 1076 | k | 1067 | -1 | 1 | -1 | 0 | 1 | 1 | 1 | 0 | 1 | 1 | 1 | 0 | 0 | 0 | -1 | 0 | 0 | 1 | 0 | -1 | 0 | 0 | 1 |
| 1077 | g | 1068 | 2 | 1 | 1 | 1 | 2 | 1 | 1 | 3 | 2 | 3 | 2 | 2 | 1 | 2 | 2 | 2 | 2 | 2 | 2 | 2 | 2 | 3 | 2 |

FIG. 6A (Continued)

| | | | | | | | | | | | | | | | | | | | | | | | | |
|---|---|---|---|---|---|---|---|---|---|---|---|---|---|---|---|---|---|---|---|---|---|---|---|---|
| 1078 | r | 1069 | 1087 | -1 | -1 | 1 | -2 | 0 | -1 | 0 | 1 | 0 | -1 | 0 | 0 | 0 | -1 | -1 | -2 | -1 | 0 | 0 | 0 | 1 |
| 1079 | d | 1070 | 1088 | 3 | 1 | 0 | 5 | 3 | 5 | 2 | 2 | 3 | 5 | 4 | 5 | 2 | 2 | 2 | 5 | 5 | 5 | 5 | 5 | 5 |
| 1080 | f | 1071 | 1089 | 0 | -1 | -3 | 0 | -3 | 0 | 1 | -1 | -1 | 1 | 1 | 1 | -1 | -1 | -1 | 2 | 0 | 2 | 2 | -1 | -1 |
| 1081 | a | 1072 | 1090 | 0 | 1 | -1 | 0 | 0 | 0 | 0 | 1 | 2 | 1 | 2 | 1 | 1 | 0 | 1 | 1 | 1 | 0 | 0 | 0 | 1 |
| 1082 | t | 1073 | 1091 | 4 | 1 | 1 | 4 | 1 | 1 | 4 | 1 | 1 | 1 | 4 | 1 | 2 | 0 | 1 | 2 | 0 | 0 | 4 | 0 | 0 |
| 1083 | v | 1074 | 1092 | 1 | -1 | 2 | 1 | -2 | 1 | 0 | 1 | 1 | -1 | 1 | 1 | -1 | -1 | 1 | -1 | 0 | 0 | 2 | 2 | 3 |
| 1084 | r | 1075 | 1093 | 0 | -1 | 0 | 2 | 0 | 2 | 0 | 0 | -1 | 2 | 1 | 1 | 1 | 2 | 1 | 1 | 0 | 0 | 2 | 1 | 0 |
| 1085 | k | 1076 | 1094 | 2 | 1 | 1 | 3 | 0 | 3 | -1 | 1 | 2 | 3 | 3 | 3 | 1 | 2 | 0 | 1 | 1 | 2 | 0 | 3 | 3 |
| 1086 | v | 1077 | 1095 | 0 | -2 | -3 | 2 | -3 | 2 | -3 | -1 | 2 | 1 | 0 | 1 | 0 | 2 | 1 | 0 | 1 | 2 | 1 | 0 | -1 |
| 1087 | l | 1078 | 1096 | -1 | 0 | -2 | 0 | -1 | 0 | -1 | 0 | 1 | 1 | -1 | 0 | -1 | 1 | 0 | -1 | 0 | 0 | 0 | 1 | 0 |
| 1088 | s | 1079 | 1097 | 1 | 0 | 0 | 1 | -1 | 1 | 0 | -1 | 1 | 1 | 0 | 2 | 0 | 1 | 0 | 1 | 1 | 1 | 1 | 1 | 1 |
| 1089 | m | 1080 | 1098 | -1 | -1 | -1 | 1 | -2 | 1 | 0 | 2 | 0 | 0 | -1 | 0 | -1 | 1 | 0 | 0 | 1 | -1 | 0 | -1 | 1 |
| 1090 | p | 1081 | 1099 | 1 | 0 | 0 | 1 | 0 | 1 | -1 | 0 | 0 | -1 | -1 | 1 | 0 | 0 | 0 | 0 | 1 | 1 | 0 | 1 | 1 |
| 1091 | q | 1082 | 1100 | -2 | -2 | -2 | 0 | -2 | 0 | 0 | 1 | -2 | 0 | 0 | 0 | 0 | -1 | 0 | -1 | 1 | -1 | 1 | 1 | 2 |
| 1092 | v | 1083 | 1101 | -1 | -1 | -1 | 1 | -1 | 1 | -4 | 0 | 0 | 0 | -1 | 1 | -1 | 0 | -1 | 0 | 1 | 0 | 0 | 0 | -1 |
| 1093 | n | 1084 | 1102 | 0 | -3 | -2 | 0 | -2 | 0 | -1 | 1 | 0 | -1 | -2 | 0 | -1 | 0 | -2 | 0 | 1 | -1 | 0 | -1 | -1 |
| 1094 | i | 1085 | 1103 | -2 | -2 | -1 | 2 | -4 | 2 | 0 | -1 | 1 | -3 | -1 | 0 | -2 | -1 | -2 | -2 | -1 | -1 | 0 | -1 | 0 |
| 1095 | v | 1086 | 1104 | -1 | -3 | -2 | 3 | 0 | 3 | -4 | 2 | 1 | -1 | 0 | 1 | -2 | -1 | -2 | -3 | -1 | -1 | 1 | -2 | 0 |
| 1096 | k | 1087 | 1105 | 1 | -2 | -4 | 0 | -3 | 0 | 0 | 0 | -3 | -1 | -1 | 1 | 1 | -1 | -3 | 0 | 1 | 0 | 0 | -1 | -1 |
| 1097 | k | 1088 | 1106 | 0 | 0 | 0 | -1 | -1 | -1 | -1 | 1 | -2 | 0 | -3 | -1 | -1 | -1 | 0 | 0 | -1 | 0 | 0 | 0 | 0 |
| 1098 | t | 1089 | 1107 | 2 | -1 | -3 | 2 | 0 | 2 | 1 | -1 | -1 | 0 | -1 | 0 | 1 | 0 | 1 | 2 | 0 | 2 | 2 | -1 | 0 |
| 1099 | e | 1090 | 1108 | -3 | 0 | 1 | 0 | 2 | 0 | 1 | -1 | 0 | -1 | 0 | 0 | 2 | 0 | 2 | -3 | 0 | 1 | 1 | 1 | 1 |
| 1100 | v | 1091 | 1109 | 0 | 1 | -1 | -1 | -1 | -1 | -3 | -1 | 2 | -1 | 2 | 2 | 0 | 0 | -1 | 0 | 1 | 0 | 0 | 0 | 3 |
| 1101 | q | 1092 | 1110 | 1 | 1 | 0 | 0 | 0 | 0 | -1 | 0 | 0 | 0 | -1 | 0 | 0 | 2 | 0 | 0 | 2 | 2 | 2 | 3 | -1 |
| 1102 | t | 1093 | 1111 | 1 | -1 | 0 | 0 | -2 | 0 | 1 | 2 | 2 | 2 | 1 | 2 | 2 | 0 | 0 | 0 | -1 | -2 | -1 | 0 | 0 |
| 1103 | g | 1094 | 1112 | 1 | -2 | 0 | -1 | -1 | -1 | -2 | 0 | 1 | -2 | -2 | 1 | 1 | 0 | -1 | 2 | 0 | -1 | 0 | -1 | 3 |
| 1104 | g | 1095 | 1113 | -1 | -1 | -2 | -1 | -1 | -1 | -1 | -1 | -2 | -2 | -2 | -1 | -1 | 2 | 0 | 0 | 3 | 2 | 2 | 0 | 0 |
| 1105 | f | 1096 | 1114 | 0 | -1 | -1 | 0 | 0 | 0 | -1 | 0 | -1 | 0 | -1 | 0 | -2 | 1 | -1 | -1 | 1 | 1 | 0 | -1 | -1 |
| 1106 | s | 1097 | 1115 | -1 | -1 | -1 | 4 | -1 | 4 | 0 | 0 | 4 | 4 | -1 | 4 | -1 | 0 | -1 | 0 | 0 | 0 | 4 | 4 | 4 |
| 1107 | k | 1098 | 1116 | -1 | -1 | -1 | 3 | -1 | 3 | 0 | 0 | 3 | 2 | 0 | 2 | 0 | -1 | 0 | 0 | -1 | -1 | 3 | 3 | 2 |

FIG. 6A (Continued)

| | | | | | | | | | | | | | | | | | | | | |
|---|---|---|---|---|---|---|---|---|---|---|---|---|---|---|---|---|---|---|---|---|
| 1108 | e | 1099 | 1117 | 1 | 0 | -1 | 0 | 2 | 0 | 3 | 0 | 2 | 3 | 0 | 1 | -1 | 0 | 0 | 2 | 2 |
| 1109 | s | 1100 | 1118 | 0 | -1 | -1 | -2 | 0 | 1 | 1 | 1 | 1 | 1 | 0 | 0 | 0 | 0 | 0 | 2 | 1 |
| 1110 | i | 1101 | 1119 | -2 | -3 | -3 | -4 | -3 | -1 | 0 | -1 | -3 | -1 | -3 | -2 | -1 | -1 | 0 | 0 | 0 |
| 1111 | l | 1102 | 1120 | 0 | -1 | -2 | -2 | -1 | -1 | 0 | 0 | 0 | 0 | -1 | -2 | -2 | -1 | -1 | -1 | 0 |
| 1112 | p | 1103 | 1121 | 3 | 0 | -1 | 0 | 2 | 4 | 0 | 2 | 2 | 2 | 2 | 0 | 1 | 4 | 1 | 2 | 3 |
| 1113 | k | 1104 | 1122 | 0 | -1 | 0 | -1 | 1 | 0 | 0 | 2 | 1 | 2 | 1 | 1 | -1 | 1 | 1 | 1 | -1 |
| 1114 | r | 1105 | 1123 | 1 | 2 | 2 | 2 | 2 | 1 | 1 | 1 | 1 | 2 | 2 | 1 | 0 | 0 | 2 | 2 | 2 |
| 1115 | n | 1106 | 1124 | 0 | -1 | 0 | -1 | 1 | 1 | 1 | 2 | 3 | 2 | 0 | 1 | 0 | 1 | 1 | 1 | 2 |
| 1116 | s | 1107 | 1125 | 0 | -1 | -2 | 0 | 3 | 1 | 3 | 4 | 4 | 2 | 0 | 1 | 0 | 0 | 0 | 2 | 2 |
| 1117 | d | 1108 | 1126 | 4 | 2 | 1 | 2 | 4 | 0 | 4 | 2 | 3 | 4 | 3 | 5 | 4 | 3 | 3 | 4 | 3 |
| 1118 | k | 1109 | 1127 | -1 | 0 | 1 | 1 | -1 | 2 | 2 | 3 | 1 | 2 | 1 | -1 | -1 | 1 | 0 | -1 | 4 |
| 1119 | l | 1110 | 1128 | 2 | 1 | -3 | 0 | 1 | 0 | 0 | 1 | 1 | 0 | 0 | 0 | 1 | 0 | 0 | 3 | 3 |
| 1120 | i | 1111 | 1129 | 0 | 0 | 0 | -1 | 1 | 1 | 1 | 0 | 0 | 1 | 1 | 1 | 1 | 0 | 0 | 1 | 0 |
| 1121 | a | 1112 | 1130 | 0 | 1 | -1 | 0 | 3 | 1 | 2 | 1 | 4 | 1 | 0 | 2 | 2 | 1 | -1 | -1 | 1 |
| 1122 | r | 1113 | 1131 | 1 | 0 | -1 | -3 | 1 | 0 | -1 | 2 | -1 | 4 | 2 | -1 | -1 | 0 | 0 | 3 | 3 |
| 1123 | k | 1114 | 1132 | 0 | -2 | 0 | -1 | 1 | 0 | 4 | 0 | 4 | 0 | 1 | 0 | -1 | 0 | 4 | 2 | 2 |
| 1124 | k | 1115 | 1133 | 2 | 2 | 0 | 1 | 2 | 2 | 0 | 2 | 0 | 2 | 4 | 2 | 1 | -1 | 3 | 4 | 4 |
| 1125 | d | 1116 | 1134 | 0 | 2 | 0 | 0 | 1 | 2 | 0 | 0 | 1 | 2 | 0 | 1 | 1 | -1 | 2 | 0 | 0 |
| 1126 | w | 1117 | 1135 | 0 | 0 | -3 | -1 | 0 | 0 | 0 | 3 | 3 | 1 | -1 | 1 | -1 | 0 | 1 | 0 | 3 |
| 1127 | d | 1118 | 1136 | 2 | 2 | 1 | 0 | 1 | 2 | -2 | 0 | 1 | 0 | 0 | 0 | 0 | 0 | 2 | 3 | 3 |
| 1128 | p | 1119 | 1137 | 1 | 1 | 0 | 0 | 1 | 1 | 0 | 0 | 0 | 3 | 0 | 0 | 2 | 2 | 1 | 1 | 1 |
| 1129 | k | 1120 | 1138 | 0 | 0 | 1 | -1 | 2 | 0 | -1 | 0 | 0 | 0 | 1 | 1 | -1 | -3 | 0 | 0 | 0 |
| 1130 | k | 1121 | 1139 | -1 | 1 | -1 | -2 | 1 | 2 | 1 | 1 | 1 | 0 | 2 | 2 | 3 | 0 | 1 | 1 | 2 |
| 1131 | y | 1122 | 1140 | 0 | 0 | 0 | 1 | 2 | 0 | 0 | 1 | 0 | -1 | 1 | 1 | 2 | 1 | 0 | 0 | 0 |
| 1132 | g | 1123 | 1141 | 1 | 0 | 0 | 0 | 1 | 1 | 1 | 1 | 1 | 1 | 0 | 1 | 1 | -3 | 1 | 1 | -1 |
| 1133 | g | 1124 | 1142 | -1 | -1 | -1 | 0 | 2 | 1 | -1 | 0 | -1 | 1 | 0 | 2 | -1 | -1 | -1 | 1 | 2 |
| 1134 | f | 1125 | 1143 | 1 | 1 | 0 | 0 | 0 | -1 | 0 | 1 | 1 | 0 | -1 | 1 | 0 | 0 | 2 | -1 | -1 |
| 1135 | d | 1126 | 1144 | 1 | 0 | 0 | 0 | 0 | -1 | 0 | 0 | 0 | 0 | 0 | 0 | 1 | 0 | 0 | 1 | 3 |
| 1136 | s | 1127 | 1145 | -1 | -1 | 0 | -1 | 0 | 0 | -1 | 0 | 0 | 0 | 0 | 0 | 1 | 0 | 0 | 1 | 1 |
| 1137 | p | 1128 | 1146 | 1 | 0 | -1 | -1 | 1 | 1 | 1 | 1 | 1 | -1 | 1 | -1 | 1 | -1 | 1 | 0 | 0 |

FIG. 6A (Continued)

| | | | | | | | | | | | | | | | | | | | | | | | |
|---|---|---|---|---|---|---|---|---|---|---|---|---|---|---|---|---|---|---|---|---|---|---|---|
| 1138 | t | 1129 | 1147 | 0 | -1 | -1 | 0 | 0 | 0 | 1 | 1 | 0 | 0 | 0 | 1 | 0 | -1 | -1 | 0 | 0 | 1 | 1 | 1 |
| 1139 | v | 1130 | 1148 | 0 | 0 | 0 | -2 | -1 | -2 | 0 | 0 | 0 | 0 | 0 | 0 | -1 | -1 | -2 | 0 | 0 | 0 | 0 | 0 |
| 1140 | a | 1131 | 1149 | 0 | 0 | 0 | -1 | 0 | -1 | 0 | 0 | -2 | 0 | 0 | -1 | 0 | -1 | 0 | -1 | 0 | 0 | 0 | 0 |
| 1141 | y | 1132 | 1150 | -1 | -2 | -2 | -2 | 0 | 0 | 0 | -4 | -4 | 0 | 0 | -2 | -2 | -3 | -2 | -1 | 0 | 0 | 0 | 0 |
| 1142 | s | 1133 | 1151 | 0 | -1 | -1 | -1 | 1 | 1 | 0 | -1 | -1 | 0 | 0 | 0 | -2 | -2 | 0 | 0 | 0 | 1 | 1 | 0 |
| 1143 | v | 1134 | 1152 | -1 | -2 | -3 | -2 | 0 | 0 | 0 | -1 | -1 | 0 | 0 | -1 | 0 | -3 | -3 | -1 | 0 | 0 | 0 | 0 |
| 1144 | l | 1135 | 1153 | -1 | -3 | -2 | -1 | 0 | 0 | -1 | -2 | -2 | 0 | -2 | -2 | -1 | 0 | 0 | -1 | -2 | 0 | 0 | 0 |
| 1145 | v | 1136 | 1154 | -3 | -3 | -3 | -3 | 0 | 0 | 0 | -3 | -3 | 0 | 0 | -3 | -3 | 0 | 0 | 0 | -3 | 0 | 0 | 0 |
| 1146 | v | 1137 | 1155 | -2 | -4 | -4 | -3 | 0 | 0 | 0 | -3 | -3 | 0 | -1 | -2 | -4 | 0 | 0 | 0 | -3 | 0 | 0 | 0 |
| 1147 | a | 1138 | 1156 | 0 | 0 | 0 | -2 | 0 | 0 | 0 | -1 | -1 | 0 | 0 | -1 | -1 | -1 | -1 | 0 | -1 | 0 | 0 | 0 |
| 1148 | k | 1139 | 1157 | 0 | -1 | 0 | -2 | 0 | -2 | 0 | -1 | -1 | 0 | 0 | -2 | 0 | 0 | 0 | -1 | 0 | 0 | 0 | 0 |
| 1149 | v | 1140 | 1158 | -3 | -3 | -3 | -3 | 0 | -2 | 0 | -3 | -3 | 0 | -2 | -3 | -3 | -1 | -3 | -3 | -3 | 0 | 0 | 1 |
| 1150 | e | 1141 | 1159 | 0 | 0 | 0 | -4 | 1 | -2 | 0 | 0 | 0 | 1 | 0 | 1 | 0 | 1 | 1 | 1 | 0 | 1 | 0 | 1 |

| | | | | | | | | | | | | | | |
|---|---|---|---|---|---|---|---|---|---|---|---|---|---|---|
| 1129 | 1130 | 1131 | 1132 | 1133 | 1134 | 1135 | 1136 | 1137 | 1138 | 1139 | 1140 | 1141 | 1142 | 1143 |
| k | k | y | g | g | f | d | s | p | t | v | a | y | s | v |
| 1120 | 1121 | 1122 | 1123 | 1124 | 1125 | 1126 | 1127 | 1128 | 1129 | 1130 | 1131 | 1132 | 1133 | 1134 |
| 1138 | 1139 | 1140 | 1141 | 1142 | 1143 | 1144 | 1145 | 1146 | 1147 | 1148 | 1149 | 1150 | 1151 | 1152 |
| -28.4 | -0.3 | -61.7 | 0 | -37.5 | -2.9 | 6.2 | -7.2 | 5.2 | -71.2 | 2.3 | 0 | -64 | -5.2 | 0 |
| 81.4 | -127 | -78.1 | -4.9 | -49.6 | -2.6 | 3.9 | 15 | -40.8 | -72.5 | -23.9 | 85 | -101 | 4.7 | |
| 33.6 | -61.6 | -61.8 | -18 | -69.6 | 16.3 | -27.2 | -24 | 0 | -65.2 | 4.69999 | -30.1 | -62 | -33.3 | 23 |
| 17.6 | -40.7 | -39.2 | -16.7 | -70.1 | 2 | -27.2 | -45.9 | -5.2 | -22.2 | 4.7 | -32.7 | -63 | -53.9 | -12.1 |
| 49 | 58.5 | -32 | -43.5 | 0.700027 | -45.7 | 6.3 | 26.8 | 36.1 | 0 | 24 | 35.7 | 6.3 | 4.7 | 4.7 |
| 60.1 | -6.20001 | -8.2 | -22.9 | -39.5 | -8.8 | -22.2 | -17.3 | -2.6 | 73.8 | 0 | 0 | -60 | -5.2 | 0 |
| 56.2 | 8 | -5.5 | -22.9 | -55.2 | 12.8 | 4.50002 | -29.7 | -3.1 | 65.3 | -4.7 | 0.9999 | 57 | -138.2 | 0 |
| 24.5 | -2.6000 | -62.4 | 0 | 33.3 | 7.5 | 8.1000 | 24.5 | 25.8 | -62.4 | 23.6 | 3.9 | 11 | 0 | 4.7 |
| 39.2 | -28.6 | -80.1 | -60.5 | -51.4 | 18.9 | -38.9 | -59.6 | 15 | 93.3 | -23.7 | -29.7 | 68 | 0 | 0 |
| 25.8 | -39.6 | -40.5 | -11.1 | -8.79999 | 14.7 | 30 | 10 | -3.3 | -64.7 | 54.1 | 7.3 | -6.2 | -0.3 | 4.7 |
| -18.3 | -53.3 | -39.2 | -30.5 | -23.8 | 2.6 | -58.1 | 16.7 | 2.9 | -65.3 | 49.4 | 8.6 | 29 | 0 | 0 |
| 58.5 | -53.6 | -68.4 | -6.2 | -48.3 | -5.2 | -3.6 | -11.6 | -35.6 | 49.3 | 2.39999 | 3.39999 | 68 | -33.3 | 0 |
| 39.5 | -39.2 | -10.7 | -15 | -71.2 | 7.8 | 0 | -44.4 | -11.4 | 100 | -1.5 | -8.7 | 63 | -56.2 | 23 |
| 43.4 | -35.6 | -9.5 | -74.2 | 5.6 | -55.8 | -44.1 | 2.2000 | 23 | -11.1 | -95.2 | 7.7 | -7.5 | -56.2 | 23 |
| 60.3 | -19.8 | -10.8 | -50.2 | 5.11 | -10.3 | -34.8 | 40 | 13.6 | -2.7 | -7.2 | -17.3 | 58 | -11.2 | 5.9 |
| 33.3 | 0 | -72.2 | -1.2 | -4.2.4 | -2.6 | -3.6 | 0 | -3.8999 | -71.2 | 17.7 | -26.8 | 62 | -5.2 | 0 |
| 33 | -4.2 | -72.2 | -9.6 | -4.2.4 | -13.3 | 20.3 | 9.1 | -71.2 | -36.4 | -1 | -60 | 11.4 | 0 |
| 0 | -6.20001 | -63.5 | 8.6 | 0 | 0 | 12 | 14.4 | 2.9 | -69.9 | -27.5 | -23 | 35 | -5.2 | 2.3 |
| 40.2 | -78.8 | -16.7 | -29.7 | -0.8998 | 73.9 | -62.8 | -20.6 | 34.3 | -61.1 | 3.8999 | 9.9999 | 11 | -4.7 | -4.7 |
| 1.6 | -49.7 | 4.7 | 0 | -36.7 | 3.00002 | -36.9 | -65.9 | -22.9 | 5.7 | -36.6 | 27.6 | -57.3 | 0 | 6.2 | 0 |

Critical epitope count: 891 (all allotypes)

B score: 19754.8 (Global)

| Pos | Residue | r_start | r_end | A | C | D | E | F | G | H | I | K | L | M | N | P | Q | R | S | T | V | W | Y |
|---|---|---|---|---|---|---|---|---|---|---|---|---|---|---|---|---|---|---|---|---|---|---|---|
| 1026 | e | 1017 | 1035 | 0 | 0 | 0 | 0 | 0 | 0 | 0 | 0 | 0 | 0 | 0 | 0 | 0 | 0 | 0 | 0 | 0 | 0 | 0 | 0 |
| 1027 | q | 1018 | 1036 | 0 | 0 | 0 | 0 | 0 | 0 | 8.5 | 0 | 0 | 8.5 | 0 | 0 | 0 | 0 | 0 | 0 | 0 | 0 | 10 | 19 |
| 1028 | e | 1019 | 1037 | 0 | 0 | 0 | 0 | 0 | 0 | 0 | 0 | 0 | 0 | 0 | 0 | 5.8 | 0 | 2.3 | 8.5 | 0 | 0 | 8.6 | 8.5 |
| 1029 | i | 1020 | 1038 | 0 | 0 | 0 | 9.1 | 13.5 | 0 | 0 | 8.5 | 0 | 0 | 0 | 0 | 0 | 8.5 | 0 | 0 | 0 | 0 | 13.6 | 11.7 |
| 1030 | g | 1021 | 1039 | 0 | 8.5 | 0 | 18.5 | 21.2 | 13 | 7.7 | 8.5 | 0 | 16.2 | 16.2 | 8.5 | 8.4 | 8.5 | 0 | 8.5 | 8.5 | 8.5 | 13.7 | 21.2 |
| 1031 | k | 1022 | 1040 | 88 | 16.6 | 0 | 11 | 97.8 | 0 | 8 | 24.6 | 0 | 21.6 | 24.6 | 14.6 | 12.7 | 8.6 | 8 | 24.3 | 16.6 | 34.3 | 82 | 80 |
| 1032 | a | 1023 | 1041 | 0 | 8.6 | 0 | 5 | 0 | 0 | 8 | 5 | 0 | 4.1 | 0 | 0 | 8 | 0 | 0 | 8.6 | 4.1 | 0 | 8 | 5 |
| 1033 | t | 1024 | 1042 | 8.6 | 8.6 | 0 | 0 | 8.6 | 0 | 5 | 8 | 0 | 5 | 5 | 0 | 8.4 | 0 | 0 | 8.6 | 0 | 0 | 8.6 | 8.6 |
| 1034 | a | 1025 | 1043 | 0 | 3 | 5 | 18.6 | 13.5 | 0 | 5.3 | 8 | 7.3 | 5 | 5 | 8 | 16.6 | 16.6 | 0 | 8.6 | 8.6 | 8.6 | 5 | 7.3 |
| 1035 | k | 1026 | 1044 | 17.1 | 8.6 | 8.6 | 92 | 8.6 | 8.6 | 8.5 | 8.6 | 0 | 8.6 | 8.6 | 8.6 | 22.1 | 8.6 | 10.9 | 17.1 | 17.1 | 17.1 | 8.6 | 8.6 |

FIG. 6C (Continued)

| | | | | | | | | | | | | | | | | | | | | | | | |
|---|---|---|---|---|---|---|---|---|---|---|---|---|---|---|---|---|---|---|---|---|---|---|---|
| 1036 | y | 1027 | 1045 | -8.5 | 0 | -8.5 | 3.9 | 0 | -8.5 | 6 | -8.5 | -2.5 | 12.4 | 0 | -8.5 | -8.5 | -8.5 | -2.5 | 0 | -8.5 | 0 | 2.3 | 0 |
| 1037 | f | 1028 | 1046 | 2.4 | -2.1 | -10.6 | -14.2 | 0 | -6.2 | -19.2 | -10.6 | -21.7 | -2.1 | 8.6 | -10.6 | 0.1 | -19.2 | -19.4 | 6.4 | -10.6 | -2.1 | 8.6 | 5.6 |
| 1038 | f | 1029 | 1047 | -2.9 | -2.9 | -11.5 | -6.5 | 0 | -11.4 | -16.1 | -3 | -27.7 | -11.5 | 0 | -3 | -20 | -11.5 | -19.2 | -2.9 | -2.9 | -3 | 8.7 | -3 |
| 1039 | y | 1030 | 1048 | 8.5 | -19.2 | -30.8 | -18.4 | 0 | -24.8 | -19.2 | -2.1 | -22.2 | -22.2 | -16.2 | -8.6 | -20.1 | -27.8 | -22.2 | -16.2 | -27.8 | -19.2 | -5.6 | 0 |
| 1040 | s | 1031 | 1049 | -13.3 | -3 | -3 | -11.6 | -16.2 | -13.3 | -14.1 | -11.5 | -19.3 | -27.8 | -8.5 | -8.6 | 3 | -11.6 | -20.8 | 0 | -11.6 | -24.8 | -13.8 | -16.2 |
| 1041 | n | 1032 | 1050 | -26.1 | -16.2 | -18.1 | -21.1 | -3 | -14.6 | -15.8 | -14.5 | -22.3 | -11.5 | -11.5 | 0 | -22.3 | -23.1 | -33.8 | -7.7 | -14.6 | -17.5 | -11.5 | -11.5 |
| 1042 | i | 1033 | 1051 | -6 | -11.6 | -11.6 | -4 | -11.6 | -11.6 | -12.3 | 0 | -20 | -11.6 | -8.6 | -8.6 | -8.5 | -3 | -23 | -3 | -11.6 | -11.6 | -14.6 | -11.6 |
| 1043 | m | 1034 | 1052 | -6 | -13.7 | -14.6 | -14.6 | -8.6 | -19.3 | -33.8 | -7.7 | -33.3 | -22.3 | 0 | -22.3 | -17.1 | -27.8 | -25.3 | 2.6 | 3 | -7.7 | -11.6 | -11.6 |
| 1044 | n | 1035 | 1053 | 12.4 | 1.7 | -6.5 | 11.4 | 7.7 | 4.7 | 3 | 12.4 | -25.2 | 17.1 | 23.9 | 0 | 23.8 | -5.2 | -10.7 | 15.4 | 4.7 | 18.4 | 5.6 | 4.7 |
| 1045 | f | 1036 | 1054 | -23.1 | -20.1 | -30.7 | -26.6 | 0 | -23.1 | -30.8 | -30.7 | -39.3 | -19.2 | -27.7 | -30.7 | -14.5 | -39.3 | -36.3 | -20.1 | -11.5 | -14.5 | -14 | -10.7 |
| 1046 | f | 1037 | 1055 | -25.3 | -26.1 | -17.6 | -9.6 | 0 | -33.8 | -3 | -27.8 | -33.8 | -30.8 | -30.8 | -23.1 | -27.8 | -23.1 | -33.8 | -23.1 | -20.1 | -30.8 | 4.8 | -23.1 |
| 1047 | k | 1038 | 1056 | 13.7 | 3 | -0.9 | 20.7 | 23.4 | 15.7 | 1.7 | 10.7 | 0 | 15.7 | 18.4 | -0.9 | 3 | 4.7 | 3 | 3 | 10.7 | 10.7 | 27 | 18.4 |
| 1048 | t | 1039 | 1057 | -12 | -6.4 | -2.4 | -5.4 | 11.5 | -12 | -2.6 | 0 | -12 | -3.6 | 0 | -24 | -4.7 | -12 | -12 | 0 | 0 | -8.6 | 3 | 7.7 |
| 1049 | e | 1040 | 1058 | -15.4 | -9.4 | -15.4 | 0 | 1.1 | -15.4 | -10.4 | -3.8 | -15.4 | -6.8 | -6.8 | -15.4 | -9.4 | -9.4 | -15.4 | -6.4 | -12.4 | -15.4 | -10.4 | -15.4 |

| | | | | | | | | | | | | | | | |
|---|---|---|---|---|---|---|---|---|---|---|---|---|---|---|---|
| 1078 | r | 1069 | 1087 | 6 | 11.6 | 22 | -9 | 8.6 | -0.6 | 8.4 | 6 | 6.7 | 9.4 | 13.3 | 5.8 | 0 |
| 1079 | d | 1070 | 1088 | 0 | 11.6 | 17 | 3 | -7.7 | 2.1 | 13.9 | -9 | 5 | 2 | 16 | 15.7 | 3.5 | 0 |
| 1080 | f | 1071 | 1089 | 0 | 11.6 | 25 | 14.5 | 25.3 | 9 | 0 | -9 | 8 | 9.7 | -2.2 | 21.7 | 0 | 0 |
| 1081 | a | 1072 | 1090 | 0 | 11.6 | 25 | -13 | 20.3 | -9 | 8.5 | -9 | 0 | 8 | -17 | 21.7 | 12 | 12 |
| 1082 | t | 1073 | 1091 | 14.5 | 11.6 | 0 | 25 | 8.5 | 0 | 0 | -9 | 8.5 | -0.3 | -2.2 | 0 | 2.7 | 0 |
| 1083 | v | 1074 | 1092 | 0 | 11.6 | 18 | 28 | 19.3 | 0 | -9 | -9 | 16 | -12.7 | 16 | 21.7 | 3.5 | 0 |
| 1084 | r | 1075 | 1093 | -3 | 9.3 | 28 | -25 | -7.7 | -16.7 | 28.3 | -3.7 | 11.8 | 6.4 | -2.3 | 16.7 | 3.5 | -5 |
| 1085 | k | 1076 | 1094 | 0 | 11.6 | -11 | 25 | -3 | 0 | 20.8 | -9 | 0 | 3.6 | 11 | 21.7 | 5 | 0 |
| 1086 | v | 1077 | 1095 | 3 | 11.6 | 28 | 25 | 10.7 | 0 | 0 | 0 | 8 | 15.7 | 13 | 21.7 | 2.7 | 0 |
| 1087 | l | 1078 | 1096 | 6 | 11.6 | -14 | 25 | 0 | 0 | 16.9 | -9 | 6 | 4.7 | 0.599998 | 3 | -5 | 0 |
| 1088 | s | 1079 | 1097 | 6 | 11.6 | 0 | 25 | -3 | 0 | 8.4 | -9 | 6 | 3.6 | 11 | 3.4 | 5.8 | 0 |
| 1089 | m | 1080 | 1098 | 0 | 11.6 | 20 | 25 | 10.7 | 0 | -9 | -9 | -6 | 5 | -13 | 15.7 | 12.7 | 0 |
| 1090 | p | 1081 | 1099 | 3 | 0 | -25 | 25 | -5.8 | 2.4 | 0 | -13.7 | 12 | -4.7 | 8.4 | 16.7 | 12 | -5 |
| 1091 | q | 1082 | 1100 | 0 | 11.6 | 25 | 19 | 10.7 | 0 | 8.4 | -9 | -5 | -9.7 | 8.3 | 21.7 | 5.8 | 0 |

| 1148 | k | 1139 | 1157 | 6.3 | 6.3 | -2.3 | 6.3 | 25.6 | 6.3 | 6.3 | 14 | 0 | 6.3 | 14 | 14 | 6.3 | 17 | 6.3 | 0 | 6.3 | 6.3 | 14 | 28.7 | 5.4 |
| --- | --- | --- | --- | --- | --- | --- | --- | --- | --- | --- | --- | --- | --- | --- | --- | --- | --- | --- | --- | --- | --- | --- | --- | --- |
| 1149 | v | 1140 | 1158 | 0 | -2.3 | -2.3 | -2.3 | 0 | -2.3 | -2.3 | 0 | 2.3 | 0 | 0 | 2.3 | 6.1 | -2.3 | -2.3 | 2.3 | -2.3 | -2.3 | 0 | 0 | 0 |
| 1150 | e | 1141 | 1159 | 0 | -2.3 | -2.3 | -2.3 | 14 | 0 | -2.3 | 0 | 0 | 0 | 0 | 0 | -2.3 | -2.3 | 8.4 | -2.3 | 0 | 0 | 0 | 17 | 5.4 |

FIG. 6D

| Critical epitope count: 891 (all allotypes) | | | | DRB1 score: 12545.7 (Global) | | | | | | | | | | | | | | | | | | | | |
|---|---|---|---|---|---|---|---|---|---|---|---|---|---|---|---|---|---|---|---|---|---|---|---|---|
| Pos | Residue | r_start | r_end | A | C | D | E | F | G | H | I | K | L | M | N | P | Q | R | S | T | V | W | Y |
| 1026 | e | 1017 | 1035 | 99.3 | 55.5 | 131.6 | 101.9 | 54.7 | 28.8 | 94.2 | 77.4 | 0 | 40.6 | 75.5 | 28.7 | 61.2 | 11.5 | 4.6 | -1.1 | 71.6 | 25.6 | 28 | 53 |
| 1027 | q | 1018 | 1036 | 17.7 | 57.7 | 107.1 | 107.1 | -22.3 | 91.6 | 67.8 | 20.2 | 0 | 6.2 | 21.5 | 4.7 | -6.1 | 78.2 | 72.4 | 34.3 | 4.7 | 8.2 | 18.2 | -1.9 |
| 1028 | e | 1019 | 1037 | 32 | 59.3 | 50.8 | -23.2 | 22.3 | 24.7 | 49.3 | 32.5 | 23.3 | 31.9 | 34.6 | 21.9 | 40.9 | 7.7 | 32 | -15.3 | 49.9 | 8.5 | 6.5 | 62.3 |
| 1029 | i | 1020 | 1038 | 0 | 49.5 | -79.4 | -66.3 | 49.8 | 153.1 | -124 | 40.8 | 0 | 43.4 | 27.3 | -73.9 | -17.8 | 133.3 | 40.7 | 44.3 | 40.9 | 9.5 | 3.8 | 34.3 |
| 1030 | g | 1021 | 1039 | 10.8 | 19.5 | 57.5 | 25.8 | 128.3 | 247 | 42.2 | 32.5 | 51 | 51.4 | 27.3 | 57.5 | 49 | 31.6 | 13.5 | 15.5 | 18.8 | 9.5 | 85 | 109.8 |
| 1031 | k | 1022 | 1040 | 96.8 | 86 | 96.8 | 98 | 40.5 | 96.8 | 65 | 120.7 | 29.3 | 156.7 | 19.9 | 19 | 59.2 | 40.5 | 82.5 | 79.6 | 90.4 | 106.7 | 41.2 | 147.2 |
| 1032 | a | 1023 | 1041 | 10.8 | 19.6 | -1.5 | 0 | 136 | 35.5 | 22.4 | 0 | 82.5 | 13.5 | 19.9 | 24.2 | 30.9 | 38.1 | 57.8 | 48.9 | 31.4 | 30.7 | 64.9 | 47.2 |
| 1033 | t | 1024 | 1042 | 62.7 | 24 | -17 | -17 | 28 | 15 | 30.8 | 147 | 28.8 | 58.9 | 16.3 | 11.9 | 3.9 | 0 | 11.4 | 6.7 | 11 | 22.5 | 41 | 16.7 |
| 1034 | a | 1025 | 1043 | 17.7 | 63.1 | -17 | -17 | 28 | -15 | -30.8 | 31.4 | 14.7 | 35.5 | 22.5 | 11.9 | 3.9 | 0 | 11.4 | 6.7 | 11 | 22.5 | 41 | 2.8 |
| 1035 | k | 1026 | 1044 | 99.3 | 55.5 | 131.6 | 101.9 | 54.7 | 38.6 | 137 | 77.4 | 67.9 | 20.7 | 20.0 | 6.1 | 51.3 | 44.9 | 77.4 | 90.1 | 10.3 | 25.6 | 8.2 | 53 |

| | | | | | | | | | | | | | | |
|---|---|---|---|---|---|---|---|---|---|---|---|---|---|---|
| 1050 | | 1041 | 1059 | 1.5 | 22 | -20 | 26.3 | 29.1 | -9.1 | 48.6 | 49.5 | 25.4 | 0 | 41.7 | 0.79999 | 57.9 |
| 1051 | t | 1042 | 1060 | 9.1 | 13 | 47 | 20 | 8.5 | 24.8 | 15 | 22.9 | 12 | 103 | 34.8 | 62.8 | 145 | 45.7 |
| 1052 | _ | 1043 | 1061 | 13 | -20 | -6.2 | -19.6 | -41 | 25.4 | 24 | -18 | -15.9 | -25.7 | -95.7 | 105 | -112.2 |
| 1053 | a | 1044 | 1062 | 13 | 20 | 14 | -20 | -7.4 | -19.6 | 19.6 | 0 | 18 | -13.5 | 43.6 | 91.2 | -126 |
| 1054 | n | 1045 | 1063 | 5 | 5 | 17 | 6 | 37.1 | 42.2 | -3.9 | 109 | 32.7 | 28.9 | 9 | 21.2 | -28.7 |
| 1055 | g | 1046 | 1064 | 9.1 | 20 | 4.9 | -20 | 1.5 | 9 | -11.5 | 24.9 | 0 | 10.7 | 22.6 | 61.4 | 30.2 | 77.6 |
| 1056 | e | 1047 | 1065 | 16 | 7.4 | 6.3 | -20 | 22.8 | 17.2 | 10 | -39.6 | 22.2 | 19.3 | 2.6 | 10009.5 | -27.2 |
| 1057 | _ | 1048 | 1066 | 0 | -5 | 19 | 7.5 | 3.17E+01 | 75.4 | 0 | 113 | 63.2 | 849 | 22.2 | -112 | 63.7 | 0 |
| 1058 | r | 1049 | 1067 | 17 | 3.4 | 6.3 | 19 | 0 | 7.6 | 1.5 | 93.3 | 37.1 | 51 | 36.3 | 211 | 19000.1 | 69.4 |
| 1059 | k | 1050 | 1068 | 14 | 0 | 32 | -9.5 | 32.3 | 82.7 | 10.5 | 132 | 48.3 | 106 | 36 | 0 | 42.7 | 30.2 |
| 1060 | r | 1051 | 1069 | 4.9 | -5 | 17 | -7.5 | 57.5 | 27.2 | 0 | 108 | 48.3 | 113 | 32.4 | -17.4 | 40.7 | -0.2 |
| 1061 | p | 1052 | 1070 | -15 | 12.1 | 4.9 | 16.9 | -9.1 | -1.8 | 49.1 | 55.3 | 0 | -29 | -139.1 | -18.9 | -58.9 |
| 1062 | _ | 1053 | 1071 | -15 | 2 | 0 | -20 | -8.5 | -24.8 | -2.9 | 43.8 | 7.4 | -14.5 | 36.3 | -35.7 | -63.7 | 31.8 |
| 1063 | _ | 1054 | 1072 | 2 | 13 | 4.9 | 15 | 29.3 | 5.4 | 9.7 | 39.2 | 9.4 | 14.7 | 13.8 | 52.8 | 9.2 | 66.4 |
| | | | | 15 | 4.7 | 6.3 | 0 | 24.3 | 0 | 12.6 | 98.1 | 47.9 | 35.7 | 2.6 | 4.3 | 27.6 | 38 |
| | | | | 19.1 | 22.8 | -2.7 | 20 | 39.2 | -9 | 7.3 | 48.2 | 46.7 | 23.7 | 20.8 | 41.3 | 36.6 | 19.3 |
| | | | | 16 | 2.6 | 4.9 | 20 | 3.9 | 18.3 | 13.2 | 32.8 | 5.9 | 23 | 22.6 | 24.2 | 0 | 32.8 |
| | | | | -15 | 2 | 19 | 19 | 26.3 | 42.2 | 1.5 | 100 | 38.5 | 109 | 21.9 | -15.6 | 53.4 | -5900.01 |
| | | | | -15 | 20 | 14 | 5.1 | 43.9 | -1.8 | -0.4 | 93.3 | 17.4 | 91 | 5.6 | 55.3 | -2400.01 | 90.9 |
| | | | | -15 | -13 | 41 | 5.1 | 36.5 | 42.2 | -1.9 | 98 | 33 | 120 | 28.3 | -11 | 25.8 | -21.1 |

FIG. 6D (Continued)

| | | | | | | | | | | | | | | | | | | | | | | | |
|---|---|---|---|---|---|---|---|---|---|---|---|---|---|---|---|---|---|---|---|---|---|---|---|
| 1064 | e | 1055 | 1073 | 10.9 | 10.9 | 2 | 0 | 36.1 | 10.9 | 31.1 | 46.1 | 63.4 | 46.1 | 46.1 | 32 | 14.5 | 14.5 | 70.5 | 14.5 | 14.5 | 46.1 | 21.8 | 46.1 |
| 1065 | t | 1056 | 1074 | 2 | -1.5 | -1.5 | -1.5 | 18.5 | -9.1 | 2 | 0.9 | -9.1 | 5.5 | 7.9 | -1.5 | -1.5 | -1.5 | -9.1 | 2 | 0 | 0.9 | -2.5 | 9.7 |
| 1066 | n | 1057 | 1075 | 8.4 | 2 | 2 | 2 | 2.9 | 2 | 2 | 2.9 | 2 | 9.3 | 2.9 | 0 | 2 | 2.9 | 2 | 2 | 2 | 2.9 | 2.9 | 2.9 |
| 1067 | g | 1058 | 1076 | 0 | 7.3 | 0.9 | 0.9 | 7.3 | 0 | 6.8 | 7.3 | 5.8 | 7.3 | 12.8 | 0.9 | 6.4 | 7.3 | 23 | 7.3 | 0.9 | 7.3 | 6.4 | 6.4 |
| 1068 | e | 1059 | 1077 | 6.8 | 0.9 | 0.9 | 0 | 0.9 | 1.3 | 0 | 6.4 | 8.9 | 0.9 | 6.4 | 21.4 | 6.8 | 6.8 | 9.8 | 6.8 | 6.8 | 6.4 | 0 | 0.9 |
| 1069 | t | 1060 | 1078 | 0.9 | 0 | 0 | 0 | 0 | 0 | 6.4 | 0 | 0 | 0 | 0 | 6.4 | 0 | 6.4 | 0 | 0 | 0 | 0 | 0 | 0 |
| 1070 | g | 1061 | 1079 | 0 | 0.9 | 0 | 0 | 2.7 | 0 | 0.9 | 19.1 | 0 | 19.1 | 2.7 | 0 | 0.9 | 0.9 | 0.9 | 0.9 | 0 | 2.7 | 0 | 0.9 |
| 1071 | e | 1062 | 1080 | 0 | 0 | -13 | 0 | 33.4 | 0 | 8.9 | 43.5 | 8.9 | 43.5 | 24.6 | -13 | -13 | 0 | 8.9 | 0 | 0 | 24.6 | 38.9 | 33.4 |
| 1072 | i | 1063 | 1081 | -41 | -41 | -41 | -41 | -4.3 | -41 | -28 | 0 | -29 | -26 | -15 | -40 | -41 | -40 | -29 | -41 | -41 | -15 | -27 | -27 |
| 1073 | v | 1064 | 1082 | -34.7 | -41.1 | -41.1 | -41.1 | 8.6 | -41.1 | -41.1 | 41.1 | -14 | 1.5 | 0 | -25.8 | -41.1 | 25 | 22.8 | -28.6 | -25.8 | 0 | 16 | 15.8 |
| 1074 | w | 1065 | 1083 | -27 | -41 | -38 | -40 | 3.5 | -28 | -38 | -9 | -11 | 2 | 3.5 | -25 | -13 | -17 | -9 | -27 | -17 | -13 | 0 | -11 |
| 1075 | d | 1066 | 1084 | 41.7 | 30.5 | 0 | -9.8 | 47.2 | -5.6 | 52.8 | 70.1 | 35.5 | 58.3 | 81.1 | -6.90001 | -23.8 | 35.9 | 31.5 | 32.4 | -7.40001 | 82.6 | 38.2 | 56.7 |
| 1076 | k | 1067 | 1085 | -20.7 | 10.1 | 3 | -12.5 | 11.2 | -20.7 | -10.7 | 18 | 0 | 10.9 | 17.6 | -12.5 | -28 | -12.5 | 3.5 | 1.5 | 3 | 10.9 | 4.5 | 28.8 |
| 1077 | g | 1068 | 1086 | 44.9 | 5.5 | -25.3 | -25.3 | 19.6 | 0 | -10.3 | 46.5 | 13.3 | 36.5 | 0.8 | 30.8 | 18.6 | 21.9 | 16.6 | 44.9 | 20.6 | 7.2 | 26.9 | 44 |

| | | 1083 | 1084 | 1085 | 1086 | 1087 | 1088 | 1089 | 1090 | 1091 | 1092 | 1093 | 1094 | 1095 | 1096 |
|---|---|---|---|---|---|---|---|---|---|---|---|---|---|---|---|
| | | 1101 | 1102 | 1103 | 1104 | 1105 | 1106 | 1107 | 1108 | 1109 | 1110 | 1111 | 1112 | 1113 | 1114 |
| 1092 | v | | | | | | | | | | | | | | |
| 1093 | u | | | | | | | | | | | | | | |
| 1094 | i | | | | | | | | | | | | | | |
| 1095 | v | | | | | | | | | | | | | | |
| 1096 | k | | | | | | | | | | | | | | |
| 1097 | k | | | | | | | | | | | | | | |
| 1098 | t | | | | | | | | | | | | | | |
| 1099 | e | | | | | | | | | | | | | | |
| 1100 | v | | | | | | | | | | | | | | |
| 1101 | q | | | | | | | | | | | | | | |
| 1102 | t | | | | | | | | | | | | | | |
| 1103 | g | | | | | | | | | | | | | | |
| 1104 | g | | | | | | | | | | | | | | |
| 1105 | f | | | | | | | | | | | | | | |

| | | | | 1143 | 1144 | 1145 | 1146 | 1147 | 1148 | 1149 | 1150 | 1151 | 1152 | 1153 | 1154 | 1155 | 1156 |
|---|---|---|---|---|---|---|---|---|---|---|---|---|---|---|---|---|---|
| 1134 | f | 1125 | | 0 | 8 | 32.7 | 13.11 | 11.5 | 31.1 | 100 | 0 | -12.3 | 15.4 | 64 | 4.2 | 69.4 | 7.59999 |
| 1135 | d | 1126 | | 59.9 | 72.3 | 75 | 20.7 | 17.3 | 68.9 | 109 | 33.8 | 48.6 | 4.6 | 9.39999 | 29.7 | 49.6 | 11.3 |
| 1136 | s | 1127 | | 66.3 | 109.1 | 122.9 | 135.4 | 101.2 | 68.3 | 118 | 104.3 | 79.2 | 7.3 | 38.5 | 0 | 30.9 |
| 1137 | p | 1128 | | 53.2 | 112.9 | 104.6 | 136.9 | 116.7 | 64.4 | 109 | 71.5 | 104.3 | 52 | 63.6 | 29.7 | 33.2 | 26.1 |
| 1138 | t | 1129 | | 144.9 | 4.1 | 27.2 | 42.9 | 6.60001 | 96.3 | 25 | 132.1 | 51.3 | 143.6 | 123.6 | 133.3 | 98 | 0 |
| 1139 | v | 1130 | | 52.9 | 76.8 | 82.8 | 175.7 | 0.699997 | 56 | 109 | 60.3 | 42.6 | 38.5 | 20.6 | 55.6 | 25.7 |
| 1140 | a | 1131 | | 64.6 | 4.8 | 28.6 | 41.2 | 23.5 | 19.4 | 94.8 | 48 | 9.6 | 42.9 | 27.7 | 2.5 | 25.3 |
| 1141 | y | 1132 | | 128.4 | 7.40001 | 42.8 | 35.3 | 21.9 | 127.5 | 44.3 | 135.7 | 70.3 | 163.5 | 150.9 | 22.1 | 111.7 | -1.3 |
| 1142 | s | 1133 | | 3.19999 | 43.1 | 24.2 | 23.7 | 9.79999 | 46.7 | 49.1 | 46.7 | 0.2 | 75.2 | 20.5 | 14.6 | 81.9 | 29.7 |
| 1143 | v | 1134 | | 149.8 | 61.1 | 50.1 | 0 | 37.8 | 121.9 | 23 | 134.7 | 57.2 | 160.7 | 138.2 | 144 | 103.9 | 0.299999 |
| 1144 | l | 1135 | | 162.1 | 8 | 54.3 | 16 | 48.1 | 103.2 | 33.8 | 134.7 | 53.9 | 149.9 | 157.9 | 29.7 | 88.6 | 0.299999 |
| 1145 | v | 1136 | | 4.60001 | 3.8 | 71.8 | 23.4 | 9.69999 | 9.3 | 44.5 | 99.5 | 44.1 | 13.5 | 4.1 | 44.8 | 31.8 |
| 1146 | v | 1137 | | 52 | 62.4 | 85.2 | 22.9 | 2.7 | 80.1 | 109 | 72 | 104.3 | 42.1 | 0 | 29.7 | 33.2 | 27.7 |
| 1147 | a | 1138 | | 28.4 | 12.8 | 64.5 | 50.8 | 0.3 | 133 | 93.7 | 20.8 | 56.5 | 49.5 | 26.7 | 13.3 | 54.4 | 24.9 |
| | | | 1143 | 79.7 | 13.3 | 4.8 | 26.9 | 52.9 | 34.8 | 28.6 | 62.9 | 51.9 | 70.3 | 20.5 | 10.5 | 75.7 | 22.7 |
| | | | 1144 | 39.3 | 24.1 | 58.7 | 66.7 | 18.3 | 0 | 109 | 14.2 | 76.9 | 16.4 | 36.9 | 0 | 49.6 | -0.20001 |
| | | | 1145 | 38.4 | 28.6 | 32.1 | 20.1 | 5.59999 | 45.6 | 71.8 | 26.7 | 58 | 0 | 9.5 | 29.7 | 49.6 | 7.8 |
| | | | 1146 | 85 | 0 | 0 | 14.8 | 0 | 62.9 | -82.4 | 119.8 | 0 | 141 | 131.3 | -29.7 | 89.6 | -1.3 |
| | | | 1147 | 91.8 | -9 | 65.8 | 11.8 | 20.6 | 79.8 | 14 | 76.5 | 52.9 | 126.3 | 128.1 | 22.1 | 82.8 | -5.40001 |
| | | | 1148 | 127.9 | 34.1 | 6.3 | 17.7 | 12.5 | 82.2 | 0 | 136.9 | 141.9 | 160 | 131.7 | 11.3 | 81.8 | 4.2 |

Protein sequence alignment

```
SEQID-NO:5   -----MDKKYSIGLDIGTNSVGWAVITDEYKVPSKKFKVLGNTDRHSIKKNLIGALLFD
SEQID-NO:8   MAAFKPNPINYILGLDIGIASVGWAMV--EIDEDENPICLID----------LGVRVFFE
SEQID-NO:6   ----MSDLVLGLDIGIGSVGVGIL--NKVTGE----IIH----------KNSRIFP
SEQID-NO:7   ----MKRNYILGLDIGITSVGYGII---DYETRD---VID----------AGVRLFK
                  : :****   *** ***   . :    .   .            .  :*

SEQID-NO:5   SGETA-------EATRLKRTARRRYTRRKNRICYLQEIFSNEMAKVDDSFFHRLEESFLV
SEQID-NO:8   RAEVPKTGDSLAMARRLARSVRRLTRRRAHRLLRARRLLKRE------------------
SEQID-NO:6   AAQAENN-----LVRRTNRQGRRLARRKKHRRVRLNRLFEES------------------
SEQID-NO:7   EANVENN-----EGRRSKRGARRLKRRRHRIQRVKKLLFDY------------------
              .         .   *  *  **    . :.*   .  :*

SEQID-NO:5   EEDKKHERHPIFGNIVDEVAYHE-----KYPTIYHLRKKLVDSTDKADLRLIYLALAHMIK
SEQID-NO:8   ---------GVLQAADFDENGLIKSLPNTPWQLRAAALDRKLTPLEWSAVLLHLIK
SEQID-NO:6   ------GLI--TDFTK-----ISINLNPYQLRVKGLTDELSNEELFIALKNMVK
SEQID-NO:7   ------NLL--TDHSE-----LS-GINPYEARVKGLSQKLSEEEFSAALLHLAK
                   .:         .        :           .   * .  : *

SEQID-NO:5   FRG-HFLIEGDLNPDNSDVDKLFIQLVQTYNQLFEENPINASGVDAKAILSARLSKSRRL
SEQID-NO:8   HRG--YLSQRKNEGETADKE------LGALLKGVADN----------AHAL
SEQID-NO:6   HRGISYLDDASDDGNSS---------VGDYAQIVKEN----------SKQL
SEQID-NO:7   RRGVHNVNEVEEDTGNE---------LSTKEQISR-N----------SKAL
              **     .            :     .   *            . :

SEQID-NO:5   ENLIAQLPGEKKNGLFGNLIALSLGLTPNFKSNFDLAEDAKLQLSKDTYDDDLDNLLAQI
SEQID-NO:8   QTGDFRTPAE----------------------------------------LAL-------
SEQID-NO:6   ET---KTPGQ----------------------------------------IQL-------
SEQID-NO:7   EE---KYVAE----------------------------------------LQL-------
              .                                                 *
```

FIG. 7 (Continued)

```
SEQID-NO:5   GDQYADLFLAAKNLSDAILLSDILRVNTEITKAPLSASMIKRYDEHQDLTLLKALVRQQ-
SEQID-NO:8   ------------------------------------------------------------
SEQID-NO:6   ------------------------------------------------------------
SEQID-NO:7   ------------------------------------------------------------

SEQID-NO:5   LPEKYKEIFFDQSKNGYAGYIDGGASQEEFYKFIKPILEKMDGTEELLVKLNREDLLRKQ
SEQID-NO:8   --NKFEK-------------ESGHIRNQ--------------------RGDYSHTFSRKDLQA-
SEQID-NO:6   --ERYQT-------------Y-GQLRGDFT-------------VEKDGKKHRLINVFPTSAYRS--
SEQID-NO:7   --ERLKK-------------D-GEVRGS--------------------INRFKTSDYVK--
                  .  :                 :.                     .

SEQID-NO:5   RTFDNGSIPHQIHLGELHAILRRQEDE-YPFLKDN-REKIEKILTFRIPYVVGPLARGNS
SEQID-NO:8   ------------------------ELILLLFEKQKEFGNPHVSGGLKEGIETLLMTQRPALSGD----AVQ
SEQID-NO:6   ------------------------EALRILQTQQEF-NPQITDEFINRYLEILTGKRKYYHGP----GNE
SEQID-NO:7   ------------------------EAKQLLKVQKAY-H-QLDQSFIDTYIDLLETRRTYEGP----GEG
                                         *           :  :*:    .   *

SEQID-NO:5   R------FAWMTRKSEETITPWNEEEVVDKGASAQSFIERMTNFDKNLPNEKVLPKHSLLYE
SEQID-NO:8   K--------------------------MLGH------------CTFE-----PAEPKAAKNTYTAE
SEQID-NO:6   KSRTDYGRY-RTSGETLDNI-FGILIGK---------------CTFY-----PDEFRAAKASYTAQ
SEQID-NO:7   S---PFGW-----KDIKEW-YEMLMGH---------------CTYF-----PEELRSVKYAYNAD
                                                        *.:         :          :

SEQID-NO:5   YFTVYNELTKVKYVTEGMRKPAFLSGEQKKAIVDLLFKTNRKVT-----VKQLKEDY-FK
SEQID-NO:8   RFIWLTKLNNLRILEQGSERP----LTDTERATLMDEPYRKS-KLT------YAQARKLLGLE
SEQID-NO:6   EFNLLNDLNNLTVPTETKK-----LSKEQKNQIIN--YVKNEKAMGPAKLFKYIAKLL-SC
SEQID-NO:7   LYNALNDLNNLVITRDENEK-----LEYYEKFQIIENVFKQKKKPT-----LKQIAKEI-LV
                 :   :                   :.                          *

SEQID-NO:5   KIECFDSVEI--SGVEDRFNASLGTYHDLLKIIKDKDFLDNE-----ENEDILEDIVLTLT
SEQID-NO:8   DTAFFKGLRYGKDNAEASTLMEMKAYHAISRALEKEGLKDKKSPLNLSPELQDEIGTAFS
SEQID-NO:6   DVADIKGYRI--DKSGKAEIHTFEAYRKMKTL----ETLDIE---QMDRETLDKLAYVLT
SEQID-NO:7   NEEDIKGYRV--TSTGKPEFTNLKVYHDIKDITARKEIIENA-----ELLDQIAKILT
                 :                       :                        ::.
```

FIG. 7 (Continued)

```
SEQID-NO:5    LFEDREMIEERLKTYAH----LFDDKVMKQLKRRRYT-------GWGRLSRKLLINGIRDKQS
SEQID-NO:8    LFKTDEDITGRLKDR------IQPEILEALLKHISFD-------KFVQISLKALR-------
SEQID-NO:6    LNTEREGIQEALEHEFADGSFSQKQVDELVQFRKANSSIFGKGWHNFSVKLMM---------
SEQID-NO:7    IYQSSEDIQEELTNLNSE--LTQEEIEQISNLKGYT-------GTHNLSLKAIN--------
                *          *               ::        *             :  .

SEQID-NO:5    GKTILDFLKSDGFANRNFMQLIHDDSLTFKEDIQKAQVSGQGDSLHEHIANLAGSPAIKK
SEQID-NO:8    --RIVPLMEQ---GKRYDEACAE----IYGDHYGKKNTEEKIYLP-PIPADEIRNPVVLR
SEQID-NO:6    --ELIPELYE---TSEEQMTILT----RLGKQKTTSSSNKTKYIDEKLLTEEIYNPVVAK
SEQID-NO:7    --LILDELWH---TNDNQIAIFN-----RLKLVPKKVDLSQQKEIPTTLVDDFILSPVVKR
                :              :            :*  .    .      :      *..

SEQID-NO:5    GILQTVKVVDELVKVMGRHKPENIVIEMARENQTT-------QKGQKNSRERMKR---IEE
SEQID-NO:8    ALSQARKVINGVVRRYG---SPARIHIETAREVGKSFKDRKEIEKRQEENRKDREK-----A
SEQID-NO:6    SVRQAIKIVNAAIKEYG---DFDNIVIEMARETNED-DEKKAIQKIQKANKDEKDAAMLKA
SEQID-NO:7    SFIQSIKVINAIIKKYG---LPNDIIELAREKNSK-DAQKMINEMQKRNRQTNER---IEE
                :: * ::: :  :         :         *   ** ***      .     :

SEQID-NO:5    GIKELGSQILKEHPVENTQLQNEKLLYLYLQNGRDMYVDQELDINRL-----SDYDVDHIV
SEQID-NO:8    AAKF--REYFPNFVGEPKSKDILKLRLYEQQHGKCLYSGKEINLGRL-NEKGYVEIDHAL
SEQID-NO:6    ANQYNGKAELPHSVFHGHKQLATKIRLWHQQGERCLYTGKTISIHDLINNSNQFEVDHIL
SEQID-NO:7    IIRTTGK-------ENAKYLIEKIKLHDMQEGKCLYSLEAIPLEDLLNNPFNYEVDHII
                               :       :     *      :: :   .   .  **

SEQID-NO:5    PQSFLKDDSIDNKVLTRSDKNRGKSDNVPSEEVKKMKNY-WRQLLNAKLITQRKFDNLT
SEQID-NO:8    PFSRTWDDSFNNKVLVLGSENQNKGNQTPYEYFNGKDNSREWQEFKARV-----ETSRFP
SEQID-NO:6    PLSITFDDSLANKVLVYATANQEKGQRTPYQALDSMDDAWSFRELKAFV----RESKTLS
SEQID-NO:7    PRSVSFDNSFNNKVLVKQEENSKKGNRTFFQYLSSSDSKISYETFKKHILNLAKGKGRIS
                .  :.* .::*:*:     .::**:    .   .   .        :

SEQID-NO:5    KAERG------GLSELD-KAGFIKRQLVETRQITKHVAQILDSRMNTKYDENDKLIREVK
SEQID-NO:8    RSKKQRIL----LQKFD-EDGFKERNLNDTRYVNRFLCQFVADRMRLTGKG------KKR
SEQID-NO:6    NKKKEYLLTEEDISKFDVRKKFIERNLVDTRYASRVVLNALQEHFRAHKI------DTK
SEQID-NO:7    KTKKEYLLEERDINRFSVQKDFINRNLVDTRYATRGLMNLLRSYFRVNNL------DVK
                  :            .:   ::*  * :**  .:  :     :             .
```

FIG. 7 (Continued)

```
SEQID-NO:5  VITLKSKLVSDFRKDFQFYKVREINNYHHAHDAYLNAVVGTALIKKYPKLESEFV-YGDY
SEQID-NO:8  VFASNGQITNLLRGFWGLRKVRAENDRHHALDAVVVA-CSTVAMQ--QKITRFVR-YKEM
SEQID-NO:6  VSVVRGQFTSQLRRHWGIEKTRD-TYHHHAVDALIIA--ASSQLNLWKKQKNTLVSYSED
SEQID-NO:7  VKSINGGFTSFLRRKWFKKERNKGYKHHAEDALIIA-NADFTFKEWKKLDKAKK-VMEN
                     *         :    :*     :  **  *  ***  **  ::   .

SEQID-NO:5  KVYDVRKMIAKSEQEIGKATAKYFFYSNIMNFFKTEITLANGEIRKRPLIETNGETGE--
SEQID-NO:8  NAFD----GKTIDKETGEVLHQKTHFPQPWEFFAQEVMIRVFGKPDGKPEFEEADTPEKLR
SEQID-NO:6  QLDIETGELISDDE----YKESVFKAPYQHFVDTLKSKEFEDS-----------------
SEQID-NO:7  QMFEEKQAESMPEIETEQEYKE-IFITPHQ-----IKHIKDFKD----------------
             :  :                              .                    .

SEQID-NO:5  IVWDKGRDFATVRKVLSMPQVNIVKKTEVQTGGFSKESILPKRNS------DKLI----A
SEQID-NO:8  TLLAEKLSSRPEAVHEYVTPLFVSRAPNRKMSGQGHMETVKSAKRL--DEGVSVLRVPLT
SEQID-NO:6  ILFSYQVDSKFNRKISDAT-IYATRQAKVGKDKADETYVLGKIKDIYTQDGYDAFM----
SEQID-NO:7  YKYSHRVDKKPNRELINDT-LYSTR-----KDDKGNTLIVNNLNGLYDKDN-DKLK----
                         :    *                     . :           .

SEQID-NO:5  RKKDWDPKKYGGFDSPTVAYSVLVVAKVEKG------KSKK------LKSVKELLGITIM
SEQID-NO:8  QLKLKDLEKMVNREREPKLYEA-LKARLEAH------KDDPAKAFAEPFYKY-DKAG---
SEQID-NO:6  KIYKKDKSKFLMYRHDPQTFEKVIEPILENYPNKQINDKGKEVPCNPFLKYKEEHG-YIR
SEQID-NO:7  KLINKSPEKLLMYHHDPQTYQK-LKLIMEQY-----GDEK------NPLYKYYEETGNYLT
             :  .   :  *             :   :         .  :       .  *

SEQID-NO:5  ERSSFEKNPIDFLEAKGYKEVKKDLIIKLPKYSLFELENGRKRMLASAGELQKGNELALP
SEQID-NO:8  NRTQQVKAVR--VEQQVQKTGVWVRNHNGIAD----N------ATMVRVDVFEKG
SEQID-NO:6  KYSKKGNGPE--IKSLKYYDSKLGNHIDITP-----KDSNNKVVLQSVSPWRADVYFNK
SEQID-NO:7  KYSKKDNGPV--IKKIKYYGNKLNAHLDITD-----DYPNSRNKVVKLSLKPYRFDVYLDN
                       :    * : .  . : :                   .

SEQID-NO:5  --SKYVNFLYLASHYEKLKGSPEDNEQKQLFVE-QHKHYLDEIIEQISEFSKRVIL----
SEQID-NO:8  --DKYYLVPIY--SWQVAKGILPDRAVVQGKDE-EDWQLIDDSFNFKEFSLHPNDLV--E
SEQID-NO:6  TTGKYEILGLKYADLQFDKGTGTYKISQEKYNDIKKKEGVDSDSEFKFTLYKNDLLLVKD
SEQID-NO:7  --GVYKFVTVK--NLDVIKKENYYEVNSKCYEEAKKLKKISNQAEFIASFYNNDLI----
                                                  .  :
```

FIG. 7 (Continued)

```
SEQID-NO:5  ---ADANLDKVLSAYNKHRDKPIREQAENIIHLFTLTNL--------GAPAAFKYFDTTI
SEQID-NO:8  VITKKARMFGYFASCHRGTGN-INIRIHDLDHKIGKNGI--------LEGIGVKT
SEQID-NO:6  TETKEQLFRFLSRTMPKQKHYVELKPYDKQKFEGGEALIKVLGNVANSGQCKKGLG-KS
SEQID-NO:7  ---KINGELYRVIGVNNDLLNR--IEVNMIDITYREYLENM----NDKRPPRIIKTIASKT
              .  :    .  :          :      .   :          ..  :: .

SEQID-NO:5  DRKRYTSTKEVLDATLIHQSITGLYETRIDLSQLGGD
SEQID-NO:8  ALSFQKYQIDELGKEIRPCRLK--KRPPVR-------
SEQID-NO:6  NISIYKVRTDVLGNQHIIKNEG--DKPKLDF------
SEQID-NO:7  Q-SIKKYSTDILGNLYEVKSKK--HPQIIKKG-----
               . *.            .
```

Streptococcus pyogenes (HLA Class I 9mer)- <-20 threshold applied.

FIG. 8C

Streptococcus pyogenes (HLA Class I and II 10mer)

FIG. 8D

Streptococcus pyogenes (HLA Class I and II 10mer) - <-20 threshold applied.

FIG. 9

| Sequence/HLA | Target amino acid positions for substitution (single and consecutive) |
|---|---|
| Streptococcus pyogenes (HLA Class I 9mer) | 16, 18, 31, 71, 81-82, 86, 97, 98, 105, 118, 126, 128, 132, 135, 136, 138-139, 155, 158, 164, 168, 185, 188, 192, 196, 216, 244, 271, 275, 278-279, 290, 300, 321, 333, 337, 351-352, 359, 362, 373, 375, 383, 395, 418, 419, 422-423, 430, 432-433, 462, 511-517, 553, 575, 578, 580, 583, 591, 594, 598, 626-627, 653-655, 694, 702, 704, 741, 746-748, 772, 775, 778, 780, 796, 799-800, 812, 814-816, 823, 950, 1001, 1008, 1013, 1015-1016, 1018, 1023, 1028-29, **1033-34

FIG. 9 (Continued)

| | |
|---|---|
| Staphylococcus aureus (HLA Class I 9mer) | 722, 725-726, 728, 747, 753, 755, 761, 764, 769-770, 772, 778, 792, 795-796, 798-799, 804, 810, 818, 822, 861, 865, 882, 884-885, 889-890, 895-896, 898-899, 919-920, 932, 935, 937-938, 942, 946, 965, 970-971, 999, 1004, 1019, 1021, 1023-1024, 1031, 1042-1043, 1066, 1069, 1096, 1099, 1104 |
| Staphylococcus aureus (HLA Class I and Class II 10mer) | 18, 48, 51, 55, 70, 72, 86, 89, 176, 197, 211-212, 219-221, 223, 233, 235-236, 239-241, 256, 277, 345, 347, 351, 358, 389, 407-408, 415, 420-421, 444, 468, 500, 519, 565, 568-569, 573, 604, 609, 625, 651, 657, 664, 666, 669, 675, 683, 688, 698-703, 705, 707-708, 713, 744, 754, 760, 769-771, 773-774, 808-809, 837, 855, 857-858, 897, 904-905, 912, 914, 918, 931, 939, 942, 947, 962, 966-967, 971, 974, 996, 1001, 1004, 5, 18, 21, 23, 26, 29, 34, 35, 51, 66-67, 70-72, 74, 76, 110, 118, 124, 132, 140, 145, 165, 170-171, 176, 190, 193, 197-198, 201-202, 204, 212, 216, 223, 229-230, 232, 234, 240, 244-245, 247, 249, 251, 262, 269, 277-278, 281, 283-284, 303, 305, 313, 329-330, 332, 335, 347-348, 351, 354-355, 358, 362, 364, 366, 368, 383, 386-387, 404, 407-408, 420, 423, 430, 444, 464, 470, 474-476, 478-480, 508-510, 519, 523-527, 529, 532, 535-536, 538, 541, 543, 555, 558, 565, 601, 615, 625, 627, 630, 632, 635, 637-638, 641, 644, 646, 680, 687-690, 694, 713-715, 718, 720-721, 732, 745, 771, 809, 816, 827-828, 847, 857, 864-865, 868, 877, 897, 912, 914, 916-917, 947, 974, 982, 989, 992, 1001, 1004, 1015-1016, 1019, 1030, 1032, 1038, 1041, 1046, 1048 |
| Neisseria meningitidis (HLA Class I 9mer) | 24-26, 74-75, 77-78, 97, 106, 111, 113, 116, 118, 127, 136-138, 144, 226, 231, 272, 279-280, 287-288, 297, 304-305, 310, 317, 331-332, 335, 337, 342, 417, 423, 425, 427-430, 435, 441, 467, 472, 487, 516, 547, 554, 590, 592, 595-596, 599-600, 623, 632, 635-637, 639, 643-644, 646, 671-672, 675-676, 680, 686, 690, 692-694, 707, 710, 744, 746-748, 750, 752-753, 778-779, 806-807, 836, 844, 858-860, 864, 876, 878, 880-881, 883, 885, 888-892, 894-895, 936, 938, 948, 950, 952-953, 960-961, 965, 967, 988, 991, 1006, 1009, 1019-1020, 1033, 1035, 1057-1058, 1066 |
| Neisseria meningitidis (HLA Class I and Class II 10mer) | 12, 17, 41, 43-46, 49, 68, 95, 97, 120, 122, 125, 130, 158, 174, 185, 196, 199, 203, 205, 208, 212-213, 227, 235, 238-239, 254-255, 257, 260, 262-263, 283, 287, 289, 304, 311, 329-332, 337, 360, 365, 372, 374, 386, 388-391, 407-408, 410-412, 434, 439, 448, 458, 472, 478, 481, 487-488, 491-495, 497, 511, 513-515, 519, 537, 541, 545, 553-554, 556, 558-559, 568, 573, 577, 596, 604, 611, 632, 635, 643-644, 651, 662, 680-681, 685, 694, 702, 705-707, 709, 712, 716, 723, 725, 729, 747, 766, 791, 797, 821, 824, 828-830, 832, 838, 844, 852, 857, 859-862, 867, 875, 885, 891, 903, 907, 910, 919-920, 923-925, 928, 935, 941, 953, 959, 961-962, 964-965, 967, 973, 985, 988, 995, 999, 1001, 1010, 1016-1017, 1019-1020, 1028, 1030, 1058, 1001, 1063 |

FIG. 11

Cas9

| Protein Coverage | Supporting Peptides |

Protein Coverage:

SEQ ID NO: 5

```
   1  MDKKYSIGLD IGTNSVGWAV ITDEYKVPSK KFKVLGNTDR HSIKKNLIGA LLFDSGETAE ATRLKRTARR RYTRRKNRIC
  81  YLQEIFSNEM AKVDDSFFHR LEESFLVEED KKHERHPIFG NIVDEVAYHE KYPTIYHLRK KLVDSTDKAD LRLIYLALAH
 161  MIKFRGHFLI EGDLNPDNSD VDKLFIQLVQ TYNQLFEENP INASGVDAKA ILSARLSKSR RLENLIAQLP GEKKNGLFGN
 241  LIALSLGLTP NFKSNFDLAE DAKLQLSKDT YDDDLDNLLA QIGDQYADLF LAAKNLSDAI LLSDILRVNT EITKAPLSAS
 321  MIKRYDEHHQ DLTLLKALVR QQLPEKYKEI FFDQSKNGYA GYIDGGASQE EFYKFIKPIL EKMDGTEELL VKLNREDLLR
 401  KQRTFDNGSI PHQIHLGELH AILRRQEDFY PFLKDNREKI EKILTFRIPY YVGPLARGNS RFAWMTRKSE ETITPWNFEE
 481  VVDKGASAQS FIERMTNFDK NLPNEKVLPK HSLLYEYFTV YNELTKVKYV TEGMRKPAFL SGEQKKAIVD LLFKTNRKVT
 561  VKQLKEDYFK KIECFDSVEI SGVEDRFNAS LGTYHDLLKI IKDKDFLDNE ENEDILEDIV LTLTLFEDRE MIEERLKTYA
 641  HLFDDKVMKQ LKRRRYTGWG RLSRKLINGI RDKQSGKTIL DFLKSDGFAN RNFMQLIHDD SLTFKEDIQK AQVSGQGDSL
 721  HEHIANLAGS PAIKKGILQT VKVVDELVKV MGRHKPENIV IEMARENQTT QKGQKNSRER MKRIEEGIKE LGSQILKEHP
 801  VENTQLQNEK LYLYYLQNGR DMYVDQELDI NRLSDYDVDH IVPQSFLKDD SIDNKVLTRS DKNRGKSDNV PSEEVVKKMK
 881  NYWRQLLNAK LITQRKFDNL TKAERGGLSE LDKAGFIKRQ LVETRQITKH VAQILDSRMN TKYDENDKLI REVKVITLKS
 961  KLVSDFRKDF QFYKVREINN YHHAHDAYLN AVVGTALIKK YPKLESEFVY GDYKVYDVRK MIAKSEQEIG KATAKYFFYS
1041  NIMNFFKTEI TLANGEIRKR PLIETNGETG EIVWDKGRDF ATVRKVLSMP QVNIVKKTEV QTGGFSKESI LPKRNSDKLI
1121  ARKKDWDPKK YGGFDSPTVA YSVLVVAKVE KGKSKKLKSV KELLGITIME RSSFEKNPID FLEAKGYKEV KKDLIIKLPK
1201  YSLFELENGR KRMLASAGEL QKGNELALPS KYVNFLYLAS HYEKLKGSPE DNEQKQLFVE QHKHYLDEII EQISEFSKRV
1281  IIADANLDKV LSAYNKHRDK PIREQAENII HLFTLTNLGA PAAFKYFDTT IDRKRYTSTK EVLDATLIHQ SITGLYETRI
1361  DLSQLGGDSR ADPKKKRKV
```

CRISPR-ASSOCIATED (CAS) PROTEINS WITH REDUCED IMMUNOGENICITY

SEQUENCE LISTING

The instant application contains a Sequence Listing which was submitted electronically in ASCII format on May 10, 2018 and is hereby incorporated by reference in its entirety. Said ASCII copy, created on May 10, 2018, is named 0132-0015US1_seqlist.txt and is 149,983 bytes in size.

FIELD OF THE INVENTION

The field of the invention is cellular and molecular biology and genetic engineering. Specifically, the invention relates to methods of reducing the immunogenicity of CRISPR-associated (Cas) proteins and the modified Cas proteins produced therefrom. In addition, the invention relates to methods for cell and gene therapy, including any and all genetic modifications and alterations of gene expression (and/or genetic elements) made in-vivo or ex-vivo, using Cas proteins with reduced immunogenicity.

BACKGROUND OF THE INVENTION

The Clustered Regularly Interspaced Short Palindromic Repeats (CRISPR) and associated proteins (Cas proteins), which comprise the CRISPR-Cas system, were first identified in selected bacterial species and form part of a prokaryotic adaptive immune system. See Sorek, et al., "CRISPR—a widespread system that provides acquired resistance against phages in bacteria and archaea," *Nat. Rev. Microbiol.* 6(3)181-6 (2008), which is incorporated by reference herein in its entirety. CRISPR-Cas systems have been classified into three main types: Type I, Type II, and Type III. The main defining features of the separate Types are the various cas genes, and the respective proteins they encode, that are employed. The cas1 and cas2 genes appear to be universal across the three main Types, whereas cas3, cas9, and cas10 are thought to be specific to the Type I, Type II, and Type III systems, respectively. See, e.g., Barrangou, R. and Marraffini, L. A., "CRISPR-Cas systems: prokaryotes upgrade to adaptive immunity," *Mol. Cell.* 54(2):234-44 (2014), which is incorporated by reference herein in its entirety.

In general, the CRISPR-Cas system functions by capturing short regions of invading viral or plasmid DNA and integrating the captured DNA into the host genome to form so-called CRISPR arrays that are interspaced by repeated sequences within the CRISPR locus. This acquisition of DNA into CRISPR arrays is followed by transcription and RNA processing.

Depending on the bacterial species, CRISPR RNA processing proceeds differently. For example, in the Type II system, originally described in the bacterium *Streptococcus pyogenes*, the transcribed RNA is paired with a transactivating RNA (tracrRNA) before being cleaved by RNase III to form an individual CRISPR-RNA (crRNA). The crRNA is further processed after binding by the Cas9 nuclease to produce the mature crRNA. The crRNA/Cas9 complex subsequently binds to DNA containing sequences complimentary to the captured regions (termed protospacers). The Cas9 protein then cleaves both strands of DNA in a site-specific manner, forming a double-strand break (DSB). This provides a DNA-based memory, resulting in rapid degradation of viral or plasmid DNA upon repeat exposure and/or infection. The native CRISPR system has been comprehensively reviewed (see, e.g., Barrangou, R. and Marraffini, L. A., 2014).

Since its original discovery, multiple groups have done extensive research around potential applications of the CRISPR system in genetic engineering, including gene editing (Jinek et al., "A programmable dual-RNA-guided DNA endonuclease in adaptive bacterial immunity," *Science* 337(6096):816-21 (2012); Cong et al., "Multiplex genome engineering using CRISPR/Cas systems," *Science* 339 (6121):819-23 (2013); and Mali et al., "RNA-guided human genome engineering via Cas9," *Science* 339(6121):823-26; each of which is incorporated by reference herein in its entirety). One major development was utilization of a chimeric RNA to target the Cas9 protein, designed around individual units from the CRISPR array fused to the tracrRNA. This creates a single RNA species, called a small guide RNA (gRNA) where modification of the sequence in the protospacer region can target the Cas9 protein site-specifically. Considerable work has been done to understand the nature of the base-pairing interaction between the chimeric RNA and the target site, and its tolerance to mismatches, which is highly relevant in order to predict and assess off-target effects (see, e.g., Fu et al., "Improving CRISPR-Cas nucleases using truncated guide RNAs," *Nature Biotechnology* 32(3):279-84 (2014), and supporting material, which is incorporated by reference herein in its entirety).

The CRISPR-Cas9 gene editing system has been used successfully in a wide range of organisms and cell lines, both in order to induce DSB formation using the wild type Cas9 protein or to nick a single DNA strand using a mutant protein termed Cas9n/Cas9 D10A (see, e.g., Mali et al., (2013) and Sander and Joung, "CRISPR-Cas systems for editing, regulating and targeting genomes," *Nature Biotechnology* 32(4): 347-55 (2014), each of which is incorporated by reference herein in its entirety). While double-strand break (DSB) formation results in creation of small insertions and deletions (indels) that can disrupt gene function, the Cas9n/Cas9 D10A nickase avoids indel creation (the result of repair through non-homologous end-joining) while stimulating the endogenous homologous recombination machinery. Thus, the Cas9n/Cas9 D10A nickase can be used to insert regions of DNA into the genome with high-fidelity.

In addition to genome editing, the CRISPR system has a multitude of other applications, including regulating gene expression, genetic circuit construction, and functional genomics, amongst others. Reviewed in Sander, J. D. and Joung, J. K. "CRISPR-Cas systems for editing, regulating and targeting genomes," *Nature Biotech.* 32(4):347-55 (2014), which is incorporated by reference herein in its entirety.

There is wide spread interest in using CRISPR both in vivo and ex vivo for gene and cell therapy applications. Such applications are particularly relevant where single (monogenic) genetic modifications have been associated with specific disease conditions. Furthermore, CRISPR can be used to aid insertion of heterologous DNA sequences to support cell engineering. A good example of this is in the generation of immunotherapies involving genetically engineered T cells, or CAR-T (chimeric antigen receptors) T-cell mediated therapies. See, e.g., Maus et al., "Adoptive immunotherapy for cancer or viruses," *Annual Rev. Immunol.* 32:189-225 (2014), which is incorporated by reference herein in its entirety. However, the broad applicability of CRISPR, particularly in the generation of new therapeutic treatments, comes with a number of challenges, many of which are described in Cox et al., "Therapeutic genome editing: prospects and challenges," *Nature Medicine* 21(2): 121-31 (2015) ("Cox 2015"), which is incorporated by reference herein in its entirety.

One key challenge identified by Cox et al., "Therapeutic genome editing: prospects and challenges," *Nature Medicine* 21(2):121-31 (2015), is the immunogenicity of the Cas9 protein. The use of polypeptides as therapeutics has the associated risk of generating undesirable immune responses in patients, typically defined by the generation of anti-drug antibody (ADA) responses. Such responses can be motivated by the presence of "foreign" epitopes in the molecule and can be exacerbated by extrinsic factors, such as the genomic and disease background of the patient, the dosing and administration regime utilized, the formulation, and the route of administration and impurities, amongst others. These immune responses can have a variety of consequences, from altered pharmacology, to increased drug clearance or neutralization and loss of therapeutic efficacy. In extreme cases, protein therapeutics can cause the development of severe allergic and anaphylactic reactions, with considerable risk to the patient.

Another well-characterized immune reaction to "foreign" agents is the so-called graft or transplant rejection (also termed host-versus-graft reaction), in which the endogenous immune system reacts against, causing the destruction of, foreign tissue. Tissue rejection can be mediated by humoral and cellular immune responses. In the case of genetically modified cells generated for the purpose of incorporating a missing copy of a gene (gene therapy) or to help the patient eliminating cancerous cells (e.g., CAR-T therapies), there is a risk that some of the "machinery" utilized for the genetic modification of the cells could be "presented" by the modified cells and be recognized by the host as a "foreign" agent. Such recognition would trigger a rejection reaction, which could potentially render ineffective such treatments or, in severe cases, potentially cause auto-immune reactions. For example, depending on the method of delivery for the Cas protein, there are different associated risks in relation to unwanted immune responses. Where the Cas protein is encoded by the cell (e.g. following viral delivery), there is a potential risk that cells engineered to express Cas proteins could present Cas peptides on their HLA (human leukocyte antigen) Class I proteins and trigger an immune reaction. Where Cas9 protein is "transfected" (ex vivo) there is additional potential risk of HLA Class II-mediated humoral or anaphylactic responses.

Various publications are cited herein, the disclosures of which are incorporated by reference herein in their entireties.

SUMMARY OF THE INVENTION

The present invention reduces the immunogenicity of Cas proteins, e.g., Cas9 proteins. As Cas9 is a bacterial protein, it is highly likely that it will contain immunogenic epitopes, as has been confirmed by a recent study (Wang et al., Human Gene Therapy 26(7):432-442 (2015), incorporated herein by reference in its entirety). The role of Cas protein immunogenicity in the use of CRISPR for therapeutic applications will depend on factors such as the method utilized to engineer the therapeutic cells (including the Cas9 delivery method) and the duration for which the Cas9 protein is required to be present in the recipient cell in order for the engineering to be efficacious. Thus, there is a need for methods for producing Cas proteins with reduced immunogenicity and the availability of such Cas proteins for use in genetic engineering, including gene and cell therapies.

In some embodiments, the invention is directed to a method for reducing the immunogenicity of a CRISPR-associated (Cas) protein, the method comprising introducing one or more amino acid substitutions into one or more residues corresponding to one or more major histocompatibility (MHC) Class I and/or Class II binding sites of the Cas protein to form a recombinant Cas protein.

In some embodiments, the position of the one or more amino acid substitutions is selected through epitope mapping. In some embodiments, the epitope mapping is in silico epitope mapping. In some embodiments, the epitope mapping comprises incubating an antigen presenting cell (APC) in the presence of a Cas protein, and identifying one or more peptides derived from the Cas protein bound to a major histocompatibility (MHC) Class I and/or Class II protein of the APC.

In some embodiments, the method of the invention further comprises isolating at least a portion of the MHC Class I and/or MHC Class II proteins from the APC. In some embodiments, the MHC Class I and/or MHC Class II proteins are isolated by immunoprecipitation. In some embodiments, at least one or more Cas peptides bound to the MHC Class I and/or MHC Class II proteins is identified by mass spectrometry.

In some embodiments, the method further comprises assaying the immunogenicity of the recombinant Cas protein by exposing the recombinant Cas protein to a population of T-cells and comparing the level of T-cell activation to the level of T-cell activation induced by a corresponding wild-type Cas protein. In some embodiments, the T-cell activation is determined by measuring T-cell proliferation. In some embodiments, the T-cell proliferation is measured by flow cytometry or ELISpot. In some embodiments, the T-cells are CD4+ T-cells. In some embodiments, the T-cells are CD8+ T-cells.

In some embodiments, the method further comprises assaying the immunogenicity of the recombinant Cas protein by exposing the recombinant Cas protein to a population of B-cells and comparing the level of B-cell activation to the level of B-cell activation induced by a corresponding wild-type Cas protein.

In some embodiments, the MHC Class I and MHC Class II proteins are HLA Class I and HLA Class II proteins, respectively.

In some embodiments, the recombinant Cas protein is derived from a prokaryote. In some embodiments, the prokaryote is a bacterium. In some embodiments, the bacterium is from the genera *Streptococcus, Staphylococcus,* or *Neisseria*. In some embodiments, the bacterium is *Streptococcus pyogenes, Streptococcus thermophilus, Staphylococcus aureus,* or *Neisseria meningitidis*. In some embodiments, the recombinant Cas protein is derived from Cas3, Cas9, or Cas10. In some embodiments, the recombinant Cas protein is derived from a Cas9-like protein, such as Cpf1, disclosed in Zetsche et al., "Cpf1 is a Single RNA-Guided Endonuclease of a Class 2 CRISPR-Cas System," Cell 163:759-771 (2015), incorporated herein by reference in its entirety. In some embodiments, the recombinant Cas protein is derived from Cas9.

In some embodiments, residues selected for substitution, which are contained within the one or more major histocompatibility (MHC) Class I and/or Class II bound epitopes are selected from the residues designated in FIG. 9. In some embodiments, the residues for substitution are selected from residues 16, 18, 31, 71, 81-82, 86, 97, 98, 105, 118, 126, 128, 132, 135, 136, 138-139, 155, 158, 164, 168, 185, 188, 192, 196, 216, 244, 271, 275, 278-279, 290, 300, 321, 333, 337, 351-352, 359, 362, 373, 375, 383, 395, 418, 419, 422-423, 430, 432-433, 462, 511-517, 553, 575, 578, 580, 583, 591, 594, 598, 626-627, 653-655, 694, 702, 704, 741, 746-748, 772, 775, 778, 780, 796, 799-800, 812, 814-816, 823, 950, 1001, 1008, 1013, 1015-1016, 1018, 1023, 1028-29, 1033-34, 1036, 1038-1039, 1043, 1045-1046, 1050-1051, 1067, 1072-1074, 1080, 1086-1089, 1094, 1137-1144, 1146, 1174, 1179, 1181, 1195-1196, 1198, 1200-1202, 1204, 1213-1215, 1217-1218, 1220, 1235, 1237, 1242, 1294, 1297-98, 1309, 1313, 1318, 1348, 1352, 1355-1356, and/or 1362 of *Streptococcus pyogenes* Cas9, or corresponding residues of *Streptococcus thermophilus* Cas9, *Staphylococcus aureus* Cas9, or *Neisseria meningitidis* Cas9.

In some embodiments, the residues for substitution are selected from residues 5, 7, 9-11, 25-27, 31, 33, 43, 47, 51, 85, 90, 97-98, 118-119, 128, 136, 168-170, 181, 184, 186, 188, 196, 211, 222, 229, 248, 252, 256, 264, 266-267, 278, 292, 300, 302, 305-306, 308, 312, 321, 322, 324, 334, 335, 351, 352, 359, 362, 363, 372, 375, 377, 380, 383, 390-391, 399, 403, 405, 409, 410, 432, 450-451, 455-456, 462, 469, 471, 473, 476, 488, 491-492, 529-530, 534, 539, 548, 553, 557-559, 561, 564, 578, 594-595, 598, 600-601, 606, 615, 631-632, 636, 639, 643, 651-653, 655-656, 661, 666, 679-680, 683, 704, 720, 724, 727, 733, 735, 738, 741, 747-751, 753, 758-761, 763, 765-766, 788, 791, 793, 795-796, 830-834, 836, 838, 841, 845-847, 867, 869-870, 872, 891, 914, 916-917, 919, 922, 925, 927, 931, 934-935, 943, 953-954, 970, 972-973, 988, 1008-1009, 1013, 1015, 1019, 1021, 1029, 1036-1039, 1042, 1045-1046, 1060, 1092, 1096, 1100, 1105, 1110, 1131, 1141, 1143, 1145-1146, 1149, 1157-1160, 1163-1164, 1181-1182, 1187, 1190, 1210, 1212, 1238, 1265, 1266, 1273, 1276, 1280, 1298, 1302, 1310, 1313, 1315, 1326-1327, 1335-1336, 1342, 1347-1348, 1352, 1355, and/or 1360 of *Streptococcus pyogenes* Cas9, or corresponding residues of *Streptococcus thermophilus* Cas9, *Staphylococcus aureus* Cas9, or *Neisseria meningitidis* Cas9.

In some embodiments, the residues for substitution are selected from residues 8, 50, 53-54, 76, 77, 79, 82, 89, 92-93, 135, 147, 169, 176-180, 183-184, 203, 208, 211, 240-241, 248, 251-252, 266, 268, 271-273, 278, 280, 305, 307-308, 347-348, 350, 353, 356, 372, 375-377, 379, 381, 412, 467, 595, 607, 628, 631, 643, 649, 676, 688-690, 702, 718, 724-726, 728, 735, 754-756, 764, 788, 792, 795-796, 799, 828, 835, 864-865, 871-873, 875-876, 932, 934-935, 990, 1024, 1030, 1055, 1069, 1071-1072, and/or 1097 of *Streptococcus thermophilus* Cas9, or corresponding residues of *Streptococcus pyogenes* Cas9, *Staphylococcus aureus* Cas9, or *Neisseria meningitidis* Cas9.

In some embodiments, the residues for substitution are selected from residues 5, 6, 8, 10, 12, 15, 19, 20, 23, 28, 33-35, 37-38, 40, 43-47, 50, 69-70, 75-76, 79, 82, 93, 118, 120-121, 135-139, 159, 162, 165,169, 183-184, 186, 189, 196, 207, 211, 234, 238, 241, 251-252, 254, 256, 273, 298, 304-307, 309, 314, 347, 350, 356-357, 359, 362, 364, 367-368, 372, 375, 377-378, 381, 384, 386, 388, 396, 400, 401, 427, 429, 431-432, 455, 457, 467, 478, 506-511, 523, 528-529, 538-539, 545, 554-556, 567-568, 577, 588, 597, 600, 607, 631, 641, 643, 670, 673, 675-676, 678-700, 684-685, 689, 692, 701-704, 707, 715, 718, 722, 725-726, 728, 747, 753, 755, 761, 764, 769-770, 772, 778, 792, 795-796, 798-799, 804, 810, 818, 822, 861, 865, 882, 884-885, 889-890, 895-896, 898-899, 919-920, 932, 935, 937-938, 942, 946, 965, 970-971, 999, 1004, 1019, 1021, 1023-1024, 1031, 1042-1043, 1066, 1069, 1096, 1099, and/or 1104 of *Streptococcus thermophilus* Cas9, or corresponding residues of *Streptococcus pyogenes* Cas9, *Staphylococcus aureus* Cas9, or *Neisseria meningitidis* Cas9.

In some embodiments, the residues for substitution are selected from residues 18, 48, 51, 55, 70, 72, 86, 89, 176, 197, 211-212, 219-221, 223, 233, 235-236, 239-241, 256, 277, 345, 347, 351, 358, 389, 407-408, 415, 420-421, 444, 468, 500, 519, 565, 568-569, 573, 604, 609, 625, 651, 657, 664, 666, 669, 675, 683, 688, 698-703, 705, 707-708, 713, 744, 754, 760, 769-771, 773-774, 808-809, 837, 855, 857-858, 897, 904-905, 912, 914, 918, 931, 939, 942, 947, 962, 966-967, 971, 974, 996, 1001 and/or 1004 of *Staphylococcus aureus* Cas9, or corresponding residues of *Streptococcus pyogenes* Cas9, *Streptococcus thermophilus* Cas9, or *Neisseria meningitidis* Cas9.

In some embodiments, the residues for substitution are selected from residues 5, 18, 21, 23, 26, 29, 34, 35, 51, 66-67, 70-72, 74, 76, 110, 118, 124, 132, 140, 145, 165, 170-171, 176, 190, 193, 197-198, 201-202, 204, 212, 216, 223, 229-230, 232, 234, 240, 244-245, 247, 249, 251, 262, 269, 277-278, 281, 283-284, 303, 305, 313, 329-330, 332, 335, 347-348, 351, 354-355, 358, 362, 364, 366, 368, 383, 386-387, 404, 407-408, 420, 423, 430, 444, 464, 470, 474-476, 478-480, 508-510, 519, 523-527, 529, 532, 535-536, 538, 541, 543, 555, 558, 565, 601, 615, 625, 627, 630, 632, 635, 637-638, 641, 644, 646, 680, 687-690, 694, 713-715, 718, 720-721, 732, 745, 771, 809, 816, 827-828, 847, 857, 864-865, 868, 877, 897, 912, 914, 916-917, 947, 974, 982, 989, 992, 1001, 1004, 1015-1016, 1019, 1030, 1032, 1038, 1041, 1046, and/or 1048 of *Staphylococcus aureus* Cas9, or corresponding residues of *Streptococcus pyogenes* Cas9, *Streptococcus thermophilus* Cas9, or *Neisseria meningitidis* Cas9.

In some embodiments, the one or more residues corresponding to the one or more major histocompatibility (MHC) Class I and/or Class II binding sites is selected from residues 24-26, 74-75, 77-78, 97, 106, 111, 113, 116, 118, 127, 136-138, 144, 226, 231, 272, 279-280, 287-288, 297, 304-305, 310, 317, 331-332, 335, 337, 342, 417, 423, 425, 427-430, 435, 441, 467, 472, 487, 516, 547, 554, 590, 592, 595-596, 599-600, 623, 632, 635-637, 639, 643-644, 646, 671-672, 675-676, 680, 686, 690, 692-694, 707, 710, 744, 746-748, 750, 752-753, 778-779, 806-807, 836, 844, 858-860, 864, 876, 878, 880-881, 883, 885, 888-892, 894-895, 936, 938, 948, 950, 952-953, 960-961, 965, 967, 988, 991, 1006, 1009, 1019-1020, 1033, 1035, 1057-1058, and/or 1066 of *Neisseria meningitidis* Cas9, or corresponding residues of *Streptococcus pyogenes* Cas9, *Streptococcus thermophilus* Cas9, or *Staphylococcus aureus* Cas9.

In some embodiments, the residues for substitution are selected from residues 12, 17, 41, 43-46, 49, 68, 95, 97, 120, 122, 125, 130, 158, 174, 185, 196, 199, 203, 205, 208, 212-213, 227, 235, 238-239, 254-255, 257, 260, 262-263, 283, 287, 289, 304, 311, 329-332, 337, 360, 365, 372, 374, 386, 388-391, 407-408, 410-412, 434, 439, 448, 458, 472, 478, 481, 487-488, 491-495, 497, 511, 513-515, 519, 537, 541, 545, 553-554, 556, 558-559, 568, 573, 577, 596, 604, 611, 632, 635, 643-644, 651, 662, 680-681, 685, 694, 702, 705-707, 709, 712, 716, 723, 725, 729, 747, 766, 791, 797, 821, 824, 828-830, 832, 838, 844, 852, 857, 859-862, 867, 875, 885, 891, 903, 907, 910, 919-920, 923-925, 928, 935, 941, 953, 959, 961-962, 964-965, 967, 973, 985, 988, 995, 999, 1001, 1010, 1016-1017, 1019-1020, 1028, 1030, 1058, 1001, and/or 1063 of *Neisseria meningitidis* Cas9, or corresponding residues of *Streptococcus pyogenes* Cas9, *Streptococcus thermophilus* Cas9, or *Staphylococcus aureus* Cas9.

In some embodiments, the MHC Class I and/or Class II binding sites of the Cas protein comprises a peptide comprising 9 (9mer) or 10 (10mer) amino acids. In some embodiments, the introduced amino acid substitution is a naturally occurring amino acid.

In some embodiments, the invention is directed to a recombinant CRISPR-associated (Cas) protein comprising one or more amino acid substitutions in one or more residues corresponding to one or more MHC Class I and/or MHC Class II binding sites in a wild-type Cas protein, wherein the recombinant Cas protein has reduced immunogenicity compared to a wild-type Cas protein. In some embodiments, wherein the MHC Class I and/or Class II binding sites of the Cas protein comprises a peptide comprising 9 (9mer) or 10 (10mer) amino acids. In some embodiments, the introduced amino acid substitution is a naturally occurring amino acid.

In some embodiments, the wild-type Cas protein comprises an amino sequence having at least 95% identity to the amino acid sequence of any one of SEQ ID NOs: 1-4.

In some embodiments, the invention is directed to a recombinant CRISPR-associated (Cas) protein made by a process comprising introducing one or more amino acid substitutions into one or more residues corresponding to one or more MHC Class I and/or MHC Class II binding sites of a wild-type Cas protein to form the recombinant Cas protein, wherein the recombinant Cas protein has reduced immunogenicity compared to the wild-type Cas protein. In some embodiments, the position of the one or more amino acid substitutions is determined by epitope mapping. In some embodiments, the epitope mapping is performed using in silico methods. In some embodiments, the epitope mapping is performed by a method comprising incubating an antigen presenting cell (APC) in the presence of a Cas protein and identifying peptides derived from the Cas protein bound to major histocompatibility (MHC) Class I and/or Class II proteins. In some embodiments, at least a portion of the MHC Class I and/or MHC Class II proteins bound to the Cas peptides is isolated. In some embodiments, the MHC Class I and/or MHC Class II proteins bound to the Cas peptides are isolated by immunoprecipitation.

In some embodiments, the invention is directed to a recombinant CRISPR-associated (Cas) protein comprising one or more substitutions in one or more amino acid residues of a wild-type Cas protein as designated in FIG. 9, wherein the recombinant Cas protein has reduced immunogenicity compared to the wild-type Cas protein.

In some embodiments, the invention is directed to an isolated nucleic acid molecule comprising a nucleotide sequence that encodes a recombinant CRISPR-associated (Cas) protein, wherein the recombinant Cas protein has one or more amino acid substitutions in one or more residues corresponding to one or more MHC Class I and/or MHC Class II binding sites of a wild-type Cas protein, wherein the recombinant Cas protein has reduced immunogenicity compared to a wild-type Cas protein.

In some embodiments, the invention is directed to a vector comprising the nucleic acid as described herein. In some embodiments, the vector is a viral vector. In some embodiments, the viral vector is an adeno-associated viral vector or a lentiviral vector.

In some embodiments, the invention is directed to a cell comprising the recombinant Cas protein as described herein. In some embodiments, the invention is directed to a cell comprising the nucleic acid as described herein. In some embodiments, the invention is directed to a cell comprising a vector as described herein. In some embodiments, the cell is a prokaryotic cell. In some embodiments, the cell is an *E. coli* cell. In some embodiments, the cell is a eukaryotic cell. In embodiments, the cell is a mammalian cell. In some embodiments, the cell is a lymphocytic cell, a myeloid cell, an induced pluripotent stem cell (iPSC), or a T cell, although all mammalian cell types are envisaged as being used in the invention.

In some embodiments, the invention is directed to a library for identifying a CRISPR-associated (Cas) protein with reduced immunogenicity, the library comprising at least one recombinant Cas protein comprising one or more amino acid substitutions in one or more residues corresponding to one or more MHC Class I and/or MHC Class II binding sites of a wild-type Cas protein.

In some embodiments, the invention is directed to a method for altering the DNA sequence and/or gene expression at a genomic location containing a target sequence, the method comprising introducing into a cell containing the genetic element a guide RNA that hybridizes to the target sequence and a recombinant CRISPR-associated (Cas) protein comprising one or more amino acid substitutions in one or more residues corresponding to one or more MHC Class I and/or MHC Class II binding sites in a wild-type Cas protein, wherein expression of the one or more genetic elements is altered. In some embodiments, the guide RNA and/or the recombinant Cas protein are transfected into the cell. In some embodiments, the guide RNA and/or the recombinant Cas protein are located on a vector. In some embodiments, the guide RNA and the recombinant Cas protein are located on the same vector. In some embodiments, the vector is a viral vector. In some embodiments, the viral vector is an adeno-associated viral vector or a lentiviral vector.

In some embodiments, the disclosure is directed to a recombinant CRISPR-associated (Cas) protein, wherein said protein comprises one or more amino acid variation compared to a while-type Cas protein, wherein the one or more amino acid variation is at one or more positions corresponding to amino acid residues in the polypeptide of SEQ ID NO: 5, wherein the variation is at a position selected from the group consisting of (i) residues 100 to 120, (ii) residues 250 to 280, (iii) residues 690 to 710, (iv) residues 840 to 860, and (v) residues 1270 to 1295.

In some embodiments, the variation is at a position selected from the group consisting of (i) residues 102 to 120, (ii) residues 253 to 277, (iii) residues 692 to 709, (iv) residues 692 to 709, and (v) residues 1276 to 1292.

In some embodiments, the variation is at a position selected from residues 102 to 120. In some embodiments, the variation is at a position selected from residues 253 to 277. In some embodiments, the variation is at a position selected from residues 692 to 709. In some embodiments, the variation is at a position selected from residues 692 to 709. In some embodiments, the variation is at a position selected from residues 1276 to 1292.

In some embodiments, the recombinant Cas protein comprises two or more amino acid variations. In some embodiments, the recombinant Cas protein comprises three or more amino acid variations. In some embodiments, the recombinant Cas protein comprises five or more amino acid variations. In some embodiments, the amino acid variation is a substitution of SEQ ID NO: 5 selected from the group consisting of one or more of the following:

| Position | Original residue | Possible substitutions |
| --- | --- | --- |
| 105 | F | D, E |
| 106 | L | D, E, G, K, P, Q, R |
| 107 | V | D, E, G |
| 258 | L | D, E, G, K, P |
| 263 | K | A, D, E, G, N, P, S, T |
| 264 | L | A, D, E, G, H, K, N, P, Q, R, S, T, V |
| 265 | Q | D, E, G, N, P, T |
| 266 | L | A, D, E, G, N, P, Q, S, T, V |
| 267 | S | A, D, E, G, H, P, T |
| 696 | L | E, G, P |
| 846 | F | E, W |
| 847 | L | D, E, F, G, H, K, N, P, Q, S, T, W |
| 852 | I | D, E, F, G, Y |
| 855 | K | D, E, G, P, S |
| 1278 | K | A, D, E, F, G, N, P, Q, S, T, V, W |
| 1279 | R | D, E, H, K, Q |
| 1280 | V | A, D, E, G, K, N, P, Q, S, T |
| 1281 | I | A, D, E, F, G, H, K, N, P, Q, R, S, T, W |
| 1282 | L | A, D, E, G, H, N, P, S, T |

In some embodiments, the amino acid variation is a substitution of SEQ ID NO: 5, wherein said amino acid substitutions include the following: L106D, K263D, L696G, L847D, and I1281D.

In some embodiments, the amino acid variation is determined using in silico epitope mapping.

In some embodiments, the amino acid variation is a substitution of one or more amino acids with one or more different amino acids.

In some embodiments, the amino acid variation comprises replacing one or more of aspargine, glutamine, leucine, lysine, methionine, serine, threonine, and valine residues with a different amino acid.

In some embodiments, the amino acid variation comprises replacing a polar amino acid with a nonpolar amino acid.

In some embodiments, the amino acid variation comprises replacing a hydrophilic amino acid with a hydrophobic amino acid.

In some embodiments, the amino acid variation is an insertion of one or more amino acids residues. In some embodiments, the amino acid variation is a deletion of one or more amino acid residues.

In some embodiments, the wild-type Cas protein has a sequence 90% identical to SEQ ID NO: 5. In some embodiments, the wild-type Cas protein is derived from a prokaryote. In some embodiments, the prokaryote is a bacterium. In some embodiments, the bacterium is from the genera *Streptococcus*, *Staphylococcus*, or *Neisseria*. In some embodiments, the bacterium is *Streptococcus pyogenes*, *Streptococcus thermophilus*, *Staphylococcus aureus*, or *Neisseria meningitidis*.

In some embodiments, the recombinant Cas protein is derived from Cas3, Cas9, or Cas10. In some embodiments, the recombinant Cas protein is derived from Cas9.

In some embodiments, the disclosure is directed to a polynucleotide encoding any Cas protein as described herein. In some embodiments, the disclosure is directed to an expression vector comprising any polynucleotide as described herein. In some embodiments, the disclosure is directed to a host cell comprising any expression vector as described herein.

BRIEF DESCRIPTION OF THE DRAWINGS

Figure 1:
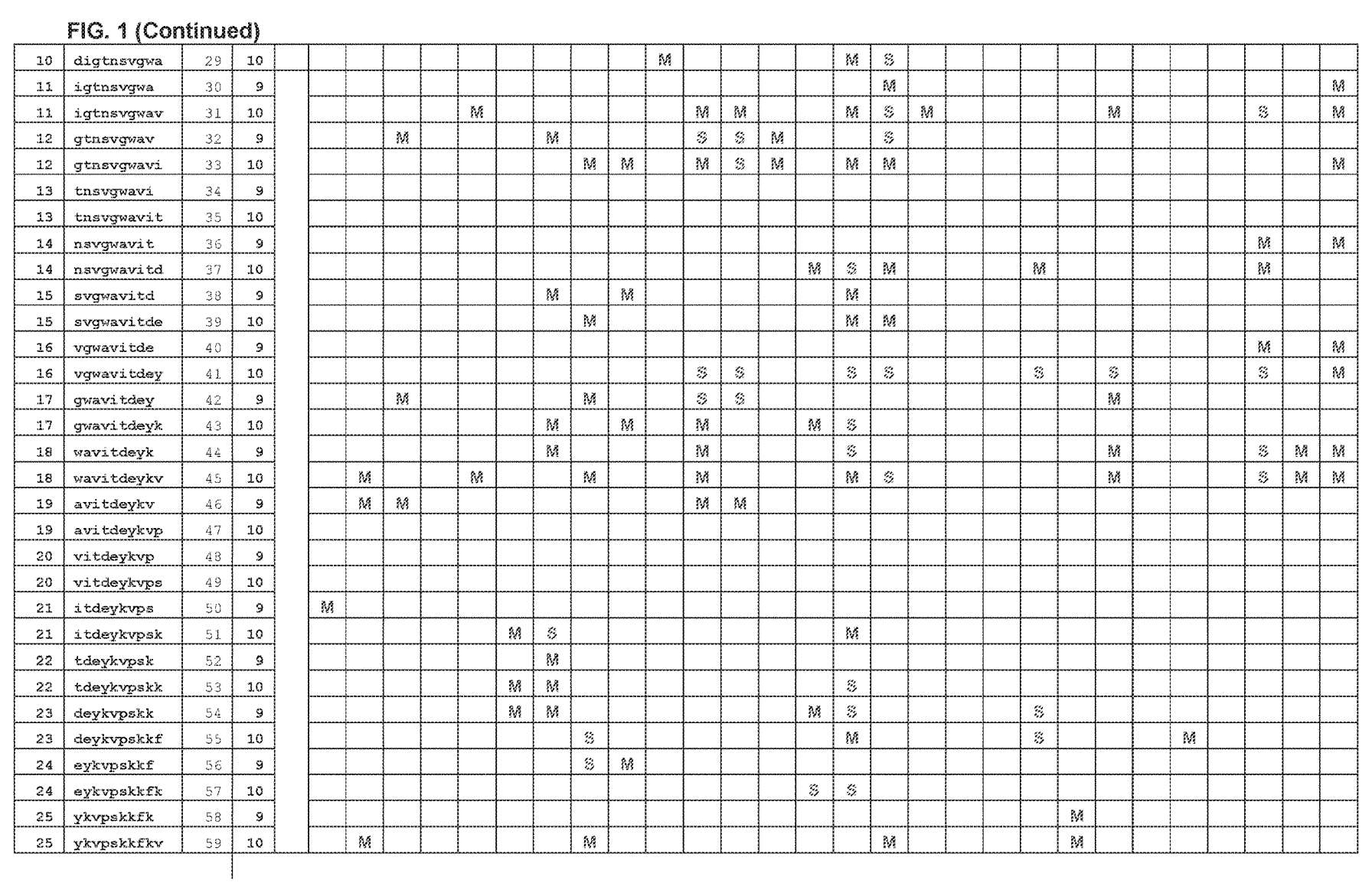
Figure 1:
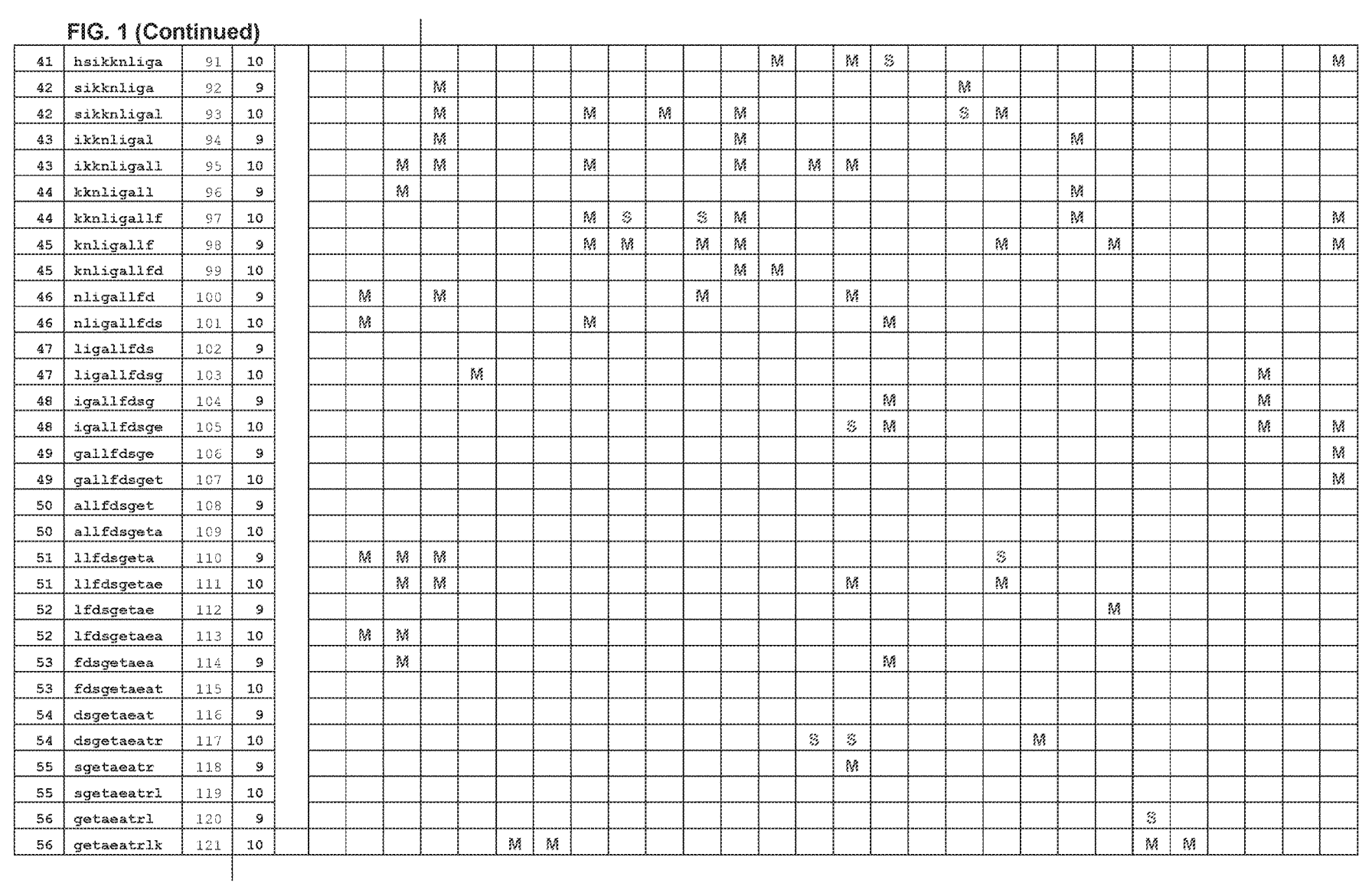
Figure 1:
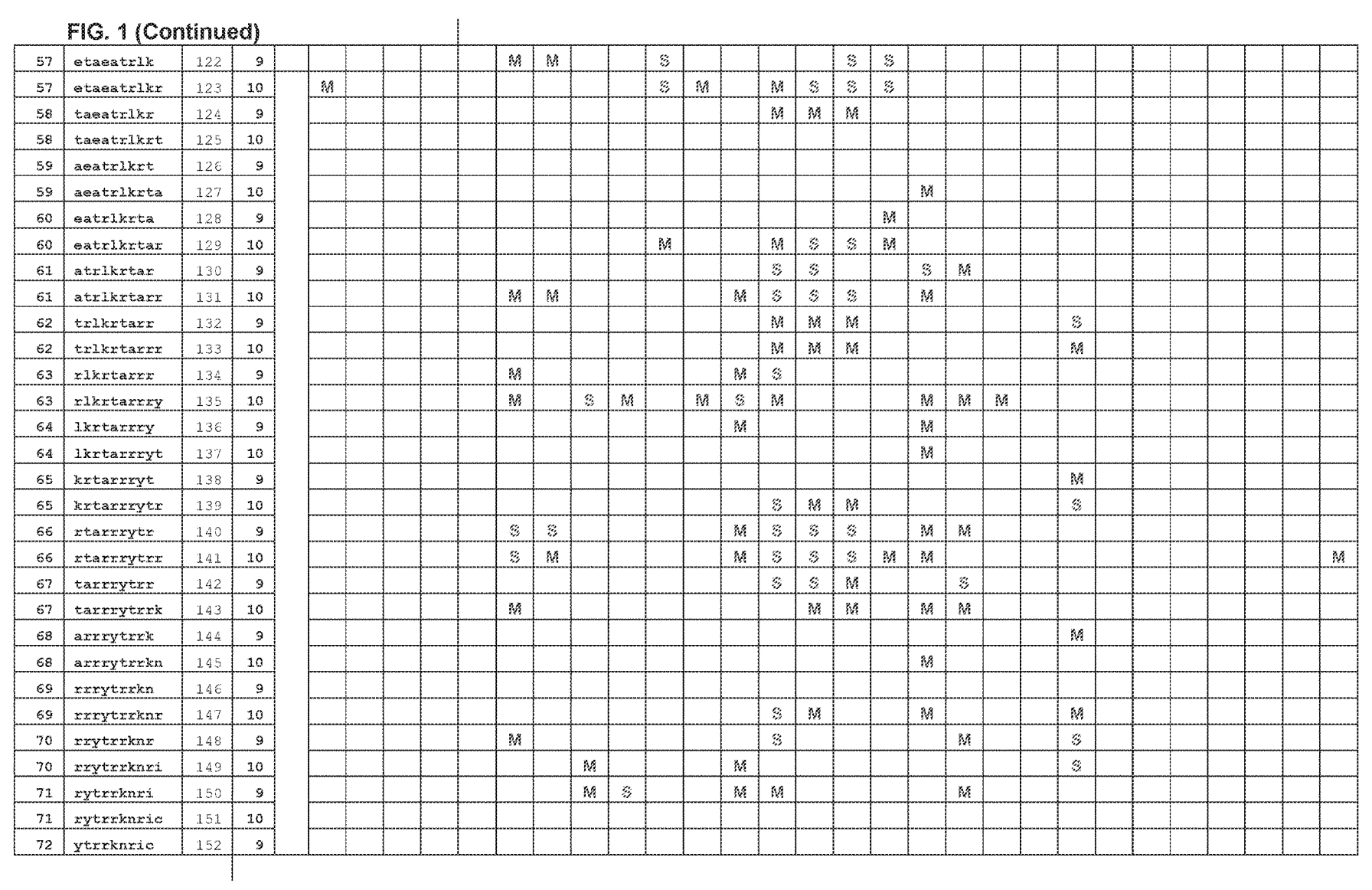
Figure 1:
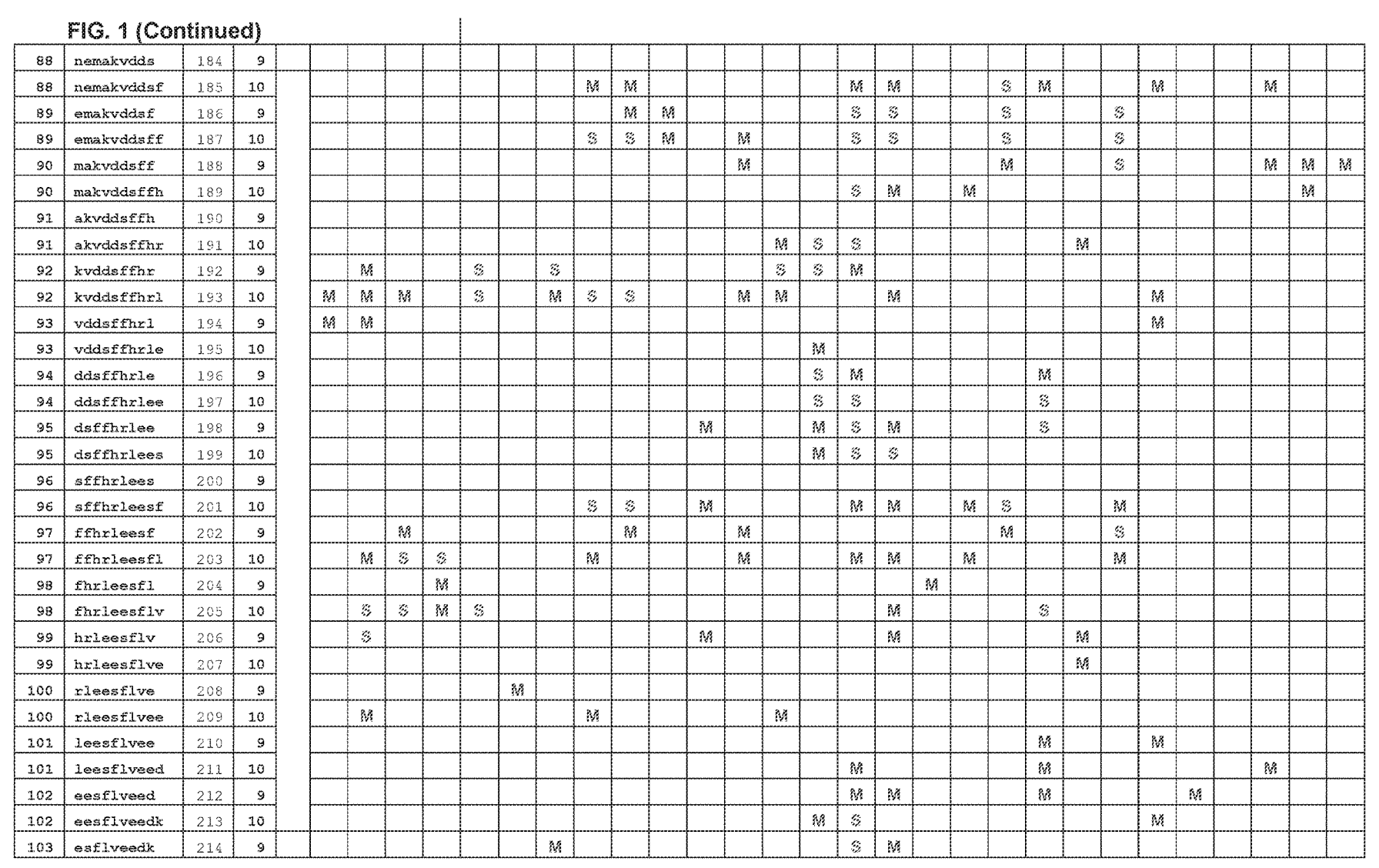

FIG. 1 is a map of strong (S) and medium (M) peptide binding sites, epitopes, derived from *Streptococcus pyogenes* Cas9 for HLA Class I allotypes. Epitopes in each category for 9-mer and 10-mer sequences are presented. Data are presented for the first 125 amino acids of the Cas9 sequence. Values for different allotypes are represented separately, with allotype references restricted to two digits.

FIGS. 2A, 2B, and 2C are maps of strong (S) and medium (M) peptide binding sites, epitopes, derived from *Streptococcus pyogenes* Cas9 for HLA Class II allotypes. Epitopes in each category for 10-mer sequences are presented. Data are presented for the first 125 amino acids of the Cas9 sequence. Values for different allotypes are represented separately, with allotype references restricted to two digits.

FIG. 3 is a map of strong (S) and medium (M) peptide binding sites, epitopes, derived from *Streptococcus pyogenes* Cas9 for HLA Class I allotypes. Epitopes in each category for 9-mer and 10-mer sequences are presented. Data are only presented for amino acids 1026-1150 of the Cas9 sequence. Values for different allotypes are represented separately, with allotype references restricted to two digits.

FIGS. 4A 4B and 4C are maps of strong (S) and medium (M) peptide binding sites, epitopes, derived from *Streptococcus pyogenes* Cas9 for HLA Class II allotypes. Epitopes in each category for 10-mer sequences are presented. Data are only presented for amino acids 1026-1150 of the Cas9 sequence. Values for different allotypes are represented separately, with allotype references restricted to two digits.

Figure 5B:
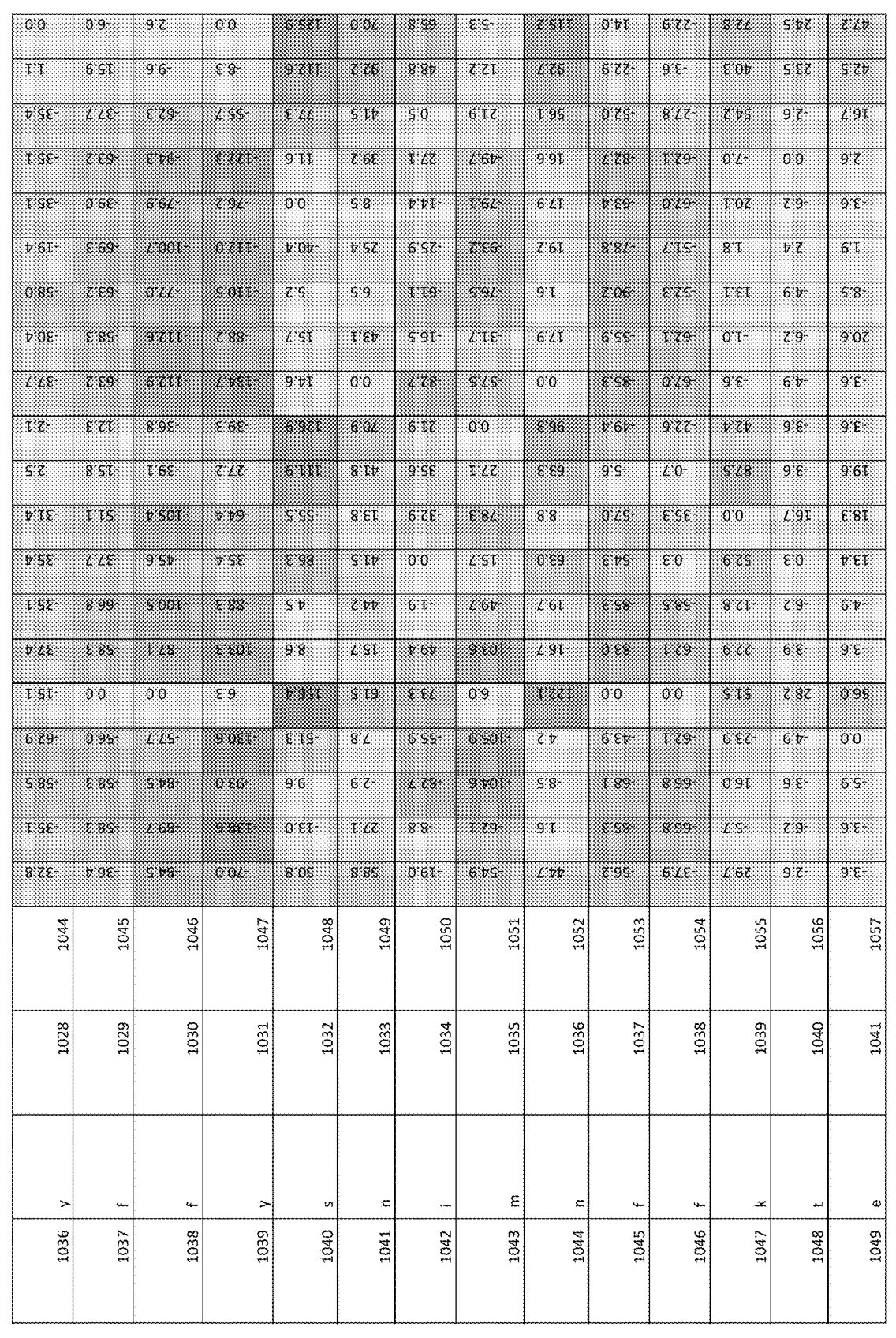
Figure 5B:
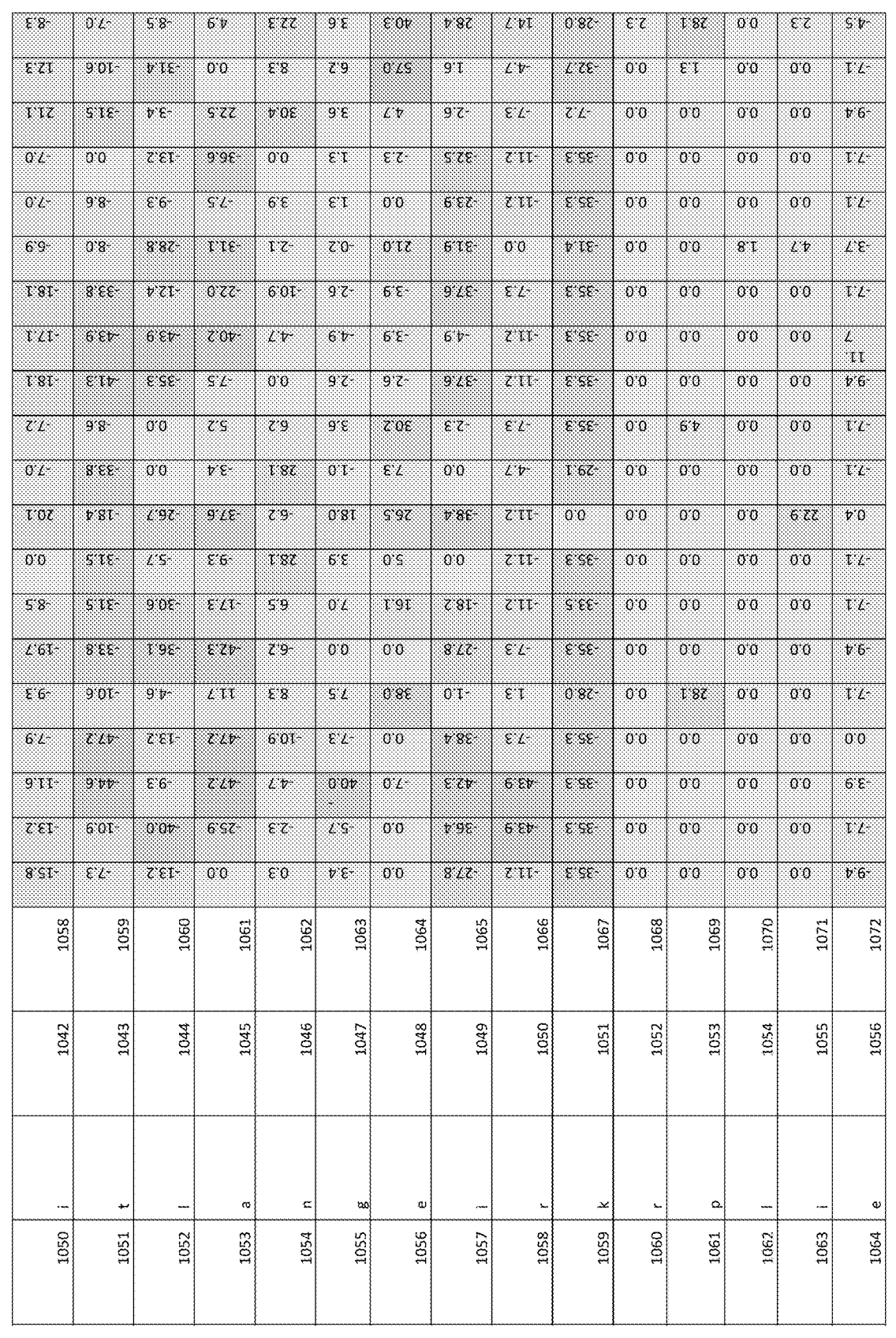
Figure 5B:
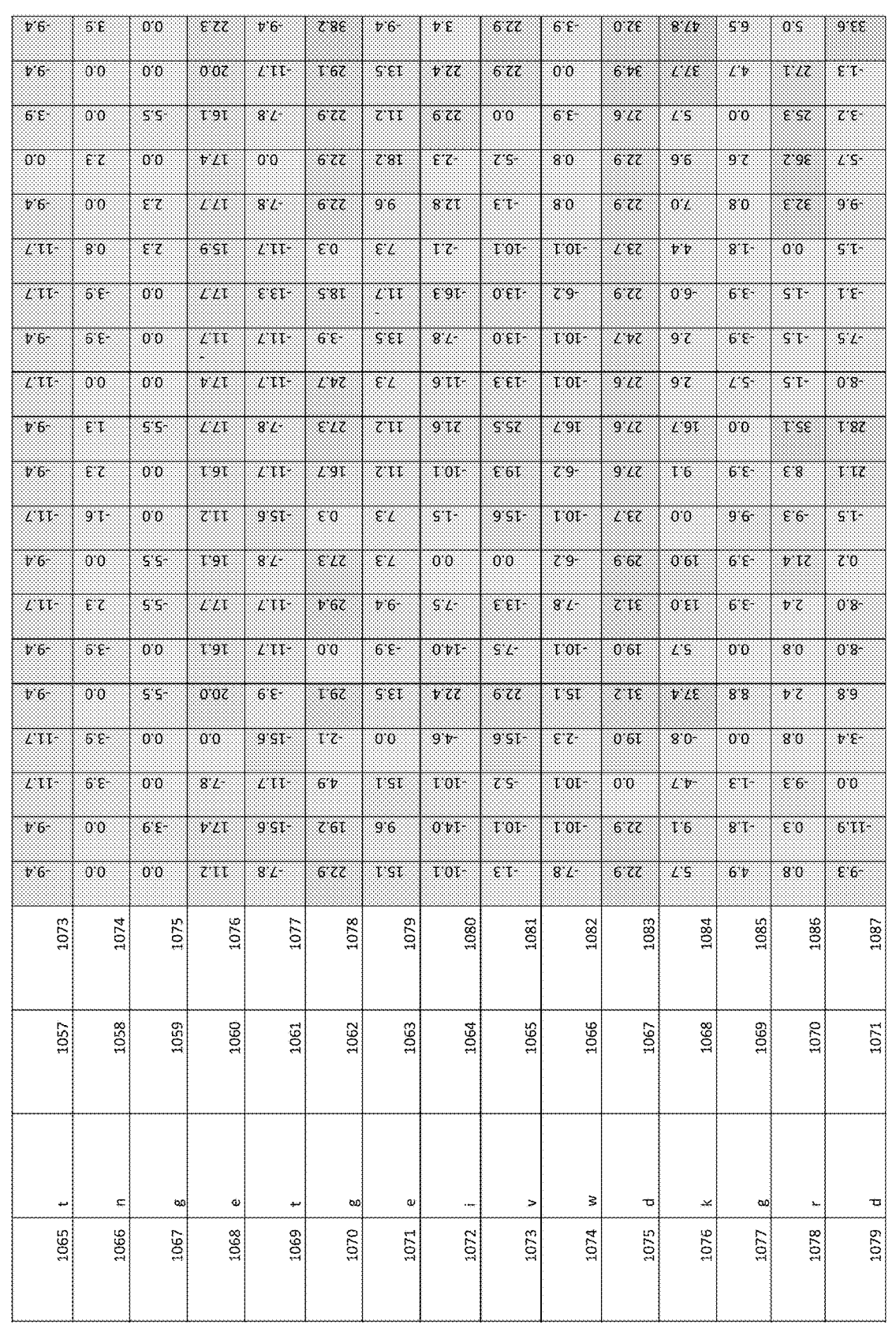
Figure 5B:
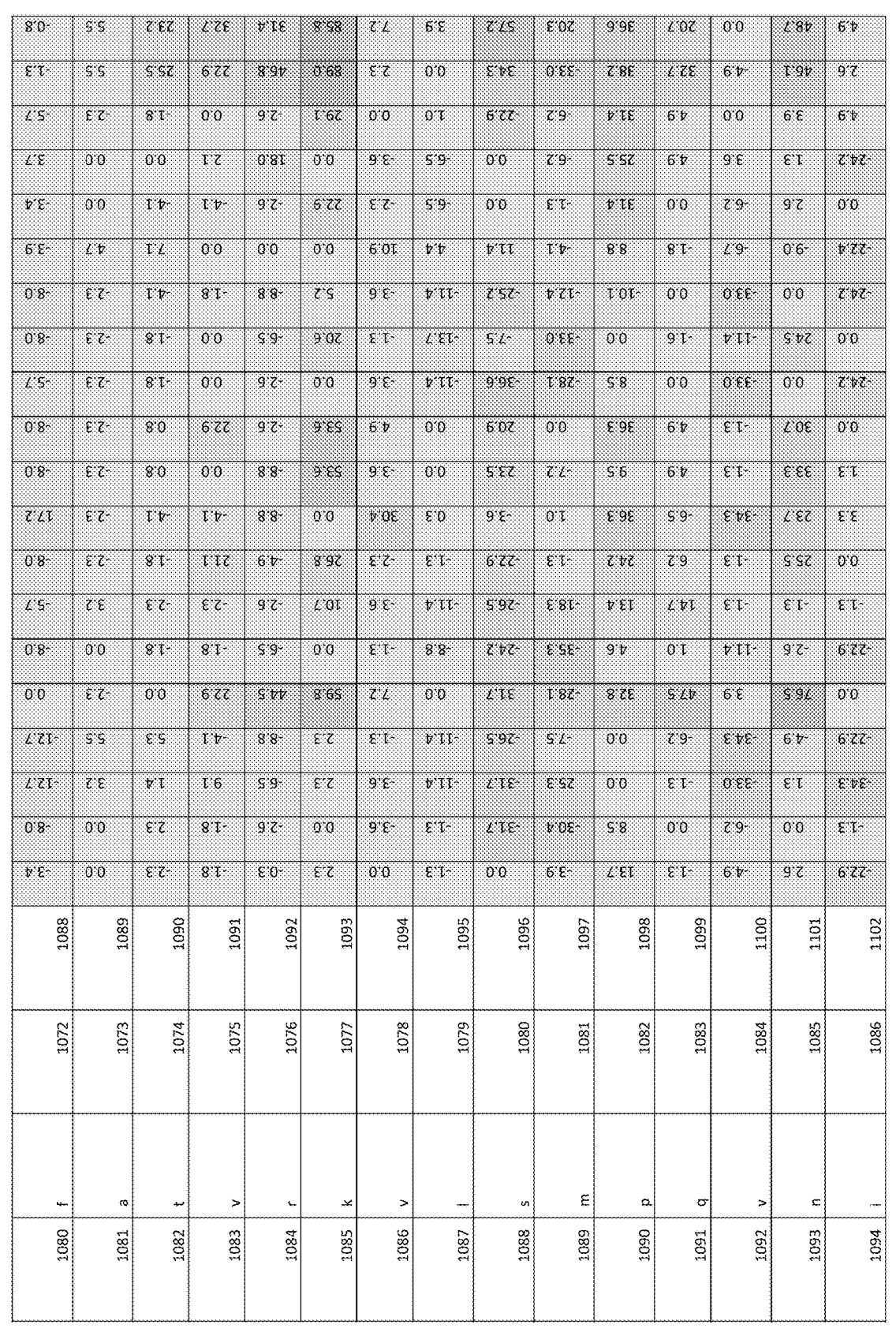
Figure 5B:
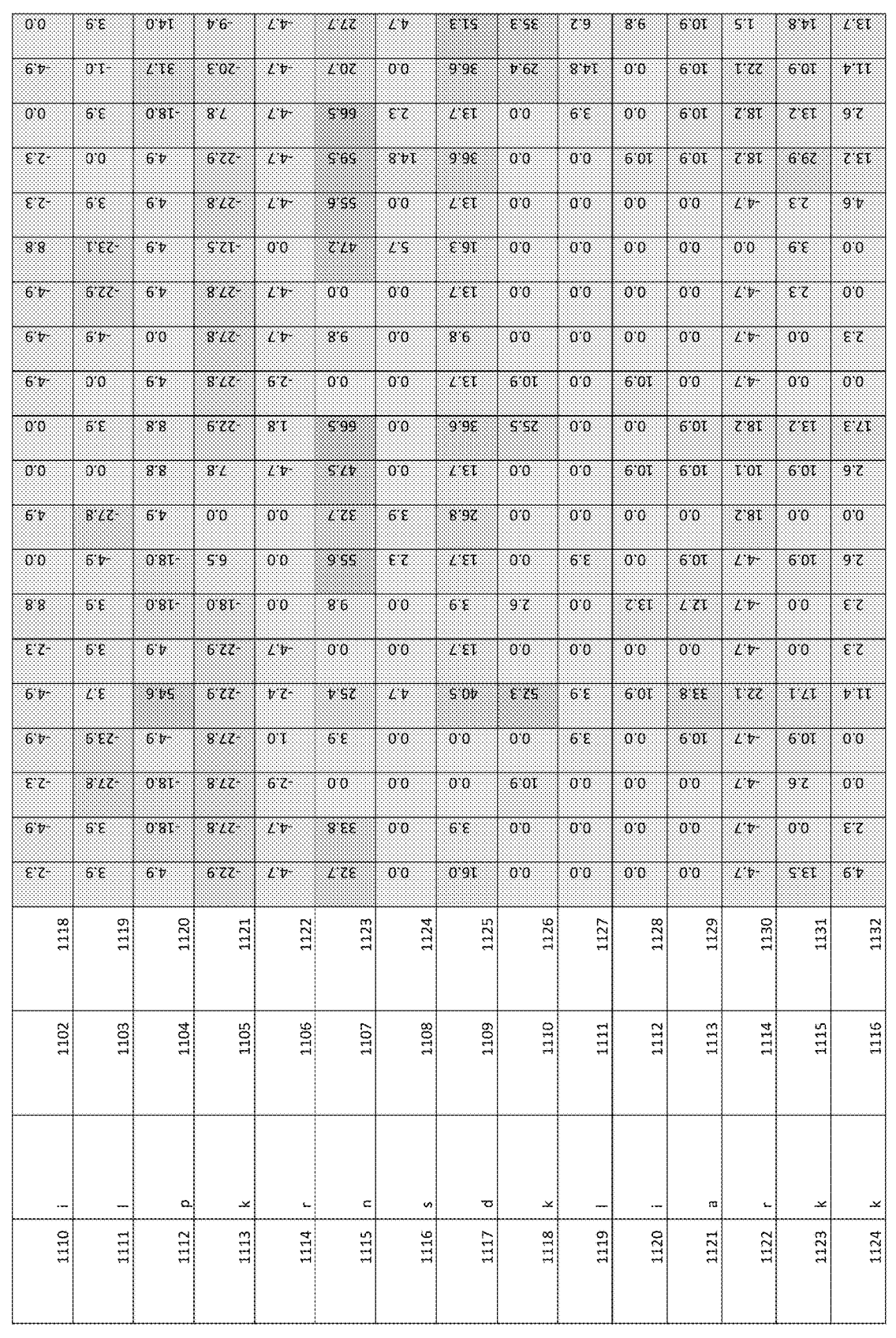
Figure 5B:
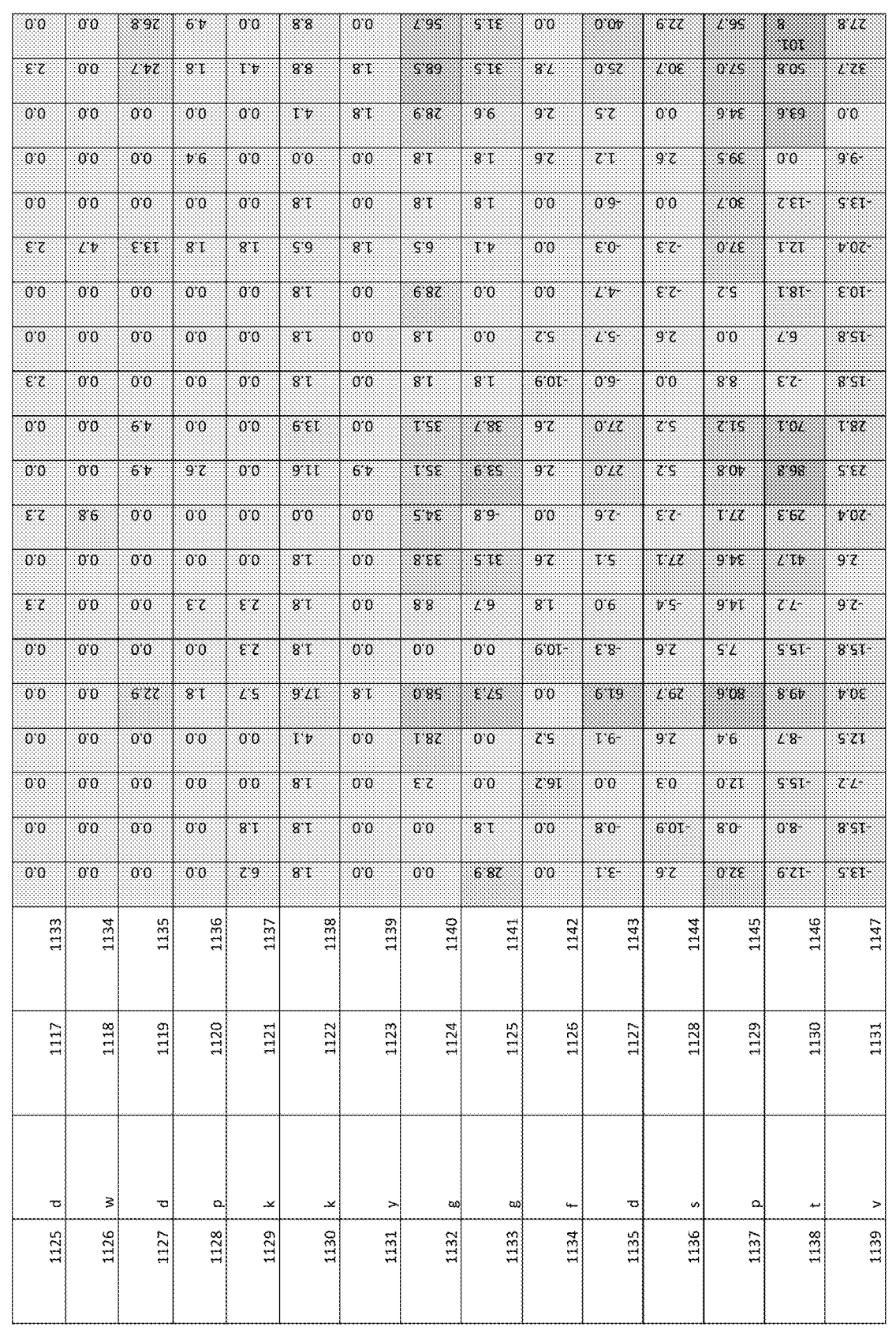
Figure 5B:
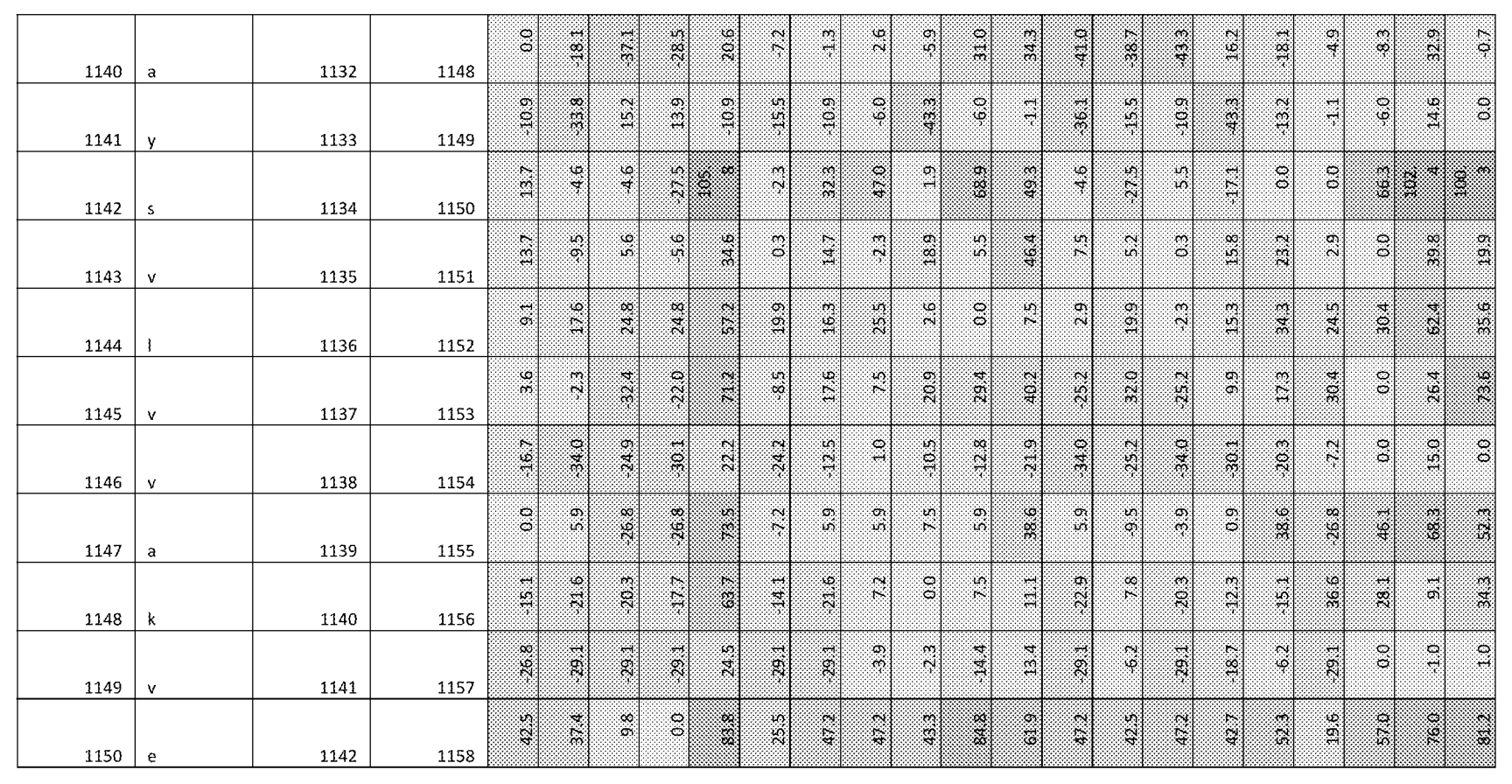
Figure 5C:
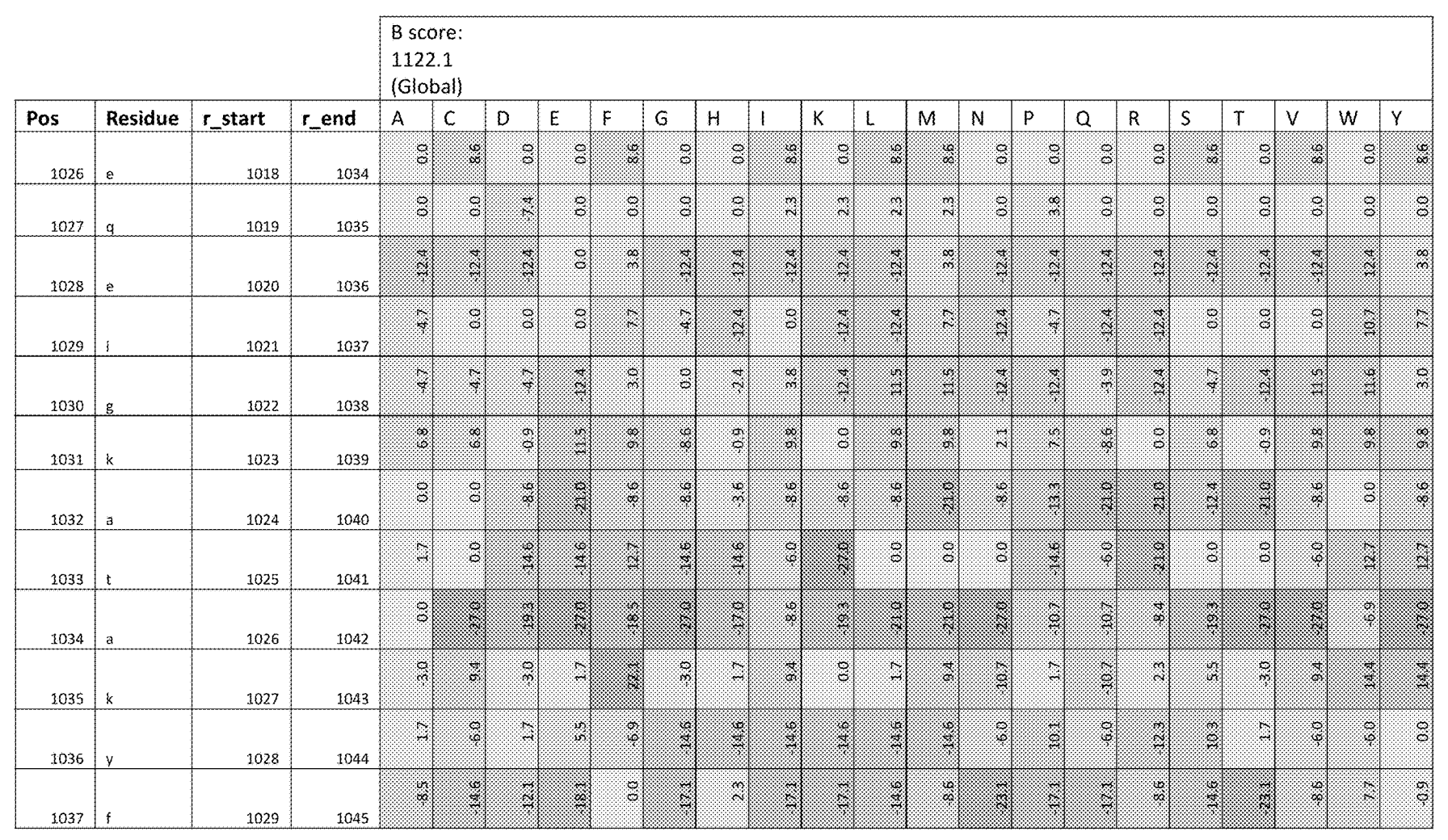
Figure 5C:
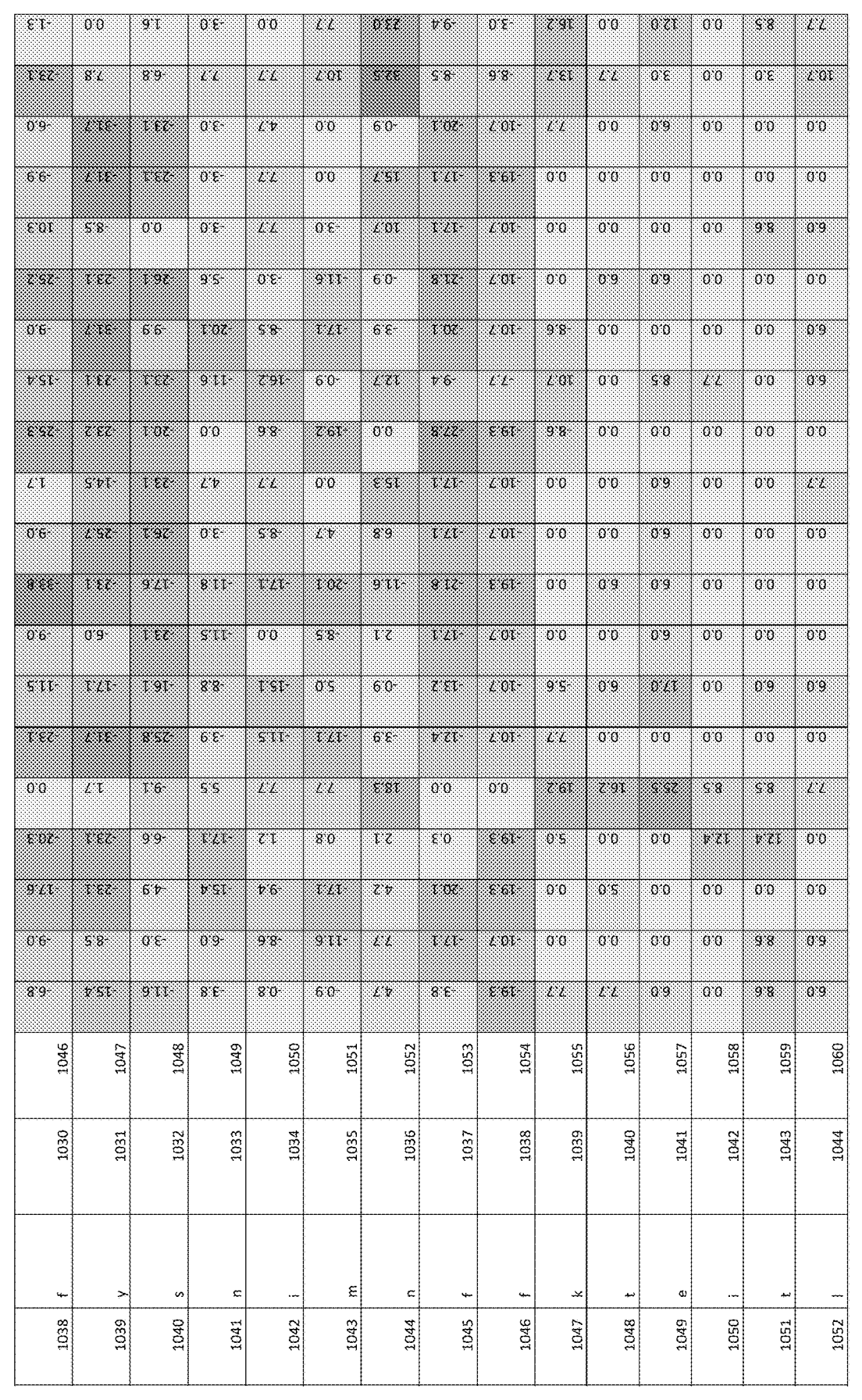
Figure 5C:
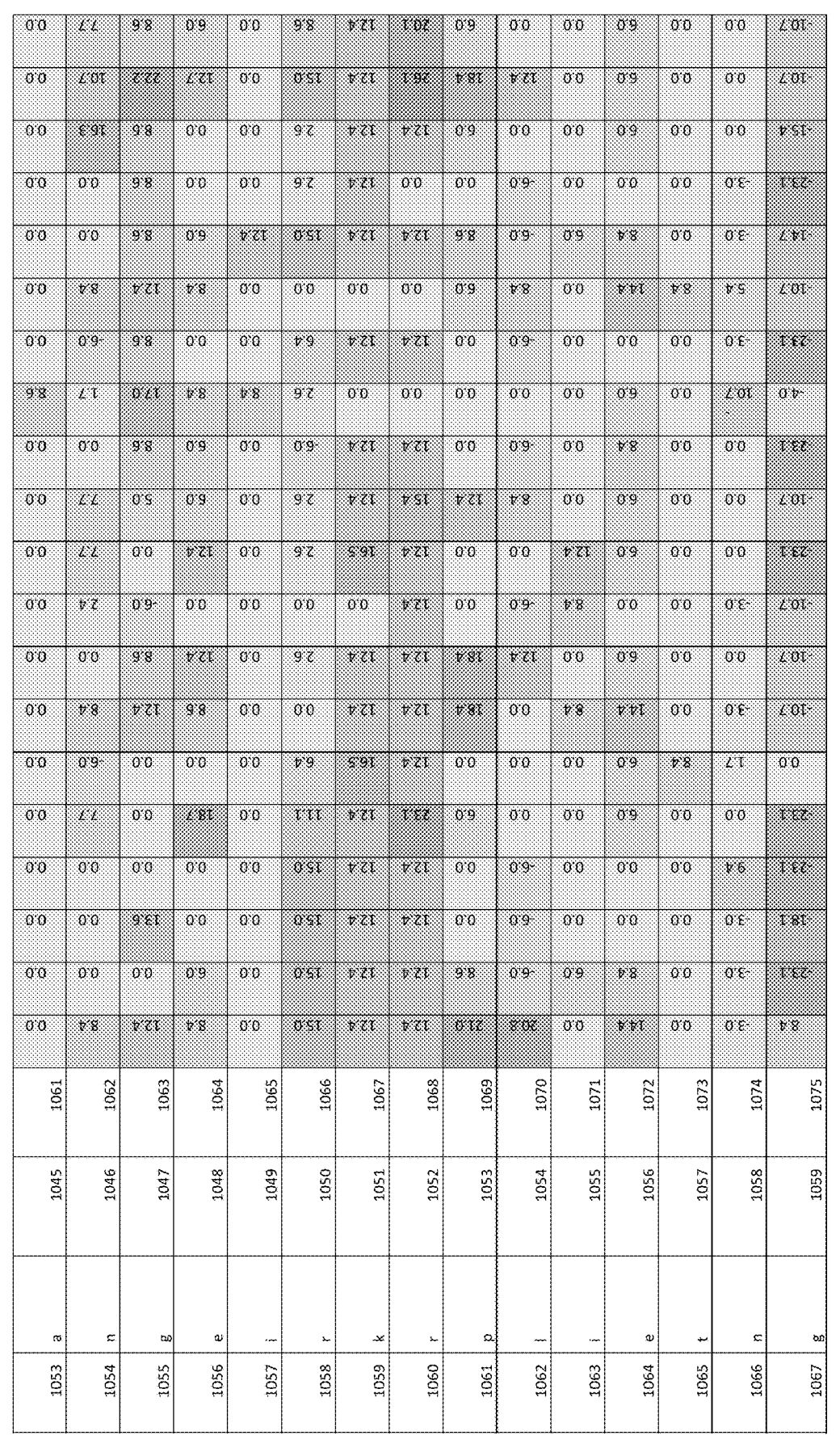
Figure 5C:
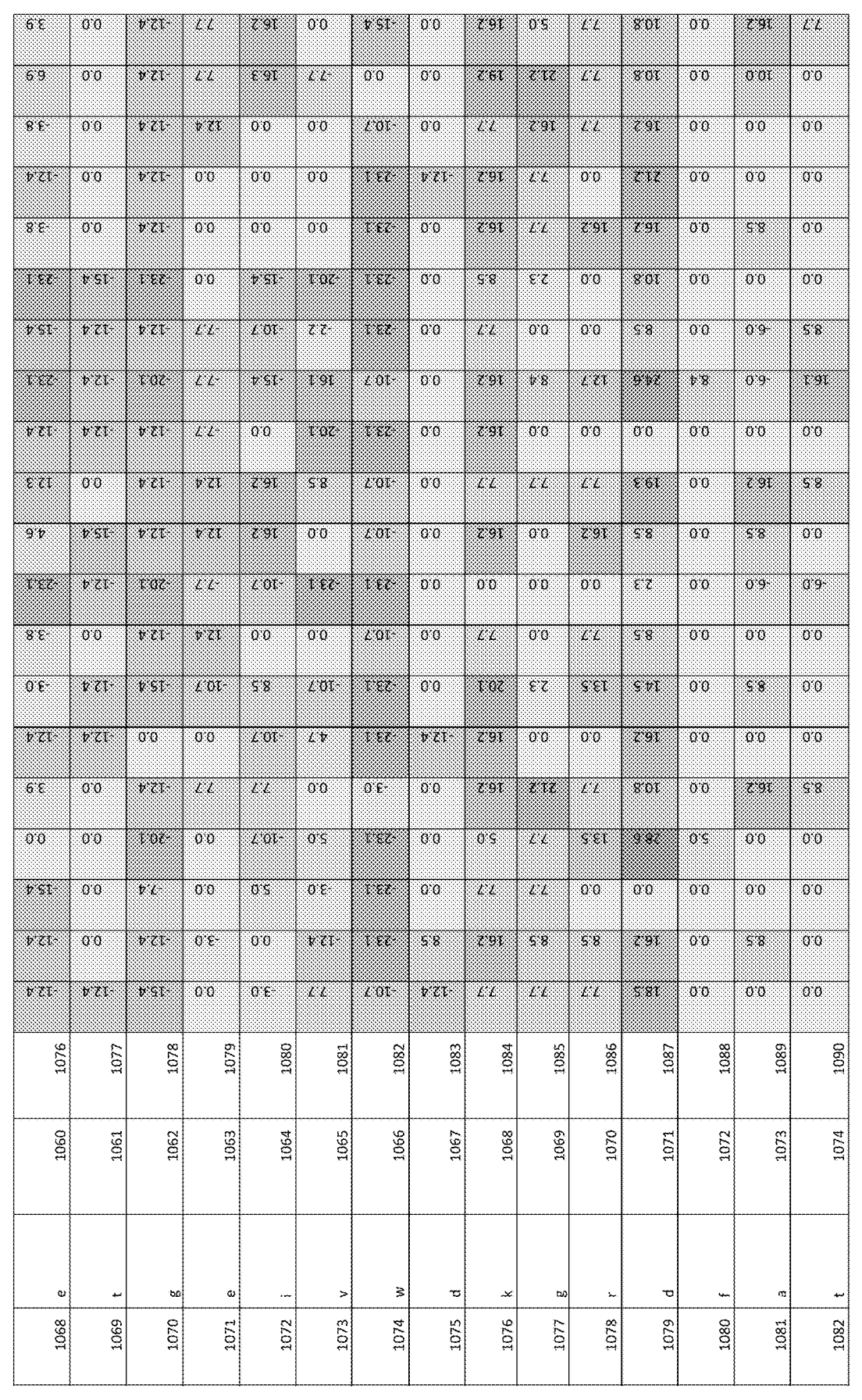
Figure 5C:
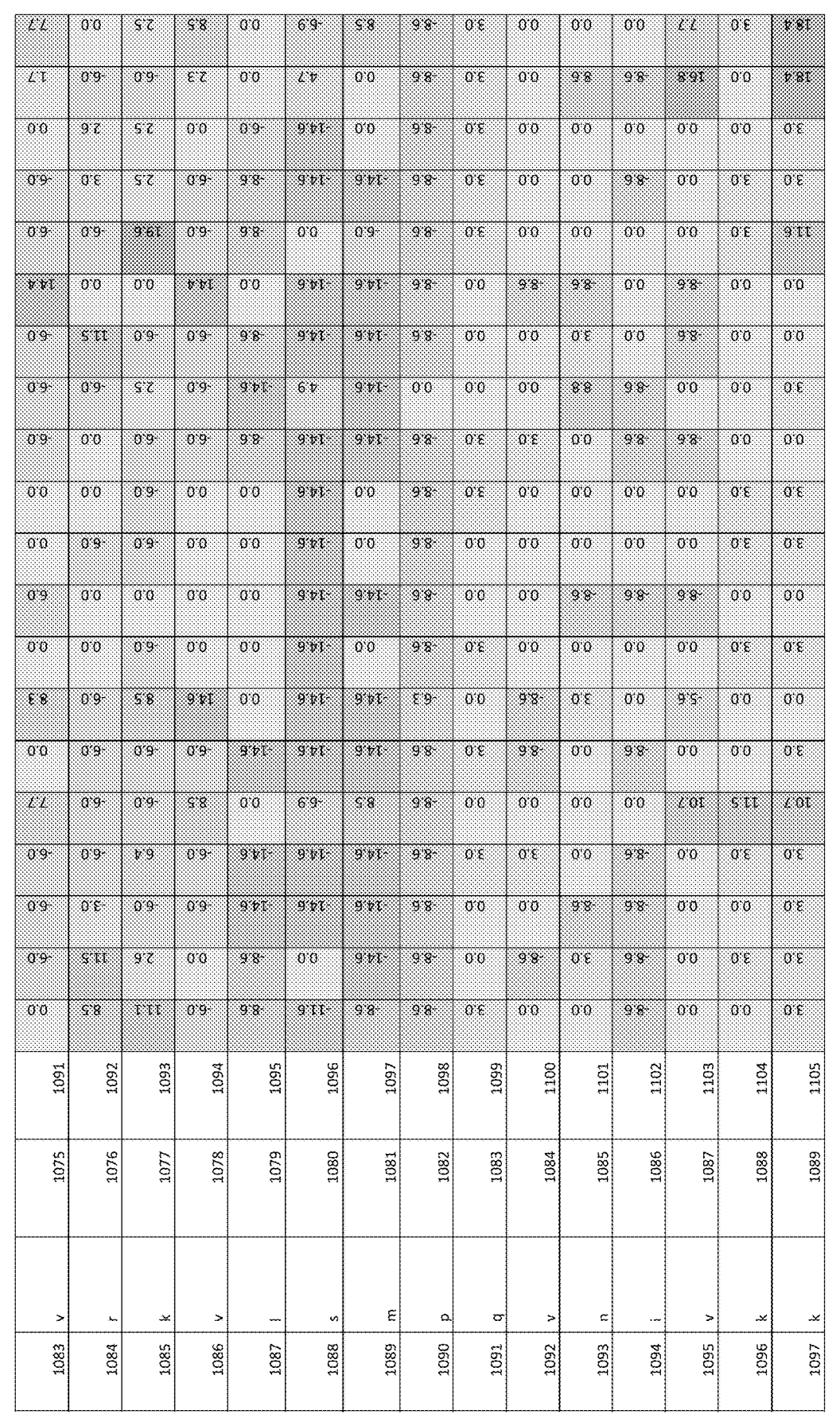
Figure 5C:
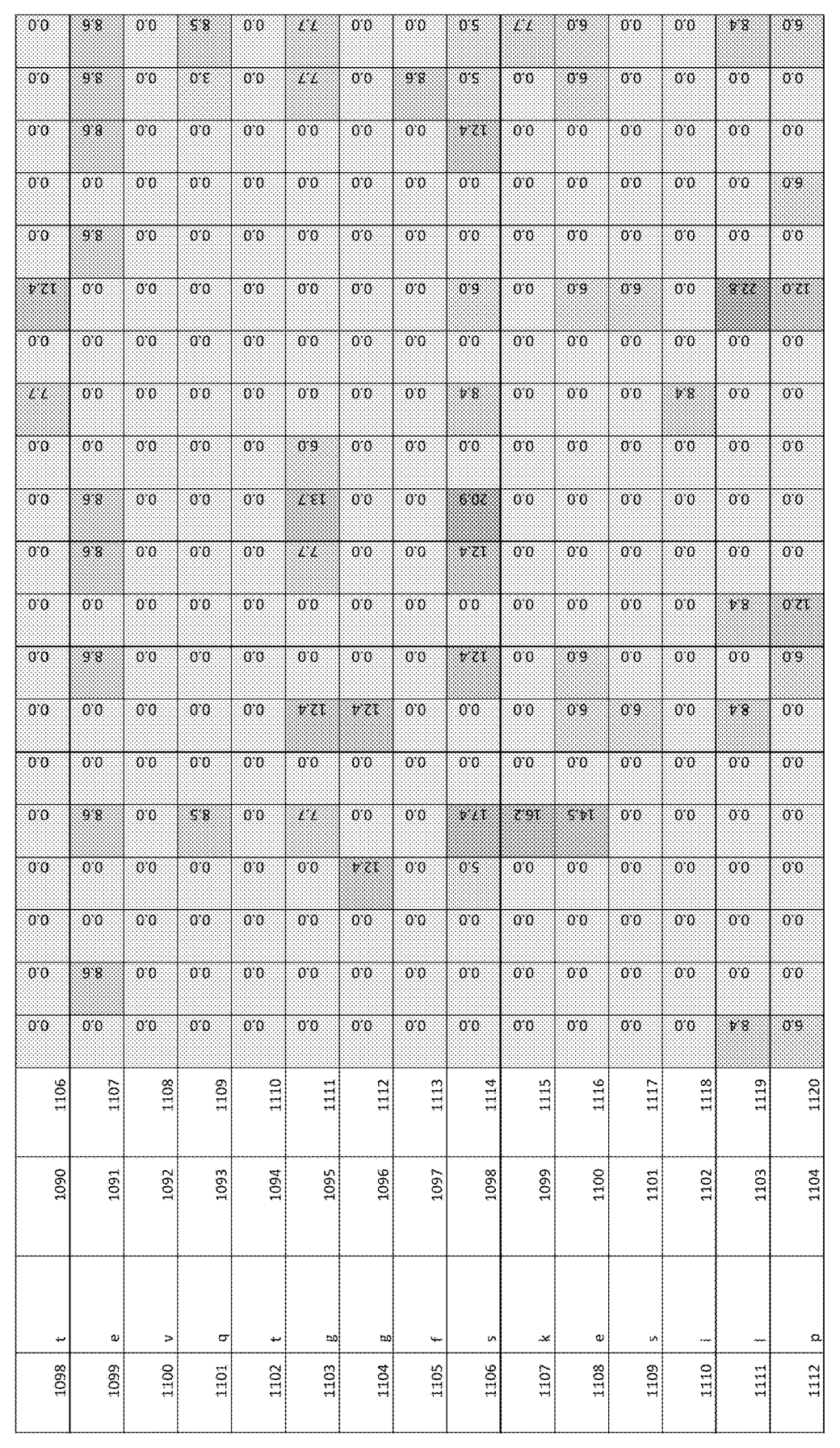
Figure 5C:
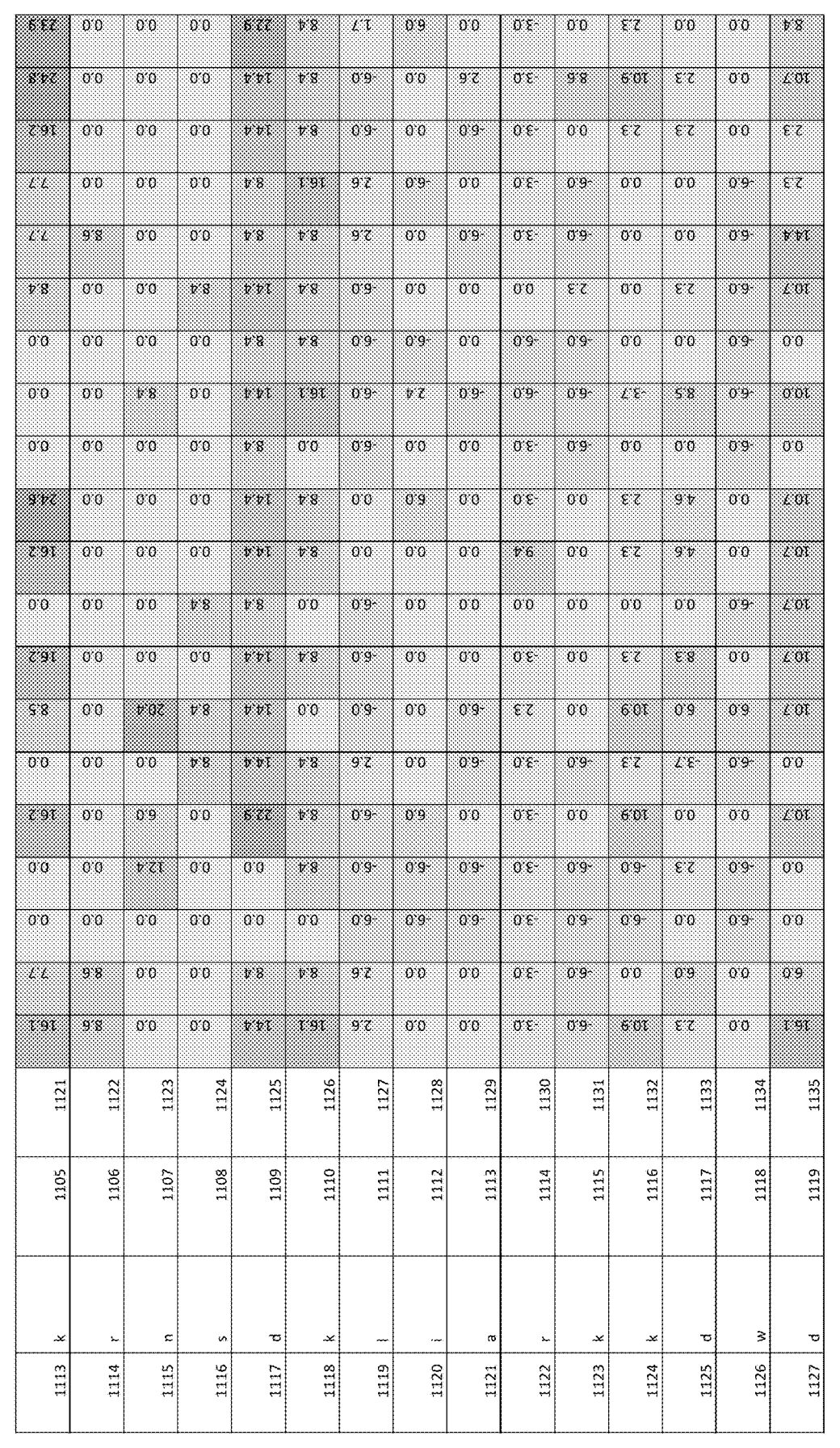
Figure 5C:
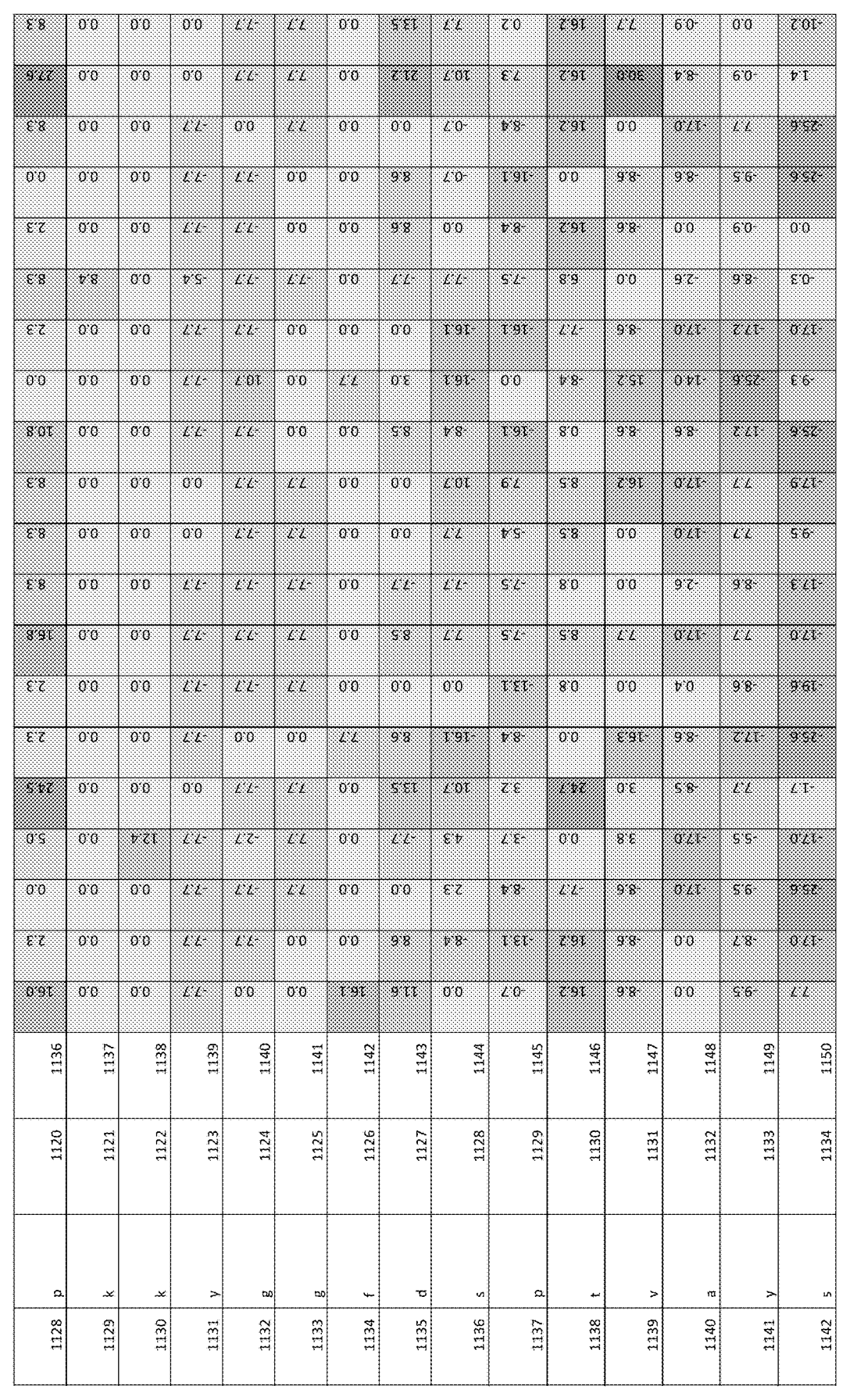
Figure 5C:
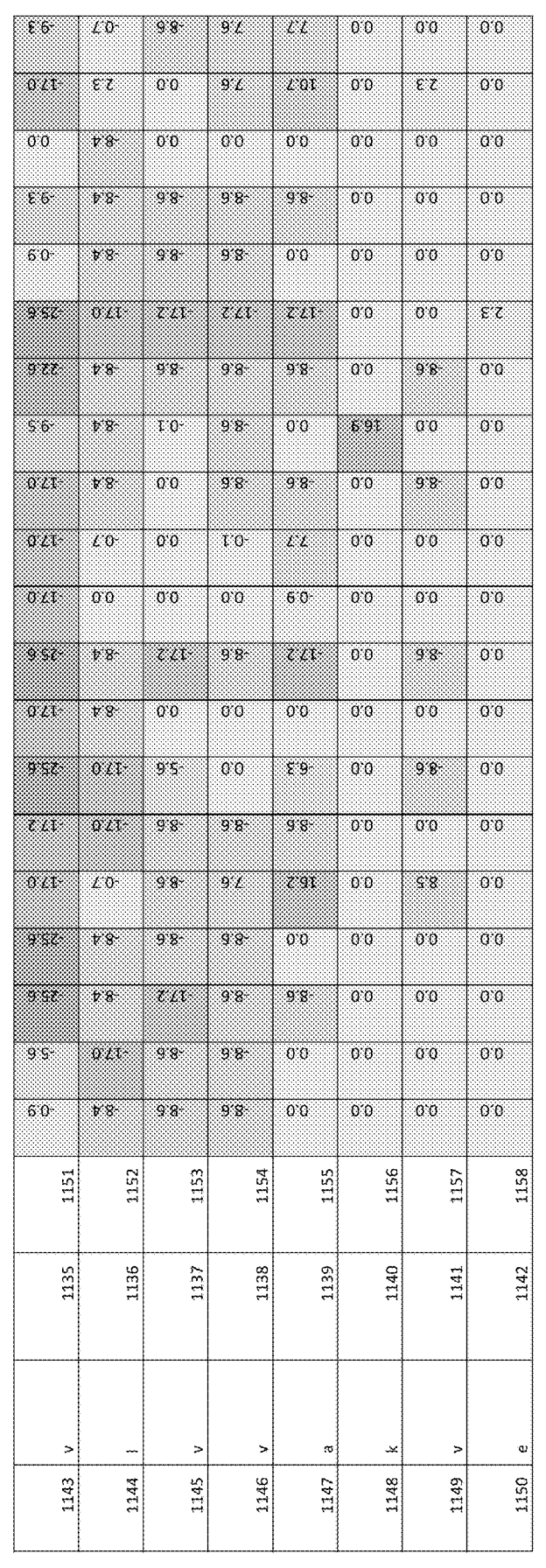

FIGS. 5A, 5B and 5C depict the randomization of amino acids 1026-1150 from *Streptococcus pyogenes* Cas9 and assessment of impact on 9mer immunogenicity. Data are presented for HLA-A and HLA-B Class I allotypes only. The left hand panel indicates the effect of amino acid substitution on the number of allotypes binding the specific epitope ("binders"). The right hand panel indicates the sum of the number of binders for each allotype multiplied by the allotype frequency in the global population (presented separately for A and B allotypes).

Figure 6B:
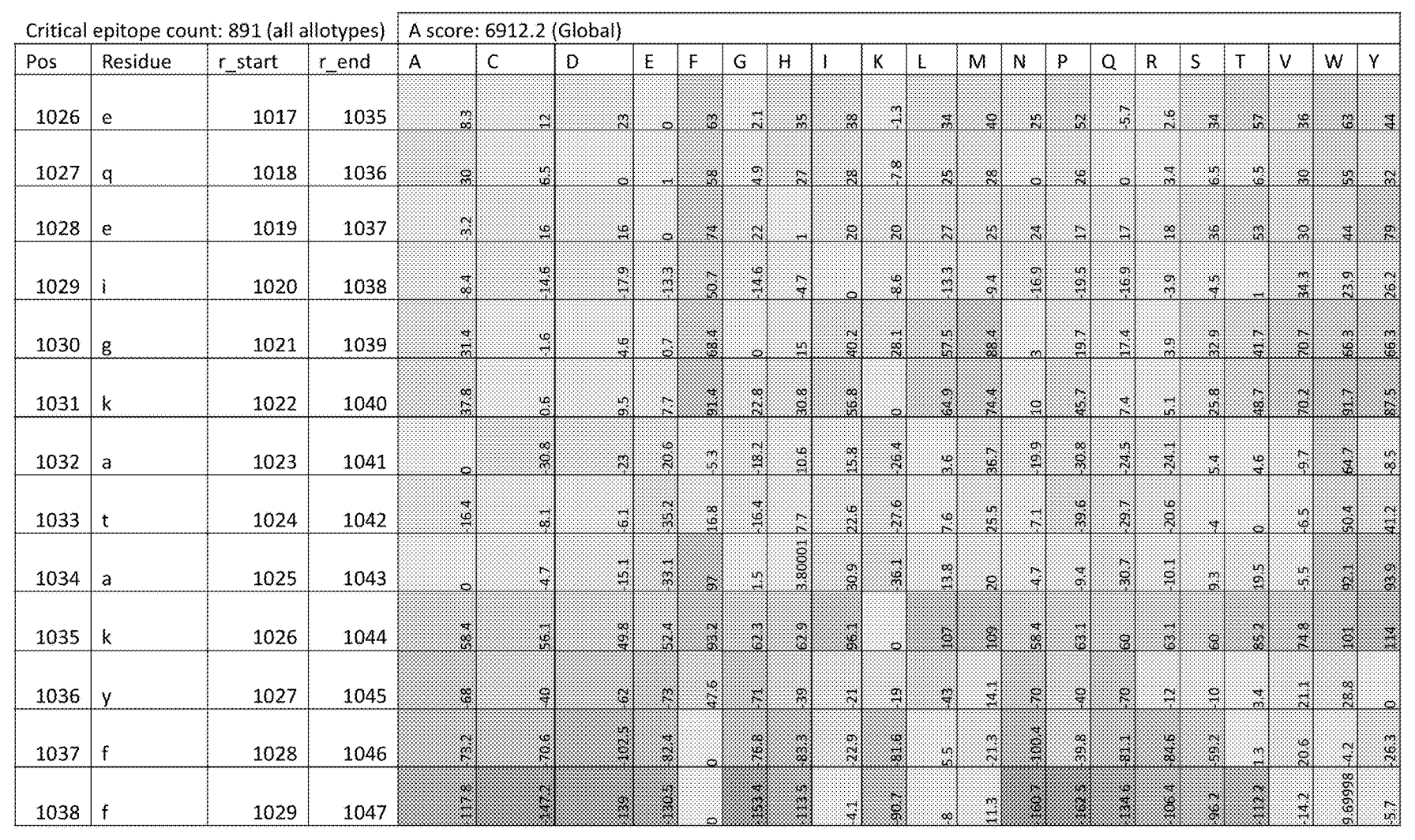
Figure 6B:
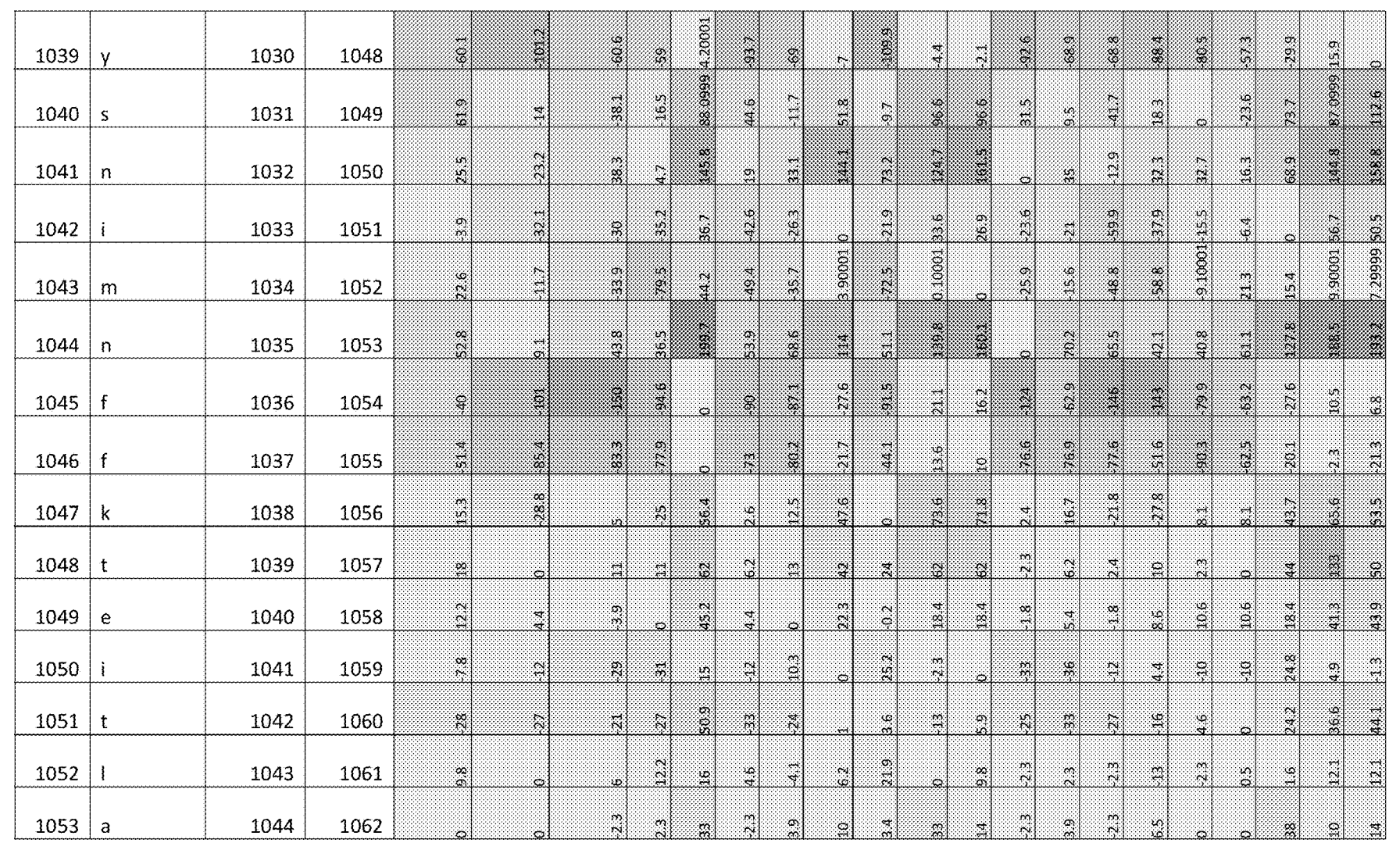
Figure 6B:
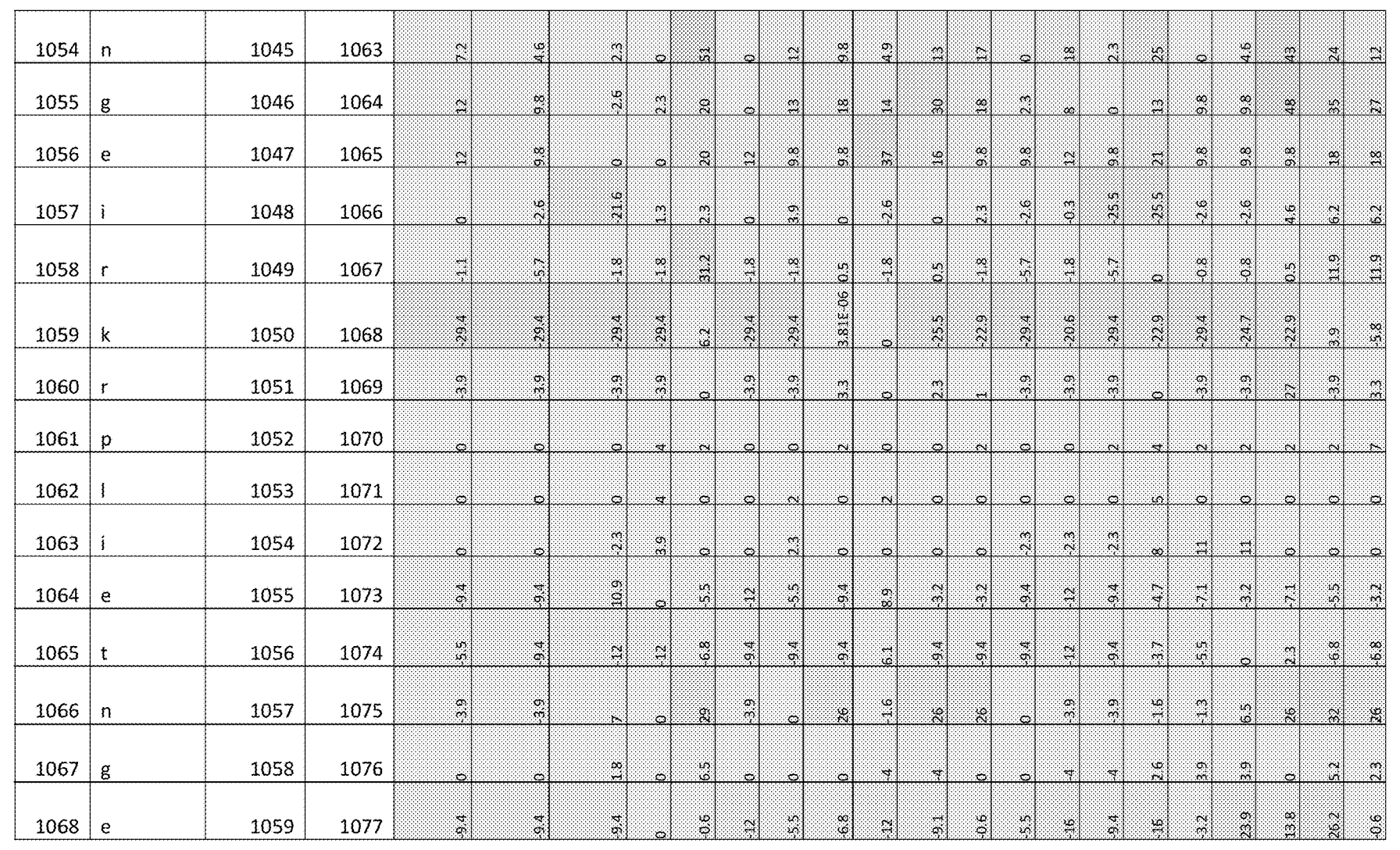
Figure 6B:
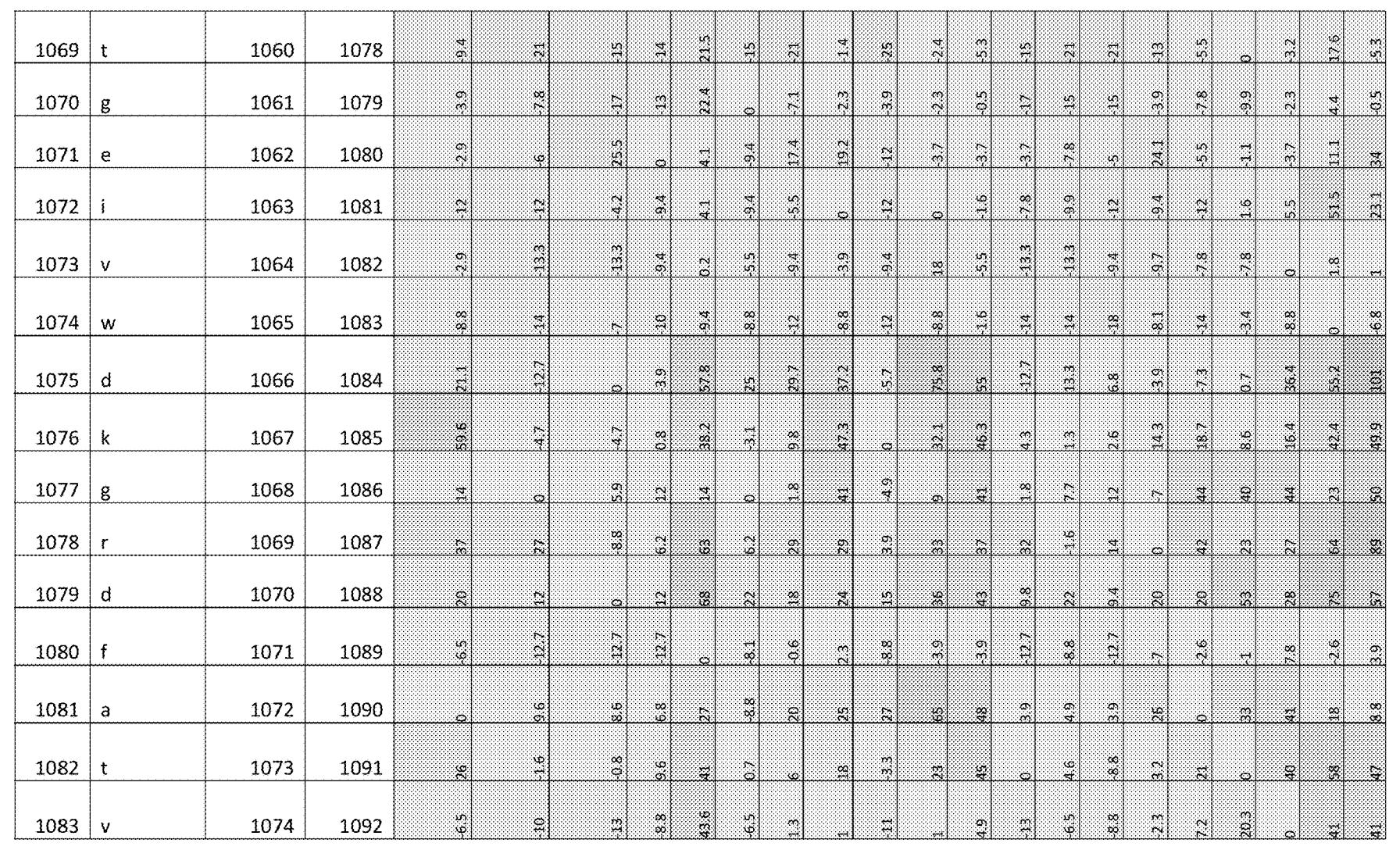
Figure 6B:
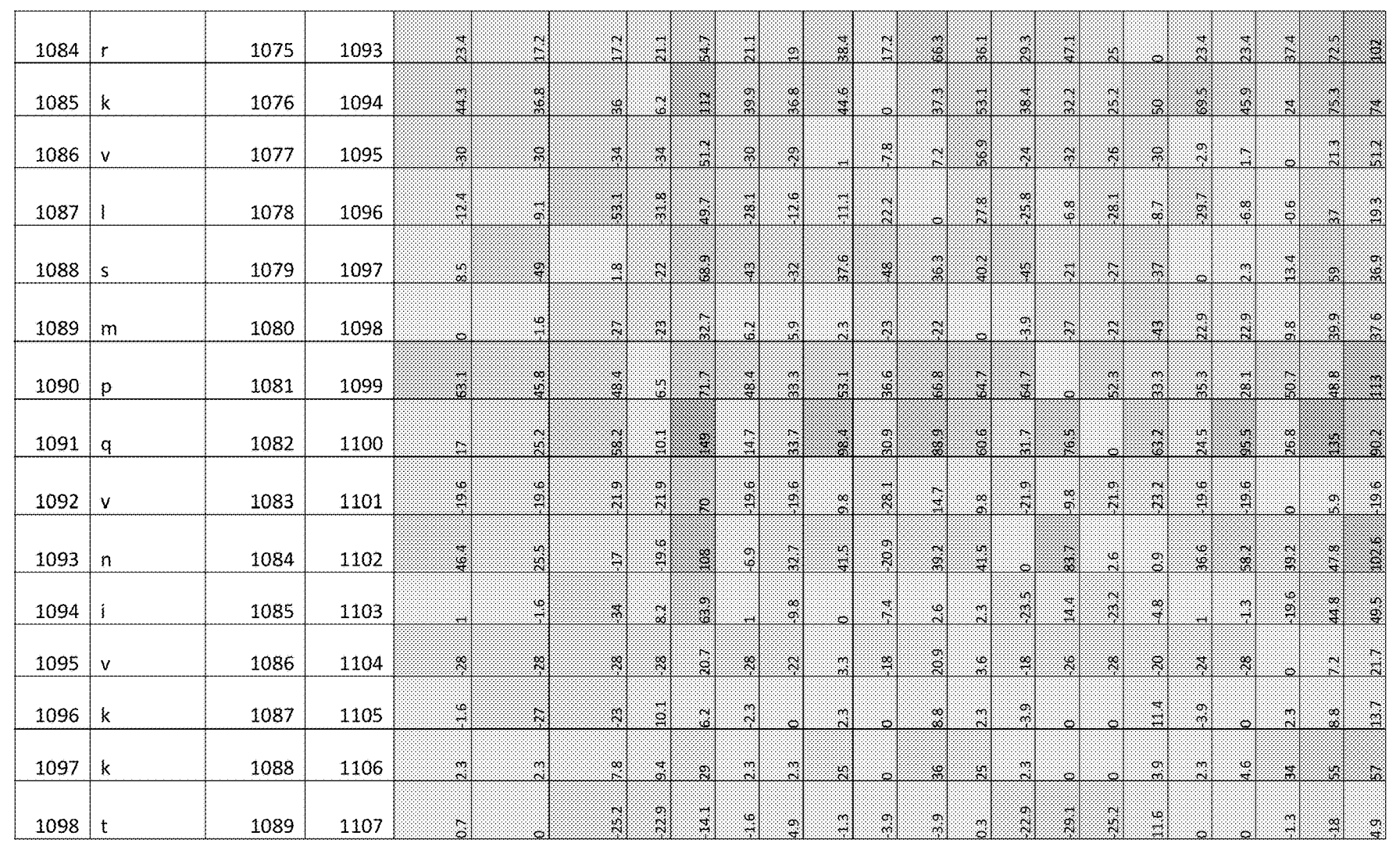
Figure 6B:
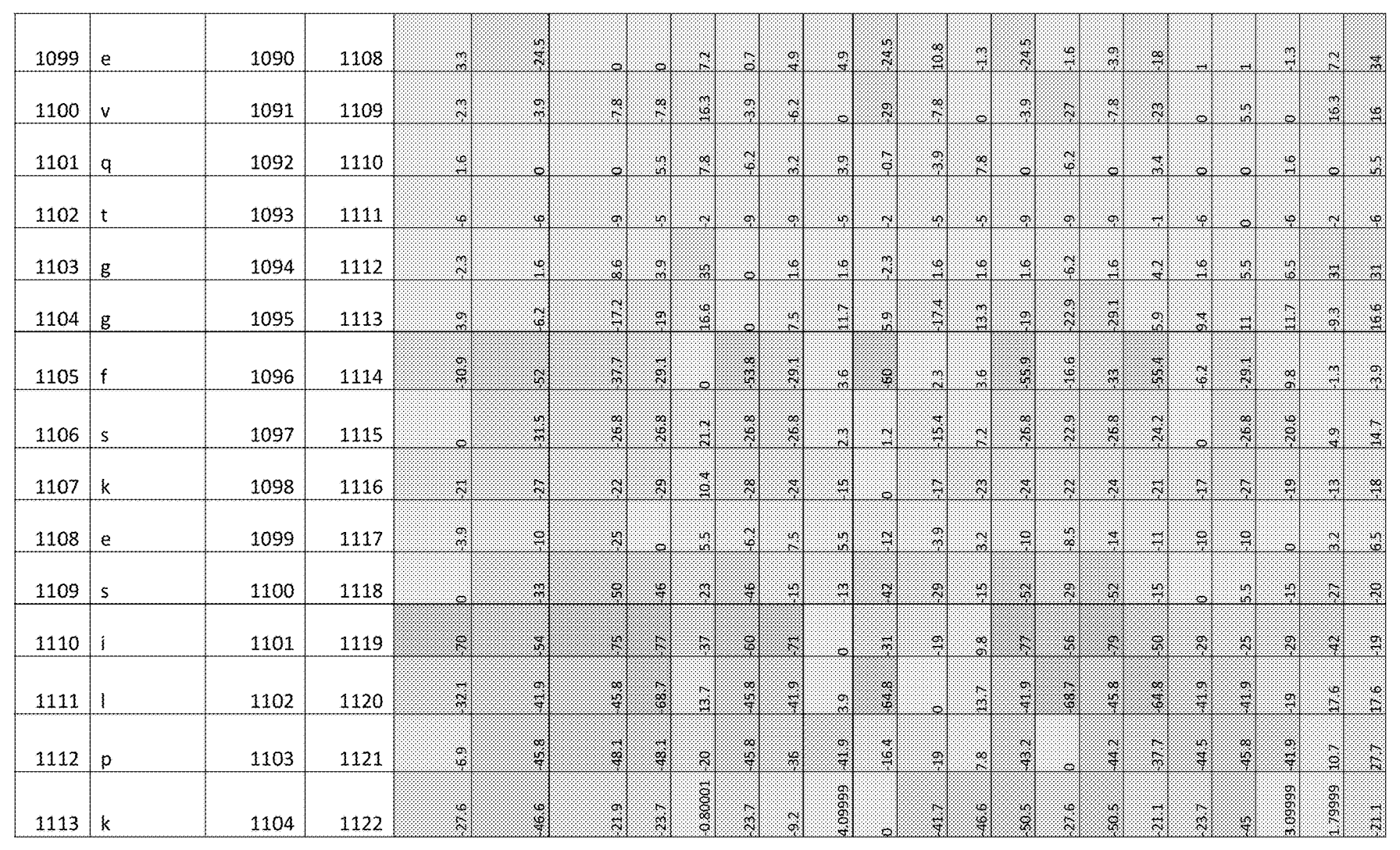
Figure 6B:
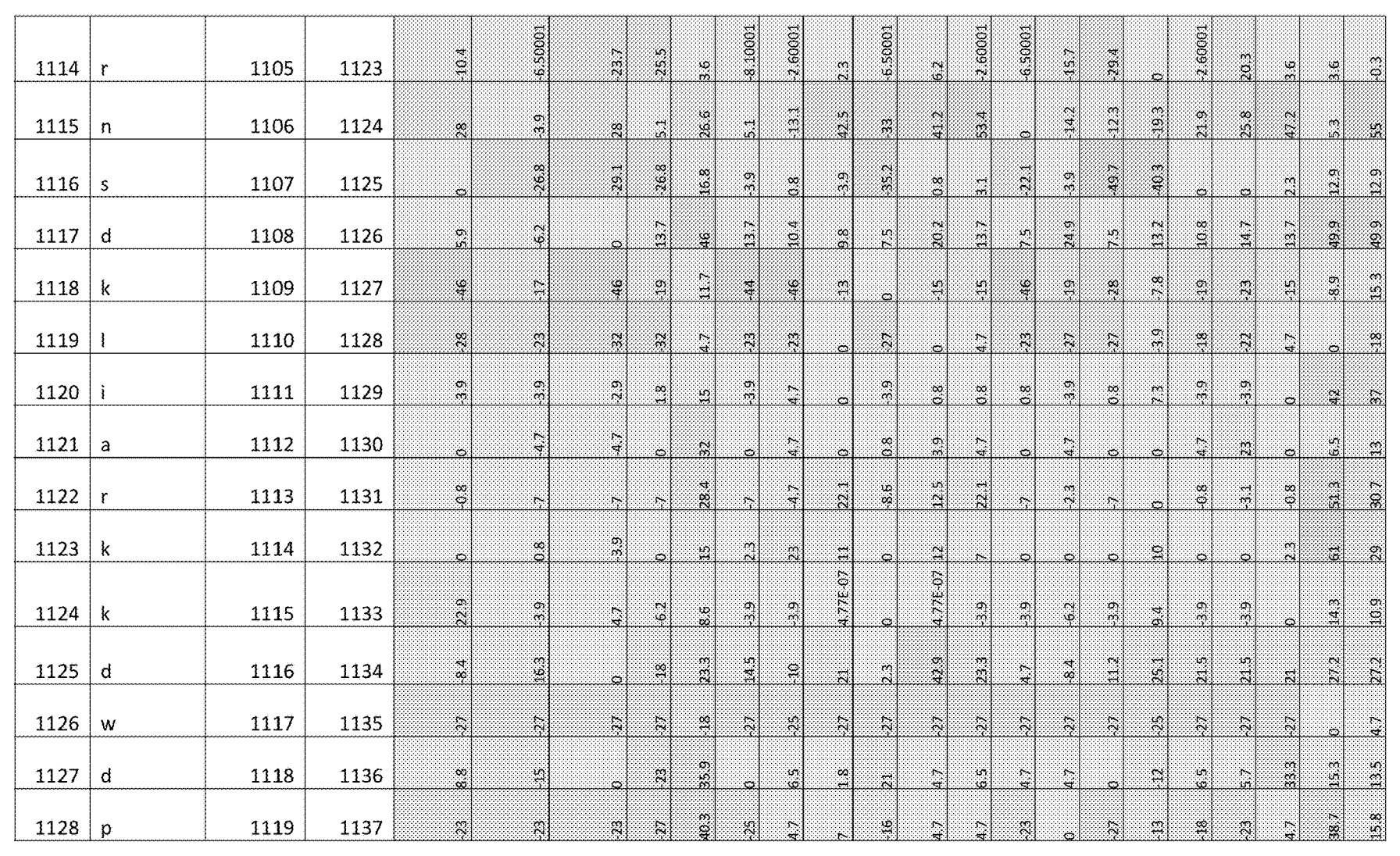
Figure 6B:
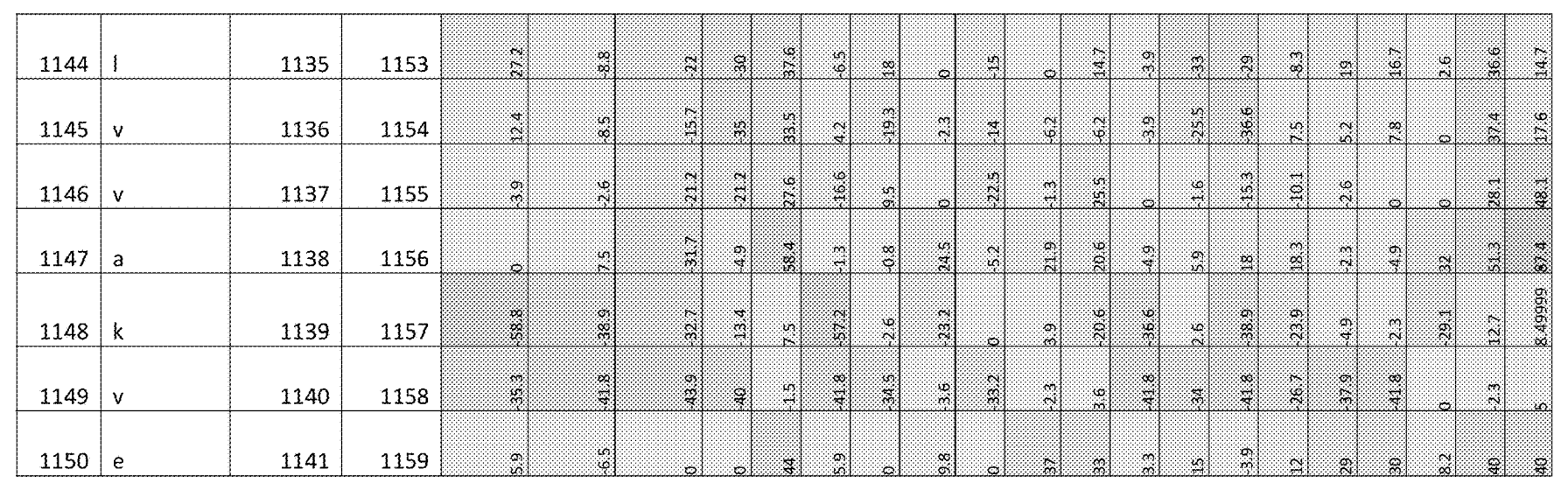
Figure 6C:
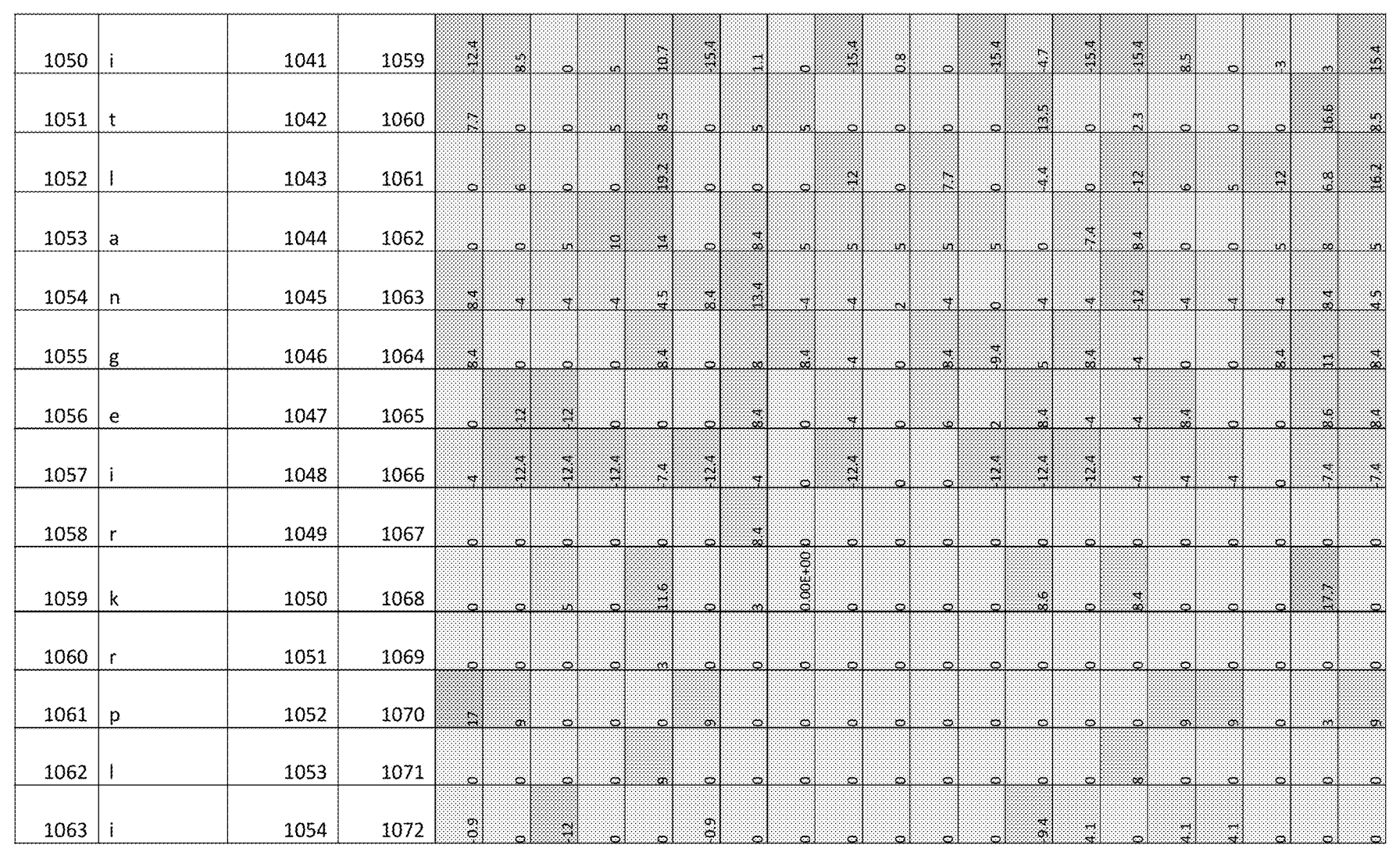
Figure 6C:
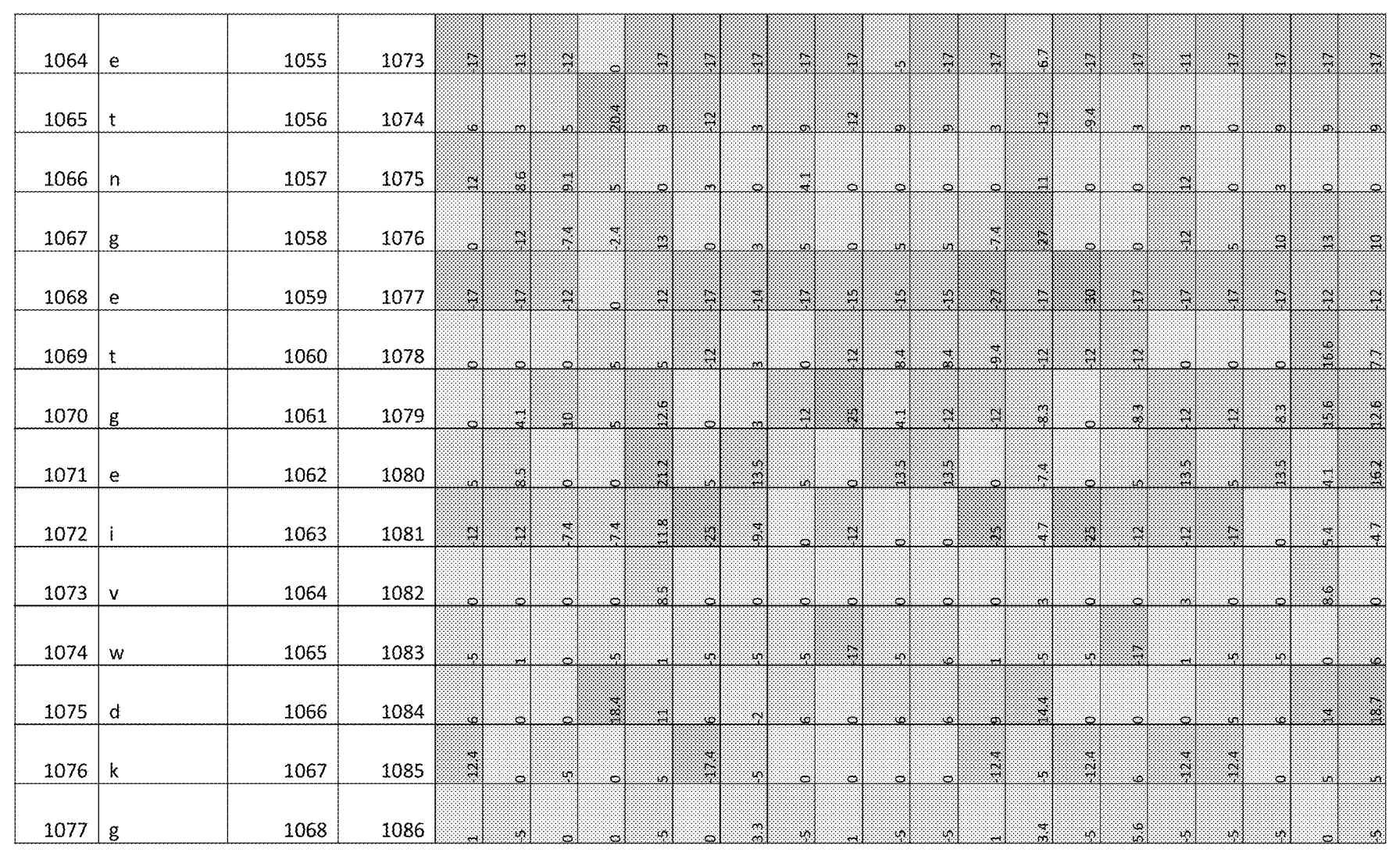
Figure 6C:
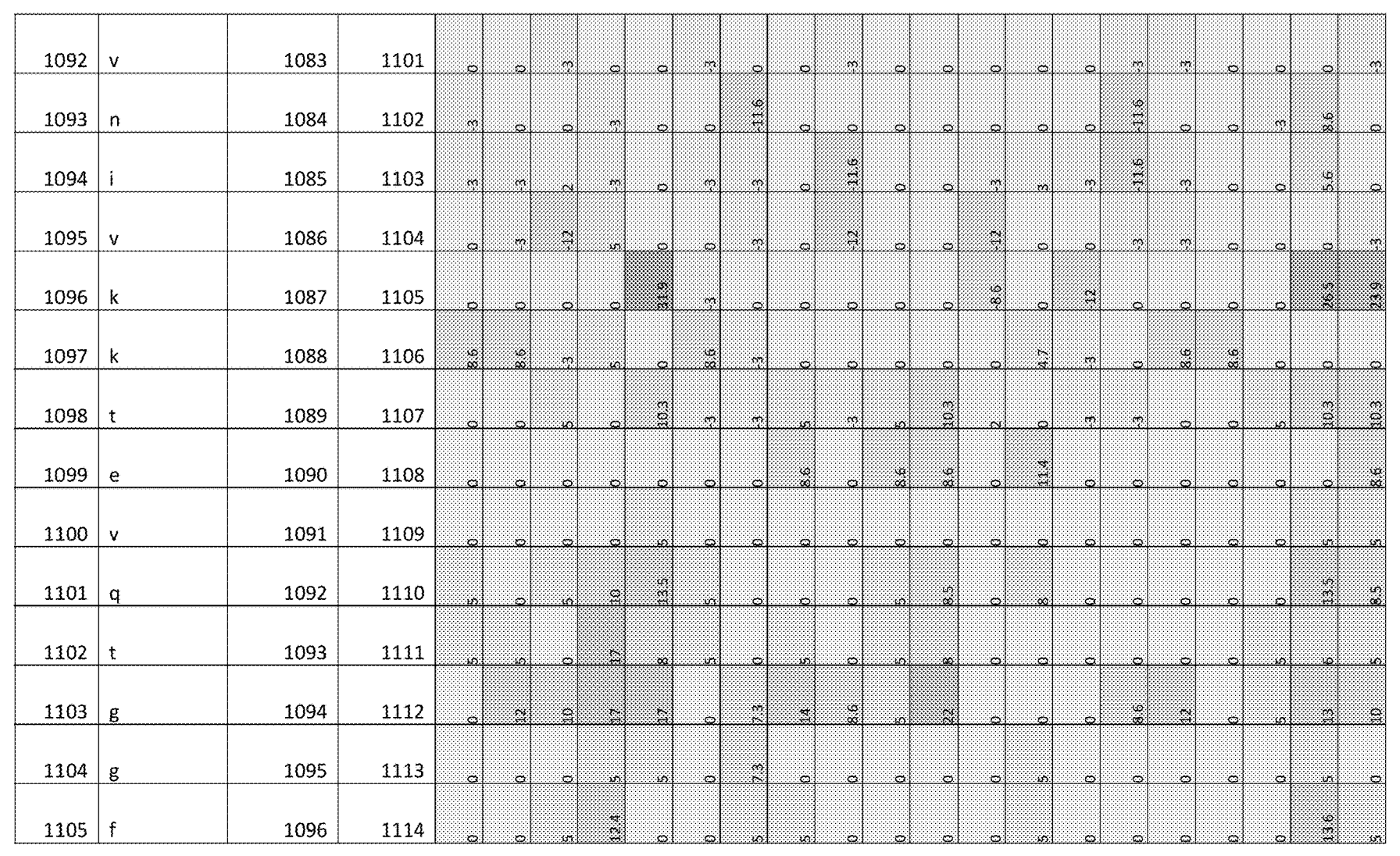
Figure 6C:
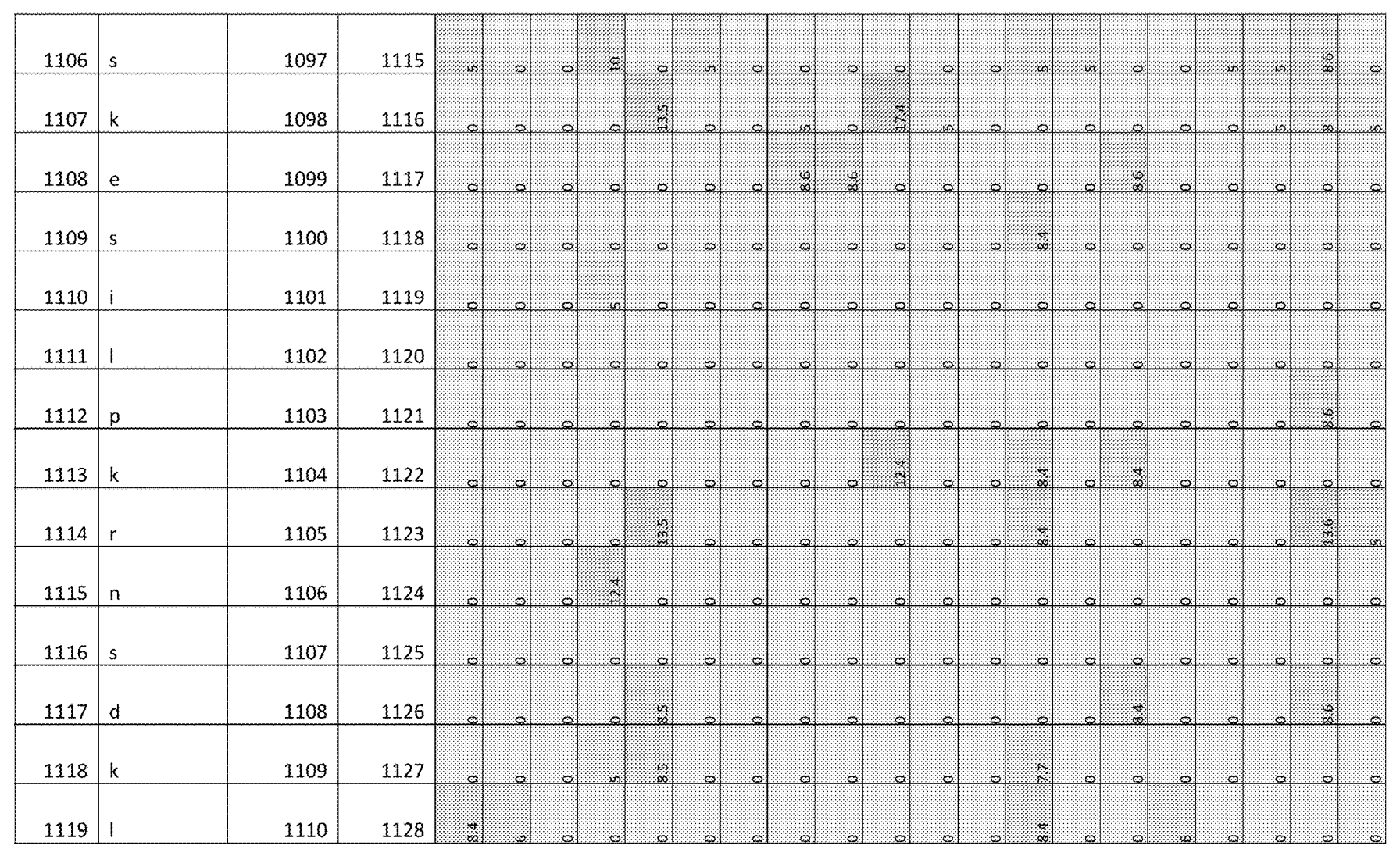
Figure 6C:
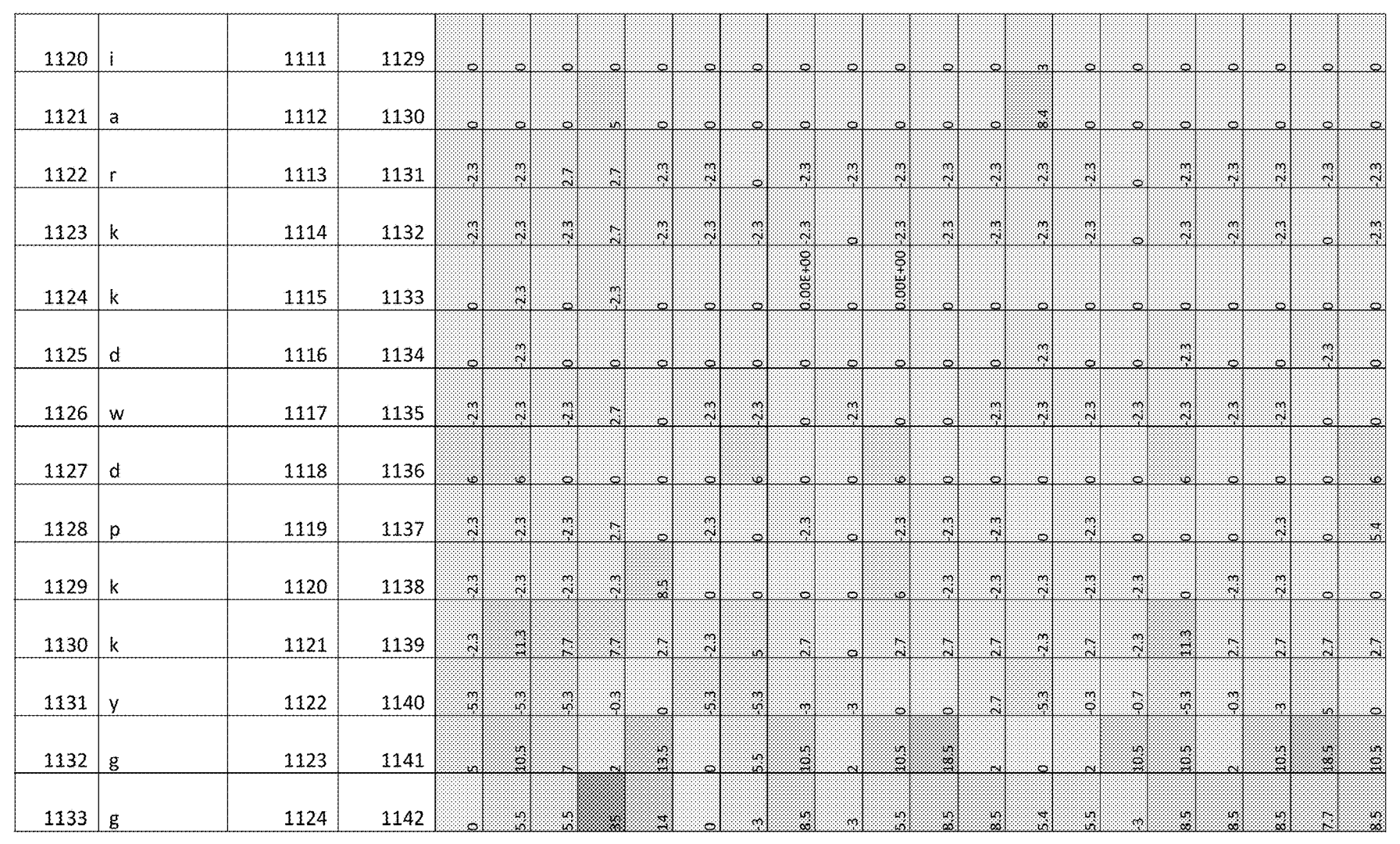
Figure 6C:
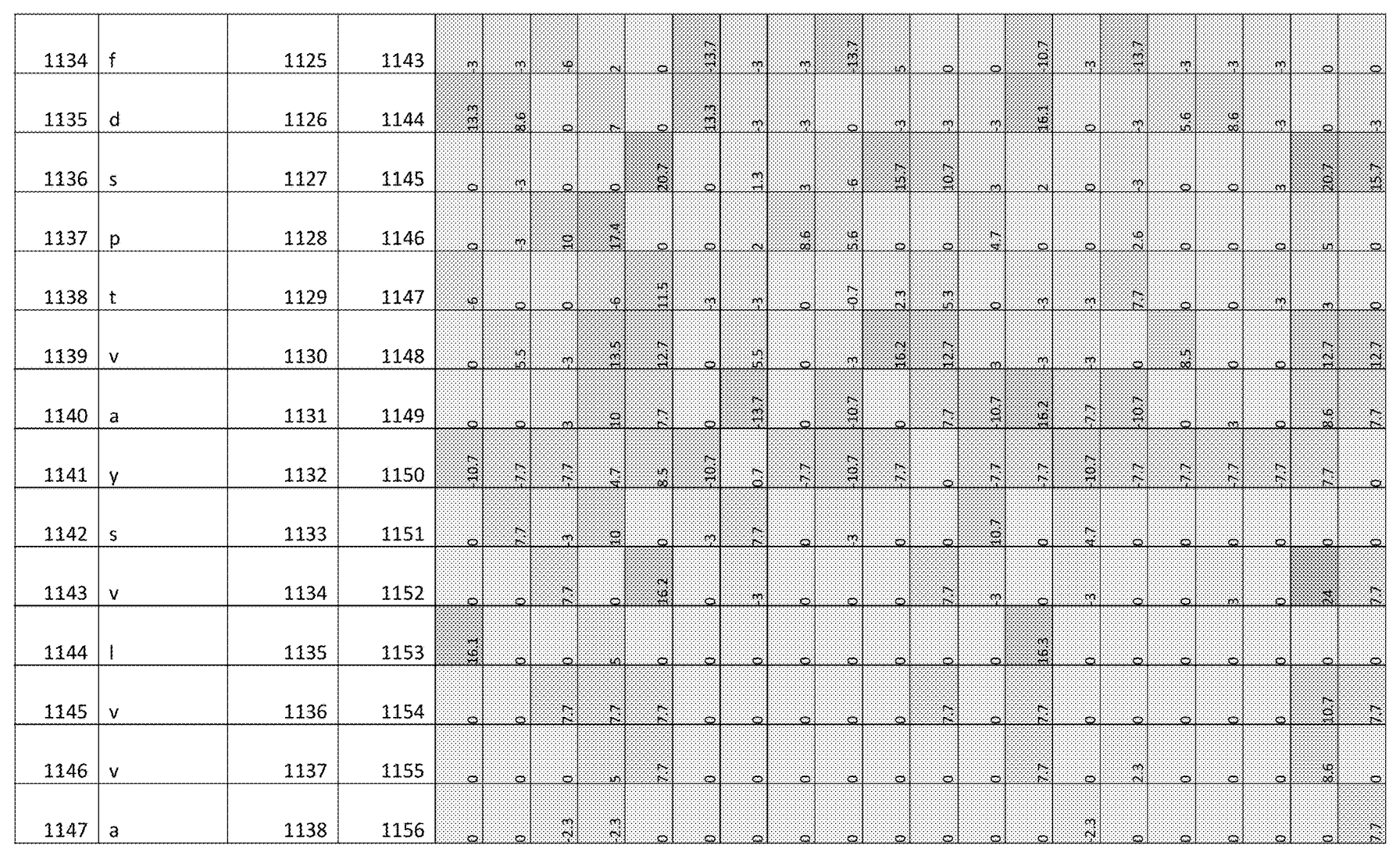
Figure 6D:
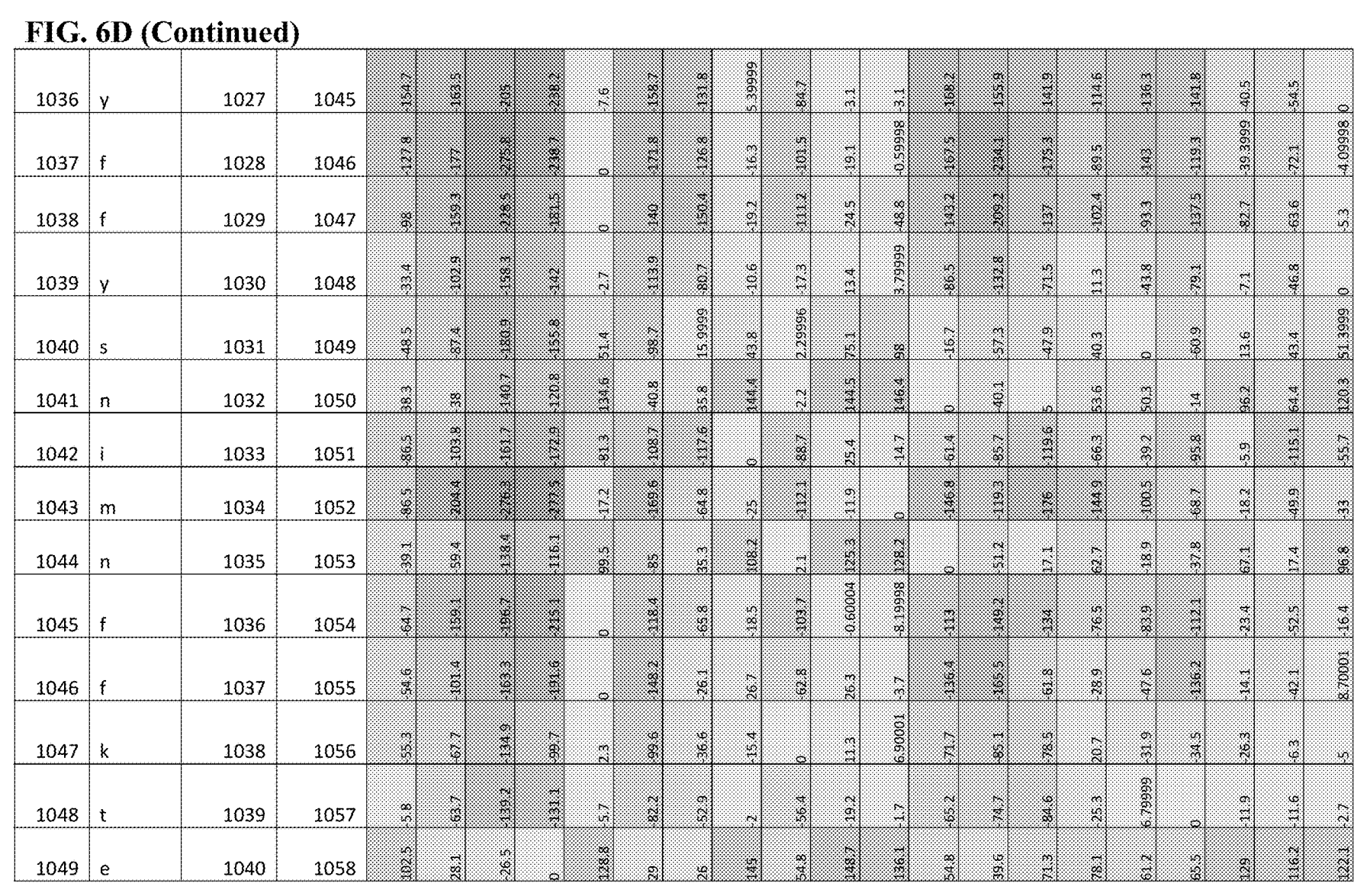
Figure 6D:
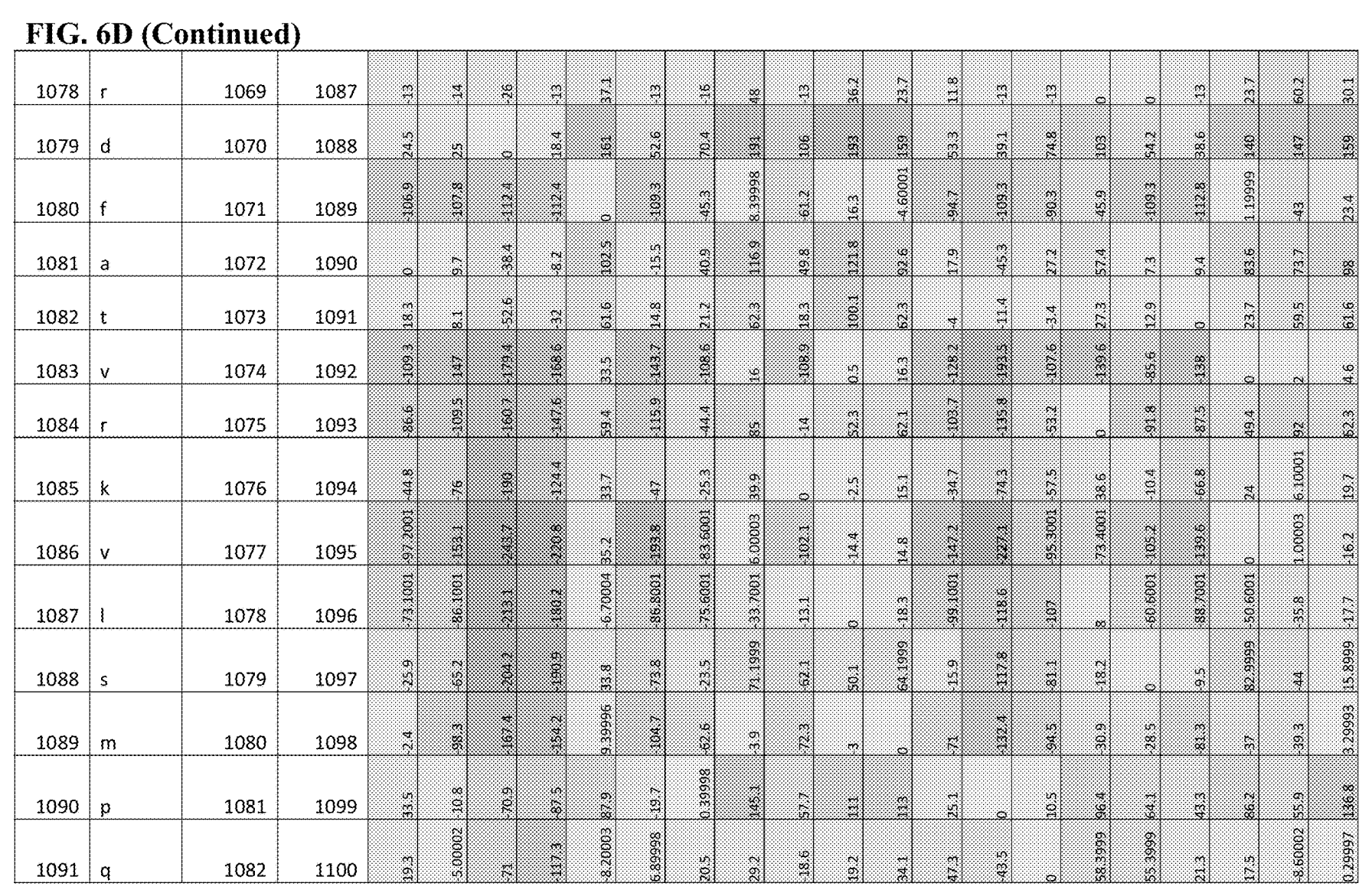
Figure 6D:
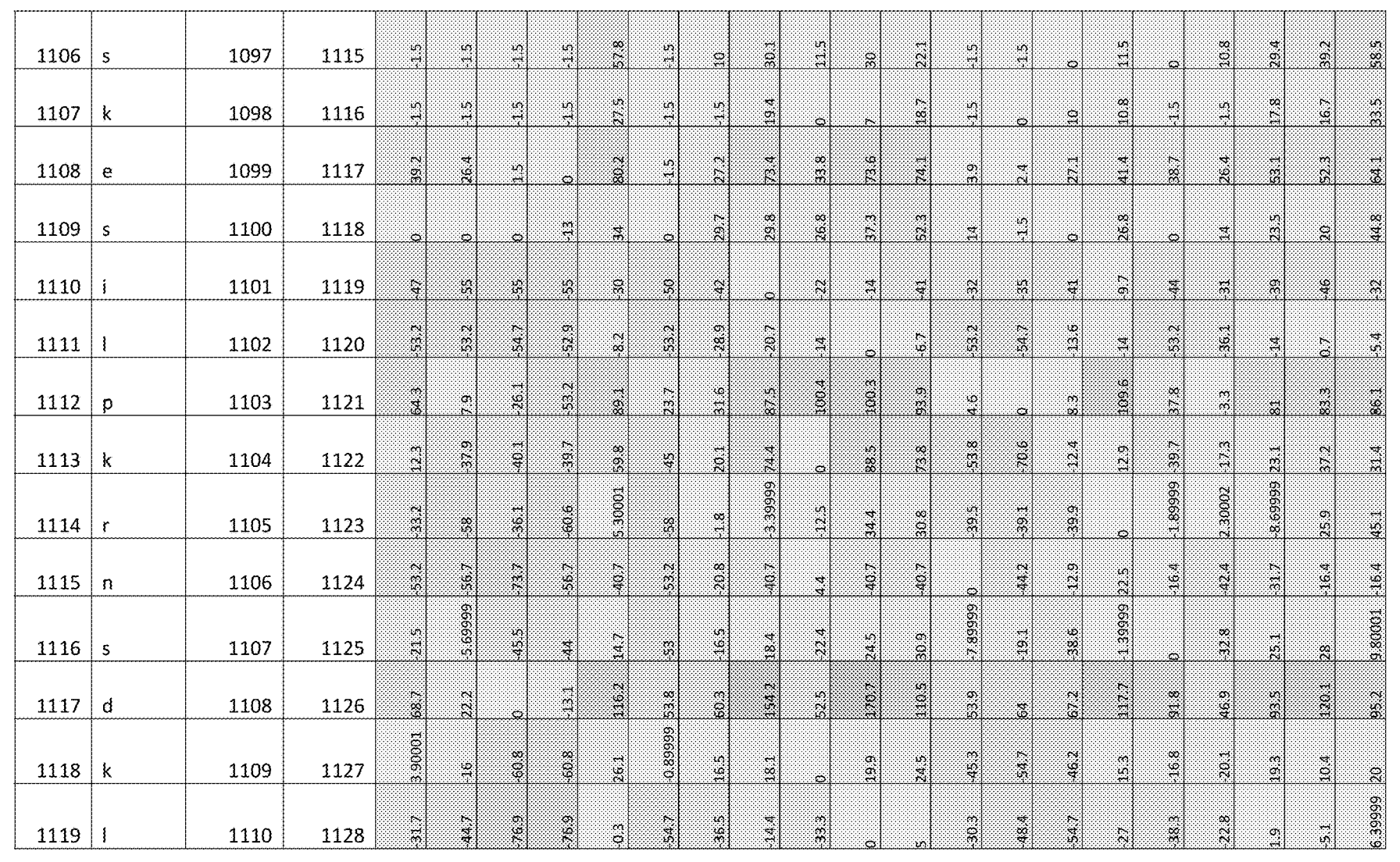
Figure 6D:
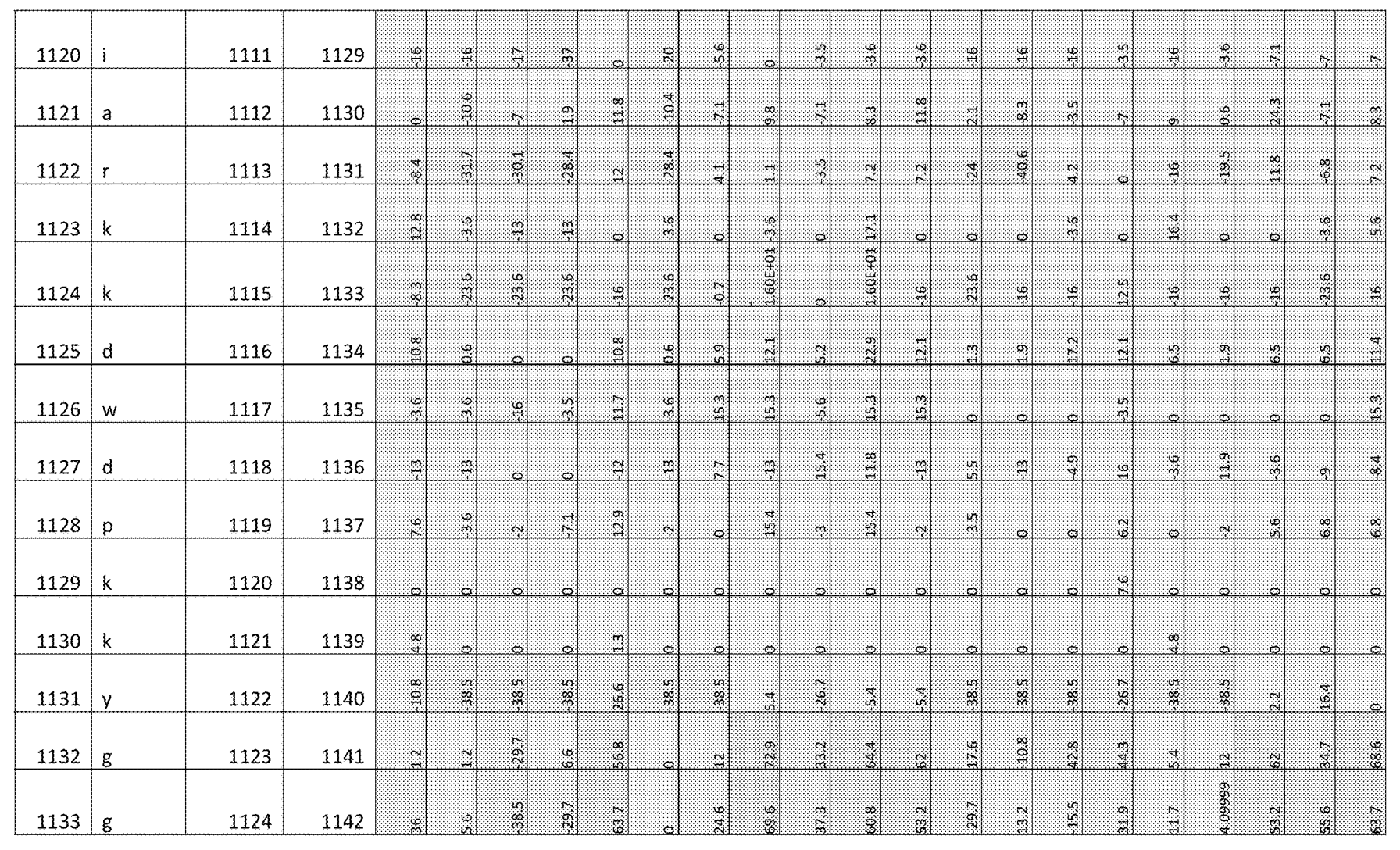
Figure 6D:
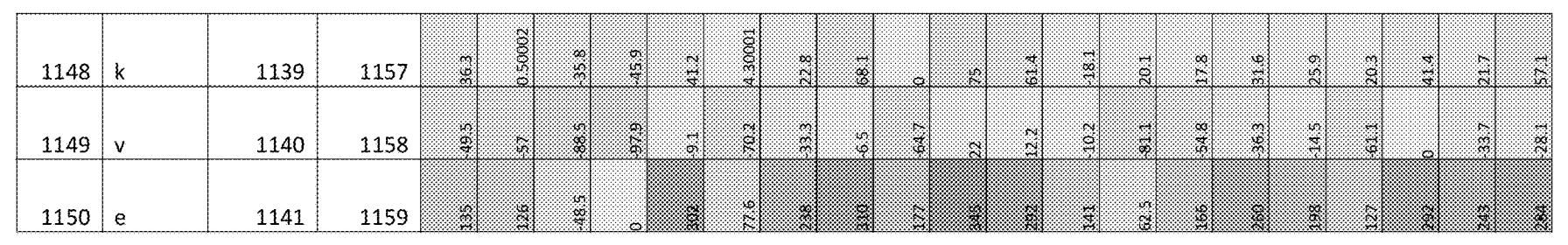

FIGS. 6A, 6B, 6C, and 6D depict the randomization of amino acids 1026-1150 from *Streptococcus pyogenes* Cas9 and assessment of impact on 10mer and global Cas9 immunogenicity. Data are presented for HLA-A and HLA-B Class I allotypes, and the DRB1 Class II allotypes only. The left hand panel indicates the effect of amino acid substitution on the number of allotypes binding the specific epitope ("binders") from the Class I and II allotypes above. The right hand panel indicates the sum of the number of binders for each allotype multiplied by the allotype frequency in the global population (presented separately for HLA-A, HLA-B and DRB1 allotypes).

FIG. 7 depicts a calculated protein sequence alignment between *Streptococcus pyogenes* Cas9 protein (SEQ ID NO: 5), *Streptococcus thermophilus* LMD-9 Cas9 protein (SEQ ID NO: 6), *Staphylococcus aureus* subsp. *aureus* Cas9 protein (SEQ ID NO: 7), and *Neisseria meningitidis* Cas9 protein (SEQ ID NO: 8).

Figure 8A:
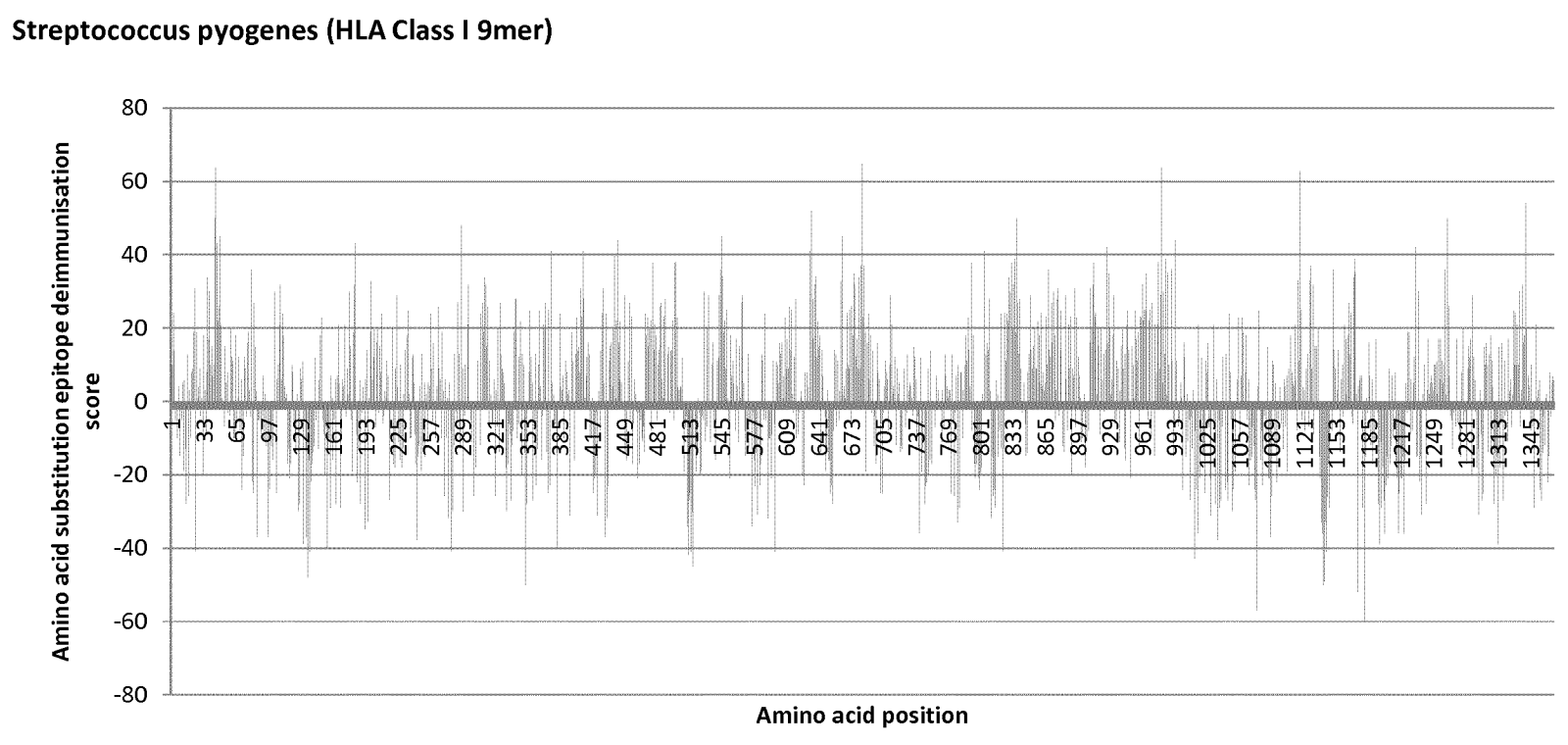
Figure 8C:
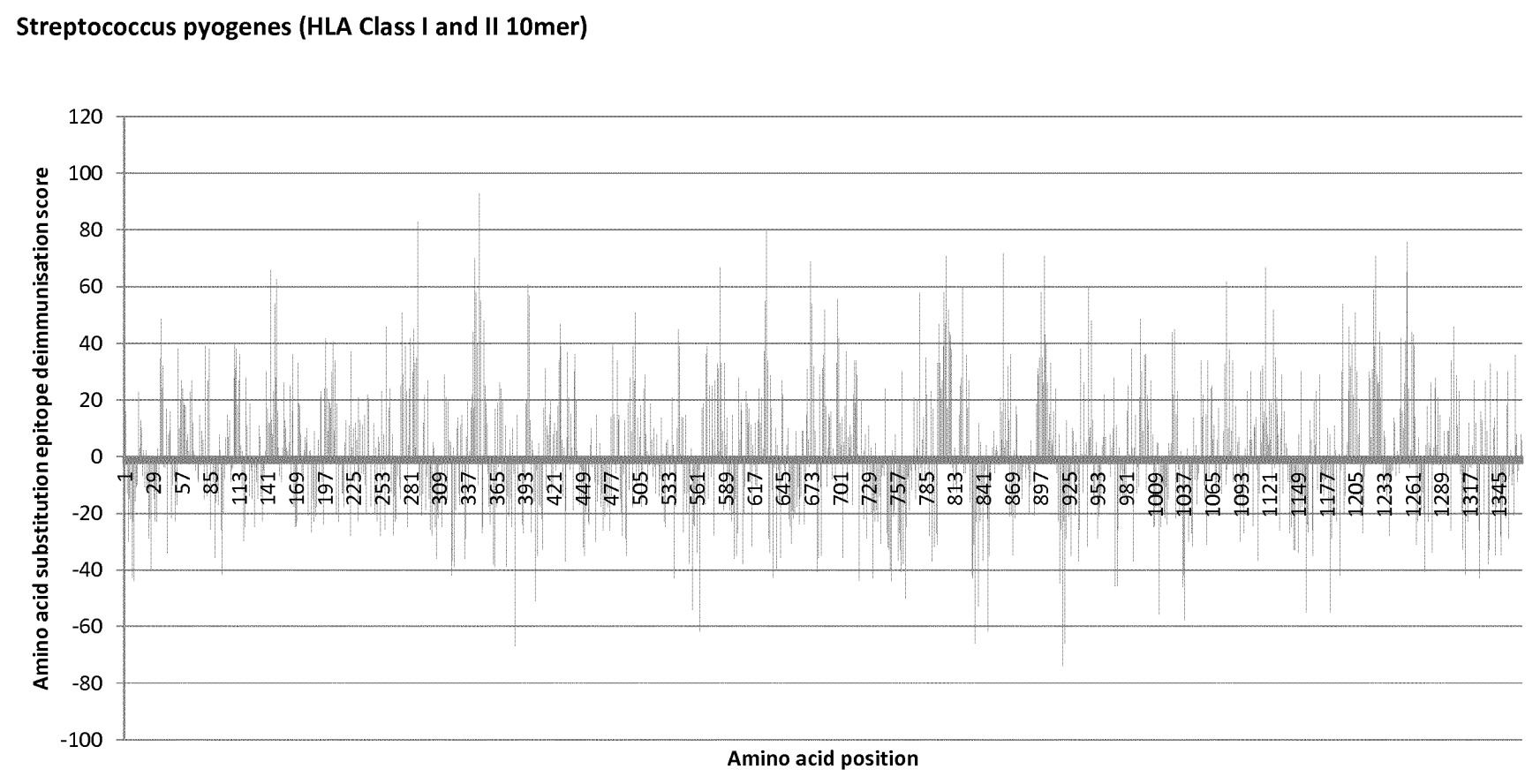

FIG. 8A depicts the amino acid substitution deimmunisation score for *Streptococcus pyogenes* Cas9 protein (SEQ ID NO: 5) for 9mers (HLA Class I only). The amino acid substitution deimmunisation score is the sum of the number of HLA allotypes binding the given epitope when all possible substitutions are assessed for a specific position. The score therefore indicates the likelihood that for any given position a substitution can be identified that will deimmunise the corresponding epitope. A positive score indicates that substitutions at that position will give a greater chance of increasing epitope immunogenicity, where a negative score indicates that substitutions will give a greater chance in decreasing epitope immunogenicity.

FIG. 8B depicts the amino acid substitution deimmunisation score for *Streptococcus pyogenes* Cas9 protein (SEQ ID NO: 5) for 9mers (HLA Class I only) where a cut-off of <−20 is applied. Amino acid positions in this category are viewed as targets for substitution in order to reduce Cas9 immunogenicity.

FIG. 8C depicts the amino acid substitution deimmunisation score for *Streptococcus pyogenes* Cas9 protein (SEQ ID NO: 5) for 10mers (HLA Class I and II). The amino acid substitution deimmunisation score is the sum of the number of HLA allotypes binding the given epitope when all possible substitutions are assessed for a specific position. The score therefore indicates the likelihood that for any given position a substitution can be identified that will deimmunise the corresponding epitope. A positive score indicates that substitutions at that position will give a greater chance of increasing epitope immunogenicity, where a negative score indicates that substitutions will give a greater chance in decreasing epitope immunogenicity.

FIG. 8D depicts the amino acid substitution deimmunisation score for *Streptococcus pyogenes* Cas9 protein (SEQ ID NO: 5) for 10mers (HLA Class I and II) where a cut-off of <−20 is applied. Amino acid positions in this category are viewed as targets for substitution in order to reduce Cas9 immunogenicity.

FIG. 9 represents target amino acid positions for substitution. Positions are identified from applying <−20 threshold to the amino acid substitution epitope deimmunisation score. Inclusion here indicates a high likelihood that a substitution can reduce epitope immunogenicity, however the specific substitutions made can be considered based on individual epitope binding scores and other related criteria such as amino acid characteristics and functional and structural localization (as discussed elsewhere).

FIG. 11 highlights the HLA-binding peptides eluted from HLA-DR molecules on the dendritic cells from a healthy donor after treatment with the whole Cas9 protein (*Streptococcus pyogenes*; SEQ ID NO: 5) using the MAPPs (MHC-associated peptide proteomics) assay. The Cas9 amino acid sequence is shown with the eluted HLA-binding peptides shown in bars underneath the sequences. The areas of the Cas9 protein highlighted by these bars represent areas of the Cas9 protein likely to be responsible for driving a CD4+ T cell response in this healthy donor. In conjunction with the in silico analysis, MAPPs analysis can help identify the area within the Cas9 protein responsible for driving the immune response and help guide protein engineering to remove these T cell epitopes.

DETAILED DESCRIPTION OF THE INVENTION

Figure 10A:
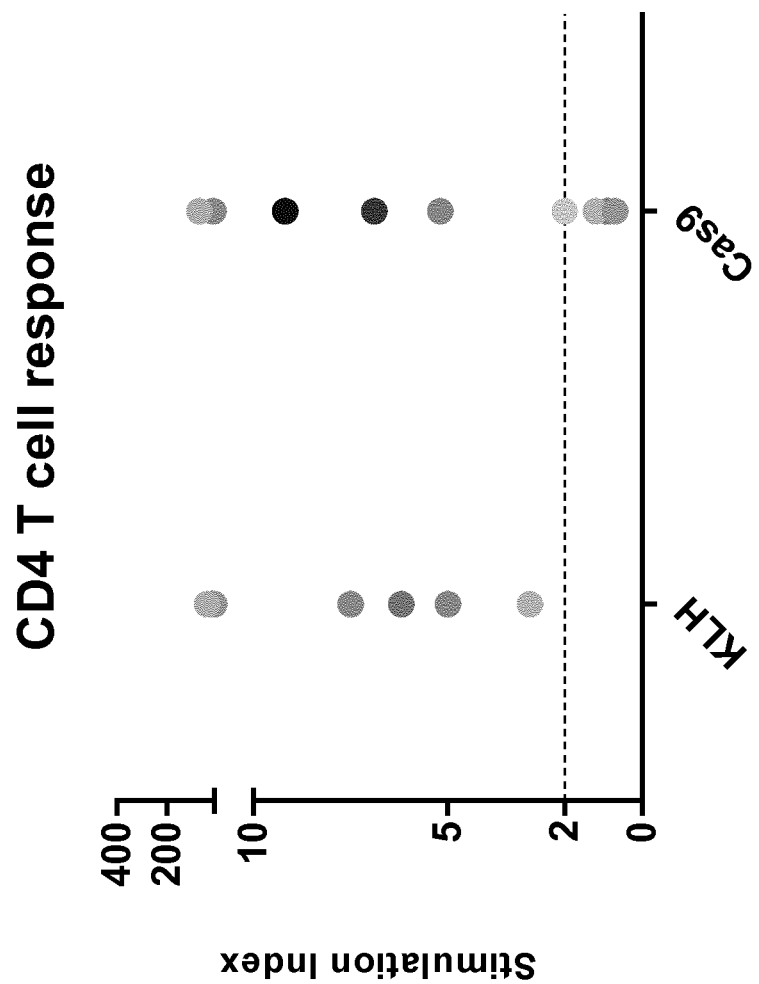
FIG. 10A represents the CD4+ T cell response induced by the whole Cas9 protein (*Streptococcus pyogenes*) in the DC:CD4 activation assay. Each dot represents a single healthy donor with a stimulation index >2 deemed a positive T cell response. KLH is a highly immunogenic protein and induces a CD4+ T cell response in all 9 healthy donors. Cas9 induced a CD4+ T cell response in 5 of the 9 (56%) healthy donors tested suggesting that Cas9 contains CD4+ T cell epitopes and is capable of raising a helper T cell response in human cells. This assay can be used to evaluate deimmunised versions of the Cas9 protein and determine which have a reduced immunogenicity compared to the wild-type Cas9 protein.

The invention provided herein uses components of the CRISPR-Cas system, which can be utilized to accomplish genomic engineering, including gene editing and altering expression of a gene and/or genetic element. Such genomic engineering can be used in various therapeutic strategies, including the treatment of genetic diseases. In addition, described herein are methods for creating Cas proteins with reduced immunogenicity that can be used in conjunction with other CRISPR components. In certain embodiments, described herein are recombinant Cas proteins with reduced immunogenicity, isolated nucleic acids that encode such recombinant Cas proteins, vectors comprising these nucleic acids, and cells comprising the nucleic acids and/or vectors. The creation of Cas proteins with reduced immunogenicity may allow for more stable, efficient, and efficacious use of the CRISPR-Cas system in a host organism, including humans.

Definitions

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the method/device being employed to determine the value, or the variation that exists among the study subjects. Typically the term is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% variability depending on the situation.

The use of the term "or" in the claims is used to mean "and/or" unless explicitly indicated to refer only to alternatives or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited, elements or method steps. It is contemplated that any embodiment discussed in this specification can be implemented with respect to any method, system, host cells, expression vectors, and/or composition of the invention. Furthermore, compositions, systems, host cells, and/or vectors of the invention can be used to achieve methods and proteins of the invention.

The use of the term "for example" and its corresponding abbreviation "e.g." (whether italicized or not) means that the specific terms recited are representative examples and embodiments of the invention that are not intended to be limited to the specific examples referenced or cited unless explicitly stated otherwise.

A "nucleic acid," "nucleic acid molecule," "oligonucleotide" or "polynucleotide" means a polymeric compound comprising covalently linked nucleotides. The term "nucleic acid" includes polyribonucleic acid (RNA) and polydeoxyribonucleic acid (DNA), both of which may be single- or double-stranded. DNA includes, but is not limited to, complimentary DNA (cDNA), genomic DNA, plasmid or vector DNA, and synthetic DNA. In some embodiments, the invention is directed to a polynucleotide encoding any one of the polypeptides disclosed herein, e.g., is directed to a polynucleotide encoding a Cas protein or variant thereof. In some embodiments, the invention is directed to a polynucleotide encoding Cas3, Cas9, Cas10 or variants thereof.

A "gene" refers to an assembly of nucleotides that encode a polypeptide, and includes cDNA and genomic DNA nucleic acid molecules. "Gene" also refers to a nucleic acid fragment that can act as a regulatory sequences preceding (5' non-coding sequences) and following (3' non-coding sequences) the coding sequence.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

An "amino acid" as used herein refers to a compound containing both a carboxyl (—COOH) and amino (—NH$_2$) group. "Amino acid" refers to both natural and unnatural, i.e., synthetic, amino acids. Natural amino acids, with their three-letter and single letter abbreviations, include Alanine (Ala; A); Arginine (Arg, R); Asparagine (Asn; N); Aspartic acid (Asp; D); Cysteine (Cys; C); Glutamine (Gln; Q); Glutamic acid (Glu; E); Glycine (Gly; G); Histidine (His; H); Isoleucine (Ile; I); Leucine (Leu; L); Lysine (Lys; K); Methionine (Met; M); Phenylalanine (Phe; F); Proline (Pro; P); Serine (Ser; S); Threonine (Thr; T); Tryptophan (Trp; W); Tyrosine (Tyr; Y); and Valine (Val; V).

An "amino acid substitution" refers to a polypeptide or protein comprising one or more substitutions of a wild-type or naturally occurring amino acid with a different amino acid relative to the wild-type or naturally occurring amino acid at that amino acid residue. The substituted amino acid of the invention may be a synthetic or naturally occurring amino acid. In certain embodiments, the substituted amino acid is a naturally occurring amino acid selected from the group consisting of: A, R, N, D, C, Q, E, G, H, I, L, K, M, F, P, S, T, W, Y, and V. Substitution mutants may be described using an abbreviated system. For example, a substitution mutation in which the fifth (5$^{th}$) amino acid residue is substituted may be abbreviated as "X5Y," wherein "X" is the wild-type or naturally occurring amino acid to be replaced, "5" is the amino acid residue within the protein or polypeptide, and "Y" is the substituted, or non-wild-type or non-naturally occurring, amino acid.

The term "recombinant" when used in reference to a nucleic acid molecule, peptide, polypeptide, or protein means of, or resulting from, a new combination of genetic material that is not known to exist in nature. A recombinant molecule can be produced by any of the well-known techniques available in the field of recombinant technology, including, but not limited to, polymerase chain reaction (PCR), gene splicing (e.g., using restriction endonucleases), and solid state synthesis of nucleic acid molecules, peptides, or proteins.

An "isolated" polypeptide, protein, peptide, or nucleic acid is a molecule that has been removed from its natural environment. It is also to be understood that "isolated" polypeptides, proteins, peptides, or nucleic acids may be formulated with excipients such as diluents or adjuvants and still be considered isolated.

The terms "sequence identity" or "% identity" in the context of nucleic acid sequences or amino acid sequences refers to the percentage of residues in the compared sequences that are the same when the sequences are aligned over a specified comparison window. A comparison window can be a segment of at least 10 to over 1000 residues in which the sequences can be aligned and compared. Methods of alignment for determination of sequence identity are well-known can be performed using publically available databases such as BLAST (blast.ncbi.nlm.nih.gov/Blast.cgi.). "Percent identity" or "% identity" when referring to amino acid sequences can be determined by methods known in the art. For example, in some embodiments, "percent identity" of two amino acid sequences is determined using the algorithm of Karlin and Altschul, *Proc. Natl. Acad. Sci. USA* 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al., *J. Mol. Biol.* 215:403-10 (1990). BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

In certain embodiments of the invention, polypeptides or nucleic acid molecules have 70%, at least 70%, 75%, at least 75%, 80%, at least 80%, 85%, at least 85%, 90%, at least 90%, 95%, at least 95%, 97%, at least 97%, 98%, at least 98%, 99%, or at least 99% or 100% sequence identity with a reference polypeptide or nucleic acid molecule, respectively (or a fragment of the reference polypeptide or nucleic acid molecule). In some embodiments, polypeptides or nucleic acid molecules have about 70%, at least about 70%, about 75%, at least about 75%, about 80%, at least about 80%, about 85%, at least about 85%, about 90%, at least about 90%, about 95%, at least about 95%, about 97%, at least about 97%, about 98%, at least about 98%, about 99%, at least about 99% or about 100% sequence identity with a reference polypeptide or nucleic acid molecule, respectively (or a fragment of the reference polypeptide or nucleic acid molecule).

The RNA molecule that binds to CRISPR-Cas components and targets them to a specific location within the target DNA is referred to herein as "guide RNA," "gRNA," or "small guide RNA" and may also be referred to herein as a "DNA-targeting RNA." A guide RNA comprises at least two nucleotide segments: at least one "DNA-binding segment" and at least one "polypeptide-binding segment." By "segment" is meant a part, section, or region of a molecule, e.g., a contiguous stretch of nucleotides of an RNA molecule. The definition of "segment," unless otherwise specifically defined, is not limited to a specific number of total base pairs.

The guide RNA can be introduced into the target cell as an isolated RNA molecule, or is introduced into the cell using an expression vector containing DNA encoding the guide RNA.

The "DNA-binding segment" (or "DNA-targeting sequence") of the guide RNA comprises a nucleotide sequence that is complementary to a specific sequence within a target DNA.

The guide RNA of the current disclosure can include one or more polypeptide-binding sequences/segments. The polypeptide-binding segment (or "protein-binding sequence") of the guide RNA interacts with the RNA-binding domain of a Cas protein of the current disclosure. Such polypeptide-binding segments or sequences are known to those of skill in the art, e.g., those disclosed in U.S. patent application publications 2014/0068797, 2014/0273037, 2014/0273226, 2014/0295556, 2014/0295557, 2014/0349405, 2015/0045546, 2015/0071898, 2015/0071899, and 2015/0071906, the disclosures of which are incorporated herein in their entireties.

"T cell" or "T-cell" are used interchangeably and refer to a type of lymphocytic cell that plays a central role in cell-mediated immunity and expresses a T-cell receptor (TCR) on its surface. T-cells include CD4+ and CD8+ T-cells but are distinguished from other lymphocytes, such as B cells and natural killer cells (NK cells).

A "major histocompatibility complex" or "MHC" protein as used herein refers to a set of cell surface molecules encoded by a large gene family that play a significant role in the immune system of vertebrates. A key function of these proteins is to bind peptide fragments derived from endogenous or exogenous (foreign) proteins and display them on the cell surface for recognition by the appropriate T-cells of the host organism. The MHC gene family is divided into three subgroups: Class I, Class II, and Class III. The human MHC Class I and Class II genes are also referred to as human leukocyte antigen (HLA)—HLA Class I and HLA Class II, respectively. Some of the most studied HLA genes in humans are the nine MHC genes: HLA-A, HLA-B, HLA-C, HLA-DPA1, HLA-DPB1, HLA-DQA1, HLA-DQB1, HLA-DRA, HLA-DRB1 and HLA-DRB345.

"Binding" or "interaction" as used herein refers to a non-covalent interaction between macromolecules (e.g., between DNA and RNA, or between a polypeptide and a polynucleotide). "Binding" may also be referred to as "associated with" or "interacting." "Binding" as used herein means that the binding partners are capable of binding to each other (e.g., will not necessarily bind to each other). Some portions of a binding interaction may be sequence-specific, but not all components of a binding interaction need be sequence-specific (e.g., contacts with phosphate residues in a DNA backbone). Binding interactions are generally characterized by a dissociation constant (Kd), e.g., less than 1 mM, less than 100 uM, less than 10 uM, less than 1 uM, less than 100 nM, less than 10 nM. "Affinity" refers to the strength of binding, increased binding affinity being correlated with a lower Kd.

As used herein, "promoter," "promoter sequence," or "promoter region" refers to a DNA regulatory region/sequence capable of binding RNA polymerase and involved in initiating transcription of a downstream coding or non-coding sequence. In some examples of the present disclosure, the promoter sequence includes the transcription initiation site and extends upstream to include the minimum number of bases or elements necessary to initiate transcription at levels detectable above background. In some embodiments, the promoter sequence includes a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present invention.

A "vector" or "expression vector" is a replicon, such as a plasmid, phage, virus, or cosmid, to which another DNA segment may be attached to bring about the replication and/or expression of the attached DNA segment in a cell. "Vector" includes episomal (e.g., plasmids) and non episomal vectors. In some embodiments of the present disclosure the vector is an episomal vector, which is removed/lost from a population of cells after a number of cellular generations, e.g., by asymmetric partitioning. The term "vector" includes both viral and nonviral means for introducing a nucleic acid molecule into a cell in vitro, in vivo, or ex vivo. Vectors may be introduced into the desired host cells by well-known methods, including, but not limited to, transfection, transduction, cell fusion, and lipofection. Vectors can comprise various regulatory elements including promoters. In some embodiments, vector designs can be based on constructs designed by Mali et al. "Cas9 as a versatile tool for engineering biology," *Nature Methods* 10:957-63 (2013). In some embodiments, the invention is directed to an expression vector comprising any of the polynucleotides described herein, e.g., an expression vector comprising polynucleotides encoding a Cas protein or variant thereof. In some embodiments, the invention is directed to an expression vector comprising polynucleotides encoding a Cas3, Cas9, or Cas10 protein or variant thereof.

"Transfection" as used herein means the introduction of an exogenous nucleic acid molecule, including a vector, into a cell. A "transfected" cell comprises an exogenous nucleic acid molecule inside the cell and a "transformed" cell is one in which the exogenous nucleic acid molecule within the cell induces a phenotypic change in the cell. The transfected nucleic acid molecule can be integrated into the host cell's genomic DNA and/or can be maintained by the cell, temporarily or for a prolonged period of time, extra-chromosomally. Host cells or organisms that express exogenous nucleic acid molecules or fragments are referred to as "recombinant," "transformed," or "transgenic" organisms. In some embodiments, the invention is directed to a host cell comprising any of the expression vectors described herein, e.g., an expression vector comprising a polynucleotide encoding a Cas protein or variant thereof. In some embodiments, the invention is directed to a host cell comprising an expression vector comprising a polynucleotide encoding a Cas3, Cas 9 or Cas10 protein or variant thereof.

The term "in silico" as used herein refers to a process or analysis preformed on a computer, including computer modeling and computer simulation. In some embodiments, the term "in silico" refers to the EPIBASE® epitope prediction method.

Recombinant CRISPR-Associated (Cas) Proteins

As described above, Cas proteins are a critical component in the CRISPR-Cas system, which can be used for, inter alia, genome editing, gene regulation, genetic circuit construction, and functional genomics. While the Cas1 and Cas2 proteins appear to be universal to all the presently identified CRISPR systems, the Cas3, Cas9, and Cas10 proteins are thought to be specific to the Type I, Type II, and Type III CRISPR systems, respectively. In certain embodiments of the present invention, the recombinant Cas protein with reduced immunogenicity, including methods of deriving such proteins, is derived from a Cas3, Cas9, or Cas10 protein. In some embodiments, the recombinant Cas protein with reduced immunogenicity, including methods of deriving such a protein, is derived from a Cas9 protein.

Following initial publications around the CRISPR-Cas9 system (Type II system), Cas9 variants have been identified in a range of bacterial species and a number have been functionally characterized. See, e.g., Chylinski, et al., "Classification and evolution of type II CRISPR-Cas systems," *Nucleic Acids Research* 42(10):6091-105 (2014), Ran, et al., "In vivo genome editing using *Staphylococcus aureus* Cas9," *Nature* 520(7546):186-91 (2015) and Esvelt, et al., "Orthogonal Cas9 proteins for RNA-guided gene regulation and editing," *Nature Methods* 10(11):1116-21 (2013), each of which is incorporated by reference herein in its entirety.

Cas9 variants from *Streptococcus pyogenes, Streptococcus thermophilus, Staphylococcus aureus*, and *Neisseria meningitidis*, in particular, have been well-characterized. In some embodiments, the recombinant Cas protein with reduced immunogenicity, including methods of deriving such a protein, is derived from a Cas9 protein from a bacterium of the genera, *Streptococcus, Staphylococcus*, or *Neisseria*. In certain embodiments, the recombinant Cas9 protein is derived from a Cas9 protein from *Streptococcus pyogenes, Streptococcus thermophilus, Staphylococcus aureus*, or *Neisseria meningitidis*. In some embodiments, the recombinant Cas9 protein is derived from a *Streptococcus pyogenes* Cas9 protein. In other embodiments, the recombinant Cas9 protein is derived from a *Staphylococcus aureus* Cas9 protein.

Following is an exemplary nucleotide sequence (SEQ ID NO: 1) that encodes the *Streptococcus pyogenes* Cas9 protein:

ATGGACAAGAAGTACTCCATTGGGCTCGATATCGGCACAAACAGCGTC

GGCTGGGCCGTCATTACGGACGAGTACAAGGTGCCGAGCAAAAATT

CAAAGTTCTGGGCAATACCGATCGCCACAGCATAAAGAAGAACCTCA

TTGGCGCCCTCCTGTTCGACTCCGGGGAGACGGCCGAAGCCACGCGGC

TCAAAAGAACAGCACGGCGCAGATATACCCGCAGAAAGAATCGGATC

TGCTACCTGCAGGAGATCTTTAGTAATGAGATGGCTAAGGTGGATGAC

TCTTTCTTCCATAGGCTGGAGGAGTCCTTTTTGGTGGAGGAGGATAAA

AAGCACGAGCGCCACCCAATCTTTGGCAATATCGTGGACGAGGTGGC

GTACCATGAAAAGTACCCAACCATATATCATCTGAGGAAGAAGCTTGT

AGACAGTACTGATAAGGCTGACTTGCGGTTGATCTATCTCGCGCTGGC

GCATATGATCAAATTTCGGGGACACTTCCTCATCGAGGGGGACCTGAA

CCCAGACAACAGCGATGTCGACAAACTCTTTATCCAACTGGTTCAGAC

TTACAATCAGCTTTTCGAAGAGAACCCGATCAACGCATCCGGAGTTGA

CGCCAAAGCAATCCTGAGCGCTAGGCTGTCCAAATCCCGGCGGCTCGA

AAACCTCATCGCACAGCTCCCTGGGGAGAAGAAGAACGGCCTGTTTG

GTAATCTTATCGCCCTGTCACTCGGGCTGACCCCCAACTTTAAATCTAA

CTTCGACCTGGCCGAAGATGCCAAGCTTCAACTGAGCAAAGACACCTA

CGATGATGATCTCGACAATCTGCTGGCCCAGATCGGCGACCAGTACGC

AGACCTTTTTTTGGCGGCAAAGAACCTGTCAGACGCCATTCTGCTGAG

TGATATTCTGCGAGTGAACACGGAGATCACCAAAGCTCCGCTGAGCGC

TAGTATGATCAAGCGCTATGATGAGCACCACCAAGACTTGACTTTGCT

GAAGGCCCTTGTCAGACAGCAACTGCCTGAGAAGTACAAGGAAATTTT

CTTCGATCAGTCTAAAAATGGCTACGCCGGATACATTGACGGCGGAGC

AAGCCAGGAGGAATTTTACAAATTTATTAAGCCCATCTTGGAAAAAAT

GGACGGCACCGAGGAGCTGCTGGTAAAGCTTAACAGAGAAGATCTGT

TGCGCAAACAGCGCACTTTCGACAATGGAAGCATCCCCCACCAGATTC

ACCTGGGCGAACTGCACGCTATCCTCAGGCGGCAAGAGGATTTCTACC

CCTTTTTGAAAGATAACAGGGAAAAGATTGAGAAAATCCTCACATTTC

GGATACCCTACTATGTAGGCCCCCTCGCCCGGGGAAATTCCAGATTCG

CGTGGATGACTCGCAAATCAGAAGAGACCATCACTCCCTGGAACTTCG

AGGAAGTCGTGGATAAGGGGGCCTCTGCCCAGTCCTTCATCGAAAGG

ATGACTAACTTTGATAAAAATCTGCCTAACGAAAAGGTGCTTCCTAAA

CACTCTCTGCTGTACGAGTACTTCACAGTTTATAACGAGCTCACCAAG

GTCAAATACGTCACAGAAGGGATGAGAAAGCCAGCATTCCTGTCTGG

AGAGCAGAAGAAAGCTATCGTGGACCTCCTCTTCAAGACGAACCGGA

AAGTTACCGTGAAACAGCTCAAAGAAGACTATTTCAAAAAGATTGAA

TGTTTCGACTCTGTTGAAATCAGCGGAGTGGAGGATCGCTTCAACGCA

TCCCTGGGAACGTATCACGATCTCCTGAAAATCATTAAAGACAAGGAC

TTCCTGGACAATGAGGAGAACGAGGACATTCTTGAGGACATTGTCCTC

ACCCTTACGTTGTTTGAAGATAGGGAGATGATTGAAGAACGCTTGAAA

ACTTACGCTCATCTCTTCGACGACAAAGTCATGAAACAGCTCAAGAGG

CGCCGATATACAGGATGGGGCGGCTGTCAAGAAAACTGATCAATGG

GATCCGAGACAAGCAGAGTGGAAAGACAATCCTGGATTTTCTTAAGTC

CGATGGATTTGCCAACCGGAACTTCATGCAGTTGATCCATGATGACTC

TCTCACCTTTAAGGAGGACATCCAGAAAGCACAAGTTTCTGGCCAGGG

GGACAGTCTTCACGAGCACATCGCTAATCTTGCAGGTAGCCCAGCTAT

CAAAAAGGGAATACTGCAGACCGTTAAGGTCGTGGATGAACTCGTCA

AAGTAATGGGAAGGCATAAGCCCGAGAATATCGTTATCGAGATGGCC

CGAGAGAACCAAACTACCCAGAAGGGACAGAAGAACAGTAGGGAAA

GGATGAAGAGGATTGAAGAGGGTATAAAAGAACTGGGGTCCCAAATC

CTTAAGGAACACCCAGTTGAAAACACCCAGCTTCAGAATGAGAAGCT

CTACCTGTACTACCTGCAGAACGGCAGGGACATGTACGTGGATCAGGA

ACTGGACATCAATCGGCTCTCCGACTACGACGTGGATCATATCGTGCC

CCAGTCTTTTCTCAAAGATGATTCTATTGATAATAAAGTGTTGACAAG

ATCCGATAAAAATAGAGGGAAGAGTGATAACGTCCCCTCAGAAGAAG

TTGTCAAGAAAATGAAAAATTATTGGCGGCAGCTGCTGAACGCCAAA

CTGATCACACAACGGAAGTTCGATAATCTGACTAAGGCTGAACGAGGT

GGCCTGTCTGAGTTGGATAAAGCCGGCTTCATCAAAAGGCAGCTTGTT

GAGACACGCCAGATCACCAAGCACGTGGCCCAAATTCTCGATTCACGC

ATGAACACCAAGTACGATGAAAATGACAAACTGATTCGAGAGGTGAA

AGTTATTACTCTGAAGTCTAAGCTGGTCTCAGATTTCAGAAAGGACTT

-continued
```
TCAGTTTTATAAGGTGAGAGAGATCAACAATTACCACCATGCGCATGA
TGCCTACCTGAATGCAGTGGTAGGCACTGCACTTATCAAAAAATATCC
CAAGCTTGAATCTGAATTTGTTTACGGAGACTATAAAGTGTACGATGT
TAGGAAAATGATCGCAAAGTCTGAGCAGGAAATAGGCAAGGCCACCG
CTAAGTACTTCTTTTACAGCAATATTATGAATTTTTTCAAGACCGAGAT
TACACTGGCCAATGGAGAGATTCGGAAGCGACCACTTATCGAAACAA
ACGGAGAAACAGGAGAAATCGTGTGGGACAAGGGTAGGGATTTCGCG
ACAGTCCGGAAGGTCCTGTCCATGCCGCAGGTGAACATCGTTAAAAAG
ACCGAAGTACAGACCGGAGGCTTCTCCAAGGAAAGTATCCTCCCGAA
AAGGAACAGCGACAAGCTGATCGCACGCAAAAAGATTGGGACCCCA
AGAAATACGGCGGATTCGATTCTCCTACAGTCGCTTACAGTGTACTGG
TTGTGGCCAAAGTGGAGAAAGGGAAGTCTAAAAAACTCAAAAGCGTC
AAGGAACTGCTGGGCATCACAATCATGGAGCGATCAAGCTTCGAAAA
AAACCCCATCGACTTTCTCGAGGCGAAAGGATATAAAGAGGTCAAAA
AAGACCTCATCATTAAGCTTCCCAAGTACTCTCTCTTTGAGCTTGAAAA
CGGCCGGAAACGAATGCTCGCTAGTGCGGGCGAGCTGCAGAAAGGTA
ACGAGCTGGCACTGCCCTCTAAATACGTTAATTTCTTGTATCTGGCCAG
CCACTATGAAAAGCTCAAAGGGTCTCCCGAAGATAATGAGCAGAAGC
AGCTGTTCGTGGAACAACACAAACACTACCTTGATGAGATCATCGAGC
AAATAAGCGAATTCTCCAAAAGAGTGATCCTCGCCGACGCTAACCTCG
ATAAGGTGCTTTCTGCTTACAATAAGCACAGGGATAAGCCCATCAGGG
AGCAGGCAGAAAACATTATCCACTTGTTTACTCTGACCAACTTGGGCG
CGCCTGCAGCCTTCAAGTACTTCGACACCACCATAGACAGAAAGCGGT
ACACCTCTACAAAGGAGGTCCTGGACGCCACACTGATTCATCAGTCAA
TTACGGGGCTCTATGAAACAAGAATCGACCTCTCTCAGCTCGGTGGAG
ACTGA
```

Following is an exemplary nucleotide sequence (SEQ ID NO: 2) that encodes the *Streptococcus thermophilus* Cas9 protein:

```
ATGAGCGACCTGGTGCTGGGCCTGGACATCGGCATCGGCAGCGTGGG
CGTGGGCATCCTGAACAAGGTGACCGGCGAGATCATCCACAAGAACA
GTCGCATCTTCCCTGCTGCTCAGGCTGAGAACAACCTGGTGCGCCGCA
CCAACCGCCAGGGTCGCCGGCTTGCTCGCCGCAAGAAGCACCGGCGC
GTGCGCCTGAACCGCCTGTTCGAGGAGAGCGGCCTGATCACCGACTTC
ACCAAGATCAGCATCAACCTGAACCCCTACCAGCTGCGCGTGAAGGG
CCTGACCGACGAGCTGAGCAACGAGGAGCTGTTCATCGCCCTGAAGA
ACATGGTGAAGCACCGCGGCATCAGCTACCTGGACGACGCCAGCGAC
GACGGCAACAGCAGCGTGGGCGACTACGCCCAGATCGTGAAGGAGAA
CAGCAAGCAGCTGGAGACCAAGACCCCCGGCCAGATCCAGCTGGAGC
GCTACCAGACCTACGGCCAGCTGCGCGGCGACTTCACCGTGGAGAAG
GACGGCAAGAAGCACCGCCTGATCAACGTGTTCCCCACCAGCGCCTAC
CGCAGCGAGGCCCTGCGCATCCTGCAGACCCAGCAGGAGTTCAACCC
CCAGATCACCGACGAGTTCATCAACCGCTACCTGGAGATCCTGACCGG
CAAGCGCAAGTACTACCACGGCCCCGGCAACGAGAAGAGCCGCACCG
ACTACGGCCGCTACCGCACCAGCGGCGAGACCCTGGACAACATCTTCG
GCATCCTGATCGGCAAGTGCACCTTCTACCCCGACGAGTTCCGCGCCG
CCAAGGCCAGCTACACCGCCCAGGAGTTCAACCTGCTGAACGACCTG
AACAACCTGACCGTGCCCACCGAGACCAAGAAGCTGAGCAAGGAGCA
GAAGAACCAGATCATCAACTACGTGAAGAACGAGAAGGCCATGGGCC
CCGCCAAGCTGTTCAAGTACATCGCCAAGCTGCTGAGCTGCGACGTGG
CCGACATCAAGGGCTACCGCATCGACAAGAGCGGCAAGGCCGAGATC
CACACCTTCGAGGCCTACCGCAAGATGAAGACCCTGGAGACCCTGGA
CATCGAGCAGATGGACCGCGAGACCCTGGACAAGCTGGCCTACGTGC
TGACCCTGAACACCGAGCGCGAGGGCATCCAGGAGGCCCTGGAGCAC
GAGTTCGCCGACGGCAGCTTCAGCCAGAAGCAGGTGGACGAGCTGGT
GCAGTTCCGCAAGGCCAACAGCAGCATCTTCGGCAAGGGCTGGCACA
ACTTCAGCGTGAAGCTGATGATGGAGCTGATCCCCGAGCTGTACGAGA
CCAGCGAGGAGCAGATGACCATCCTGACCCGCCTGGGCAAGCAGAAG
ACCACCAGCAGCAGCAACAAGACCAAGTACATCGACGAGAAGCTGCT
GACCGAGGAGATCTACAACCCCGTGGTGGCCAAGAGCGTGCGCCAGG
CCATCAAGATCGTGAACGCCGCCATCAAGGAGTACGGCGACTTCGAC
AACATCGTGATCGAGATGGCCCGCGAGACCAACGAGGACGACGAGAA
GAAGGCCATCCAGAAGATCCAGAAGGCCAACAAGGACGAGAAGGAC
GCCGCCATGCTGAAGGCCGCCAACCAGTACAACGGCAAGGCCGAGCT
GCCCCACAGCGTGTTCCACGGCCACAAGCAGCTGGCCACCAAGATCC
GCCTGTGGCACCAGCAGGGCGAGCGCTGCCTGTACACCGGCAAGACC
ATCAGCATCCACGACCTGATCAACAACAGCAACCAGTTCGAGGTGGA
CCACATCCTGCCCCTGAGCATCACCTTCGACGACAGCCTGGCCAACAA
GGTGCTGGTGTACGCCACCGCCAACCAGGAGAAGGGCCAGCGCACCC
CCTACCAGGCCCTGGACAGCATGGACGACGCCTGGAGCTTCCGCGAG
CTGAAGGCCTTCGTGCGCGAGAGCAAGACCCTGAGCAACAAGAAGAA
GGAGTACCTGCTGACCGAGGAGGACATCAGCAAGTTCGACGTGCGCA
AGAAGTTCATCGAGCGCAACCTGGTGGACACCCGCTACGCCAGCCGC
GTGGTGCTGAACGCCCTGCAGGAGCACTTCCGCGCCCACAAGATCGAC
ACCAAGGTGAGCGTGGTGCGCGGCCAGTTCACCAGCCAGCTGCGCCG
CCACTGGGGCATCGAGAAGACCCGCGACACCTACCACCACCACGCCG
TGGACGCCCTGATCATTGCGGCTTCTAGCCAGCTGAACCTGTGGAAGA
AGCAGAAGAACACCCTGGTGAGCTACAGCGAGGACCAGCTGCTGGAC
ATCGAGACCGGCGAGCTGATCAGCGACGACGAGTACAAGGAGAGCGT
GTTCAAGGCCCCCTACCAGCACTTCGTGGACACCCTGAAGAGCAAGG
AGTTCGAGGACAGCATCCTGTTCAGCTACCAGGTGGACAGCAAGTTCA
```

```
ACCGCAAGATCAGCGACGCCACCATCTACGCCACCCGCCAGGCCAAG
GTGGGCAAGGACAAGGCCGACGAGACCTACGTGCTGGGCAAGATCAA
GGACATCTACACCCAGGACGGCTACGACGCCTTCATGAAGATCTACAA
GAAGGACAAGAGCAAGTTCCTGATGTACCGCCACGACCCCCAGACCT
TCGAGAAGGTGATCGAGCCCATCCTGGAGAACTACCCCAACAAGCAG
ATCAACGATAAAGGCAAGGAGGTGCCCTGCAACCCCTTCCTGAAGTA
CAAGGAGGAGCACGGCTACATCCGCAAGTACAGCAAGAAGGGCAACG
GCCCCGAGATCAAGAGCCTGAAGTACTACGACAGCAAGCTGGGCAAC
CACATCGACATCACCCCCAAGGACAGCAACAACAAGGTGGTGCTGCA
GAGCGTGAGCCCCTGGCGCGCCGACGTGTACTTCAACAAGACCACCG
GCAAGTACGAGATCCTGGGCCTGAAGTACGCCGACCTGCAGTTTGATA
AGGGCACCGGCACCTACAAGATCAGCCAGGAGAAGTACAACGACATC
AAGAAGAAGGAGGGCGTGGACAGCGACAGCGAGTTCAAGTTCACCCT
GTACAAGAACGACCTTCTGCTGGTGAAGGACACCGAGACCAAGGAGC
AACAGCTGTTCCGCTTCCTGAGCCGCACCATGCCCAAGCAGAAGCACT
ACGTGGAGCTGAAGCCCTACGACAAGCAGAAGTTCGAGGGCGGCGAG
GCCCTGATCAAGGTGCTGGGCAACGTGGCCAACAGCGGCCAGTGCAA
GAAGGGCCTGGGCAAGAGCAACATCAGCATCTACAAGGTGCGCACCG
ACGTGCTGGGCAACCAGCACATCATCAAGAACGAGGGCGACAAGCCC
AAGCTGGACTTCTGA
```

Following is an exemplary nucleotide sequence (SEQ ID NO: 3) that encodes the *Staphylococcus aureus* Cas9 protein:

```
ATGAAGCGGAACTACATCCTGGGCCTGGACATCGGCATCACCAGCGT
GGGCTACGGCATCATCGACTACGAGACACGGGACGTGATCGATGCCG
GCGTGCGGCTGTTCAAAGAGGCCAACGTGGAAAACAACGAGGGCAGG
CGGAGCAAGAGAGGCGCCAGAAGGCTGAAGCGGCGGAGGCGGCATA
GAATCCAGAGAGTGAAGAAGCTGCTGTTCGACTACAACCTGCTGACCG
ACCACAGCGAGCTGAGCGGCATCAACCCCTACGAGGCCAGAGTGAAG
GGCCTGAGCCAGAAGCTGAGCGAGGAAGAGTTCTCTGCCGCCCTGCT
GCACCTGGCCAAGAGAAGAGGCGTGCACAACGTGAACGAGGTGGAAG
AGGACACCGGCAACGAGCTGTCCACCAAAGAGCAGATCAGCCGGAAC
AGCAAGGCCCTGGAAGAGAAATACGTGGCCGAACTGCAGCTGGAACG
GCTGAAGAAAGACGGCGAAGTGCGGGGCAGCATCAACAGATTCAAGA
CCAGCGACTACGTGAAAGAAGCCAAACAGCTGCTGAAGGTGCAGAAG
GCCTACCACCAGCTGGACCAGAGCTTCATCGACACCTACATCGACCTG
CTGGAAACCCGGCGGACCTACTATGAGGGACCTGGCGAGGGCAGCCC
CTTCGGCTGGAAGGACATCAAGGAATGGTACGAGATGCTGATGGGCC
ACTGCACCTACTTCCCCGAGGAACTGCGGAGCGTGAAGTACGCCTACA
ACGCCGACCTGTACAACGCCCTGAACGACCTGAACAATCTCGTGATCA
CCAGGGACGAGAACGAGAAGCTGGAATATTACGAGAAGTTCCAGATC
ATCGAGAACGTGTTCAAGCAGAAGAAGAAGCCCACCCTGAAGCAGAT
CGCCAAAGAAATCCTCGTGAACGAAGAGGATATTAAGGGCTACAGAG
TGACCAGCACCGGCAAGCCCGAGTTCACCAACCTGAAGGTGTACCAC
GACATCAAGGACATTACCGCCCGGAAAGAGATTATTGAGAACGCCGA
GCTGCTGGATCAGATTGCCAAGATCCTGACCATCTACCAGAGCAGCGA
GGACATCCAGGAAGAACTGACCAATCTGAACTCCGAGCTGACCCAGG
AAGAGATCGAGCAGATCTCTAATCTGAAGGGCTATACCGGCACCCAC
AACCTGAGCCTGAAGGCCATCAACCTGATCCTGGACGAGCTGTGGCAC
ACCAACGACAACCAGATCGCTATCTTCAACCGGCTGAAGCTGGTGCCC
AAGAAGGTGGACCTGTCCCAGCAGAAAGAGATCCCCACCACCCTGGT
GGACGACTTCATCCTGAGCCCCGTCGTGAAGAGAAGCTTCATCCAGAG
CATCAAAGTGATCAACGCCATCATCAAGAAGTACGGCCTGCCCAACG
ACATCATTATCGAGCTGGCCCGCGAGAAGAACTCCAAGGACGCCCAG
AAAATGATCAACGAGATGCAGAAGCGGAACCGGCAGACCAACGAGC
GGATCGAGGAAATCATCCGGACCACCGGCAAAGAGAACGCCAAGTAC
CTGATCGAGAAGATCAAGCTGCACGACATGCAGGAAGGCAAGTGCCT
GTACAGCCTGGAAGCCATCCCTCTGGAAGATCTGCTGAACAACCCCTT
CAACTATGAGGTGGACCACATCATCCCCAGAAGCGTGTCCTTCGACAA
CAGCTTCAACAACAAGGTGCTCGTGAAGCAGGAAGAAAACAGCAAGA
AGGGCAACCGGACCCCATTCCAGTACCTGAGCAGCAGCGACAGCAAG
ATCAGCTACGAAACCTTCAAGAAGCACATCCTGAATCTGGCCAAGGG
CAAGGGCAGAATCAGCAAGACCAAGAAAGAGTATCTGCTGGAAGAAC
GGGACATCAACAGGTTCTCCGTGCAGAAAGACTTCATCAACCGGAAC
CTGGTGGATACCAGATACGCCACCAGAGGCCTGATGAACCTGCTGCG
GAGCTACTTCAGAGTGAACAACCTGGACGTGAAAGTGAAGTCCATCA
ATGGCGGCTTCACCAGCTTTCTGCGGCGGAAGTGGAAGTTTAAGAAAG
AGCGGAACAAGGGGTACAAGCACCACGCCGAGGACGCCCTGATCATT
GCCAACGCCGATTTCATCTTCAAAGAGTGGAAGAAACTGGACAAGGC
CAAAAAAGTGATGGAAAACCAGATGTTCGAGGAAAAGCAGGCCGAGA
GCATGCCCGAGATCGAAACCGAGCAGGAGTACAAAGAGATCTTCATC
ACCCCCCACCAGATCAAGCACATTAAGGACTTCAAGGACTACAAGTA
CAGCCACCGGGTGGACAAGAAGCCTAATAGAGAGCTGATTAACGACA
CCCTGTACTCCACCCGAAGGACGACAAGGGCAACACCCTGATCGTG
AACAATCTGAACGGCCTGTACGACAAGGACAATGACAAGCTGAAAAA
GCTGATCAACAAGAGCCCCGAAAAGCTGCTGATGTACCACCACGACC
CCCAGACCTACCAGAAACTGAAGCTGATTATGGAACAGTACGGCGAC
GAGAAGAATCCCCTGTACAAGTACTACGAGGAAACCGGGAACTACCT
GACCAAGTACTCCAAAAAGGACAACGGCCCCGTGATCAAGAAGATTA
AGTATTACGGCAACAAACTGAACGCCCATCTGGACATCACCGACGACT
ACCCCAACAGCAGAAACAAGGTCGTGAAGCTGTCCCTGAAGCCCTAC
```

AGATTCGACGTGTACCTGGACAATGGCGTGTACAAGTTCGTGACCGTG
AAGAATCTGGATGTGATCAAAAAAGAAAACTACTACGAAGTGAATAG
CAAGTGCTATGAGGAAGCTAAGAAGCTGAAGAAGATCAGCAACCAGG
CCGAGTTTATCGCCTCCTTCTACAACAACGATCTGATCAAGATCAACG
GCGAGCTGTATAGAGTGATCGGCGTGAACAACGACCTGCTGAACCGG
ATCGAAGTGAACATGATCGACATCACCTACCGCGAGTACCTGGAAAA
CATGAACGACAAGAGGCCCCCAGGATCATTAAGACAATCGCCTCCA
AGACCCAGAGCATTAAGAAGTACAGCACAGACATTCTGGGCAACCTG
TATGAAGTGAAATCTAAGAAGCACCCTCAGATCATCAAAAAGGGCTA
A

Following is an exemplary nucleotide sequence (SEQ ID NO: 4) that encodes the *Neisseria meningitidis* Cas9 protein:

ATGGCCGCCTTCAAGCCCAACCCCATCAACTACATCCTGGGCCTGGAC
ATCGGCATCGCCAGCGTGGGCTGGGCCATGGTGGAGATCGACGAGGA
CGAGAACCCCATCTGCCTGATCGACCTGGGTGTGCGCGTGTTCGAGCG
CGCTGAGGTGCCCAAGACTGGTGACAGTCTGGCTATGGCTCGCCGGCT
TGCTCGCTCTGTTCGGCGCCTTACTCGCCGGCGCGCTCACCGCCTTCTG
CGCGCTCGCCGCCTGCTGAAGCGCGAGGGTGTGCTGCAGGCTGCCGAC
TTCGACGAGAACGGCCTGATCAAGAGCCTGCCCAACACTCCTTGGCAG
CTGCGCGCTGCCGCTCTGGACCGCAAGCTGACTCCTCTGGAGTGGAGC
GCCGTGCTGCTGCACCTGATCAAGCACCGCGGCTACCTGAGCCAGCGC
AAGAACGAGGGCGAGACCGCCGACAAGGAGCTGGGTGCTCTGCTGAA
GGGCGTGGCCGACAACGCCCACGCCCTGCAGACTGGTGACTTCCGCAC
TCCTGCTGAGCTGGCCCTGAACAAGTTCGAGAAGGAGAGCGGCCACA
TCCGCAACCAGCGCGGCGACTACAGCCACACCTTCAGCCGCAAGGAC
CTGCAGGCCGAGCTGATCCTGCTGTTCGAGAAGCAGAAGGAGTTCGGC
AACCCCCACGTGAGCGGCGGCCTGAAGGAGGGCATCGAGACCCTGCT
GATGACCCAGCGCCCCGCCCTGAGCGGCGACGCCGTGCAGAAGATGC
TGGGCCACTGCACCTTCGAGCCAGCCGAGCCCAAGGCCGCCAAGAAC
ACCTACACCGCCGAGCGCTTCATCTGGCTGACCAAGCTGAACAACCTG
CGCATCCTGGAGCAGGGCAGCGAGCGCCCCCTGACCGACACCGAGCG
CGCCACCCTGATGGACGAGCCCTACCGCAAGAGCAAGCTGACCTACG
CCCAGGCCCGCAAGCTGCTGGGTCTGGAGGACACCGCCTTCTTCAAGG
GCCTGCGCTACGGCAAGGACAACGCCGAGGCCAGCACCCTGATGGAG
ATGAAGGCCTACCACGCCATCAGCCGCGCCCTGGAGAAGGAGGGCCT
GAAGGACAAGAAGAGTCCTCTGAACCTGAGCCCCGAGCTGCAGGACG
AGATCGGCACCGCCTTCAGCCTGTTCAAGACCGACGAGGACATCACCG
GCCGCCTGAAGGACCGCATCCAGCCCGAGATCCTGGAGGCCCTGCTG
AAGCACATCAGCTTCGACAAGTTCGTGCAGATCAGCCTGAAGGCCCTG
CGCCGCATCGTGCCCCTGATGGAGCAGGGCAAGCGCTACGACGAGGC
CTGCGCCGAGATCTACGGCGACCACTACGGCAAGAAGAACACCGAGG
AGAAGATCTACCTGCCTCCTATCCCCGCCGACGAGATCCGCAACCCCG
TGGTGCTGCGCGCCCTGAGCCAGGCCCGCAAGGTGATCAACGGCGTG
GTGCGCCGCTACGGCAGCCCCGCCCGCATCCACATCGAGACCGCCCGC
GAGGTGGGCAAGAGCTTCAAGGACCGCAAGGAGATCGAGAAGCGCCA
GGAGGAGAACCGCAAGGACCGCGAGAAGGCCGCCGCCAAGTTCCGCG
AGTACTTCCCCAACTTCGTGGGCGAGCCCAAGAGCAAGGACATCCTGA
AGCTGCGCCTGTACGAGCAGCAGCACGGCAAGTGCCTGTACAGCGGC
AAGGAGATCAACCTGGGCCGCCTGAACGAGAAGGGCTACGTGGAGAT
CGACCACGCCCTGCCCTTCAGCCGCACCTGGGACGACAGCTTCAACAA
CAAGGTGCTGGTGCTGGGCAGCGAGAACCAGAACAAGGGCAACCAGA
CCCCCTACGAGTACTTCAACGGCAAGGACAACAGCCGCGAGTGGCAG
GAGTTCAAGGCCCGCGTGGAGACCAGCCGCTTCCCCCGCAGCAAGAA
GCAGCGCATCCTGCTGCAGAAGTTCGACGAGGACGGCTTCAAGGAGC
GCAACCTGAACGACACCCGCTACGTGAACCGCTTCCTGTGCCAGTTCG
TGGCCGACCGCATGCGCCTGACCGGCAAGGGCAAGAAGCGCGTGTTC
GCCAGCAACGGCCAGATCACCAACCTGCTGCGCGGCTTCTGGGGCCTG
CGCAAGGTGCGCGCCGAGAACGACCGCCACCACGCCCTGGACGCCGT
GGTGGTGGCCTGCAGCACCGTGGCCATGCAGCAGAAGATCACCCGCTT
CGTGCGCTACAAGGAGATGAACGCCTTCGACGGTAAAACCATCGACA
AGGAGACCGGCGAGGTGCTGCACCAGAAGACCCACTTCCCCCAGCCC
TGGGAGTTCTTCGCCCAGGAGGTGATGATCCGCGTGTTCGGCAAGCCC
GACGGCAAGCCCGAGTTCGAGGAGGCCGACACCCCCGAGAAGCTGCG
CACCCTGCTGGCCGAGAAGCTGAGCAGCCGCCCTGAGGCCGTGCACG
AGTACGTGACTCCTCTGTTCGTGAGCCGCGCCCCCAACCGCAAGATGA
GCGGTCAGGGTCACATGGAGACCGTGAAGAGCGCCAAGCGCCTGGAC
GAGGGCGTGAGCGTGCTGCGCGTGCCCCTGACCCAGCTGAAGCTGAA
GGACCTGGAGAAGATGGTGAACCGCGAGCGCGAGCCCAAGCTGTACG
AGGCCCTGAAGGCCCGCCTGGAGGCCCACAAGGACGACCCCGCCAAG
GCCTTCGCCGAGCCCTTCTACAAGTACGACAAGGCCGGCAACCGCACC
CAGCAGGTGAAGGCCGTGCGCGTGGAGCAGGTGCAGAAGACCGGCGT
GTGGGTGCGCAACCACAACGGCATCGCCGACAACGCCACCATGGTGC
GCGTGGACGTGTTCGAGAAGGGCGACAAGTACTACCTGGTGCCCATCT
ACAGCTGGCAGGTGGCCAAGGGCATCCTGCCCGACCGCGCCGTGGTG
CAGGGCAAGGACGAGGAGGACTGGCAGCTGATCGACGACAGCTTCAA
CTTCAAGTTCAGCCTGCACCCCAACGACCTGGTGGAGGTGATCACCAA
GAAGGCCCGCATGTTCGGCTACTTCGCCAGCTGCCACCGCGGCACCGG
CAACATCAACATCCGCATCCACGACCTGGACCACAAGATCGGCAAGA
ACGGCATCCTGGAGGGCATCGGCGTGAAGACCGCCCTGAGCTTCCAG
AAGTACCAGATCGACGAGCTGGGCAAGGAGATCCGCCCCTGCCGCCT
GAAGAAGCGCCCTCCTGTGCGCTGA

In some embodiments of the present invention, the recombinant Cas protein is derived from a Cas protein encoded by a nucleic acid molecule comprising a nucleotide sequence having at least 70%, at least 75%, at least 80%, at least 85%, at least 90%, at least 95%, at least 96%, at least 97%, at least 98%, at least 99%, or 100% identity with the nucleotide sequence of SEQ ID NO: 1.

In certain embodiments, the recombinant Cas protein is derived from a Cas protein encoded by a nucleic acid molecule comprising a nucleotide sequence having at least 70%, at least 75%, at least 80%, at least 85%, at least 90%, at least 95%, at least 96%, at least 97%, at least 98%, at least 99%, or 100% identity with the nucleotide sequence of SEQ ID NO: 2.

In some embodiments, the recombinant Cas protein is derived from a Cas protein encoded by a nucleic acid molecule comprising a nucleotide sequence having at least 70%, at least 75%, at least 80%, at least 85%, at least 90%, at least 95%, at least 96%, at least 97%, at least 98%, at least 99%, or 100% identity with the nucleotide sequence of SEQ ID NO: 3.

In certain embodiments, the recombinant Cas protein is derived from a Cas protein encoded by a nucleic acid molecule comprising a nucleotide sequence having at least 70%, at least 75%, at least 80%, at least 85%, at least 90%, at least 95%, at least 96%, at least 97%, at least 98%, at least 99%, or 100% identity with the nucleotide sequence of SEQ ID NO: 4.

Following is the amino acid sequence of the *Streptococcus pyogenes* Cas9 protein (SEQ ID NO: 5) (see Esvelt, et al., "Orthogonal Cas9 proteins for RNA-guided gene regulation and editing," *Nature Methods* 10(11):1116-21 (2013), which is incorporated by reference herein in its entirety):

MDKKYSIGLDIGTNSVGWAVITDEYKVPSKKFKVLGNTDRHSIKKNLI
GALLFDSGETAEATRLKRTARRRYTRRKNRICYLQEIFSNEMAKVDDS
FFHRLEESFLVEEDKKHERHPIFGNIVDEVAYHEKYPTIYHLRKKLVD
STDKADLRLIYLALAHMIKFRGHFLIEGDLNPDNSDVDKLFIQLVQTY
NQLFEENPINASGVDAKAILSARLSKSRRLENLIAQLPGEKKNGLFGN
LIALSLGLTPNFKSNFDLAEDAKLQLSKDTYDDDLDNLLAQIGDQYAD
LFLAAKNLSDAILLSDILRVNTEITKAPLSASMIKRYDEHHQDLTLLK
ALVRQQLPEKYKEIFFDQSKNGYAGYIDGGASQEEFYKFIKPILEKMD
GTEELLVKLNREDLLRKQRTFDNGSIPHQIHLGELHAILRRQEDFYPF
LKDNREKIEKILTFRIPYYVGPLARGNSRFAWMTRKSEETITPWNFEE
VVDKGASAQSFIERMTNFDKNLPNEKVLPKHSLLYEYFTVYNELTKVK
YVTEGMRKPAFLSGEQKKAIVDLLFKTNRKVTVKQLKEDYFKKIECFD
SVEISGVEDRFNASLGTYHDLLKIIKDKDFLDNEENEDILEDIVLTLT
LFEDREMIEERLKTYAHLFDDKVMKQLKRRRYTGWGRLSRKLINGIRD
KQSGKTILDFLKSDGFANRNFMQLIHDDSLTFKEDIQKAQVSGQGDSL
HEHIANLAGSPAIKKGILQTVKVVDELVKVMGRHKPENIVIEMARENQ
TTQKGQKNSRERMKRIEEGIKELGSQILKEHPVENTQLQNEKLYLYYL
QNGRDMYVDQELDINRLSDYDVDHIVPQSFLKDDSIDNKVLTRSDKNR
GKSDNVPSEEVVKKMKNYWRQLLNAKLITQRKFDNLTKAERGGLSELD

KAGFIKRQLVETRQITKHVAQILDSRMNTKYDENDKLIREVKVITLKS
KLVSDFRKDFQFYKVREINNYHHAHDAYLNAVVGTALIKKYPKLESEF
VYGDYKVYDVRKMIAKSEQEIGKATAKYFFYSNIMNFFKTEITLANGE
IRKRPLIETNGETGEIVWDKGRDFATVRKVLSMPQVNIVKKTEVQTGG
FSKESILPKRNSDKLIARKKDWDPKKYGGFDSPTVAYSVLVVAKVEKG
KSKKLKSVKELLGITIMERSSFEKNPIDFLEAKGYKEVKKDLIIKLPK
YSLFELENGRKRMLASAGELQKGNELALPSKYVNFLYLASHYEKLKGS
PEDNEQKQLFVEQHKYLDEIIEQISEFSKRVILADANLDKVLSAYNK
HRDKPIREQAENIIHLFTLTNLGAPAAFKYFDTTIDRKRYTSTKEVLD
ATLIHQSITGLYETRIDLSQLGGD

Following is the amino acid sequence of the *Streptococcus thermophilus* LMD-9 Cas9 protein (SEQ ID NO: 6) (see Esvelt, et al., "Orthogonal Cas9 proteins for RNA-guided gene regulation and editing," *Nature Methods* 10(11):1116-21 (2013), which is incorporated by reference herein in its entirety):

MSDLVLGLDIGIGSVGVGILNKVTGEIIHKNSRIFPAAQAENNLVRRT
NRQGRRLARRKKHRRVRLNRLFEESGLITDFTKISINLNPYQLRVKGL
TDELSNEELFIALKNMVKHRGISYLDDASDDGNSSVGDYAQIVKENSK
QLETKTPGQIQLERYQTYGQLRGDFTVEKDGKKHRLINVFPTSAYRSE
ALRILQTQQEFNPQITDEFINRYLEILTGKRKYYHGPGNEKSRTDYGR
YRTSGETLDNIFGILIGKCTFYPDEFRAAKASYTAQEFNLLNDLNNLT
VPTETKKLSKEQKNQIINYVKNEKAMGPAKLFKYIAKLLSCDVADIKG
YRIDKSGKAEIHTFEAYRKMKTLETLDIEQMDRETLDKLAYVLTLNTE
REGIQEALEHEFADGSFSQKQVDELVQFRKANSSIFGKGWHNFSVKLM
MELIPELYETSEEQMTILTRLGKQKTTSSSNKTKYIDEKLLTEEIYNP
VVAKSVRQAIKIVNAAIKEYGDFDNIVIEMARETNEDDEKKAIQKIQK
ANKDEKDAAMLKAANQYNGKAELPHSVFHGHKQLATKIRLWHQQGERC
LYTGKTISIHDLINNSNQFEVDHILPLSITFDDSLANKVLVYATANQE
KGQRTPYQALDSMDDAWSFRELKAFVRESKTLSNKKKEYLLTEEDISK
FDVRKKFIERNLVDTRYASRVVLNALQEHFRAHKIDTKVSVVRGQFTS
QLRRHWGIEKTRDTYHHHAVDALIIAASSQLNLWKKQKNTLVSYSEDQ
LLDIETGELISDDEYKESVFKAPYQHFVDTLKSKEFEDSILFSYQVDS
KFNRKISDATIYATRQAKVGKDKADETYVLGKIKDIYTQDGYDAFMKI
YKKDKSKFLMYRHDPQTFEKVIEPILENYPNKQINDKGKEVPCNPFLK
YKEEHGYIRKYSKKGNGPEIKSLKYYDSKLGNHIDITPKDSNNKVVLQ
SVSPWRADVYFNKTTGKYEILGLKYADLQFDKGTGTYKISQEKYNDIK
KKEGVDSDSEFKFTLYKNDLLLVKDTETKEQQLFRFLSRTMPKQKHYV
ELKPYDKQKFEGGEALIKVLGNVANSGQCKKGLGKSNISIYKVRTDVL
GNQHIIKNEGDKPKLDF

Following is the amino acid sequence of the *Staphylococcus aureus* subsp. *aureus* Cas9 protein (SEQ ID NO: 7) (see Ran, et al., "In vivo genome editing using *Staphylo-* coccus aureus Cas9," Nature 520(7546):186-91 (2015), which is incorporated by reference herein in its entirety):

MKRNYILGLDIGITSVGYGIIDYETRDVIDAGVRLFKEANVENNEGRR

SKRGARRLKRRRRHRIQRVKKLLFDYNLLTDHSELSGINPYEARVKGL

SQKLSEEEFSAALLHLAKRRGVHNVNEVEEDTGNELSTKEQISRNSKA

LEEKYVAELQLERLKKDGEVRGSINRFKTSDYVKEAKQLLKVQKAYHQ

LDQSFIDTYIDLLETRRTYYEGPGEGSPFGWKDIKEWYEMLMGHCTYF

PEELRSVKYAYNADLYNALNDLNNLVITRDENEKLEYYEKFQIIENVF

KQKKKPTLKQIAKEILVNEEDIKGYRVTSTGKPEFTNLKVYHDIKDIT

ARKEIIENAELLDQIAKILTIYQSSEDIQEELTNLNSELTQEEIEQIS

NLKGYTGTHNLSLKAINLILDELWHTNDNQIAIFNRLKLVPKKVDLSQ

QKEIPTTLVDDFILSPVVKRSFIQSIKVINAIIKKYGLPNDIIIELAR

EKNSKDAQKMINEMQKRNRQTNERIEEIIRTTGKENAKYLIEKIKLHD

MQEGKCLYSLEAIPLEDLLNNPFNYEVDHIIPRSVSFDNSENNKVLVK

QEENSKKGNRTPFQYLSSSDSKISYETFKKHILNLAKGKGRISKTKKE

YLLEERDINRFSVQKDFINRNLVDTRYATRGLMNLLRSYFRVNNLDVK

VKSINGGFTSFLRRKWKFKKERNKGYKHHAEDALIIANADFIFKEWKK

LDKAKKVMENQMFEEKQAESMPEIETEQEYKEIFITPHQIKHIKDFKD

YKYSHRVDKKPNRELINDTLYSTRKDDKGNTLIVNNLNGLYDKDNDKL

KKLINKSPEKLLMYHHDPQTYQKLKLIMEQYGDEKNPLYKYYEETGNY

LTKYSKKDNGPVIKKIKYYGNKLNAHLDITDDYPNSRNKVVKLSLKPY

RFDVYLDNGVYKFVTVKNLDVIKKENYYEVNSKCYEEAKKLKKISNQA

EFIASFYNNDLIKINGELYRVIGVNNDLLNRIEVNMIDITYREYLENM

NDKRPPRIIKTIASKTQSIKKYSTDILGNLYEVKSKKHPQIIKKG

Following is the amino acid sequence of the *Neisseria meningitidis* Cas9 protein (SEQ ID NO: 8) (see Esvelt, et al., "Orthogonal Cas9 proteins for RNA-guided gene regulation and editing," *Nature Methods* 10(11):1116-21 (2013), which is incorporated by reference herein in its entirety):

MAAFKPNPINYILGLDIGIASVGWAMVEIDEDENPICLIDLGVRVFER

AEVPKTGDSLAMARRLARSVRRLTRRRAHRLLRARRLLKREGVLQAAD

FDENGLIKSLPNTPWQLRAAALDRKLTPLEWSAVLLHLIKHRGYLSQR

KNEGETADKELGALLKGVADNAHALQTGDFRTPAELALNKFEKESGHI

RNQRGDYSHTFSRKDLQAELILLFEKQKEFGNPHVSGGLKEGIETLLM

TQRPALSGDAVQKMLGHCTFEPAEPKAAKNTYTAERFIWLTKLNNLRI

LEQGSERPLTDTERATLMDEPYRKSKLTYAQARKLLGLEDTAFFKGLR

YGKDNAEASTLMEMKAYHAISRALEKEGLKDKKSPLNLSPELQDEIGT

AFSLFKTDEDITGRLKDRIQPEILEALLKHISFDKFVQISLKALRRIV

PLMEQGKRYDEACAEIYGDHYGKKNTEEKIYLPPIPADEIRNPVVLRA

LSQARKVINGVVRRYGSPARIHIETAREVGKSFKDRKEIEKRQEENRK

DREKAAAKFREYFPNFVGEPKSKDILKLRLYEQQHGKCLYSGKEINLG

RLNEKGYVEIDHALPFSRTWDDSFNNKVLVLGSENQNKGNQTPYEYFN

GKDNSREWQEFKARVETSRFPRSKKQRILLQKFDEDGFKERNLNDTRY

VNRFLCQFVADRMRLTGKGKKRVFASNGQITNLLRGFWGLRKVRAEND

RHHALDAVVVACSTVAMQQKITRFVRYKEMNAFDGKTIDKETGEVLHQ

KTHFPQPWEFFAQEVMIRVFGKPDGKPEFEEADTPEKLRTLLAEKLSS

RPEAVHEYVTPLFVSRAPNRKMSGQGHMETVKSAKRLDEGVSVLRVPL

TQLKLKDLEKMVNREREPKLYEALKARLEAHKDDPAKAFAEPFYKYDK

AGNRTQQVKAVRVEQVQKTGVWVRNHNGIADNATMVRVDVFEKGDKYY

LVPIYSWQVAKGILPDRAVVQGKDEEDWQLIDDSFNFKFSLHPNDLVE

VITKKARMFGYFASCHRGTGNINIRIHDLDHKIGKNGILEGIGVKTAL

SFQKYQIDELGKEIRPCRLKKRPPVR

In some embodiments of the present invention, the recombinant Cas protein is derived from a Cas protein comprising an amino acid sequence having at least 70%, at least 75%, at least 80%, at least 85%, at least 90%, at least 95%, at least 96%, at least 97%, at least 98%, at least 99%, or 100% identity with the amino acid sequence of SEQ ID NO: 5.

In certain embodiments, the recombinant Cas protein is derived from a Cas protein comprising an amino acid sequence having at least 70%, at least 75%, at least 80%, at least 85%, at least 90%, at least 95%, at least 96%, at least 97%, at least 98%, at least 99%, or 100% identity with the amino acid sequence of SEQ ID NO: 6.

In some embodiments, the recombinant Cas protein is derived from a Cas protein comprising an amino acid sequence having at least 70%, at least 75%, at least 80%, at least 85%, at least 90%, at least 95%, at least 96%, at least 97%, at least 98%, at least 99%, or 100% identity with the amino acid sequence of SEQ ID NO: 7.

In certain embodiments, the recombinant Cas protein is derived from a Cas protein comprising an amino acid sequence having at least 70%, at least 75%, at least 80%, at least 85%, at least 90%, at least 95%, at least 96%, at least 97%, at least 98%, at least 99%, or 100% identity with the amino acid sequence of SEQ ID NO: 8.

The present invention is also directed to recombinant Cas proteins comprising one or more amino acid substitutions in one or more residues corresponding to one or more MHC Class I and/or MHC Class II binding sites in a wild-type Cas protein. In certain embodiments, the recombinant Cas protein is derived from the wild-type protein containing the corresponding MHC Class I and/or Class II binding sites. In some embodiments, the recombinant Cas protein has reduced immunogenicity compared to the wild-type Cas protein from which it is derived. In some embodiments, the recombinant Cas protein is isolated and in other embodiments it is located within a cell.

In some embodiments, the recombinant Cas protein is derived from a Cas9-like protein, such as Cpf1, disclosed in Zetsche et al., "Cpf1 is a Single RNA-Guided Endonuclease of a Class 2 CRISPR-Cas System," Cell 163:759-771 (2015), incorporated herein by reference in its entirety.

In some embodiments, the disclosure is directed to a recombinant CRISPR-associated (Cas) protein, wherein said protein comprises one or more amino acid variation compared to a while-type Cas protein, wherein the one or more amino acid variation is at one or more positions corresponding to amino acid residues in the polypeptide of SEQ ID NO: 5, wherein the variation is at a position selected from the group consisting of (i) residues 100 to 120, (ii) residues 250 to 280, (iii) residues 690 to 710, (iv) residues 840 to 860, and (v) residues 1270 to 1295. In some embodiments, the variation is at a position selected from the group consisting of (i) residues 102 to 120, (ii) residues 253 to 277, (iii) residues 692 to 709, (iv) residues 692 to 709, and (v) residues 1276 to 1292.

In some embodiments, the variation is at a position selected from residues 102 to 120. In some embodiments, the variation is at a position selected from residues 253 to 277. In some embodiments, the variation is at a position selected from residues 692 to 709. In some embodiments, the variation is at a position selected from residues 692 to 709. In some embodiments, the variation is at a position selected from residues 1276 to 1292.

In some embodiments, the recombinant Cas protein comprises two or more amino acid variations. In some embodiments, the recombinant Cas protein comprises three or more amino acid variations. In some embodiments, the amino acid variation is determined using in silico epitope mapping.

The term "variation," when referring to a variation at a given polypeptide residue position, refers to any modifications at those residues. For example, the term variation can refer to substituting (i.e., replacing) an amino acid (i.e., residue) at a given position with a different amino acid. In some embodiments, the amino acid can be substituted with a different amino acid having a different property. Various predictive algorithms for determining the immunogenic properties of a polypeptide are known in the art, and can include (1) the ratio between the frequencies of aspargine, glutamine, leucine, lysine, methionine, serine, threonine, and valine residues in the stretch and the remaining antigen sequence; (2) Grantham polarity scale (Grantham et al., *Science.* 185: 862-864 (1974)); (3) Karplus and Schulz flexibility scale (Karplus et al., *Naturwissenschaften* 72: 212-213 (1985)); (4) Kolaskar and Tongaonkar antigenicity scale (Kolaskar et al., *FEBS Lett.* 276: 172-174 (1990)); (5) Parker hydrophilicity scale (Parker et al., *Biochemistry* 25: 5425-5432 (1986)); (6) Ponnuswamy polarity scale (Ponnuswamy et al., *Biochim. Biophys. Acta.* 623: 301-326 (1980)); and, (7) Atchley et al. factor1 scale (Atchley et al., *Proc. Natl. Acad. Sci. U.S.A.* 102: 6395-6400 (2005)). In some embodiments, EPIBASE® can be used to determine what amino acid can be used to reduce immunogenicity of the polypeptide.

For example, in some embodiments, one or more of aspargine, glutamine, leucine, lysine, methionine, serine, threonine, and valine residues can be replaced with a different amino acid. In some embodiments, the amino acid variation comprises replacing a polar amino acid with a nonpolar amino acid. In some embodiments, the amino acid variation comprises replacing a hydrophilic amino acid with a hydrophobic amino acid. In some embodiments, and amino acid with a large side chain can be replaced with an amino acid with a smaller side chain.

In some embodiments, the term variation can refer to deleting one or more amino acids residues into the Cas protein. For example, in some embodiments, 2, 3, 4, 5, 6, 7, 8, 9, 10, 12, 14, 16, 18 or 20 amino acids can be deleted in one epitope. In some embodiments, one or more amino acids can be deleted from two or more epitopes on the same protein. In some embodiments, the deletions are not contiguous on the polypeptide, e.g., one deletion can occur on one region of the polypeptide, and a separate deletion can occur on a separate part of the polypeptide.

In some embodiments, the term variation can refer to inserting one or more amino acid residues into the Cas protein. For example, in some embodiments, 2, 3, 4, 5, 6, 7, 8, 9, 10, 12, 14, 16, 18 or 20 amino acids can be inserted in one epitope. In some embodiments, one or more amino acids can be inserted into two or more epitopes on the same protein. In some embodiments, the insertions are not contiguous on the polypeptide, e.g., one insertion can occur on one region of the polypeptide, and a separate insertion can occur on a separate part of the polypeptide.

In some embodiments, the Cas protein can have various types of variations. For example, in some embodiments, the Cas protein can have one or more amino acid substitutions, one or more amino acid deletions, and one or more amino acid insertions.

In some embodiments, the wild-type Cas protein has a sequence 90% identical to SEQ ID NO: 5. In some embodiments, the wild-type Cas protein has a sequence 90% identical to SEQ ID NO: 6. In some embodiments, the wild-type Cas protein has a sequence 90% identical to SEQ ID NO: 7. In some embodiments, the wild-type Cas protein has a sequence 90% identical to SEQ ID NO: 8. In some embodiments, the wild-type Cas protein has a sequence 91%, 92%, 93%, 94%, 95%, 96%, 97%, 98% or 99% identical to SEQ ID NO: 5. In some embodiments, the wild-type Cas protein has a sequence 91%, 92%, 93%, 94%, 95%, 96%, 97%, 98% or 99% identical to SEQ ID NO: 6. In some embodiments, the wild-type Cas protein has a sequence 91%, 92%, 93%, 94%, 95%, 96%, 97%, 98% or 99% identical to SEQ ID NO: 7. In some embodiments, the wild-type Cas protein has a sequence 91%, 92%, 93%, 94%, 95%, 96%, 97%, 98% or 99% identical to SEQ ID NO: 8.

In some embodiments, the wild-type Cas protein is derived from a prokaryote. In some embodiments, the prokaryote is a bacterium. In some embodiments, the bacterium is from the genera *Streptococcus, Staphylococcus,* or *Neisseria*. In some embodiments, the bacterium is *Streptococcus pyogenes, Streptococcus thermophilus, Staphylococcus aureus,* or *Neisseria meningitidis*.

In some embodiments, the recombinant Cas protein is derived from Cas3, Cas9, or Cas10. In some embodiments, the recombinant Cas protein is derived from Cas9.

Polynucleotides, Expression Vectors, and Host Cells

In some embodiments, the polynucleotides or expression vectors encoding Cas proteins (or variants thereof) are placed in a host cell, e.g, a prokaryote or eukaryote cell. The devices, facilities and methods described herein are suitable for culturing any desired cell line including prokaryotic and/or eukaryotic cell lines. Further, in some embodiments, the devices, facilities and methods are suitable for culturing suspension cells or anchorage-dependent (adherent) cells and are suitable for production operations configured for production of pharmaceutical and biopharmaceutical products—such as polypeptide products, nucleic acid products (for example DNA or RNA).

In embodiments, the host cells express or produce a product, such as a Cas protein or variant thereof, or expression vectors encoding the Cas protein or variant thereof.

In some embodiments, devices, facilities and methods allow for the production of host eukaryotic cells comprising the described expression vectors, e.g., mammalian cells or lower eukaryotic cells such as for example yeast cells or filamentous fungi cells, or prokaryotic cells such as Gram-positive or Gram-negative cells, synthesised by the host cells in a large-scale manner. Unless stated otherwise herein, the devices, facilities, and methods can include any desired volume or production capacity including but not limited to bench-scale, pilot-scale, and full production scale capacities.

Moreover and unless stated otherwise herein, the host cells can be generated using devices, facilities, and methods including any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermentor or fermentation unit, or any other reaction vessel and the term "reactor" is used interchangeably with "fermentor." For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and CO2 levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316 L or any other suitable stainless steel) and Inconel, plastics, and/or glass.

In some embodiments and unless stated otherwise herein, the methods described herein can also include any suitable unit operation and/or equipment not otherwise mentioned, such as operations and/or equipment for separation, purification, and isolation of Cas proteins or variants thereof, or expression vectors expressing the Cas proteins or variants thereof. Any suitable facility and environment can be used, such as traditional stick-built facilities, modular, mobile and temporary facilities, or any other suitable construction, facility, and/or layout. For example, in some embodiments modular clean-rooms can be used. Additionally and unless otherwise stated, the devices, systems, and methods described herein can be housed and/or performed in a single location or facility or alternatively be housed and/or performed at separate or multiple locations and/or facilities.

By way of non-limiting examples and without limitation, U.S. Publication Nos. 2013/0280797; 2012/0077429; 2011/0280797; 2009/0305626; and U.S. Pat. Nos. 8,298,054; 7,629,167; and 5,656,491, which are hereby incorporated by reference in their entirety, describe example facilities, equipment, and/or systems that may be suitable.

In some embodiments, the host cells are eukaryotic cells, e.g., mammalian cells. The mammalian cells can be for example human or rodent or bovine cell lines or cell strains. Examples of such cells, cell lines or cell strains are e.g. mouse myeloma (NSO)-cell lines, Chinese hamster ovary (CHO)-cell lines, HT1080, H9, HepG2, MCF7, MDBK Jurkat, NIH3T3, PC12, BHK (baby hamster kidney cell), VERO, SP2/0, YB2/0, Y0, C127, L cell, COS, e.g., COS1 and COS7, QC1-3,HEK-293, VERO, PER.C6, HeLA, EB1, EB2, EB3, oncolytic or hybridoma-cell lines. Preferably the mammalian cells are CHO-cell lines. In one embodiment, the cell is a CHO cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1 SV GS knockout cell. The CHO FUT8 knockout cell is, for example, the Potelligent® CHOK1 SV (Lonza Biologics, Inc.). Eukaryotic cells can also be avian cells, cell lines or cell strains, such as for example, EBx® cells, EB14, EB24, EB26, EB66, or EBvl3.

In some embodiments, the host cells are stem cells. The stem cells can be, for example, pluripotent stem cells, including embryonic stem cells (ESCs), adult stem cells, induced pluripotent stem cells (iPSCs), tissue specific stem cells (e.g., hematopoietic stem cells) and mesenchymal stem cells (MSCs).

In some embodiments, the host cell is a differentiated form of any of the cells described herein. In one embodiment, the host cell is a cell derived from any primary cell in culture.

In some embodiments, the host cell is a hepatocyte such as a human hepatocyte, animal hepatocyte, or a non-parenchymal cell. For example, the host cell can be a plateable metabolism qualified human hepatocyte, a plateable induction qualified human hepatocyte, plateable Qualyst Transporter Certified™ human hepatocyte, suspension qualified human hepatocyte (including 10-donor and 20-donor pooled hepatocytes), human hepatic kupffer cells, human hepatic stellate cells, dog hepatocytes (including single and pooled Beagle hepatocytes), mouse hepatocytes (including CD-1 and C57Bl/6 hepatocytes), rat hepatocytes (including Sprague-Dawley, Wistar Han, and Wistar hepatocytes), monkey hepatocytes (including Cynomolgus or Rhesus monkey hepatocytes), cat hepatocytes (including Domestic Shorthair hepatocytes), and rabbit hepatocytes (including New Zealand White hepatocytes). Example hepatocytes are commercially available from Triangle Research Labs, LLC, 6 Davis Drive Research Triangle Park, N.C., USA 27709.

In one embodiment, the host cell is a lower eukaryotic cell such as e.g. a yeast cell (e.g., *Pichia* genus (e.g. *Pichia pastoris, Pichia methanolica, Pichia kluyveri*, and *Pichia angusta*), Komagataella genus (e.g. *Komagataella pastoris, Komagataella pseudopastoris* or *Komagataella phaffii*), Saccharomyces genus (e.g. *Saccharomyces cerevisae, cerevisiae, Saccharomyces kluyveri, Saccharomyces uvarum*), Kluyveromyces genus (e.g. *Kluyveromyces lactis, Kluyveromyces marxianus*), the *Candida* genus (e.g. *Candida utilis, Candida cacaoi, Candida boidinii*,), the Geotrichum genus (e.g. *Geotrichum fermentans*), Hansenula polymorpha, Yarrowia lipolytica, or Schizosaccharomyces pombe. Preferred is the species *Pichia pastoris*. Examples for *Pichia pastoris* strains are X33, GS115, KM71, KM71H; and CBS7435.

In some embodiments, the host cell is a fungal cell (e.g. Aspergillus (such as *A. niger, A. fumigatus, A. orzyae, A. nidula*), Acremonium (such as *A. thermophilum*), Chaetomium (such as *C. thermophilum*), Chrysosporium (such as *C. thermophile*), Cordyceps (such as *C. militaris*), Corynascus, Ctenomyces, Fusarium (such as *F. oxysporum*), Glomerella (such as *G. graminicola*), *Hypocrea* (such as *H. jecorina*), *Magnaporthe* (such as *M. orzyae*), *Mycelioph-thora* (such as *M. thermophile*), *Nectria* (such as *N. heamatococca*), *Neurospora* (such as *N. crassa*), *Penicillium, Sporotrichum* (such as *S. thermophile*), *Thielavia* (such as *T. terrestris, T. heterothallica*), *Trichoderma* (such as *T. reesei*), or *Verticillium* (such as *V. dahlia*)).

In some embodiments, the host cell is an insect cell (e.g., Sf9, Mimic™ Sf9, Sf21, High Five™ (BT1-TN-5B1-4), or BT1-Ea88 cells), an algae cell (e.g., of the genus *Amphora, Bacillariophyceae, Dunaliella, Chlorella, Chlamydomonas, Cyanophyta* (cyanobacteria), *Nannochloropsis, Spirulina*, or *Ochromonas*), or a plant cell (e.g., cells from monocotyledonous plants (e.g., maize, rice, wheat, or Setaria), or from a dicotyledonous plants (e.g., cassava, potato, soybean, tomato, tobacco, alfalfa, *Physcomitrella patens* or Arabidopsis).

In some embodiments, the host cell is a bacterial or prokaryotic cell.

In some embodiments, the host cell is a Gram-positive cells such as *Bacillus, Streptomyces Streptococcus, Staphylococcus* or *Lactobacillus. Bacillus* that can be used is, e.g. the *B. subtilis, B. amyloliquefaciens, B. licheniformis, B. natto*, or *B. megaterium*. In embodiments, the cell is *B. subtilis*, such as *B. subtilis* 3NA and *B. subtilis* 168. *Bacillus* is obtainable from, e.g., the *Bacillus* Genetic Stock Center, Biological Sciences 556, 484 West 12$^{th}$ Avenue, Columbus Ohio 43210-1214.

In some embodiments, the host cell is a Gram-negative cell, such as *Salmonella* spp. or *Escherichia coli*, such as e.g., TG1, TG2, W3110, DH1, DHB4, DH5a, HMS174, HMS174 (DE3), NM533, C600, HB101, JM109, MC4100, XL1-Blue and Origami, as well as those derived from *E. coli* B-strains, such as for example BL-21 or BL21 (DE3), all of which are commercially available.

Suitable host cells are commercially available, for example, from culture collections such as the DSMZ (Deutsche Sammlung von Mikroorganismen and Zellkulturen GmbH, Braunschweig, Germany) or the American Type Culture Collection (ATCC).

Immunogenicity and T-cell Responses in Humans

In humans, a cytotoxic T lymphocyte (CTL) response is initiated when a T-cell's unique T-cell receptor (TCR) recognizes a peptide bound to the HLA Class I molecules, displayed on the surface of most nucleated cells. Only those peptides with sufficient affinity for the HLA Class I receptor can be presented on the cell's surface, and potentially trigger a CTL response. Knowing which peptides within a protein have a strong affinity for HLA Class I receptors is therefore an important step towards determining the immunogenic regions of the protein.

The HLA Class I molecule is made of up two polypeptide chains: the α chain and β-2 microglobulin, each of which is derived from a different gene. Individuals express multiple genes encoding the α-chain: A, B, C, E, F, G, K and L. The dominant α-chain genes, A-C, are highly polymorphic. Different HLA Class I molecules are described as HLA allotypes.

For a complete analysis of the immunogenicity of a protein or peptide, one should therefore test the affinity/immunogenicity of each peptide for each possible HLA Class I allotype. Fortunately, however, some allotypes have a higher prevalence in a given population than others. As a result, the analysis for any population can be done in most cases by focusing on a limited number of allotypes. In general, an individual's T-cell population has been selected not to contain cells that recognize "self-peptides" (peptides derived from endogenous proteins) presented on HLA Class I receptors. Therefore, peptides from an exogenous protein that correspond to (known) self-peptides will normally not induce a CTL response, even if they have a high affinity for HLA Class I receptors. It is not always clear which endogenous proteins are presented and as such give rise to self-peptides.

A $T_h$ (T-helper) response is sparked when a $T_h$ Cell's unique T-Cell receptor (TCR) recognizes a peptide bound to the HLA Class II molecules displayed on antigen presenting cells (APCs). These peptides are generated from proteins internalized by an antigen presenting cell, and then cleaved through its endosomal cleavage pathway. Only those peptides with sufficient affinity for the HLA Class II receptor can be presented on the cells surface and potentially trigger a $T_h$ response. Knowing which peptides within a protein have a strong affinity for HLA Class II receptors is therefore an important step towards determining the protein's immunogenic regions.

The picture, however, can be complicated by the fact that there are several HLA Class II genes, almost all of which are highly polymorphic. Each HLA Class II molecule consists of an α and β chain, each derived from a different gene, which further increases the number of possible HLA Class II molecules. Specifically, every human individual expresses the following genes: DRA/DRB, DQA/DQB and DPA/DPB. Of these, only DRA is non-polymorphic. In addition, a "second" DRB gene (DRB3, DRB4 or DRB5) may also be present, whose product also associates with the DRA chain.

For a complete analysis of the immunogenicity of a protein or peptide, one should therefore test the affinity/immunogenicity of each peptide for each possible HLA Class II allotype. Fortunately however, some allotypes have a higher prevalence in a given population than others. As a result, the analysis for any population can be performed in most cases by focusing on a limited number of allotypes.

Furthermore, the expression levels of receptors of the DQ and DP gene families are known to be significantly lower than those of DRB, making the latter the primary focus of immunogenicity profiling. See Laupeze et al., "Differential expression of major histocompatibility complex class Ia, Ib, and II molecules on monocytes-derived dendritic and macrophagic cells," *Hum. Immunol.* 60(7):591-7 (1999); Gansbacher and Zier, "Regulation of HLA-DR, DP, and DQ expression in activated T cells," *Cell Immunol.* 117(1):22-34 (1988); Berdoz, et al., "Constitutive and induced expression of the individual HLA-DR beta and alpha chain loci in different cell types," *J. Immunol.* 139(4):1336-41 (1987); and Stunz, et al., "HLA-DRB1 and -DRB4 genes are differentially regulated at the transcriptional level," *J. Immunol.* 143(9):3081-6 (1989), each of which is incorporated by reference herein in its entirety.

Differences of expression exist between presenting cells, e.g., dendritic cells vs. macrophages. See Laupeze, et al. Also, differences in HLA expression levels have been correlated with the magnitude of the T-cell response. Vader, et al., "The HLA-DQ2 gene dose effect in celiac disease is directly related to the magnitude and breadth of gluten-specific T cell responses," *PNAS* 100(21):12390-5 (2003), which is incorporated by reference herein in its entirety. Cases of DQ- and DP-restricted T-cell response have been documented (see e.g., Castelli, et al., "HLA-DP4, the most frequent HLA II molecule, defines new supertype of peptide-binding specificity," *J. Immunol.* 169(12):6928-34 (2002), which is incorporated by reference herein in its entirety), thus it is recommended that strong DQ and DP binders are not ignored when analyzing the immunogenicity of a protein.

In general, an individual's T-cell population has been selected not to contain cells that recognize "self-peptides" presented on HLA Class II receptors. These are peptides derived from endogenous proteins after internalization by an antigen presenting cell. Therefore, peptides from an exogenous protein which correspond to (known) self-peptides will normally not induce a $T_h$ response, even if they have a high affinity for HLA Class II receptors. It is not clear which endogenous proteins are internalized and as such give rise to self-peptides. See Kirschmann, et al., "Naturally processed peptides from rheumatoid arthritis associated and non-associated HLA-DR alleles," *J. Immunol.* 155(12):5655-62 (1995) and Verreck, et al., "Natural peptides isolated from Gly86/Val86-containing variants of HLA-DR1, -DR11, -DR13, and -DR52," *Immunogenetics* 43(6):392-7 (1996), each of which is incorporated by reference herein in its entirety.

In addition to epitopes bound to HLA molecules, as described above, it is also important to consider presence of epitopes bound by surface IgG molecules (B cell receptors) found on B cells. B cell receptors are responsible for selective uptake of antigens and presentation on B cells via HLA Class II, for subsequent interaction with T cell receptors found on T helper cells. In contrast to peptides bound by HLA molecules which have been processed such that they are considered only in linear terms, B cell epitopes can also be conformational, as they are found in the native context of the protein.

The conformational aspect of B cell epitopes makes in silico prediction problematic relative to T cell epitopes (HLA binding). In vitro assays, however, can be used to identify B cell activation in response to either full length proteins (conformational and linear epitopes) or derived peptides (linear epitopes) covering the relevant regions.

Methods for Reducing Immunogenicity

Certain embodiments of the present invention are directed to methods for making a recombinant Cas protein having reduced immunogenicity, i.e., with a reduced ability to elicit a CTL or $T_h$ response in a host, such as a human. In some embodiments, the method comprises introducing one or more amino acid residues corresponding to one or more histocompatibility (MHC) Class I and/or Class II binding sites of the Cas protein to form a recombinant Cas protein, wherein the recombinant Cas protein has reduced immunogenicity compared to the Cas protein from which it was derived. In some embodiments of the invention, the position of the amino acid substitution(s) is determined through epitope mapping. In certain embodiments, the position of the amino acid substitution(s) is determined using in silico epitope mapping and in some embodiments the position of the amino acid substitution(s) is determined using cell-based epitope mapping.

Methods for Epitope Mapping

In certain embodiments of the invention, the position of one or more amino acid substitutions for reducing the immunogenicity of a Cas protein is selected through in silico epitope mapping. Methods for in silico prediction of immunogenicity that can be used in the present invention are available from academic and commercial sources. Examples include those provided by Lonza (EPIBASE®; see, e.g., U.S. Pat. No. 7,702,465 and EP1516275, each of which is incorporated by reference herein in its entirety) and the Centre of Biological Sequence Analysis at the Technical University of Denmark (NetMHC; cbs.dtu.dk/services/NetMHC/). Such tools, on occasion, can be over-predictive of immunogenic epitopes and are therefore frequently combined with in vitro or ex vivo assays, such as those provided herein, in order to further refine results. A description of such in silico methodologies in combination with cell-based assays, as well as its utilization to reduce the impact of immunogenicity risks in therapeutics, has been reviewed elsewhere (see e.g., Zurdo 2013 and Zurdo et al. 2015, each of which is incorporated by reference herein in its entirety).

In some embodiments of the present invention, epitope mapping of Cas proteins is performed using cell-based methods. For example, in certain embodiments, antigen presenting cells (APCs) are incubated in the presence of Cas proteins. Subsequently, MHC Class I and Class II proteins (e.g., HLA Class I and Class II proteins) are isolated from the APCs and the Cas9-derived peptides bound the MHC Class I and/or Class II proteins are identified. In certain embodiments, the MHC Class I and Class II proteins are isolated by immunoprecipitation. In some embodiments, the Cas9 derived peptides bound the MHC Class I and Class II proteins are identified by mass spectrometry (MS).

In other embodiments of the invention, short synthetic peptides representing putative T-cell epitopes from the Cas proteins are incubated with cells (e.g., dendritic cells (DCs)). The cells are co-cultured with CD4+ and/or CD8+ T-cells and T-cell activation is determined. The amount of T-cell activation is indicative of the immunogenicity of the putative epitope where higher T-cell activation indicates a more immunogenic peptide or epitope. In certain embodiments, T-cell activation is measured by flow cytometry or FluoroSpot.

Assaying Immunogenicity of Cas-Derived Proteins

In certain embodiments of the invention, the immunogenicity of recombinant Cas proteins made by the methods described herein is determined by measuring the level of T-cell activation induced by such recombinant proteins. In some embodiments, the T-cells comprise CD4+ and/or CD8+ T-cells. In certain embodiments, the level of activation of T-cells is measured using methods well-known in the art, including, but not limited to, flow cytometry and/or FluoroSpot. In some embodiments, the level of T-cell activation induced by the recombinant Cas protein is compared to the level of T-cell activation induced by the wild-type Cas protein from which the recombinant Cas protein was derived. If the level of T-cell activation induced by the recombinant Cas protein is lower than that induced by the wild-type Cas protein from which the recombinant Cas protein was derived, then the recombinant Cas protein is considered to have reduced immunogenicity.

MHC-Associated Peptide Proteomics (MAPPs) Assay

In some embodiments, MHC-associated Peptide Proteomics (MAPPs) assays are used to identify prominent epitopes from the Cas protein. MAPPs technology is a high-throughput approach yielding hundreds of peptide sequences from a small amount of starting material, allowing sequence analysis of self-peptide repertoires from low abundance cell types. See, e.g., Rohn, et al., *Nature Immunol.* 5:909-918 (2004), and Penna et al., *J. Immunol.* 167:

1862-1866 (2001). The MHC-associated Peptide Proteomics (MAPPs) assay involves in vitro identification of HLA class II or class I associated peptides, which are processed by professional antigen presenting cells (APCs) such as dendritic cells, and used to identify specific peptides that are bound to either Class II or Class I antigens. Antigen uptake, processing and presentation processes are taken into account. The naturally processed HLA class II-associated peptides or class I-associated peptides are identified by liquid chromatography-mass spectrometry (Kropshofer and Spindeldreher (2005) in Antigen Presenting Cells: From Mechanisms to Drug Development, eds. Kropshofer and Vogt, Wiley-VCH, Weinheim, 159-98).

Recombinant Cas Proteins Made by the Methods Described Herein

The present invention is also directed to recombinant Cas proteins made by the methods described above. For example, in certain embodiments, the invention is directed to a recombinant Cas protein made by a process comprising introducing one or more amino acid substitutions into one or more residues corresponding to one or more MHC Class I and/or Class II binding sites of a wild-type Cas protein to form the recombinant protein. In some embodiments, the recombinant Cas protein made by the methods disclosed herein has reduced immunogenicity compared to a wild-type Cas protein.

Vectors of the Invention

Viral transduction with adeno-associated virus (AAV) and lentiviral vectors (where administration can be local, targeted or systemic) have been used as delivery methods for in-vivo gene therapy. In certain embodiments of the present invention, the Cas protein can be expressed intracellularly by transduced cells Immunogenicity responses to the Cas would thus be largely mediated by MHC Class I receptors (e.g., HLA Class I receptors), which are present in all nucleated cells, thereby activating CD8+ T cells.

For many therapeutic strategies, included those envisaged by the present invention, Cas protein expression may only be required transiently. As a result, in certain embodiments of the invention, delivery of the Cas protein into cells can be achieved using non-integrative viral vectors. In addition, there are certain embodiments where the expression of CRISPR-Cas system components is required for extended periods—for example, when used in gene circuits which are permanently integrated into the genome of target cells. Such applications have been discussed by Agustín-Pavón, et al., "Synthetic biology and therapeutic strategies for the degenerating brain," *Bioessays* 36(10):979-990 (2014), which is incorporated by reference herein in its entirety. In some embodiments of the present invention, immunogenicity can have elevated relevance in relation to potential selective clearance of cells stably expressing Cas protein by the immune system.

In certain embodiments, the Cas proteins and methods of the present invention can be used in ex vivo gene editing, such as CAR-T type therapies. These embodiments may involve modification of cells from human donors. In these instances, viral vectors can be also used; however, there is the additional option to directly transfect the Cas protein (along with in-vitro transcribed guide RNA and donor DNA) into cultured cells. In this case both MHC Class I and Class II (e.g., HLA Class 1 and HLA Class 2) receptors may be involved. Furthermore, a phenomenon known as "cross-presentation" can result in presentation of peptides derived from extracellular proteins by HLA Class I receptors, adding additional weight to considering immunogenicity of Cas proteins in relation to both Class I and Class II HLA presentation.

Cell-Types of the Invention

The present invention is also directed to a cell comprising the recombinant Cas protein of the invention, a nucleic acid expressing the recombinant protein of the invention, and/or a vector comprising a nucleic acid of the invention. In certain embodiments, the cell is a prokaryotic cell, for example an *E. coli* cell. In some embodiments, the cell is a mammalian cell. In some embodiments, the cell is a eukaryotic cell, for example, a lymphocytic cell, a myeloid cell, an induced pluripotent stem cell (iPSC), or a T cell, although all mammalian cell types are envisage as being used in the invention.

Library for Identifying Cas Proteins with Reduced Immunogenicity

The present invention also encompasses a library comprising at least one recombinant Cas protein comprising one or more amino acid substitutions in one or more residues corresponding to one or more MHC Class I and/or MHC Class II binding sites of a wild-type Cas protein. In certain embodiments, the library can be used to screen for functional recombinant Cas proteins, including recombinant Cas proteins with reduced immunogenicity. This is important as it is highly likely that many amino acid substitutions that reduce immunogenicity may also reduce Cas functionality that is essential to its application. The immunogenicity of functional recombinant Cas proteins in the library can be assessed using well-known techniques, including those described herein.

Methods for Altering Gene Expression Using the Recombinant Cas Proteins

The invention is also directed to methods for altering the DNA sequence at defined genomic locations containing a target sequence comprising introducing into a cell containing the target genetic element a guide RNA that hybridizes to the target sequence and a recombinant Cas protein of the invention.

EXAMPLES

Described below are experimental procedures for reducing the immunogenicity of Cas proteins, in particular Cas9 variants from *S. pyogenes* and *S. aureus*. *S. pyogenes* Cas9 has been more extensively characterized for in vitro gene-editing studies, whereas *S. aureus* Cas9 has also been utilized for in vivo gene editing, in part due to its smaller size facilitating delivery via adeno-associated virus (AAV) vectors.

Example 1: In-Silico Prediction of Cas9 Immunogenic Epitopes for Cas9 Variants and Cell Based Immunogenicity Assays for Wildtype Cas9 (*S. Pyogenes*)

Example 1.1: In Silico Prediction of HLA Class I and Class II Binding for Cas9 Proteins This process involves creating a profile sequence for HLA Class I & Class II T-cell epitopes using in silico methods such as those described above, for Cas9 sequences from *Streptococcus pyogenes, Streptococcus thermophilus, Staphylococcus aureus*, and *Neisseria meningitidis*

A randomizer algorithm was applied to assess effects of amino acid substitutions on immunogenicity of all 9 and 10mer (containing 9 or 10 amino acid residues, respectively) sequences within the Cas9 proteins. This indicates whether potential substitutions can increase or decrease the immunogenicity of the associated 9mer or 10mer.

HLA Class I Mapping

HLA Class I epitopes were mapped for the four Cas9 variant sequences provided above (SEQ ID NOs: 1-4), but are exemplified for *Streptococcus pyogenes* Cas9 (SEQ ID NO: 5) below. In short, the platform analyzes the HLA binding specificities of all 9 and 10-mer peptides derived from a target sequence (for more details refer to paragraphs below). Profiling is performed at the allotype level for a total of 28 HLA Class I receptors.

EPIBASE® calculates binding affinity of a peptide for each of the 28 HLA Class I receptors. Based on this, peptides are classified as strong (S), medium (M), or non (N) binders.

The allotypes predicted were selected based on frequencies in a variety of populations (Caucasian, Indo-European, Oriental, North Oriental, West African, East African, Mestizo and Austronesian).

Compiled data are presented in Table 1, indicating the number of *Streptococcus pyogenes* Cas9 epitopes specific to each HLA allotype. Peptides in the two binding classes (S and M) are counted separately.

TABLE 1

Strong and medium binding *Streptococcus pyogenes* Cas9 epitopes for HLA-A and HLA-B. Total numbers of epitopes in each category for 9-mer and 10-mer sequences are presented (values for different allotypes are represented separately, with allotype references restricted to two digits).

| HLA | 9-mer | | 10-mer | |
|---|---|---|---|---|
| Allotype | Strong | Medium | Strong | Medium |
| A*01 | 8 | 60 | 6 | 43 |
| A*02 | 30 | 110 | 37 | 99 |
| A*02 | 39 | 110 | 43 | 99 |
| A*02 | 51 | 127 | 53 | 112 |
| A*02 | 22 | 64 | 18 | 69 |
| A*03 | 34 | 88 | 29 | 106 |
| A*11 | 43 | 89 | 41 | 84 |
| A*23 | 32 | 93 | 114 | 233 |
| A*24 | 18 | 57 | 51 | 135 |
| A*26 | 15 | 66 | 22 | 78 |
| A*29 | 45 | 119 | 61 | 142 |
| A*30 | 24 | 104 | 58 | 190 |
| A*31 | 60 | 159 | 50 | 169 |
| A*33 | 24 | 113 | 74 | 226 |
| A*68 | 59 | 143 | 234 | 300 |
| A*68 | 48 | 128 | 107 | 218 |
| B*07 | 14 | 47 | 6 | 62 |
| B*08 | 26 | 105 | 15 | 80 |
| B*15 | 16 | 64 | 23 | 73 |
| B*18 | 21 | 84 | 46 | 121 |
| B*27 | 7 | 100 | 13 | 105 |
| B*35 | 24 | 110 | 21 | 73 |
| B*40 | 19 | 49 | 11 | 57 |
| B*44 | 0 | 25 | 1 | 28 |
| B*51 | 0 | 7 | 0 | 11 |
| B*53 | 14 | 77 | 35 | 132 |
| B*57 | 0 | 15 | 0 | 25 |
| B*58 | 15 | 94 | 11 | 119 |

HLA Class I epitope maps for two regions of *Streptococcus pyogenes* Cas9 (positions 1-125 and 1026-1150) are shown in FIGS. 1 and 3 respectively. The latter region was selected as an exemplar region with high S epitope counts.

Information regarding allotype frequencies can be helpful to further assess the global immunogenic response of the protein of interest. It is remarked that allotype frequencies cannot just be added up to estimate total population response: epitope processing, clustering of binders into short sequence fragments, immunodominance, T-cell receptor properties, presence of B-cell epitopes (antigenicity) and Mendelian genetics are all factors that complicate global immunogenicity assessment. As a result, the population response can be different from the sum of allotype frequencies.

HLA Class II Mapping

HLA Class II epitopes have been mapped for the four Cas9 variants sequences provided above (SEQ ID NOs: 1-4), but are exemplified for *Streptococcus pyogenes* Cas9 (SEQ ID NO: 5), below. In short, the platform analyzes the HLA binding specificities of all 10-mer peptides derived from a target sequence (for more details refer to the paragraphs below). Profiling is performed at the allotype level for a number of HLA Class II receptors. Table 2 indicates the number of *Streptococcus pyogenes* Cas9 epitopes specific to each receptor.

EPIBASE® calculates the binding affinity of a peptide for each of the available HLA Class II receptors. Based on this, peptides are classified as strong (S), medium (M), or non-binders (N). We refer to Kapoerchan et al., for the successful usage of EPIBASE® in predicting binders against selected HLA Class II receptors.

TABLE 2

Strong and medium binding *Streptococcus pyogenes* Cas9 epitopes for different HLA Class II allotypes. Total numbers of epitopes in each category for 10-mer sequences are presented (values for different allotypes are represented separately, with allotype references restricted to two digits).

| | 10-mer | |
|---|---|---|
| Allotype | Strong | Medium |
| DRB1*01 | 16 | 65 |
| DRB1*01 | 21 | 81 |
| DRB1*03 | 7 | 46 |
| DRB1*03 | 6 | 33 |
| DRB1*03 | 7 | 46 |
| DRB1*04 | 8 | 26 |
| DRB1*04 | 10 | 35 |
| DRB1*04 | 10 | 35 |
| DRB1*04 | 16 | 45 |
| DRB1*04 | 16 | 46 |
| DRB1*04 | 9 | 32 |
| DRB1*04 | 19 | 68 |
| DRB1*04 | 19 | 68 |
| DRB1*07 | 8 | 39 |
| DRB1*08 | 4 | 64 |
| DRB1*08 | 5 | 67 |
| DRB1*08 | 4 | 64 |
| DRB1*08 | 7 | 70 |
| DRB1*09 | 6 | 30 |
| DRB1*10 | 15 | 67 |
| DRB1*11 | 21 | 70 |
| DRB1*11 | 6 | 24 |
| DRB1*11 | 27 | 86 |
| DRB1*11 | 27 | 86 |
| DRB1*11 | 21 | 70 |
| DRB1*12 | 12 | 92 |

TABLE 2-continued

Strong and medium binding *Streptococcus pyogenes* Cas9 epitopes for different HLA Class II allotypes. Total numbers of epitopes in each category for 10-mer sequences are presented (values for different allotypes are represented separately, with allotype references restricted to two digits).

| | 10-mer | |
|---|---|---|
| Allotype | Strong | Medium |
| DRB1*12 | 12 | 92 |
| DRB1*13 | 8 | 28 |
| DRB1*13 | 5 | 29 |
| DRB1*13 | 26 | 59 |
| DRB1*13 | 1 | 31 |
| DRB1*13 | 26 | 59 |
| DRB1*14 | 27 | 73 |
| DRB1*14 | 32 | 77 |
| DRB1*14 | 27 | 73 |
| DRB1*14 | 27 | 86 |
| DRB1*14 | 33 | 87 |
| DRB1*15 | 16 | 6 |
| DRB1*15 | 13 | 52 |
| DRB1*15 | 16 | 67 |
| DRB1*15 | 16 | 67 |
| DRB1*16 | 16 | 78 |
| DRB1*16 | 16 | 78 |
| DRB3*01 | 4 | 44 |
| DRB3*02 | 0 | 48 |
| DRB3*02 | 1 | 40 |
| DRB3*03 | 7 | 67 |
| DRB4*01 | 9 | 37 |
| DRB5*01 | 28 | 82 |
| DRB5*01 | 2 | 40 |
| DRB5*02 | 5 | 45 |
| DQA1*01 | 2 | 43 |
| DQA1*01 | 2 | 43 |
| DQA1*01 | 3 | 33 |
| DQA1*01 | 2 | 33 |
| DQA1*01|DQB1*05 | 2 | 33 |
| DQA1*01|DQB1*06 | 4 | 36 |
| DQA1*01|DQB1*06 | 4 | 36 |
| DQA1*01|DQB1*06 | 3 | 49 |
| DQA1*01|DQB1*06 | 3 | 49 |
| DQA1*01|DQB1*06 | 3 | 49 |
| DQA1*02|DQB1*02 | 0 | 42 |
| DQA1*03|DQB1*03 | 5 | 36 |
| DQA1*03|DQB1*03 | 3 | 39 |
| DQA1*03|DQB1*03 | 0 | 34 |
| DQA1*03|DQB1*04 | 3 | 54 |
| DQA1*03|DQB1*04 | 3 | 54 |
| DQA1*04|DQB1*03 | 7 | 37 |
| DQA1*04|DQB1*04 | 1 | 36 |
| DQA1*05|DQB1*02 | 0 | 42 |
| DQA1*05|DQB1*03 | 9 | 36 |
| DQA1*06|DQB1*03 | 7 | 37 |
| DPA1*01|DPB1*02 | 3 | 76 |
| DPA1*01|DPB1*03/05 | 4 | 79 |
| DPA1*01|DPB1*04 | 11 | 44 |
| DPA1*01|DPB1*04/06 | 11 | 84 |
| DPA1*02|DPB1*01 | 7 | 82 |
| DPA1*02|DPB1*05 | 7 | 49 |
| DPA1*02|DPB1*09 | 3 | 77 |
| DPA1*02|DPB1*09/13 | 8 | 99 |
| DPA1*02|DPB1*17 | 3 | 65 |
| DPA1*02|DPB1*01 | 7 | 82 |
| DPA1*02|DPB1*05 | 7 | 49 |
| DPA1*03|DPB1*04/06 | 6 | 80 |

HLA Class II epitope maps for two regions of *Streptococcus pyogenes* Cas9 (positions 1-125 and 1026-1150) are shown in FIGS. 2 and 4 respectively. The latter region was selected as an exemplar region with high S epitope counts.

In the humoral response raised against an antigen, the observed $T_h$ Cell activation/proliferation is generally interpreted in terms of the DRB1 specificity. However, it can also be important to take into account the possible contribution of the DRB3/4/5, DQ and DP genes.

Given the lower expression levels of the DQ and DP receptors compared to the DRB receptors, the class of medium epitopes for DQ and DP was ignored. Those epitopes that are strong binders (or better) to any allotype or are medium binders for DRB1 or DRB3/4/5 are operationally defined as "critical epitopes."

Information regarding allotype frequencies can be beneficial for further assessment of the global immunogenicity risk of therapeutic proteins. Allotype frequencies cannot simply be added together to estimate the total population response: epitope processing, clustering of binders into short sequence fragments, immunodominance, T-cell receptor properties, presence of B-cell epitopes (antigenicity) and Mendelian genetics are all factors which contribute to a global immunogenicity assessment. As a result, the population response can be different from the sum of allotype frequencies.

Randomization of Cas9 Sequences for Reduced Immunogenicity

Randomization was carried out in relation to HLA Class I and Class II for all four Cas9 sequences (*Streptococcus pyogenes*, *Streptococcus thermophilus*, *Staphylococcus aureus*, and *Neisseria meningitides*). Data is presented on a single identified immunogenic region from *Streptococcus pyogenes* Cas9. This can be found between amino acids 1035 and 1038 of the Cas9 sequence (originally identified from the HLA Class I epitope profile). The epitope maps for amino acids 1026-1150 (i.e., including this region) are shown for HLA Class I and HLA Class II in FIG. 3 and FIGS. 4A-C, respectively. It is interesting to note that this region appears to be strongly immunogenic for both HLA Classes.

The randomization data and plots are shown in for 9-mers and 10-mers in FIGS. 5A-C and FIGS. 6A-D respectively. In these plots, substitutions can be clearly identified, which reduce immunogenicity of the specific epitope for both HLA Class I and Class II.

FIGS. 5A and 6A in the randomization plots indicates the effect of each amino acid substitution on the number of HLA allotypes binding the specific epitope. A positive score indicates that the substitution increases the number of binders, where a negative score does the opposite.

The amino acid substitution deimmunisation scores for 9-mers and 10-mers for *Streptococcus pyogenes* Cas9 are presented in FIGS. 8A-D. This indicates the likelihood that for any given position a substitution can be identified that will deimmunise the corresponding epitope. This does not exclude the fact that some epitopes may only be deimmunised by a single substitution. The method used for data collation means that scores for 9-mers are applicable to HLA Class I epitopes and scores for 10-mers are applicable to both HLA Class I and Class II epitopes.

Amino acid substitution deimmunisation scores (and their corresponding amino acid positions) were subsequently filtered based on those which gave scores lower than a cut-off threshold of −20. These are exemplified for *Streptococcus pyogenes* Cas9 in FIGS. 8B and 8D. The positions identified are also presented in table form in FIG. 9 for *Streptococcus pyogenes*, *Streptococcus thermophilus*, *Staphylococcus aureus*, and *Neisseria meningitidis* Cas9 variants.

Example 1.2: Assessment of Cas9 Structural and Functional Regions

A three-dimensional model was generated using the coordinates of a publically available Cas9 complex crystal structure in the protein data-bank (PDB) (see Nishimasu, et al., "Crystal structure of Cas9 in complex with guide RNA and target DNA," Cell 156(5):935-49 (2014), which is incorporated by reference herein in its entirety). This structural model can be used to assess structural criteria for each amino acid residue. This information can be combined with immunogenicity data from Example 1.1 to prioritize sequence modifications of the Cas9 protein which are likely to maintain functionality while reducing immunogenicity.

Further to the data generated in the preceding paragraph, the proximity of prioritized/relevant HLA Class I and HLA Class II epitopes to key structural or functional motifs of the Cas9 sequence were performed. The Cas9 proteins from *S. pyogenes* and *S. aureus* were used for illustrative purposes.

While the macro-homology across Cas9 variants is limited—see FIG. 7—it is possible to identify relevant epitopes, as well as structural features, that are conserved in multiple Cas9 variants. In order to do this, known three-dimensional structures deposited in the PDB were compared to the target Cas9 proteins. The quality of the comparison (e.g., percent homology on macro- and micro-scale) was determined and only those sequences with a relevant level of sequence homology selected for subsequent analysis.

Those epitopes that were chosen for further characterization were aligned to corresponding domains of other species. Based, at least in part, on these alignments, three-dimensional molecular models of the target epitopes were generated. Functionally relevant positions/regions in the Cas9 proteins were identified and mapped into the three-dimensional structure of the proteins.

Example 1.3: Prioritisation of Cas9 Amino Acid Substitutions Based on Examples 1.1 and 1.2

The data compiled from Examples 1.1 and 1.2 were used to identify which epitopes could be targeted to both minimize immunogenicity risks while also retaining as much biological activity as possible in the recombinant, i.e., engineered, protein. Such domains have been described by Nishimasu et al. (2014). For example, one criterion utilized was to avoid changing amino acids present within 5 angstroms of the known nuclease domains of Cas9. For those epitopes selected to effectuate reduced immunogenicity, amino acid substitutions were selected to preserve structural features of the Cas9 protein (e.g., alpha helices/beta-sheets) as much as possible.

A global list of positions/regions that can be randomized/changed for potential reduced immunogenicity can be generated. Assessment of the effect of amino acid substitution of the identified regions can be carried out in multiple ways.

Limitations exist in the number of Cas9 variants that can be practically screened for immunogenicity in Example 2, below. It therefore highly likely that the final Cas9 variants assessed will contain multiple substitutions. However, there is considerable flexibility in how the Cas9 functionality screens can be carried out. A step-wise approach can be utilized to minimize the potential impact of the deimmunising substitutions in Cas9 function. In this method more variants can be screened (e.g., using a library approach), exhibiting larger numbers of substitutions, individually and in combination, and also to utilize multiple subsequent rounds of screening-selection, where results from primary screens are used to inform library design for subsequent rounds.

Example 1.4: In-Vitro Immunogenicity Assays on Purified Cas9 Protein

Figure 10B:
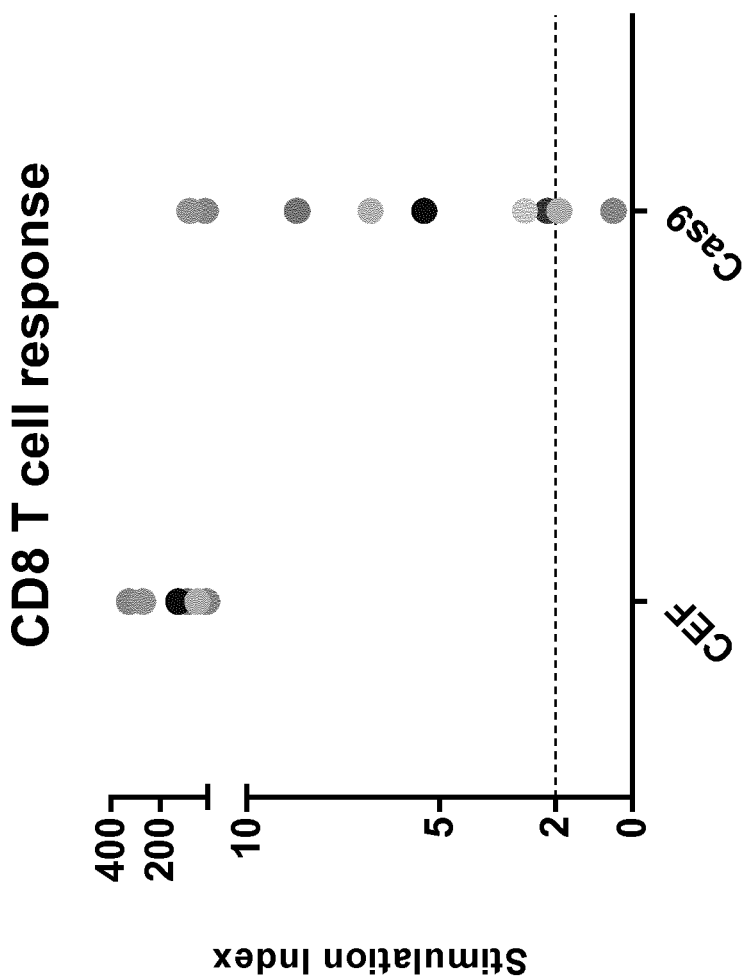
FIG. 10B represents the CD8+ T cell response induced by the whole Cas9 protein (*Streptococcus pyogenes*) in the DC:CD8 activation assay. Each dot represents a single healthy donor with a stimulation index >2 deemed a positive T cell response. CEF is a highly immunogenic peptide pool and induces a CD4+ T cell response in all 9 healthy donors. Cas9 induced a CD8+ T cell response in 6 of the 9 (67%) healthy donors tested suggesting that Cas9 contains CD8+ T cell epitopes and is capable of raising a cytotoxic T cell response in human cells.

Assays were carried out, using purified, non-deimmunised ("wildtype"), Cas9 proteins, i.e., SEQ ID NOs: 5-8, in order to assess the starting level of immunogenicity relative to proteins of known immunogenicity (shown in FIGS. 10A and 10B). A histidine purification tag (his-tag), known to be non-immunogenic, was added in order to facilitate purification.

Assays were performed using peripheral blood mononuclear cells (PBMCs) from healthy human donors corresponding to different HLA allotypes. Typically PBMCs from at least 10 or 20 different donors were utilized. There was prior evidence that HLA Class I presentation can occur even in cases where cells are exposed "externally" to whole antigens (a phenomenon known as "cross-presentation"). This was used to explore how antigen presentation can influence the activation of CD4+ (helper T-cells) or CD8+ (cytotoxic T-cells) lymphocytes.

PBMCs were incubated with recombinant Cas9 protein (Cas9 protein with incorporated amino acid substitutions determined from the analysis in Examples 1.1-1.3 above). The recombinant Cas9 protein was purified to eliminate LPS (lipopolysaccharide) contamination (endotoxin can induce T cell activation and hence give false positive results). CD4+ or CD8+ T-cell activation was assessed by measuring the proliferation of the T-cells by flow cytometry or FluoroSpot. Activation of CD4+ T-cells indicated the presence of HLA Class II T-cell epitopes, whereas the activation of CD8+ T-cells indicated that HLA Class I epitopes were present in the Cas9 protein sequence.

Example 1.5: HLA Class I and HLA Class II MAPPS (MHC-Associated Peptide Proteomics) Assay Further to use of the EPIBASE® platform for in silico prediction of immunogenic epitopes, an in vitro approach was applied to experimentally identify which epitopes are presented by HLA Class I and Class II molecules. Use of EPIBASE® can be helpful due to the high number of immunogenic epitopes identified in silico.

This assay involved immunoprecipitation of HLA Class I (HLA-A, B and C) or HLA Class II (HLA-DR, DP and DQ) proteins from antigen presenting cells (APCs) previously incubated in the presence of antigen, i.e., Cas9 protein. Cas9-derived peptides bound to the HLA molecules were acid-eluted and identified by Mass Spectrometry (MS). Identification of Cas9-derived HLA-binding peptides provides data on which peptides are processed and presented preferentially by these APCs. Analysis of this data helped to further define which of the in silico predicted epitopes are actually more relevant in potentially triggering an immune response (an example is shown in FIG. 11).

Analysis of HLA Class I bound peptides may additionally be carried out using cells expressing and/or transfected with Cas9.

Example 1.6: Activation of CD4+ and CD8+ T-cells by Short Peptides from Cas9

These assays evaluate the relative immunogenicity of different Cas9-derived peptides by incubating dendritic cells (DC) with short synthetic peptides representing the potential T-cell epitopes from Cas9 and co-culturing them with autologous T-cells (CD4+ or CD8+) to evaluate the impact of each peptide on T-cell activation. These assays can be utilized to rank the relative importance of different in silico-predicted epitopes and prioritize those to be removed

Example 1.7: Identification of B-cell Epitopes

In addition to epitopes bound to HLA molecules, as described above, it is also important to consider presence of epitopes bound by surface IgG molecules (B cell receptors) found on B cells. B cell receptors are responsible for selective uptake of antigens and presentation on B cells via HLA Class II, for subsequent interaction with T cell receptors found on T helper cells. In contrast to peptides bound by HLA molecules, which have been processed such that they are considered only in linear terms, B cell epitopes can also be conformational, as they are found in the native context of the protein.

The conformational aspect of B cell epitopes makes in silico prediction problematic relative to T cell epitopes (HLA binding). In vitro assays, however, can be used to identify B cell activation in response to either full length proteins (conformational and linear epitopes) or derived peptides (linear epitopes) covering the relevant regions.

Example 2: Functional Testing of Cas9 Variants in Mammalian Cell Lines

Example 2.1: Generation and Preparation of Mammalian Expression Vectors for Cas9 Variants and gRNAs Based on the data from Example 1 above, transient vectors for mammalian expression of recombinant Cas9 can be generated for a number of Cas9 variants.

Vector designs can be based on constructs designed by Mali et al. "Cas9 as a versatile tool for engineering biology," *Nature Methods* 10:957-63 (2013)—see Supplementary Figure S1, which is incorporated by reference herein in its entirety. Coding sequences for different Cas9 variants (either from different bacterial species, or containing modified immunogenic epitopes) can be inserted in place of the *S. pyogenes* sequence as appropriate. Guide RNA and Cas9 regions can be synthesized by a gene synthesis company (e.g., GeneART/DNA2.0) and cloned into a standard *E. coli* cloning vector. Guide RNA sequences can be appropriate to the Cas9 variant in question, i.e., as described by Esvelt (2013) and Ran et al. (2015). Large preparations of these vectors can be made using standard plasmid preparation procedures (e.g., Qiagen Maxi-prep) in order to produce DNA suitable for transfection.

Cas9 and guide RNA plasmids can be co-precipitated (standard sodium acetate/ethanol precipitation) and re-suspended in TE ready for transfection. Final DNA concentrations are assessed by spectrophotometry (Nanodrop instrument, or equivalent) before being adjusted to compensate for variable precipitation efficiency.

Example 2.2: Testing of In-Vitro_Functionality in CHO Cells (vs. WT Control) Using Model Cell Line Expressing eGFP A Chinese hamster ovary cell line derived from CHOK1SV and containing stably integrated copies of eGFP can be used to test functionality of the different Cas9 variants identified above as having potential reduced immunogenicity. In this cell line, expression of eGFP is constitutive and is directed by the cytomegalovirus (CMV) promoter.

A gRNA vector can be designed to target a region early in the eGFP coding sequence. Co-transfection of the gRNA and Cas9 vector will result in introduction of double-strand breaks (DSB) in the eGFP coding sequence. DSBs are repaired by the cell's endogenous DNA repair machinery but this is largely error prone, resulting in introduction of small insertions and deletions (indels). In the majority of cases, indels result in frame shift mutations to the coding sequence, which would prevent production of functional (fluorescent) eGFP.

Functionality of Cas9 variants can be assessed by knock-down of eGFP flurourescence 2-4 days after transfection and/or by analysis of genomic DNA-derived PCR products flanking the target site. In all cases, results from Cas9 variants can be compared to the unmodified sequences in order to assess relative functionality.

PCR products can be treated with an enzyme that cleaves heteroduplex DNA (e.g., T7EI) and analyzed qualitatively by gel electrophoresis. In this case, the percentage of the PCR product that is cleaved by the T7EI enzyme is indicative of the efficiency, i.e., functionality, of the Cas9 enzyme. Alternatively, the PCR products can be sequenced using next generation sequencing techniques, where the high level repeat sequencing of the PCR product gives a quantitative measure of the different modified or unmodified sequences present (again indicating Cas9 functionality).

Alternatives to Examples 2.1 and 2.2

Multiple different approaches can be employed to generate rationally designed libraries of Cas9 variants, which can be screened to identify those variants that are functional. One approach would be to utilize a cell line with an integrated, substrate dependent suicide gene. Viral transduction of the cell line with DNA encoding the Cas9 library plus a guide RNA targeting the suicide gene would result in introduction of a double strand break (DSB) early in the suicide gene coding sequence where the Cas9 is functional. Addition of the suicide gene substrate would kill cells where Cas9 had failed to cleave the suicide gene sequence. Cas9 sequences could be recovered from surviving cells and analyzed by next-generation sequencing. Limitations imposed by library construction methods and transduction efficiency, for example, would inform the number of variants that could be screened using the selected method. Results from Example 2, in which ever from, will need to be ranked/prioritized in order to provide a practical number of variants for input to the process of Example 3 below.

Example 3: Generation of Purified Cas9 Proteins for Immunogenicity Assays Using *E. Coli* Expression System

Example 3.1: Expression of *S. Pyogenes* Cas9 Protein in *E. Coli*

Cas9 from *S. pyogenes* can be expressed in *E. coli* using methods and expression constructs described by Gagnon et al. (2014), or equivalent. See Gagnon, et al. "Efficient mutagenesis by Cas9 protein-mediated oligonucleotide insertion and large-scale assessment of single-guide RNAs," *PLOS One* 9(8):e106396 (2014), which is incorporated by reference herein in its entirety. All variants will contain a 6×His-tag to aid purification.

Selected variants will feature SV40 (or alternative) nuclear localization sequences to test additional impact on immunogenicity. It is currently unclear whether such sequences would be required for the therapeutic use of Cas9.

Example 3.2: Purification of E. Coli-Derived Cas9 Protein

Cas9 purification methods can be tested and endotoxin load assessed (aim 5-10 mg, <1 EU/mg). A commercial nickel column can be used for protein purification (such as the Ni-NTA system from Life Technologies) according to the manufacturer's instructions. This can be followed by a Capto Q (GE Life Sciences) purification step to reduce endotoxin load. Endotoxin levels can be assessed by a commercial assay (such as the Endosafe-PTS system from Charles River), according to the manufacturer's instructions. Proteins can be quantified during purification procedure and in the final eluted product by Bradford assay or A280 reading on suitable spectrophotometer (Nanodrop or equivalent).

Example 3.3: Expression and Purification of Cas9 Variants for Immunogenicity Testing Based on data from Examples 1 and 2 above, a range of different recombinant Cas9 variants can be produced and purified. E. coli expression vectors tested in Example 3.1 can be modified to encode for the preferred recombinant Cas9 variant sequences using standard molecular cloning techniques. Proteins can be expressed and purified as described in Example 3.2 above.

Example 4: Evaluation of Immunogenicity of Cas9 Variants

Cas9 variants produced and purified in Example 3 above can be assessed again in PBMC samples obtained from the same donors assessed in Example 1. PBMCs can be incubated with different endotoxin-free Cas9 variants (up to 10-12). CD4+ or CD8+ T-cell activation can be assessed by measuring the proliferation of the T-cells by flow cytometry or ELISpot.

CD4+ or CD8+ T-cell activation can be assessed for each one of the new variants and compared to that of the parental (wild-type) molecule. Analysis of the response will determine whether additional cycles of re-engineering would be required to reduce even further the immunogenicity of the protein.

Example 5: Additional Iterations of the Above Examples

Optionally, additional re-design processes outlined in the above Examples can be implemented in order to refine the final designs.

Additional iterations of the procedures in the above Examples can be performed at various stages throughout the entire process above. For example, in silico mapping, or in silico re-engineering, can be performed by repeating the process of Examples 1.1-1.3 and incorporating the information obtained from Examples 1.5, 1.6, 2 and 4.

For example, deimmunising substitutions were determined for Cas9 from Streptococcus pyogenes. Several naturally presented HLA Class II binding peptides from Cas9 protein were identified using MAPPs HLA Class II assay (one donor only). These peptides form five different clusters (see Table 3 and FIG. 11).

TABLE 3

Naturally presented HLA binding regions from Cas9.

| cluster # | residues |
|---|---|
| 1 | 103-120 |
| 2 | 254-277 |
| 3 | 693-709 |
| 4 | 842-858 |
| 5 | 1277-1292 |

EPIBASE® in silico platform was used to identify residue substitutions in these clusters which are predicted to remove HLA binders from these regions. Table 4 contains a list of residues and possible amino acid substitutions (the list is not exclusive) which reduce/remove HLA binding in the identified clusters. In addition, Table 4 contains a predicted reduction in DRB1 score of the protein if one of the suggested substitutions is made.

The immunogenic risk of a protein or peptide can be represented by an approximate score, the DRB1 score, calculated taking into account a number of factors including the numbers of critical HLA binders and the population frequencies of the affected HLA allotypes.

TABLE 4

List of residues and possible amino acid substitutions removing/reducing HLA binding.

| Cluster | Position | Original residue | Possible substitutions | Reduction in DRB1 score due to substitution |
|---|---|---|---|---|
| cluster 1 | 105 | F | D, E | −34 |
| cluster 1 | 106 | L | D, E, G, K, P, Q, R | between −22 and −58 |
| cluster 1 | 107 | V | D, E, G | between −28 and −40 |
| cluster 2 | 258 | L | D, E, G, K, P | −24 |
| cluster 2 | 263 | K | A, D, E, G, N, P, S, T | between −36 and −49 |
| cluster 2 | 264 | L | A, D, E, G, H, K, N, P, Q, R, S, T, V | between −31 and −61 |
| cluster 2 | 265 | Q | D, E, G, N, P, T | between −28 and −50 |
| cluster 2 | 266 | L | A, D, E, G, N, P, Q, S, T, V | between −24 and −50 |
| cluster 2 | 267 | S | A, D, E, G, H, P, T | between −34 and −50 |
| cluster 3 | 696 | L | E, G, P | between −26 and −30 |
| cluster 4 | 846 | F | E, W | between −31 and −33 |
| cluster 4 | 847 | L | D, E, F, G, H, K, N, P, Q, S, T, W | between −33 and −58 |
| cluster 4 | 852 | I | D, E, F, G, Y | −20 |
| cluster 4 | 855 | K | D, E, G, P, S | between −23 and −25 |
| cluster 5 | 1278 | K | A, D, E, F, G, N, P, Q, S, T, V, W | between −22 and −92 |
| cluster 5 | 1279 | R | D, E, H, K, Q | between −23 and −116 |

TABLE 4-continued

List of residues and possible amino acid substitutions removing/reducing HLA binding.

| Cluster | Position | Original residue | Possible substitutions | Reduction in DRB1 score due to substitution |
|---|---|---|---|---|
| cluster 5 | 1280 | V | A, D, E, G, K, N, P, Q, S, T | between −31 and −92 |
| cluster 5 | 1281 | I | A, D, E, F, G, H, K, N, P, Q, R, S, T, W | between −47 and −116 |
| cluster 5 | 1282 | L | A, D, E, G, H, N, P, S, T | between −34 and −102 |

Substitutions listed in Table 4 were selected with the objective of removing/reducing HLA binding. Aspects of structural integrity and functionality of Cas9 were not considered at this point. In addition, deimmunising substitutions were selected only in five clusters identified based on data from one donor.

The following example demonstrates a reduction in predicted immunogenic risk if five substitutions (one in each cluster) are made. Calculations were determined using the following substitutions in the amino acid sequence of Cas9: L106D, K263D, L696G, L847D, I1281D. The deimmunised version of Cas9 protein has a reduced DRB1 score, as shown in Table 5, with overall reduction by 295. Looking at the DRB1 score restricted to the combined five clusters, the original Cas9 has a DRB1 score of 177.6 and the deimmunised Cas9 protein has a DRB1 score of 23.3, achieving an 87% reduction. Furthermore, the five substitutions completely removed DRB1 epitopes restricted by the HLA allotypes of the donor (DRB1*03 and DRB1*13).

TABLE 5

DRB1 scores of the Cas9 protein and deimmunised Cas9 protein with five substitutions.

| | DRB1 score for whole protein | DRB1 score due to five clusters * | Number of critical epitopes in five cluster regions * |
|---|---|---|---|
| Cas9 | 12693.6 | 177.6 | 16 |
| Deimmunised Cas9 with 5 substitutions | 12398.6 | 23.3 | 9 |

* Only epitopes/binders fully contained in the five clusters are included.

What is claimed is:

1. A method for reducing the immunogenicity of a CRISPR-associated 9 (Cas9) protein, the method comprising introducing one or more amino acid substitutions into one or more residues corresponding to one or more major histocompatibility (MHC) Class I and/or Class II binding sites of the Cas9 protein to form a recombinant Cas9 protein;
   wherein the amino acid sequence of the Cas9 protein is at least 95% identical to full-length SEQ ID NO:5; and
   wherein the one or more amino acid substitutions are one or more of: L106D, K263D, L696G, L847D, or I1281D.

2. The method of claim 1, wherein there are two or more amino acid substitutions selected from two of: L106D, K263D, L696G, L847D, or I1281D.

3. The method of claim 1, wherein there are three or more amino acid substitutions selected from three of: L106D, K263D, L696G, L847D, or I1281D.

4. The method of claim 1, wherein there are four or more amino acid substitutions selected from four of: L106D, K263D, L696G, L847D, or I1281D.

5. The method of claim 1, wherein there are five amino acid substitutions: L106D, K263D, L696G, L847D, and I1281D.

6. A recombinant CRISPR-associated 9 (Cas9) protein made by a method comprising introducing one or more amino acid substitutions into one or more residues corresponding to one or more major histocompatibility (MHC) Class I and/or Class II binding sites of the Cas9 protein to form the recombinant Cas9 protein;
   wherein the amino acid sequence of the Cas9 protein is at least 95% identical to full-length SEQ ID NO:5; and
   wherein the one or more amino acid substitutions are one or more of: L106D, K263D, L696G, L847D, or I1281D.

7. An isolated cell comprising the recombinant Cas9 protein of claim 6.

* * * * *

SEQUENCE LISTING

```
<160> NUMBER OF SEQ ID NOS: 510

<210> SEQ ID NO 1
<211> LENGTH: 4107
<212> TYPE: DNA
<213> ORGANISM: Streptococcus pyogenes

<400> SEQUENCE: 1
atggacaaga agtactccat tgggctcgat atcggcacaa acagcgtcgg ctgggccgtc      60
attacggacg agtacaaggt gccgagcaaa aaattcaaag ttctgggcaa taccgatcgc     120
cacagcataa agaagaacct cattggcgcc ctcctgttcg actccgggga gacggccgaa     180
gccacgcggc tcaaaagaac agcacggcgc agatatacccc gcagaaagaa tcggatctgc     240
tacctgcagg agatctttag taatgagatg gctaaggtgg atgactcttt cttccatagg     300
ctggaggagt cctttttggt ggaggaggat aaaaagcacg agcgccaccc aatctttggc     360
aatatcgtgg acgaggtggc gtaccatgaa aagtacccaa ccatatatca tctgaggaag     420
aagcttgtag acagtactga taaggctgac ttgcggttga tctatctcgc gctggcgcat     480
atgatcaaat tcgggggaca cttcctcatc gaggggggacc tgaacccaga caacagcgat     540
gtcgacaaac tctttatcca actggttcag acttacaatc agcttttcga agagaacccg     600
atcaacgcat ccggagttga cgccaaagca atcctgagcg ctaggctgtc caaatcccgg     660
cggctcgaaa acctcatcgc acagctccct ggggagaaga gaacggcct gtttggtaat     720 cttatcgccc tgtcactcgg gctgacccccc aactttaaat ctaacttcga cctggccgaa     780
gatgccaagc ttcaactgag caaagacacc tacgatgatg atctcgacaa tctgctggcc     840
cagatcggcg accagtacgc agaccttttt ttggcggcaa agaacctgtc agacgccatt     900
ctgctgagtg atattctgcg agtgaacacg gagatcacca agctccgct gagcgctagt     960 atgatcaagc gctatgatga gcaccaccaa gacttgactt tgctgaaggc ccttgtcaga    1020
```

```
cagcaactgc ctgagaagta caaggaaatt ttcttcgatc agtctaaaaa tggctacgcc   1080
ggatacattg acggcggagc aagccaggag gaatttttaca aatttattaa gcccatcttg   1140
gaaaaaatgg acggcaccga ggagctgctg gtaaagctta acagagaaga tctgttgcgc   1200
aaacagcgca ctttcgacaa tggaagcatc ccccaccaga ttcacctggg cgaactgcac   1260
gctatcctca ggcggcaaga ggatttctac cccttttga aagataacag ggaaaagatt   1320
gagaaaatcc tcacatttcg atacccctac tatgtaggcc ccctcgcccg gggaaattcc   1380
agattcgcgt ggatgactcg caaatcagaa gagaccatca ctccctggaa cttcgaggaa   1440
gtcgtggata agggggcctc tgcccagtcc ttcatcgaaa ggatgactaa ctttgataaa   1500
aatctgccta cgaaaaggt gcttcctaaa cactctctgc tgtacgagta cttcacagtt   1560
tataacgagc tcaccaaggt caaatacgtc acagaaggga tgagaaagcc agcattcctg   1620
tctggagagc agaagaaagc tatcgtggac ctcctcttca agacgaaccg gaaagttacc   1680
gtgaaacagc tcaaagaaga ctatttcaaa aagattgaat gtttcgactc tgttgaaatc   1740
agcggagtgg aggatcgctt caacgcatcc ctgggaacgt atcacgatct cctgaaaatc   1800
attaaagaca aggacttcct ggacaatgag gagaacgagg acattcttga ggacattgtc   1860 ctcacccctta cgttgtttga agatagggag atgattgaag aacgcttgaa aacttacgct   1920
catctcttcg acgacaaagt catgaaacag ctcaagaggc gccgatatac aggatggggg   1980
cggctgtcaa gaaaactgat caatgggatc cgagacaagc agagtggaaa gacaatcctg   2040
gattttctta gtccgatgg atttgccaac cggaacttca tgcagttgat ccatgatgac   2100
tctctcacct ttaaggagga catccagaaa gcacaagttt ctggccaggg ggacagtctt   2160
cacgagcaca tcgctaatct tgcaggtagc ccagctatca aaaagggaat actgcagacc   2220
gttaaggtcg tggatgaact cgtcaaagta atgggaaggc ataagcccga gaatatcgtt   2280
atcgagatgg cccgagagaa ccaaactacc cagaagggac agaagaacag tagggaaagg   2340
atgaagagga ttgaagaggg tataaaagaa ctggggtccc aaatccttaa ggaacaccca   2400
gttgaaaaca cccagcttca gaatgagaag ctctacctgt actacctgca gaacggcagg   2460
gacatgtacg tggatcagga actggacatc aatcggctct ccgactacga cgtggatcat   2520
atcgtgcccc agtctttct caaagatgat tctattgata taaagtgtt gacaagatcc   2580 gataaaaata gagggaagag tgataacgtc ccctcagaag aagttgtcaa gaaaatgaaa   2640
aattattggc ggcagctgct gaacgccaaa ctgatcacac aacggaagtt cgataatctg   2700
actaaggctg aacgaggtgg cctgtctgag ttggataaag ccggcttcat caaaaggcag   2760
cttgttgaga cacgccagat caccaagcac gtggcccaaa ttctcgattc acgcatgaac   2820
accaagtacg atgaaaatga caaactgatt cgagaggtga aagttattac tctgaagtct   2880
aagctggtct cagatttcag aaaggacttt cagtttttata aggtgagaga gatcaacaat   2940
taccaccatg cgcatgatgc ctacctgaat gcagtggtag gcactgcact tatcaaaaaa   3000
tatcccaagc ttgaatctga atttgtttac ggagactata agtgtacga tgttaggaaa   3060 atgatcgcaa agtctgagca ggaaataggc aaggccaccg ctaagtactt cttttacagc   3120
aatattatga attttttcaa gaccgagatt acactggcca atggagagat tcggaagcga   3180
ccacttatcg aaacaaacgg agaaacagga gaaatcgtgt gggacaaggg tagggatttc   3240
gcgacagtcc ggaaggtcct gtccatgccg caggtgaaca tcgttaaaaa gaccgaagta   3300
cagaccggag gcttctccaa ggaaagtatc ctcccgaaaa ggaacagcga caagctgatc   3360
```

| | |
|---|---|
| gcacgcaaaa aagattggga ccccaagaaa tacggcggat tcgattctcc tacagtcgct | 3420 |
| tacagtgtac tggttgtggc caaagtggag aaagggaagt ctaaaaaact caaaagcgtc | 3480 |
| aaggaactgc tgggcatcac aatcatggag cgatcaagct tcgaaaaaaa ccccatcgac | 3540 |
| tttctcgagg cgaaaggata taagaggtc aaaaagacc tcatcattaa gcttcccaag | 3600 |
| tactctctct ttgagcttga aaacggccgg aaacgaatgc tcgctagtgc gggcgagctg | 3660 |
| cagaaaggta acgagctggc actgccctct aaatacgtta atttcttgta tctggccagc | 3720 |
| cactatgaaa agctcaaagg gtctcccgaa gataatgagc agaagcagct gttcgtggaa | 3780 |
| caacacaaac actaccttga tgagatcatc gagcaaataa gcgaattctc caaaagagtg | 3840 |
| atcctcgccg acgctaacct cgataaggtg ctttctgctt acaataagca cagggataag | 3900 |
| cccatcaggg agcaggcaga aaacattatc cacttgttta ctctgaccaa cttgggcgcg | 3960 |
| cctgcagcct tcaagtactt cgacaccacc atagacagaa agcggtacac ctctacaaag | 4020 |
| gaggtcctgg acgccacact gattcatcag tcaattacgg ggctctatga aacaagaatc | 4080 |
| gacctctctc agctcggtgg agactga | 4107 |

<210> SEQ ID NO 2
<211> LENGTH: 3366
<212> TYPE: DNA
<213> ORGANISM: Streptococcus thermophilus

<400> SEQUENCE: 2

| | |
|---|---|
| atgagcgacc tggtgctggg cctggacatc ggcatcggca gcgtgggcgt gggcatcctg | 60 |
| aacaaggtga ccggcgagat catccacaag aacagtcgca tcttccctgc tgctcaggct | 120 |
| gagaacaacc tggtgcgccg caccaaccgc cagggtcgcc ggcttgctcg ccgcaagaag | 180 |
| caccggcgcg tgcgcctgaa ccgcctgttc gaggagagcg gcctgatcac cgacttcacc | 240 |
| aagatcagca tcaacctgaa ccccctaccag ctgcgcgtga agggcctgac cgacgagctg | 300 |
| agcaacgagg agctgttcat cgccctgaag aacatggtga agcaccgcgg catcagctac | 360 |
| ctggacgacg ccagcgacga cggcaacagc agcgtgggcg actacgccca gatcgtgaag | 420 |
| gagaacagca gcagctgga gaccaagacc cccggccaga tccagctgga gcgctaccag | 480 |
| acctacggcc agctgcgcgg cgacttcacc gtggagaagg acggcaagaa gcaccgcctg | 540 |
| atcaacgtgt tccccaccag cgcctaccgc agcgaggccc tgcgcatcct gcagacccag | 600 |
| caggagttca ccccccagat caccgacgag ttcatcaacc gctacctgga gatcctgacc | 660 |
| ggcaagcgca agtactacca cggccccggc aacgagaaga ccgcaccga ctacggccgc | 720 |
| taccgcacca gcggcgagac cctggacaac atcttcggca tcctgatcgg caagtgcacc | 780 |
| ttctaccccg acgagttccg cgccgccaag gccagctaca ccgcccagga gttcaacctg | 840 |
| ctgaacgacc tgaacaacct gaccgtgccc accgagacca agaagctgag caaggagcag | 900 |
| aagaaccaga tcatcaacta cgtgaagaac gagaaggcca tgggcccccgc caagctgttc | 960 |
| aagtacatcg ccaagctgct gagctgcgac gtggccgaca tcaagggcta ccgcatcgac | 1020 |
| aagagcggca aggccgagat ccacaccttc gaggcctacc gcaagatgaa gaccctggag | 1080 |
| accctggaca tcgagcagat ggaccgcgag accctggaca gctggccta cgtgctgacc | 1140 |
| ctgaacaccg agcgcgaggg catccaggag gccctggagc acgagttcgc cgacggcagc | 1200 |
| ttcagccaga gcaggtgga cgagctggtg cagttccgca aggccaacag cagcatcttc | 1260 |
| ggcaagggct ggcacaactt cagcgtgaag ctgatgatgg agctgatccc cgagctgtac | 1320 |
| gagaccagcg aggagcagat gaccatcctg acccgcctgg gcaagcagaa gaccaccagc | 1380 |

| | |
|---|---|
| agcagcaaca agaccaagta catcgacgag aagctgctga ccgaggagat ctacaacccc | 1440 |
| gtggtggcca agagcgtgcg ccaggccatc aagatcgtga acgccgccat caaggagtac | 1500 |
| ggcgacttcg acaacatcgt gatcgagatg gcccgcgaga ccaacgagga cgacgagaag | 1560 |
| aaggccatcc agaagatcca gaaggccaac aaggacgaga aggacgccgc catgctgaag | 1620 |
| gccgccaacc agtacaacgg caaggccgag ctgccccaca gcgtgttcca cggccacaag | 1680 |
| cagctggcca ccaagatccg cctgtggcac cagcagggcg agcgctgcct gtacaccggc | 1740 |
| aagaccatca gcatccacga cctgatcaac aacagcaacc agttcgaggt ggaccacatc | 1800 |
| ctgcccctga gcatcacctt cgacgacagc ctggccaaca aggtgctggt gtacgccacc | 1860 |
| gccaaccagg agaagggcca gcgcaccccc taccaggccc tggacagcat ggacgacgcc | 1920 |
| tggagcttcc gcgagctgaa ggccttcgtg cgcgagagca gaccctgag caacaagaag | 1980 |
| aaggagtacc tgctgaccga ggaggacatc agcaagttcg acgtgcgcaa gaagttcatc | 2040 |
| gagcgcaacc tggtggacac ccgctacgcc agccgcgtgg tgctgaacgc cctgcaggag | 2100 |
| cacttccgcg cccacaagat cgacaccaag gtgagcgtgg tgcgcggcca gttcaccagc | 2160 |
| cagctgcgcc gccactgggg catcgagaag acccgcgaca cctaccacca ccacgccgtg | 2220 |
| gacgccctga tcattgcggc ttctagccag ctgaacctgt ggaagaagca agaacacc | 2280 |
| ctggtgagct acagcgagga ccagctgctg gacatcgaga ccggcgagct gatcagcgac | 2340 |
| gacgagtaca aggagagcgt gttcaaggcc ccctaccagc acttcgtgga caccctgaag | 2400 |
| agcaaggagt cgaggacag catcctgttc agctaccagg tggacagcaa gttcaaccgc | 2460 |
| aagatcagcg acgccaccat ctacgccacc cgccaggcca aggtgggcaa ggacaaggcc | 2520 |
| gacgagacct acgtgctggg caagatcaag gacatctaca cccaggacgg ctacgacgcc | 2580 |
| ttcatgaaga tctacaagaa ggacaagagc aagttcctga tgtaccgcca cgacccccag | 2640 |
| accttcgaga aggtgatcga gcccatcctg gagaactacc ccaacaagca gatcaacgat | 2700 |
| aaaggcaagg aggtgccctg caaccccttc ctgaagtaca aggaggagca cggctacatc | 2760 |
| cgcaagtaca gcaagaaggg caacggcccc gagatcaaga gcctgaagta ctacgacagc | 2820 |
| aagctgggca accacatcga catcacccc aaggacagca caacaaggt ggtgctgcag | 2880 |
| agcgtgagcc cctggcgcgc cgacgtgtac ttcaacaaga ccaccggcaa gtacgagatc | 2940 |
| ctgggcctga gtacgccga cctgcagttt gataagggca ccggcaccta caagatcagc | 3000 |
| caggagaagt acaacgacat caagaagaag gagggcgtgg acagcgacag cgagttcaag | 3060 |
| ttcaccctgt acaagaacga ccttctgctg gtgaaggaca ccgagaccaa ggagcaacag | 3120 |
| ctgttccgct tcctgagccg caccatgccc aagcagaagc actacgtgga gctgaagccc | 3180 |
| tacgacaagc agaagttcga gggcggcgag gccctgatca aggtgctggg caacgtggcc | 3240 |
| aacagcggcc agtgcaagaa gggcctgggc aagagcaaca tcagcatcta caaggtgcgc | 3300 |
| accgacgtgc tgggcaacca gcacatcatc aagaacgagg gcgacaagcc caagctggac | 3360 |
| ttctga | 3366 |

<210> SEQ ID NO 3
<211> LENGTH: 3162
<212> TYPE: DNA
<213> ORGANISM: Staphylococcus aureus

<400> SEQUENCE: 3

| | |
|---|---|
| atgaagcgga actacatcct gggcctggac atcggcatca ccagcgtggg ctacggcatc | 60 |

```
atcgactacg agacacggga cgtgatcgat gccggcgtgc ggctgttcaa agaggccaac      120
gtggaaaaca acgagggcag gcggagcaag agaggcgcca gaaggctgaa gcggcggagg      180
cggcatagaa tccagagagt gaagaagctg ctgttcgact acaacctgct gaccgaccac      240
agcgagctga gcggcatcaa cccctacgag gccagagtga agggcctgag ccagaagctg      300
agcgaggaag agttctctgc cgccctgctg cacctggcca agagaagagg cgtgcacaac      360
gtgaacgagg tggaagagga caccggcaac gagctgtcca ccaaagagca gatcagccgg      420
aacagcaagg ccctggaaga gaaatacgtg gccgaactgc agctggaacg gctgaagaaa      480
gacggcgaag tgcggggcag catcaacaga ttcaagacca gcgactacgt gaaagaagcc      540
aaacagctgc tgaaggtgca aaaggcctac caccagctgg accagagctt catcgacacc      600
tacatcgacc tgctggaaac ccggcggacc tactatgagg acctggcga gggcagcccc      660 ttcggctgga aggacatcaa agaatggtac gagatgctga tgggccactg cacctacttc      720
cccgaggaac tgcggagcgt gaagtacgcc tacaacgccg acctgtacaa cgccctgaac      780
gacctgaaca atctcgtgat caccagggac gagaacgaga gctggaata ttacgagaag      840 ttccagatca tcgagaacgt gttcaagcag aagaagaagc cacccctgaa gcagatcgcc      900
aaagaaatcc tcgtgaacga agaggatatt aagggctaca gagtgaccag caccggcaag      960
cccgagttca ccaacctgaa ggtgtaccac gacatcaagg acattaccgc ccggaaagag     1020
attattgaga cgccgagct gctggatcag attgccaaga tcctgaccat ctaccagagc     1080
agcgaggaca tccaggaaga actgaccaat ctgaactccg agctgaccca ggaagagatc     1140
gagcagatct ctaatctgaa gggctatacc ggcacccaca acctgagcct gaaggccatc     1200
aacctgatcc tggacgagct gtggcacacc aacgacaacc agatcgctat cttcaaccgg     1260
ctgaagctgg tgcccaagaa ggtggacctg tcccagcaga aagagatccc caccaccctg     1320
gtggacgact tcatcctgag ccccgtcgtg aagagaagct tcatccagag catcaaagtg     1380
atcaacgcca tcatcaagaa gtacggcctg cccaacgaca tcattatcga gctggcccgc     1440
gagaagaact ccaaggacgc ccagaaaatg atcaacgaga tgcagaagcg gaaccggcag     1500
accaacgagc ggatcgagga aatcatccgg accaccggca agagaacgc caagtacctg     1560 atcgagaaga tcaagctgca cgacatgcag gaaggcaagt gcctgtacag cctggaagcc     1620
atccctctgg aagatctgct gaacaacccc ttcaactatg aggtggacca catcatcccc     1680
agaagcgtgt ccttcgacaa cagcttcaac aacaaggtgc tcgtgaagca ggaagaaaac     1740
agcaagaagg gcaaccggac cccattccag tacctgagca gcagcgacag caagatcagc     1800
tacgaaacct tcaagaagca catcctgaat ctggccaagg gcaagggcag aatcagcaag     1860
accaagaaag agtatctgct ggaagaacgg gacatcaaca ggttctccgt gcagaaagac     1920
ttcatcaacc ggaacctggt ggataccaga tacgccacca gaggcctgat gaacctgctg     1980
cggagctact tcagagtgaa caacctggac gtgaaagtga agtccatcaa tggcggcttc     2040
accagctttc tgcggcggaa gtggaagttt aagaaagagc ggaacaaggg gtacaagcac     2100
cacgccgagg acgccctgat cattgccaac gccgatttca tcttcaaaga gtggaagaaa     2160
ctggacaagg ccaaaaaagt gatggaaaac cagatgttcg aggaaaagca ggccgagagc     2220
atgcccgaga tcgaaaccga gcaggagtac aaagagatct catcaccccc caccagatc     2280 aagcacatta aggacttcaa ggactacaag tacagccacc gggtggacaa gaagcctaat     2340
agagagctga ttaacgacac cctgtactcc acccggaagg acgacaaggg caacaccctg     2400
atcgtgaaca atctgaacgg cctgtacgac aaggacaatg acaagctgaa aaagctgatc     2460
```

```
aacaagagcc ccgaaaagct gctgatgtac caccacgacc cccagaccta ccagaaactg    2520
aagctgatta tggaacagta cggcgacgag aagaatcccc tgtacaagta ctacgaggaa    2580
accgggaact acctgaccaa gtactccaaa aaggacaacg ccccgtgat caagaagatt     2640 aagtattacg gcaacaaact gaacgcccat ctggacatca ccgacgacta ccccaacagc    2700
agaaacaagg tcgtgaagct gtccctgaag ccctacagat cgacgtgta cctggacaat     2760 ggcgtgtaca agttcgtgac cgtgaagaat ctggatgtga tcaaaaaaga aaactactac    2820
gaagtgaata gcaagtgcta tgaggaagct aagaagctga agaagatcag caaccaggcc    2880
gagtttatcg cctccttcta caacaacgat ctgatcaaga tcaacggcga gctgtataga    2940
gtgatcggcg tgaacaacga cctgctgaac cggatcgaag tgaacatgat cgacatcacc    3000
taccgcgagt acctggaaaa catgaacgac aagaggcccc ccaggatcat taagacaatc    3060
gcctccaaga cccagagcat taagaagtac agcacagaca ttctgggcaa cctgtatgaa    3120
gtgaaatcta agaagcaccc tcagatcatc aaaaagggct aa                       3162
```

<210> SEQ ID NO 4
<211> LENGTH: 3249
<212> TYPE: DNA
<213> ORGANISM: Neiserria meningitidis
<400> SEQUENCE: 4

```
atggccgcct tcaagcccaa ccccatcaac tacatcctgg gcctggacat cggcatcgcc      60
agcgtgggct gggccatggt ggagatcgac gaggacgaga accccatctg cctgatcgac     120
ctgggtgtgc gcgtgttcga gcgcgctgag gtgcccaaga ctggtgacag tctggctatg     180
gctcgccggc ttgctcgctc tgttcggcgc cttactcgcc ggcgcgctca ccgccttctg     240
cgcgctcgcc gcctgctgaa gcgcgagggt gtgctgcagg ctgccgactt cgacgagaac     300
ggcctgatca agagcctgcc caacactcct tggcagctgc gcgctgccgc tctggaccgc    360
aagctgactc ctctggagtg gagcgccgtg ctgctgcacc tgatcaagca ccgcggctac    420
ctgagccagc gcaagaacga gggcgagacc gccgacaagg agctgggtgc tctgctgaag    480
ggcgtggccg acaacgccca cgccctgcag actggtgact ccgcactcc tgctgagctg     540 gccctgaaca gttcgagaa ggagagcggc cacatccgca accagcgcgg cgactacagc     600
cacaccttca gccgcaagga cctgcaggcc gagctgatcc tgctgttcga gaagcagaag    660
gagttcggca ccccacgt gagcggcggc ctgaaggagg gcatcgagac cctgctgatg      720
acccagcgcc ccgccctgag cggcgacgcc gtgcagaaga tgctgggcca ctgcaccttc    780
gagccagccg agcccaaggc cgccaagaac acctacaccg ccgagcgctt catctggctg    840
accaagctga caacctgcg catcctggag cagggcagcg agcgcccct gaccgacacc      900 gagcgcgcca ccctgatgga cgagccctac cgcaagagca agctgaccta cgcccaggcc    960
cgcaagctgc tgggtctgga ggacaccgcc ttcttcaagg gcctgcgcta cggcaaggac    1020
aacgccgagg ccagcaccct gatggagatg aaggcctacc acgccatcag ccgcgccctg    1080
gagaaggagg gcctgaagga caagaagagt cctctgaacc tgagccccga gctgcaggac    1140
gagatcggca ccgccttcag cctgttcaag accgacgaga catcaccgg ccgcctgaag     1200 gaccgcatcc agcccgagat cctggaggcc ctgctgaagc acatcagctt cgacaagttc    1260
gtgcagatca gcctgaaggc cctgcgccgc atcgtgcccc tgatggagca gggcaagcgc    1320
tacgacgagg cctgcgccga gatctacggc gaccactacg gcaagaagaa caccgaggag    1380
```

```
aagatctacc tgcctcctat ccccgccgac gagatccgca accccgtggt gctgcgcgcc    1440
ctgagccagg cccgcaaggt gatcaacggc gtggtgcgcc gctacggcag ccccgcccgc    1500
atccacatcg agaccgcccg cgaggtgggc aagagcttca aggaccgcaa ggagatcgag    1560
aagcgccagg aggagaaccg caaggaccgc gagaaggccg ccgccaagtt ccgcgagtac    1620
ttccccaact tcgtgggcga gcccaagagc aaggacatcc tgaagctgcg cctgtacgag    1680
cagcagcacg gcaagtgcct gtacagcggc aaggagatca acctgggccg cctgaacgag    1740
aagggctacg tggagatcga ccacgccctg cccttcagcc gcacctggga cgacagcttc    1800
aacaacaagg tgctggtgct ggcagcgag aaccagaaca agggcaacca gaccccctac    1860
gagtacttca cggcaagga caacagccgc gagtggcagg agttcaaggc ccgcgtggag    1920
accagccgct tcccccgcag caagaagcag cgcatcctgc tgcagaagtt cgacgaggac    1980
ggcttcaagg agcgcaacct gaacgacacc cgctacgtga accgcttcct gtgccagttc    2040
gtggccgacc gcatgcgcct gaccggcaag ggcaagaagc gcgtgttcgc cagcaacggc    2100
cagatcacca acctgctgcg cggcttctgg ggcctgcgca aggtgcgcgc cgagaacgac    2160
cgccaccacg ccctggacgc cgtggtggtg gcctgcagca ccgtggccat gcagcagaag    2220
atcacccgct tcgtgcgcta caaggagatg aacgccttcg acggtaaaac catcgacaag    2280
gagaccggcg aggtgctgca ccagaagacc cacttccccc agccctggga gttcttcgcc    2340
caggaggtga tgatccgcgt gttcggcaag cccgacggca gcccgagtt cgaggaggcc    2400 gacacccccg agaagctgcg caccctgctg gccgagaagc tgagcagccg ccctgaggcc    2460
gtgcacgagt acgtgactcc tctgttcgtg agccgcgccc ccaaccgcaa gatgagcggt    2520
cagggtcaca tggagaccgt gaagagcgcc aagcgcctgg acgagggcgt gagcgtgctg    2580
cgcgtgcccc tgacccagct gaagctgaag gacctggaga gatggtgaa ccgcgagcgc    2640 gagcccaagc tgtacgaggc cctgaaggcc cgcctggagg cccacaagga cgaccccgcc    2700
aaggccttcg ccgagccctt ctacaagtac gacaaggccg gcaaccgcac ccagcaggtg    2760
aaggccgtgc gcgtggagca ggtgcagaag accggcgtgt gggtgcgcaa ccacaacggc    2820
atcgccgaca cgccaccat ggtgcgcgtg gacgtgttcg agaagggcga caagtactac    2880
ctggtgccca tctacagctg gcaggtggcc aagggcatcc tgcccgaccg cgccgtggtg    2940
cagggcaagg acgaggagga ctggcagctg atcgacgaca gcttcaactt caagttcagc    3000
ctgcacccca cgacctggt ggaggtgatc accaagaagg cccgcatgtt cggctacttc    3060
gccagctgcc accgcggcac cggcaacatc aacatccgca tccacgacct ggaccacaag    3120
atcggcaaga acggcatcct ggagggcatc ggcgtgaaga ccgccctgag cttccagaag    3180
taccagatcg acgagctggg caaggagatc cgcccctgcc gcctgaagaa cgcccctcct    3240
gtgcgctga                                                            3249
```

<210> SEQ ID NO 5
<211> LENGTH: 1368
<212> TYPE: PRT
<213> ORGANISM: Streptococcus pyogenes

<400> SEQUENCE: 5

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile

```
              35                  40                  45
Gly Ala Leu Leu Phe Asp Ser Gly Glu Thr Ala Glu Ala Thr Arg Leu
         50                  55                  60
Lys Arg Thr Ala Arg Arg Tyr Thr Arg Lys Asn Arg Ile Cys
 65                  70                  75                  80
Tyr Leu Gln Glu Ile Phe Ser Asn Glu Met Ala Lys Val Asp Asp Ser
                 85                  90                  95
Phe Phe His Arg Leu Glu Glu Ser Phe Leu Val Glu Glu Asp Lys Lys
                100                 105                 110
His Glu Arg His Pro Ile Phe Gly Asn Ile Val Asp Glu Val Ala Tyr
            115                 120                 125
His Glu Lys Tyr Pro Thr Ile Tyr His Leu Arg Lys Lys Leu Val Asp
        130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
                180                 185                 190
Asn Gln Leu Phe Glu Glu Asn Pro Ile Asn Ala Ser Gly Val Asp Ala
            195                 200                 205
Lys Ala Ile Leu Ser Ala Arg Leu Ser Lys Ser Arg Arg Leu Glu Asn
        210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
            260                 265                 270
Asp Asp Leu Asp Asn Leu Leu Ala Gln Ile Gly Asp Gln Tyr Ala Asp
        275                 280                 285
Leu Phe Leu Ala Ala Lys Asn Leu Ser Asp Ala Ile Leu Leu Ser Asp
    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
```

```
Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
        850                 855                 860

Gly Lys Ser Asp Asn Val Pro Ser Glu Glu Val Val Lys Lys Met Lys
865                 870                 875                 880
```

```
Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
```

```
                    1280                1285                1290
Tyr Asn Lys His Arg Asp Lys Pro Ile Arg Glu Gln Ala Glu Asn
                1295                1300                1305
Ile Ile His Leu Phe Thr Leu Thr Asn Leu Gly Ala Pro Ala Ala
                1310                1315                1320
Phe Lys Tyr Phe Asp Thr Thr Ile Asp Arg Lys Arg Tyr Thr Ser
                1325                1330                1335
Thr Lys Glu Val Leu Asp Ala Thr Leu Ile His Gln Ser Ile Thr
                1340                1345                1350
Gly Leu Tyr Glu Thr Arg Ile Asp Leu Ser Gln Leu Gly Gly Asp
                1355                1360                1365

<210> SEQ ID NO 6
<211> LENGTH: 1121
<212> TYPE: PRT
<213> ORGANISM: Streptococcus thermophilus

<400> SEQUENCE: 6

Met Ser Asp Leu Val Leu Gly Leu Asp Ile Gly Ile Gly Ser Val Gly
1               5                   10                  15
Val Gly Ile Leu Asn Lys Val Thr Gly Glu Ile Ile His Lys Asn Ser
                20                  25                  30
Arg Ile Phe Pro Ala Ala Gln Ala Glu Asn Asn Leu Val Arg Arg Thr
            35                  40                  45
Asn Arg Gln Gly Arg Arg Leu Ala Arg Arg Lys Lys His Arg Arg Val
        50                  55                  60
Arg Leu Asn Arg Leu Phe Glu Glu Ser Gly Leu Ile Thr Asp Phe Thr
65                  70                  75                  80
Lys Ile Ser Ile Asn Leu Asn Pro Tyr Gln Leu Arg Val Lys Gly Leu
                85                  90                  95
Thr Asp Glu Leu Ser Asn Glu Glu Leu Phe Ile Ala Leu Lys Asn Met
            100                 105                 110
Val Lys His Arg Gly Ile Ser Tyr Leu Asp Asp Ala Ser Asp Asp Gly
        115                 120                 125
Asn Ser Ser Val Gly Asp Tyr Ala Gln Ile Val Lys Glu Asn Ser Lys
    130                 135                 140
Gln Leu Glu Thr Lys Thr Pro Gly Gln Ile Gln Leu Glu Arg Tyr Gln
145                 150                 155                 160
Thr Tyr Gly Gln Leu Arg Gly Asp Phe Thr Val Glu Lys Asp Gly Lys
                165                 170                 175
Lys His Arg Leu Ile Asn Val Phe Pro Thr Ser Ala Tyr Arg Ser Glu
            180                 185                 190
Ala Leu Arg Ile Leu Gln Thr Gln Gln Glu Phe Asn Pro Gln Ile Thr
        195                 200                 205
Asp Glu Phe Ile Asn Arg Tyr Leu Glu Ile Leu Thr Gly Lys Arg Lys
    210                 215                 220
Tyr Tyr His Gly Pro Gly Asn Glu Lys Ser Arg Thr Asp Tyr Gly Arg
225                 230                 235                 240
Tyr Arg Thr Ser Gly Glu Thr Leu Asp Asn Ile Phe Gly Ile Leu Ile
                245                 250                 255
Gly Lys Cys Thr Phe Tyr Pro Asp Glu Phe Arg Ala Ala Lys Ala Ser
            260                 265                 270
Tyr Thr Ala Gln Glu Phe Asn Leu Leu Asn Asp Leu Asn Asn Leu Thr
        275                 280                 285
```

-continued

Val Pro Thr Glu Thr Lys Lys Leu Ser Lys Glu Gln Lys Asn Gln Ile
290             295                 300

Ile Asn Tyr Val Lys Asn Glu Lys Ala Met Gly Pro Ala Lys Leu Phe
305             310                 315                 320

Lys Tyr Ile Ala Lys Leu Leu Ser Cys Asp Val Ala Asp Ile Lys Gly
            325                 330                 335

Tyr Arg Ile Asp Lys Ser Gly Lys Ala Glu Ile His Thr Phe Glu Ala
            340                 345                 350

Tyr Arg Lys Met Lys Thr Leu Glu Thr Leu Asp Ile Glu Gln Met Asp
            355                 360                 365

Arg Glu Thr Leu Asp Lys Leu Ala Tyr Val Leu Thr Leu Asn Thr Glu
370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
                405                 410                 415

Ser Ser Ile Phe Gly Lys Gly Trp His Asn Phe Ser Val Lys Leu Met
            420                 425                 430

Met Glu Leu Ile Pro Glu Leu Tyr Glu Thr Ser Glu Glu Gln Met Thr
            435                 440                 445

Ile Leu Thr Arg Leu Gly Lys Gln Lys Thr Thr Ser Ser Asn Lys
450                 455                 460

Thr Lys Tyr Ile Asp Glu Lys Leu Leu Thr Glu Glu Ile Tyr Asn Pro
465                 470                 475                 480

Val Val Ala Lys Ser Val Arg Gln Ala Ile Lys Ile Val Asn Ala Ala
                485                 490                 495

Ile Lys Glu Tyr Gly Asp Phe Asp Asn Ile Val Ile Glu Met Ala Arg
            500                 505                 510

Glu Thr Asn Glu Asp Asp Glu Lys Lys Ala Ile Gln Lys Ile Gln Lys
            515                 520                 525

Ala Asn Lys Asp Glu Lys Asp Ala Ala Met Leu Lys Ala Ala Asn Gln
530                 535                 540

Tyr Asn Gly Lys Ala Glu Leu Pro His Ser Val Phe His Gly His Lys
545                 550                 555                 560

Gln Leu Ala Thr Lys Ile Arg Leu Trp His Gln Gln Gly Glu Arg Cys
            565                 570                 575

Leu Tyr Thr Gly Lys Thr Ile Ser Ile His Asp Leu Ile Asn Asn Ser
            580                 585                 590

Asn Gln Phe Glu Val Asp His Ile Leu Pro Leu Ser Ile Thr Phe Asp
            595                 600                 605

Asp Ser Leu Ala Asn Lys Val Leu Val Tyr Ala Thr Ala Asn Gln Glu
610                 615                 620

Lys Gly Gln Arg Thr Pro Tyr Gln Ala Leu Asp Ser Met Asp Asp Ala
625                 630                 635                 640

Trp Ser Phe Arg Glu Leu Lys Ala Phe Val Arg Glu Ser Lys Thr Leu
            645                 650                 655

Ser Asn Lys Lys Lys Glu Tyr Leu Leu Thr Glu Glu Asp Ile Ser Lys
            660                 665                 670

Phe Asp Val Arg Lys Lys Phe Ile Glu Arg Asn Leu Val Asp Thr Arg
            675                 680                 685

Tyr Ala Ser Arg Val Val Leu Asn Ala Leu Gln Glu His Phe Arg Ala
690                 695                 700

His Lys Ile Asp Thr Lys Val Ser Val Val Arg Gly Gln Phe Thr Ser

-continued

```
            705                 710                 715                 720
        Gln Leu Arg Arg His Trp Gly Ile Glu Lys Thr Arg Asp Thr Tyr His
                        725                 730                 735

His His Ala Val Asp Ala Leu Ile Ile Ala Ala Ser Ser Gln Leu Asn
                        740                 745                 750

Leu Trp Lys Lys Gln Lys Asn Thr Leu Val Ser Tyr Ser Glu Asp Gln
                        755                 760                 765

Leu Leu Asp Ile Glu Thr Gly Glu Leu Ile Ser Asp Asp Glu Tyr Lys
                        770                 775                 780

Glu Ser Val Phe Lys Ala Pro Tyr Gln His Phe Val Asp Thr Leu Lys
        785                 790                 795                 800

Ser Lys Glu Phe Glu Asp Ser Ile Leu Phe Ser Tyr Gln Val Asp Ser
                        805                 810                 815

Lys Phe Asn Arg Lys Ile Ser Asp Ala Thr Ile Tyr Ala Thr Arg Gln
                        820                 825                 830

Ala Lys Val Gly Lys Asp Lys Ala Asp Glu Thr Tyr Val Leu Gly Lys
                        835                 840                 845

Ile Lys Asp Ile Tyr Thr Gln Asp Gly Tyr Asp Ala Phe Met Lys Ile
        850                 855                 860

Tyr Lys Lys Asp Lys Ser Lys Phe Leu Met Tyr Arg His Asp Pro Gln
        865                 870                 875                 880

Thr Phe Glu Lys Val Ile Glu Pro Ile Leu Glu Asn Tyr Pro Asn Lys
                        885                 890                 895

Gln Ile Asn Asp Lys Gly Lys Glu Val Pro Cys Asn Pro Phe Leu Lys
                        900                 905                 910

Tyr Lys Glu Glu His Gly Tyr Ile Arg Lys Tyr Ser Lys Lys Gly Asn
                        915                 920                 925

Gly Pro Glu Ile Lys Ser Leu Lys Tyr Tyr Asp Ser Lys Leu Gly Asn
                        930                 935                 940

His Ile Asp Ile Thr Pro Lys Asp Ser Asn Asn Lys Val Val Leu Gln
        945                 950                 955                 960

Ser Val Ser Pro Trp Arg Ala Asp Val Tyr Phe Asn Lys Thr Thr Gly
                        965                 970                 975

Lys Tyr Glu Ile Leu Gly Leu Lys Tyr Ala Asp Leu Gln Phe Asp Lys
                        980                 985                 990

Gly Thr Gly Thr Tyr Lys Ile Ser  Gln Glu Lys Tyr Asn  Asp Ile Lys
                        995                 1000                1005

Lys Lys  Glu Gly Val Asp Ser  Asp Ser Glu Phe Lys  Phe Thr Leu
            1010                1015                1020

Tyr Lys  Asn Asp Leu Leu Leu  Val Lys Asp Thr Glu  Thr Lys Glu
            1025                1030                1035

Gln Gln  Leu Phe Arg Phe Leu  Ser Arg Thr Met Pro  Lys Gln Lys
            1040                1045                1050

His Tyr  Val Glu Leu Lys Pro  Tyr Asp Lys Gln Lys  Phe Glu Gly
            1055                1060                1065

Gly Glu  Ala Leu Ile Lys Val  Leu Gly Asn Val Ala  Asn Ser Gly
            1070                1075                1080

Gln Cys  Lys Lys Gly Leu Gly  Lys Ser Asn Ile Ser  Ile Tyr Lys
            1085                1090                1095

Val Arg  Thr Asp Val Leu Gly  Asn Gln His Ile Ile  Lys Asn Glu
            1100                1105                1110

Gly Asp  Lys Pro Lys Leu Asp  Phe
            1115                1120
```

<210> SEQ ID NO 7
<211> LENGTH: 1053
<212> TYPE: PRT
<213> ORGANISM: Staphylococcus aureus

<400> SEQUENCE: 7

```
Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
```

-continued

```
            370                 375                 380
Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Val Asp Leu Ser Gln
                420                 425                 430

Gln Lys Glu Ile Pro Thr Thr Leu Val Asp Asp Phe Ile Leu Ser Pro
                435                 440                 445

Val Val Lys Arg Ser Phe Ile Gln Ser Ile Lys Val Ile Asn Ala Ile
                450                 455                 460

Ile Lys Lys Tyr Gly Leu Pro Asn Asp Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Arg Thr Thr
                500                 505                 510

Gly Lys Glu Asn Ala Lys Tyr Leu Ile Glu Lys Ile Lys Leu His Asp
                515                 520                 525

Met Gln Glu Gly Lys Cys Leu Tyr Ser Leu Glu Ala Ile Pro Leu Glu
530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
                580                 585                 590

Ser Ser Ser Asp Ser Lys Ile Ser Tyr Glu Thr Phe Lys Lys His Ile
                595                 600                 605

Leu Asn Leu Ala Lys Gly Lys Gly Arg Ile Ser Lys Thr Lys Lys Glu
                610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
                660                 665                 670

Val Lys Ser Ile Asn Gly Gly Phe Thr Ser Phe Leu Arg Arg Lys Trp
                675                 680                 685

Lys Phe Lys Lys Glu Arg Asn Lys Gly Tyr Lys His His Ala Glu Asp
690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Lys
                725                 730                 735

Gln Ala Glu Ser Met Pro Glu Ile Glu Thr Glu Gln Glu Tyr Lys Glu
                740                 745                 750

Ile Phe Ile Thr Pro His Gln Ile Lys His Ile Lys Asp Phe Lys Asp
                755                 760                 765

Tyr Lys Tyr Ser His Arg Val Asp Lys Lys Pro Asn Arg Glu Leu Ile
                770                 775                 780

Asn Asp Thr Leu Tyr Ser Thr Arg Lys Asp Asp Lys Gly Asn Thr Leu
785                 790                 795                 800
```

```
Ile Val Asn Asn Leu Asn Gly Leu Tyr Asp Lys Asp Asn Asp Lys Leu
            805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
            835                 840                 845

Asp Glu Lys Asn Pro Leu Tyr Lys Tyr Glu Glu Thr Gly Asn Tyr
        850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
            885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
            915                 920                 925

Lys Asn Leu Asp Val Ile Lys Lys Glu Asn Tyr Tyr Glu Val Asn Ser
            930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
            965                 970                 975

Glu Leu Tyr Arg Val Ile Gly Val Asn Asn Asp Leu Leu Asn Arg Ile
            980                 985                 990

Glu Val Asn Met Ile Asp Ile Thr Tyr Arg Glu Tyr Leu Glu Asn Met
            995                 1000                1005

Asn Asp Lys Arg Pro Pro Arg Ile Ile Lys Thr Ile Ala Ser Lys
        1010                1015                1020

Thr Gln Ser Ile Lys Lys Tyr Ser Thr Asp Ile Leu Gly Asn Leu
        1025                1030                1035

Tyr Glu Val Lys Ser Lys Lys His Pro Gln Ile Ile Lys Lys Gly
        1040                1045                1050

<210> SEQ ID NO 8
<211> LENGTH: 1082
<212> TYPE: PRT
<213> ORGANISM: Neisseria meningitidis

<400> SEQUENCE: 8

Met Ala Ala Phe Lys Pro Asn Pro Ile Asn Tyr Ile Leu Gly Leu Asp
1               5                   10                  15

Ile Gly Ile Ala Ser Val Gly Trp Ala Met Val Glu Ile Asp Glu Asp
            20                  25                  30

Glu Asn Pro Ile Cys Leu Ile Asp Leu Gly Val Arg Val Phe Glu Arg
        35                  40                  45

Ala Glu Val Pro Lys Thr Gly Asp Ser Leu Ala Met Ala Arg Arg Leu
    50                  55                  60

Ala Arg Ser Val Arg Arg Leu Thr Arg Arg Arg Ala His Arg Leu Leu
65                  70                  75                  80

Arg Ala Arg Arg Leu Leu Lys Arg Glu Gly Val Leu Gln Ala Ala Asp
            85                  90                  95

Phe Asp Glu Asn Gly Leu Ile Lys Ser Leu Pro Asn Thr Pro Trp Gln
            100                 105                 110

Leu Arg Ala Ala Ala Leu Asp Arg Lys Leu Thr Pro Leu Glu Trp Ser
```

```
                115                 120                 125
Ala Val Leu Leu His Leu Ile Lys His Arg Gly Tyr Leu Ser Gln Arg
130                 135                 140

Lys Asn Glu Gly Glu Thr Ala Asp Lys Glu Leu Gly Ala Leu Leu Lys
145                 150                 155                 160

Gly Val Ala Asp Asn Ala His Ala Leu Gln Thr Gly Asp Phe Arg Thr
                165                 170                 175

Pro Ala Glu Leu Ala Leu Asn Lys Phe Glu Lys Glu Ser Gly His Ile
            180                 185                 190

Arg Asn Gln Arg Gly Asp Tyr Ser His Thr Phe Ser Arg Lys Asp Leu
        195                 200                 205

Gln Ala Glu Leu Ile Leu Leu Phe Glu Lys Gln Lys Glu Phe Gly Asn
    210                 215                 220

Pro His Val Ser Gly Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Ala Glu Pro Lys Ala Ala Lys Asn Thr Tyr
            260                 265                 270

Thr Ala Glu Arg Phe Ile Trp Leu Thr Lys Leu Asn Asn Leu Arg Ile
        275                 280                 285

Leu Glu Gln Gly Ser Glu Arg Pro Leu Thr Asp Thr Glu Arg Ala Thr
    290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                325                 330                 335

Tyr Gly Lys Asp Asn Ala Glu Ala Ser Thr Leu Met Glu Met Lys Ala
            340                 345                 350

Tyr His Ala Ile Ser Arg Ala Leu Glu Lys Glu Gly Leu Lys Asp Lys
        355                 360                 365

Lys Ser Pro Leu Asn Leu Ser Pro Glu Leu Gln Asp Glu Ile Gly Thr
    370                 375                 380

Ala Phe Ser Leu Phe Lys Thr Asp Glu Asp Ile Thr Gly Arg Leu Lys
385                 390                 395                 400

Asp Arg Ile Gln Pro Glu Ile Leu Glu Ala Leu Leu Lys His Ile Ser
                405                 410                 415

Phe Asp Lys Phe Val Gln Ile Ser Leu Lys Ala Leu Arg Arg Ile Val
            420                 425                 430

Pro Leu Met Glu Gln Gly Lys Arg Tyr Asp Glu Ala Cys Ala Glu Ile
        435                 440                 445

Tyr Gly Asp His Tyr Gly Lys Lys Asn Thr Glu Lys Ile Tyr Leu
    450                 455                 460

Pro Pro Ile Pro Ala Asp Glu Ile Arg Asn Pro Val Val Leu Arg Ala
465                 470                 475                 480

Leu Ser Gln Ala Arg Lys Val Ile Asn Gly Val Val Arg Arg Tyr Gly
                485                 490                 495

Ser Pro Ala Arg Ile His Ile Glu Thr Ala Arg Glu Val Gly Lys Ser
            500                 505                 510

Phe Lys Asp Arg Lys Glu Ile Glu Lys Arg Gln Glu Glu Asn Arg Lys
        515                 520                 525

Asp Arg Glu Lys Ala Ala Ala Lys Phe Arg Glu Tyr Phe Pro Asn Phe
    530                 535                 540
```

```
Val Gly Glu Pro Lys Ser Lys Asp Ile Leu Lys Leu Arg Leu Tyr Glu
545                 550                 555                 560

Gln Gln His Gly Lys Cys Leu Tyr Ser Gly Lys Glu Ile Asn Leu Gly
                565                 570                 575

Arg Leu Asn Glu Lys Gly Tyr Val Glu Ile Asp His Ala Leu Pro Phe
            580                 585                 590

Ser Arg Thr Trp Asp Asp Ser Phe Asn Asn Lys Val Leu Val Leu Gly
        595                 600                 605

Ser Glu Asn Gln Asn Lys Gly Asn Gln Thr Pro Tyr Glu Tyr Phe Asn
    610                 615                 620

Gly Lys Asp Asn Ser Arg Glu Trp Gln Glu Phe Lys Ala Arg Val Glu
625                 630                 635                 640

Thr Ser Arg Phe Pro Arg Ser Lys Lys Gln Arg Ile Leu Leu Gln Lys
                645                 650                 655

Phe Asp Glu Asp Gly Phe Lys Glu Arg Asn Leu Asn Asp Thr Arg Tyr
            660                 665                 670

Val Asn Arg Phe Leu Cys Gln Phe Val Ala Asp Arg Met Arg Leu Thr
        675                 680                 685

Gly Lys Gly Lys Lys Arg Val Phe Ala Ser Asn Gly Gln Ile Thr Asn
    690                 695                 700

Leu Leu Arg Gly Phe Trp Gly Leu Arg Lys Val Arg Ala Glu Asn Asp
705                 710                 715                 720

Arg His His Ala Leu Asp Ala Val Val Ala Cys Ser Thr Val Ala
                725                 730                 735

Met Gln Gln Lys Ile Thr Arg Phe Val Arg Tyr Lys Glu Met Asn Ala
            740                 745                 750

Phe Asp Gly Lys Thr Ile Asp Lys Glu Thr Gly Glu Val Leu His Gln
        755                 760                 765

Lys Thr His Phe Pro Gln Pro Trp Glu Phe Phe Ala Gln Glu Val Met
770                 775                 780

Ile Arg Val Phe Gly Lys Pro Asp Gly Lys Pro Glu Phe Glu Glu Ala
785                 790                 795                 800

Asp Thr Pro Glu Lys Leu Arg Thr Leu Leu Ala Glu Lys Leu Ser Ser
                805                 810                 815

Arg Pro Glu Ala Val His Glu Tyr Val Thr Pro Leu Phe Val Ser Arg
            820                 825                 830

Ala Pro Asn Arg Lys Met Ser Gly Gln Gly His Met Glu Thr Val Lys
        835                 840                 845

Ser Ala Lys Arg Leu Asp Glu Gly Val Ser Val Leu Arg Val Pro Leu
    850                 855                 860

Thr Gln Leu Lys Leu Lys Asp Leu Glu Lys Met Val Asn Arg Glu Arg
865                 870                 875                 880

Glu Pro Lys Leu Tyr Glu Ala Leu Lys Ala Arg Leu Glu Ala His Lys
                885                 890                 895

Asp Asp Pro Ala Lys Ala Phe Ala Glu Pro Phe Tyr Lys Tyr Asp Lys
            900                 905                 910

Ala Gly Asn Arg Thr Gln Gln Val Lys Ala Val Arg Val Glu Gln Val
        915                 920                 925

Gln Lys Thr Gly Val Trp Val Arg Asn His Asn Gly Ile Ala Asp Asn
    930                 935                 940

Ala Thr Met Val Arg Val Asp Val Phe Glu Lys Gly Asp Lys Tyr Tyr
945                 950                 955                 960
```

```
Leu Val Pro Ile Tyr Ser Trp Gln Val Ala Lys Gly Ile Leu Pro Asp
            965                 970                 975

Arg Ala Val Val Gln Gly Lys Asp Glu Glu Asp Trp Gln Leu Ile Asp
        980                 985                 990

Asp Ser Phe Asn Phe Lys Phe Ser Leu His Pro Asn Asp Leu Val Glu
            995                1000                1005

Val Ile Thr Lys Lys Ala Arg Met Phe Gly Tyr Phe Ala Ser Cys
       1010                1015                1020

His Arg Gly Thr Gly Asn Ile Asn Ile Arg Ile His Asp Leu Asp
       1025                1030                1035

His Lys Ile Gly Lys Asn Gly Ile Leu Glu Gly Ile Gly Val Lys
       1040                1045                1050

Thr Ala Leu Ser Phe Gln Lys Tyr Gln Ile Asp Glu Leu Gly Lys
       1055                1060                1065

Glu Ile Arg Pro Cys Arg Leu Lys Lys Arg Pro Pro Val Arg
       1070                1075                1080

<210> SEQ ID NO 9
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 9

His His His His His His
1               5

<210> SEQ ID NO 10
<211> LENGTH: 9
<212> TYPE: PRT
<213> ORGANISM: Streptococcus pyogenes

<400> SEQUENCE: 10

Met Asp Lys Lys Tyr Ser Ile Gly Leu
1               5

<210> SEQ ID NO 11
<211> LENGTH: 10
<212> TYPE: PRT
<213> ORGANISM: Streptococcus pyogenes

<400> SEQUENCE: 11

Met Asp Lys Lys Tyr Ser Ile Gly Leu Asp
1               5                   10

<210> SEQ ID NO 12
<211> LENGTH: 9
<212> TYPE: PRT
<213> ORGANISM: Streptococcus pyogenes

<400> SEQUENCE: 12

Asp Lys Lys Tyr Ser Ile Gly Leu Asp
1               5

<210> SEQ ID NO 13
<211> LENGTH: 10
<212> TYPE: PRT
<213> ORGANISM: Streptococcus pyogenes

<400> SEQUENCE: 13
```

```
Asp Lys Lys Tyr Ser Ile Gly Leu Asp Ile
1               5                   10

<210> SEQ ID NO 14
<211> LENGTH: 9
<212> TYPE: PRT
<213> ORGANISM: Streptococcus pyogenes

<400> SEQUENCE: 14

Lys Lys Tyr Ser Ile Gly Leu Asp Ile
1               5

<210> SEQ ID NO 15
<211> LENGTH: 10
<212> TYPE: PRT
<213> ORGANISM: Streptococcus pyogenes

<400> SEQUENCE: 15

Lys Lys Tyr Ser Ile Gly Leu Asp Ile Gly
1               5                   10

<210> SEQ ID NO 16
<211> LENGTH: 9
<212> TYPE: PRT
<213> ORGANISM: Streptococcus pyogenes

<400> SEQUENCE: 16

Lys Tyr Ser Ile Gly Leu Asp Ile Gly
1               5

<210> SEQ ID NO 17
<211> LENGTH: 10
<212> TYPE: PRT
<213> ORGANISM: Streptococcus pyogenes

<400> SEQUENCE: 17

Lys Tyr Ser Ile Gly Leu Asp Ile Gly Thr
1               5                   10

<210> SEQ ID NO 18
<211> LENGTH: 9
<212> TYPE: PRT
<213> ORGANISM: Streptococcus pyogenes

<400> SEQUENCE: 18

Tyr Ser Ile Gly Leu Asp Ile Gly Thr
1               5

<210> SEQ ID NO 19
<211> LENGTH: 10
<212> TYPE: PRT
<213> ORGANISM: Streptococcus pyogenes

<400> SEQUENCE: 19

Tyr Ser Ile Gly Leu Asp Ile Gly Thr Asn
1               5                   10

<210> SEQ ID NO 20
<211> LENGTH: 9
<212> TYPE: PRT
<213> ORGANISM: Streptococcus pyogenes

<400> SEQUENCE: 20

Ser Ile Gly Leu Asp Ile Gly Thr Asn
```

```
1               5

<210> SEQ ID NO 21
<211> LENGTH: 10
<212> TYPE: PRT
<213> ORGANISM: Streptococcus pyogenes

<400> SEQUENCE: 21

Ser Ile Gly Leu Asp Ile Gly Thr Asn Ser
1               5                   10

<210> SEQ ID NO 22
<211> LENGTH: 9
<212> TYPE: PRT
<213> ORGANISM: Streptococcus pyogenes

<400> SEQUENCE: 22

Ile Gly Leu Asp Ile Gly Thr Asn Ser
1               5

<210> SEQ ID NO 23
<211> LENGTH: 10
<212> TYPE: PRT
<213> ORGANISM: Streptococcus pyogenes

<400> SEQUENCE: 23

Ile Gly Leu Asp Ile Gly Thr Asn Ser Val
1               5                   10

<210> SEQ ID NO 24
<211> LENGTH: 9
<212> TYPE: PRT
<213> ORGANISM: Streptococcus pyogenes

<400> SEQUENCE: 24

Gly Leu Asp Ile Gly Thr Asn Ser Val
1               5

<210> SEQ ID NO 25
<211> LENGTH: 10
<212> TYPE: PRT
<213> ORGANISM: Streptococcus pyogenes

<400> SEQUENCE: 25

Gly Leu Asp Ile Gly Thr Asn Ser Val Gly
1               5                   10

<210> SEQ ID NO 26
<211> LENGTH: 9
<212> TYPE: PRT
<213> ORGANISM: Streptococcus pyogenes

<400> SEQUENCE: 26

Leu Asp Ile Gly Thr Asn Ser Val Gly
1               5

<210> SEQ ID NO 27
<211> LENGTH: 10
<212> TYPE: PRT
<213> ORGANISM: Streptococcus pyogenes

<400> SEQUENCE: 27

Leu Asp Ile Gly Thr Asn Ser Val Gly Trp
1               5                   10
```

<210> SEQ ID NO 28
<211> LENGTH: 9
<212> TYPE: PRT
<213> ORGANISM: Streptococcus pyogenes

<400> SEQUENCE: 28

Asp Ile Gly Thr Asn Ser Val Gly Trp
1               5

<210> SEQ ID NO 29
<211> LENGTH: 10
<212> TYPE: PRT
<213> ORGANISM: Streptococcus pyogenes

<400> SEQUENCE: 29

Asp Ile Gly Thr Asn Ser Val Gly Trp Ala
1               5                   10

<210> SEQ ID NO 30
<211> LENGTH: 9
<212> TYPE: PRT
<213> ORGANISM: Streptococcus pyogenes

<400> SEQUENCE: 30

Ile Gly Thr Asn Ser Val Gly Trp Ala
1               5

<210> SEQ ID NO 31
<211> LENGTH: 10
<212> TYPE: PRT
<213> ORGANISM: Streptococcus pyogenes

<400> SEQUENCE: 31

Ile Gly Thr Asn Ser Val Gly Trp Ala Val
1               5                   10

<210> SEQ ID NO 32
<211> LENGTH: 9
<212> TYPE: PRT
<213> ORGANISM: Streptococcus pyogenes

<400> SEQUENCE: 32

Gly Thr Asn Ser Val Gly Trp Ala Val
1               5

<210> SEQ ID NO 33
<211> LENGTH: 10
<212> TYPE: PRT
<213> ORGANISM: Streptococcus pyogenes

<400> SEQUENCE: 33

Gly Thr Asn Ser Val Gly Trp Ala Val Ile
1               5                   10

<210> SEQ ID NO 34
<211> LENGTH: 9
<212> TYPE: PRT
<213> ORGANISM: Streptococcus pyogenes

<400> SEQUENCE: 34

Thr Asn Ser Val Gly Trp Ala Val Ile
1               5

<210> SEQ ID NO 35

```
<211> LENGTH: 10
<212> TYPE: PRT
<213> ORGANISM: Streptococcus pyogenes

<400> SEQUENCE: 35

Thr Asn Ser Val Gly Trp Ala Val Ile Thr
1               5                   10

<210> SEQ ID NO 36
<211> LENGTH: 9
<212> TYPE: PRT
<213> ORGANISM: Streptococcus pyogenes

<400> SEQUENCE: 36

Asn Ser Val Gly Trp Ala Val Ile Thr
1               5

<210> SEQ ID NO 37
<211> LENGTH: 10
<212> TYPE: PRT
<213> ORGANISM: Streptococcus pyogenes

<400> SEQUENCE: 37

Asn Ser Val Gly Trp Ala Val Ile Thr Asp
1               5                   10

<210> SEQ ID NO 38
<211> LENGTH: 9
<212> TYPE: PRT
<213> ORGANISM: Streptococcus pyogenes

<400> SEQUENCE: 38

Ser Val Gly Trp Ala Val Ile Thr Asp
1               5

<210> SEQ ID NO 39
<211> LENGTH: 10
<212> TYPE: PRT
<213> ORGANISM: Streptococcus pyogenes

<400> SEQUENCE: 39

Ser Val Gly Trp Ala Val Ile Thr Asp Glu
1               5                   10

<210> SEQ ID NO 40
<211> LENGTH: 9
<212> TYPE: PRT
<213> ORGANISM: Streptococcus pyogenes

<400> SEQUENCE: 40

Val Gly Trp Ala Val Ile Thr Asp Glu
1               5

<210> SEQ ID NO 41
<211> LENGTH: 10
<212> TYPE: PRT
<213> ORGANISM: Streptococcus pyogenes

<400> SEQUENCE: 41

Val Gly Trp Ala Val Ile Thr Asp Glu Tyr
1               5                   10

<210> SEQ ID NO 42
<211> LENGTH: 9
<212> TYPE: PRT
```

<213> ORGANISM: Streptococcus pyogenes

<400> SEQUENCE: 42

Gly Trp Ala Val Ile Thr Asp Glu Tyr
1               5

<210> SEQ ID NO 43
<211> LENGTH: 10
<212> TYPE: PRT
<213> ORGANISM: Streptococcus pyogenes

<400> SEQUENCE: 43

Gly Trp Ala Val Ile Thr Asp Glu Tyr Lys
1               5                   10

<210> SEQ ID NO 44
<211> LENGTH: 9
<212> TYPE: PRT
<213> ORGANISM: Streptococcus pyogenes

<400> SEQUENCE: 44

Trp Ala Val Ile Thr Asp Glu Tyr Lys
1               5

<210> SEQ ID NO 45
<211> LENGTH: 10
<212> TYPE: PRT
<213> ORGANISM: Streptococcus pyogenes

<400> SEQUENCE: 45

Trp Ala Val Ile Thr Asp Glu Tyr Lys Val
1               5                   10

<210> SEQ ID NO 46
<211> LENGTH: 9
<212> TYPE: PRT
<213> ORGANISM: Streptococcus pyogenes

<400> SEQUENCE: 46

Ala Val Ile Thr Asp Glu Tyr Lys Val
1               5

<210> SEQ ID NO 47
<211> LENGTH: 10
<212> TYPE: PRT
<213> ORGANISM: Streptococcus pyogenes

<400> SEQUENCE: 47

Ala Val Ile Thr Asp Glu Tyr Lys Val Pro
1               5                   10

<210> SEQ ID NO 48
<211> LENGTH: 9
<212> TYPE: PRT
<213> ORGANISM: Streptococcus pyogenes

<400> SEQUENCE: 48

Val Ile Thr Asp Glu Tyr Lys Val Pro
1               5

<210> SEQ ID NO 49
<211> LENGTH: 10
<212> TYPE: PRT
<213> ORGANISM: Streptococcus pyogenes

```
<400> SEQUENCE: 49

Val Ile Thr Asp Glu Tyr Lys Val Pro Ser
1               5                   10

<210> SEQ ID NO 50
<211> LENGTH: 9
<212> TYPE: PRT
<213> ORGANISM: Streptococcus pyogenes

<400> SEQUENCE: 50

Ile Thr Asp Glu Tyr Lys Val Pro Ser
1               5

<210> SEQ ID NO 51
<211> LENGTH: 10
<212> TYPE: PRT
<213> ORGANISM: Streptococcus pyogenes

<400> SEQUENCE: 51

Ile Thr Asp Glu Tyr Lys Val Pro Ser Lys
1               5                   10

<210> SEQ ID NO 52
<211> LENGTH: 9
<212> TYPE: PRT
<213> ORGANISM: Streptococcus pyogenes

<400> SEQUENCE: 52

Thr Asp Glu Tyr Lys Val Pro Ser Lys
1               5

<210> SEQ ID NO 53
<211> LENGTH: 10
<212> TYPE: PRT
<213> ORGANISM: Streptococcus pyogenes

<400> SEQUENCE: 53

Thr Asp Glu Tyr Lys Val Pro Ser Lys Lys
1               5                   10

<210> SEQ ID NO 54
<211> LENGTH: 9
<212> TYPE: PRT
<213> ORGANISM: Streptococcus pyogenes

<400> SEQUENCE: 54

Asp Glu Tyr Lys Val Pro Ser Lys Lys
1               5

<210> SEQ ID NO 55
<211> LENGTH: 10
<212> TYPE: PRT
<213> ORGANISM: Streptococcus pyogenes

<400> SEQUENCE: 55

Asp Glu Tyr Lys Val Pro Ser Lys Lys Phe
1               5                   10

<210> SEQ ID NO 56
<211> LENGTH: 9
<212> TYPE: PRT
<213> ORGANISM: Streptococcus pyogenes

<400> SEQUENCE: 56
```

```
Glu Tyr Lys Val Pro Ser Lys Lys Phe
1               5

<210> SEQ ID NO 57
<211> LENGTH: 10
<212> TYPE: PRT
<213> ORGANISM: Streptococcus pyogenes

<400> SEQUENCE: 57

Glu Tyr Lys Val Pro Ser Lys Lys Phe Lys
1               5                   10

<210> SEQ ID NO 58
<211> LENGTH: 9
<212> TYPE: PRT
<213> ORGANISM: Streptococcus pyogenes

<400> SEQUENCE: 58

Tyr Lys Val Pro Ser Lys Lys Phe Lys
1               5

<210> SEQ ID NO 59
<211> LENGTH: 10
<212> TYPE: PRT
<213> ORGANISM: Streptococcus pyogenes

<400> SEQUENCE: 59

Tyr Lys Val Pro Ser Lys Lys Phe Lys Val
1               5                   10

<210> SEQ ID NO 60
<211> LENGTH: 9
<212> TYPE: PRT
<213> ORGANISM: Streptococcus pyogenes

<400> SEQUENCE: 60

Lys Val Pro Ser Lys Lys Phe Lys Val
1               5

<210> SEQ ID NO 61
<211> LENGTH: 10
<212> TYPE: PRT
<213> ORGANISM: Streptococcus pyogenes

<400> SEQUENCE: 61

Lys Val Pro Ser Lys Lys Phe Lys Val Leu
1               5                   10

<210> SEQ ID NO 62
<211> LENGTH: 9
<212> TYPE: PRT
<213> ORGANISM: Streptococcus pyogenes

<400> SEQUENCE: 62

Val Pro Ser Lys Lys Phe Lys Val Leu
1               5

<210> SEQ ID NO 63
<211> LENGTH: 10
<212> TYPE: PRT
<213> ORGANISM: Streptococcus pyogenes

<400> SEQUENCE: 63

Val Pro Ser Lys Lys Phe Lys Val Leu Gly
1               5                   10
```

```
<210> SEQ ID NO 64
<211> LENGTH: 9
<212> TYPE: PRT
<213> ORGANISM: Streptococcus pyogenes

<400> SEQUENCE: 64

Pro Ser Lys Lys Phe Lys Val Leu Gly
1               5

<210> SEQ ID NO 65
<211> LENGTH: 10
<212> TYPE: PRT
<213> ORGANISM: Streptococcus pyogenes

<400> SEQUENCE: 65

Pro Ser Lys Lys Phe Lys Val Leu Gly Asn
1               5                   10

<210> SEQ ID NO 66
<211> LENGTH: 9
<212> TYPE: PRT
<213> ORGANISM: Streptococcus pyogenes

<400> SEQUENCE: 66

Ser Lys Lys Phe Lys Val Leu Gly Asn
1               5

<210> SEQ ID NO 67
<211> LENGTH: 10
<212> TYPE: PRT
<213> ORGANISM: Streptococcus pyogenes

<400> SEQUENCE: 67

Ser Lys Lys Phe Lys Val Leu Gly Asn Thr
1               5                   10

<210> SEQ ID NO 68
<211> LENGTH: 9
<212> TYPE: PRT
<213> ORGANISM: Streptococcus pyogenes

<400> SEQUENCE: 68

Lys Lys Phe Lys Val Leu Gly Asn Thr
1               5

<210> SEQ ID NO 69
<211> LENGTH: 10
<212> TYPE: PRT
<213> ORGANISM: Streptococcus pyogenes

<400> SEQUENCE: 69

Lys Lys Phe Lys Val Leu Gly Asn Thr Asp
1               5                   10

<210> SEQ ID NO 70
<211> LENGTH: 9
<212> TYPE: PRT
<213> ORGANISM: Streptococcus pyogenes

<400> SEQUENCE: 70

Lys Phe Lys Val Leu Gly Asn Thr Asp
1               5
```

<210> SEQ ID NO 71
<211> LENGTH: 10
<212> TYPE: PRT
<213> ORGANISM: Streptococcus pyogenes

<400> SEQUENCE: 71

Lys Phe Lys Val Leu Gly Asn Thr Asp Arg
1               5                   10

<210> SEQ ID NO 72
<211> LENGTH: 9
<212> TYPE: PRT
<213> ORGANISM: Streptococcus pyogenes

<400> SEQUENCE: 72

Phe Lys Val Leu Gly Asn Thr Asp Arg
1               5

<210> SEQ ID NO 73
<211> LENGTH: 10
<212> TYPE: PRT
<213> ORGANISM: Streptococcus pyogenes

<400> SEQUENCE: 73

Phe Lys Val Leu Gly Asn Thr Asp Arg His
1               5                   10

<210> SEQ ID NO 74
<211> LENGTH: 9
<212> TYPE: PRT
<213> ORGANISM: Streptococcus pyogenes

<400> SEQUENCE: 74

Lys Val Leu Gly Asn Thr Asp Arg His
1               5

<210> SEQ ID NO 75
<211> LENGTH: 10
<212> TYPE: PRT
<213> ORGANISM: Streptococcus pyogenes

<400> SEQUENCE: 75

Lys Val Leu Gly Asn Thr Asp Arg His Ser
1               5                   10

<210> SEQ ID NO 76
<211> LENGTH: 9
<212> TYPE: PRT
<213> ORGANISM: Streptococcus pyogenes

<400> SEQUENCE: 76

Val Leu Gly Asn Thr Asp Arg His Ser
1               5

<210> SEQ ID NO 77
<211> LENGTH: 10
<212> TYPE: PRT
<213> ORGANISM: Streptococcus pyogenes

<400> SEQUENCE: 77

Val Leu Gly Asn Thr Asp Arg His Ser Ile
1               5                   10

<210> SEQ ID NO 78
<211> LENGTH: 9

```
<212> TYPE: PRT
<213> ORGANISM: Streptococcus pyogenes

<400> SEQUENCE: 78

Leu Gly Asn Thr Asp Arg His Ser Ile
1               5

<210> SEQ ID NO 79
<211> LENGTH: 10
<212> TYPE: PRT
<213> ORGANISM: Streptococcus pyogenes

<400> SEQUENCE: 79

Leu Gly Asn Thr Asp Arg His Ser Ile Lys
1               5                   10

<210> SEQ ID NO 80
<211> LENGTH: 9
<212> TYPE: PRT
<213> ORGANISM: Streptococcus pyogenes

<400> SEQUENCE: 80

Gly Asn Thr Asp Arg His Ser Ile Lys
1               5

<210> SEQ ID NO 81
<211> LENGTH: 10
<212> TYPE: PRT
<213> ORGANISM: Streptococcus pyogenes

<400> SEQUENCE: 81

Gly Asn Thr Asp Arg His Ser Ile Lys Lys
1               5                   10

<210> SEQ ID NO 82
<211> LENGTH: 9
<212> TYPE: PRT
<213> ORGANISM: Streptococcus pyogenes

<400> SEQUENCE: 82

Asn Thr Asp Arg His Ser Ile Lys Lys
1               5

<210> SEQ ID NO 83
<211> LENGTH: 10
<212> TYPE: PRT
<213> ORGANISM: Streptococcus pyogenes

<400> SEQUENCE: 83

Asn Thr Asp Arg His Ser Ile Lys Lys Asn
1               5                   10

<210> SEQ ID NO 84
<211> LENGTH: 9
<212> TYPE: PRT
<213> ORGANISM: Streptococcus pyogenes

<400> SEQUENCE: 84

Thr Asp Arg His Ser Ile Lys Lys Asn
1               5

<210> SEQ ID NO 85
<211> LENGTH: 10
<212> TYPE: PRT
<213> ORGANISM: Streptococcus pyogenes
```

<400> SEQUENCE: 85

Thr Asp Arg His Ser Ile Lys Lys Asn Leu
1               5                   10

<210> SEQ ID NO 86
<211> LENGTH: 9
<212> TYPE: PRT
<213> ORGANISM: Streptococcus pyogenes

<400> SEQUENCE: 86

Asp Arg His Ser Ile Lys Lys Asn Leu
1               5

<210> SEQ ID NO 87
<211> LENGTH: 10
<212> TYPE: PRT
<213> ORGANISM: Streptococcus pyogenes

<400> SEQUENCE: 87

Asp Arg His Ser Ile Lys Lys Asn Leu Ile
1               5                   10

<210> SEQ ID NO 88
<211> LENGTH: 9
<212> TYPE: PRT
<213> ORGANISM: Streptococcus pyogenes

<400> SEQUENCE: 88

Arg His Ser Ile Lys Lys Asn Leu Ile
1               5

<210> SEQ ID NO 89
<211> LENGTH: 10
<212> TYPE: PRT
<213> ORGANISM: Streptococcus pyogenes

<400> SEQUENCE: 89

Arg His Ser Ile Lys Lys Asn Leu Ile Gly
1               5                   10

<210> SEQ ID NO 90
<211> LENGTH: 9
<212> TYPE: PRT
<213> ORGANISM: Streptococcus pyogenes

<400> SEQUENCE: 90

His Ser Ile Lys Lys Asn Leu Ile Gly
1               5

<210> SEQ ID NO 91
<211> LENGTH: 10
<212> TYPE: PRT
<213> ORGANISM: Streptococcus pyogenes

<400> SEQUENCE: 91

His Ser Ile Lys Lys Asn Leu Ile Gly Ala
1               5                   10

<210> SEQ ID NO 92
<211> LENGTH: 9
<212> TYPE: PRT
<213> ORGANISM: Streptococcus pyogenes

<400> SEQUENCE: 92

```
Ser Ile Lys Lys Asn Leu Ile Gly Ala
1               5
```

<210> SEQ ID NO 93
<211> LENGTH: 10
<212> TYPE: PRT
<213> ORGANISM: Streptococcus pyogenes

<400> SEQUENCE: 93

```
Ser Ile Lys Lys Asn Leu Ile Gly Ala Leu
1               5                   10
```

<210> SEQ ID NO 94
<211> LENGTH: 9
<212> TYPE: PRT
<213> ORGANISM: Streptococcus pyogenes

<400> SEQUENCE: 94

```
Ile Lys Lys Asn Leu Ile Gly Ala Leu
1               5
```

<210> SEQ ID NO 95
<211> LENGTH: 10
<212> TYPE: PRT
<213> ORGANISM: Streptococcus pyogenes

<400> SEQUENCE: 95

```
Ile Lys Lys Asn Leu Ile Gly Ala Leu Leu
1               5                   10
```

<210> SEQ ID NO 96
<211> LENGTH: 9
<212> TYPE: PRT
<213> ORGANISM: Streptococcus pyogenes

<400> SEQUENCE: 96

```
Lys Lys Asn Leu Ile Gly Ala Leu Leu
1               5
```

<210> SEQ ID NO 97
<211> LENGTH: 10
<212> TYPE: PRT
<213> ORGANISM: Streptococcus pyogenes

<400> SEQUENCE: 97

```
Lys Lys Asn Leu Ile Gly Ala Leu Leu Phe
1               5                   10
```

<210> SEQ ID NO 98
<211> LENGTH: 9
<212> TYPE: PRT
<213> ORGANISM: Streptococcus pyogenes

<400> SEQUENCE: 98

```
Lys Asn Leu Ile Gly Ala Leu Leu Phe
1               5
```

<210> SEQ ID NO 99
<211> LENGTH: 10
<212> TYPE: PRT
<213> ORGANISM: Streptococcus pyogenes

<400> SEQUENCE: 99

```
Lys Asn Leu Ile Gly Ala Leu Leu Phe Asp
```

```
<210> SEQ ID NO 100
<211> LENGTH: 9
<212> TYPE: PRT
<213> ORGANISM: Streptococcus pyogenes

<400> SEQUENCE: 100

Asn Leu Ile Gly Ala Leu Leu Phe Asp
1               5

<210> SEQ ID NO 101
<211> LENGTH: 10
<212> TYPE: PRT
<213> ORGANISM: Streptococcus pyogenes

<400> SEQUENCE: 101

Asn Leu Ile Gly Ala Leu Leu Phe Asp Ser
1               5                   10

<210> SEQ ID NO 102
<211> LENGTH: 9
<212> TYPE: PRT
<213> ORGANISM: Streptococcus pyogenes

<400> SEQUENCE: 102

Leu Ile Gly Ala Leu Leu Phe Asp Ser
1               5

<210> SEQ ID NO 103
<211> LENGTH: 10
<212> TYPE: PRT
<213> ORGANISM: Streptococcus pyogenes

<400> SEQUENCE: 103

Leu Ile Gly Ala Leu Leu Phe Asp Ser Gly
1               5                   10

<210> SEQ ID NO 104
<211> LENGTH: 9
<212> TYPE: PRT
<213> ORGANISM: Streptococcus pyogenes

<400> SEQUENCE: 104

Ile Gly Ala Leu Leu Phe Asp Ser Gly
1               5

<210> SEQ ID NO 105
<211> LENGTH: 10
<212> TYPE: PRT
<213> ORGANISM: Streptococcus pyogenes

<400> SEQUENCE: 105

Ile Gly Ala Leu Leu Phe Asp Ser Gly Glu
1               5                   10

<210> SEQ ID NO 106
<211> LENGTH: 9
<212> TYPE: PRT
<213> ORGANISM: Streptococcus pyogenes

<400> SEQUENCE: 106

Gly Ala Leu Leu Phe Asp Ser Gly Glu
1               5
```

```
<210> SEQ ID NO 107
<211> LENGTH: 10
<212> TYPE: PRT
<213> ORGANISM: Streptococcus pyogenes

<400> SEQUENCE: 107

Gly Ala Leu Leu Phe Asp Ser Gly Glu Thr
1               5                   10

<210> SEQ ID NO 108
<211> LENGTH: 9
<212> TYPE: PRT
<213> ORGANISM: Streptococcus pyogenes

<400> SEQUENCE: 108

Ala Leu Leu Phe Asp Ser Gly Glu Thr
1               5

<210> SEQ ID NO 109
<211> LENGTH: 10
<212> TYPE: PRT
<213> ORGANISM: Streptococcus pyogenes

<400> SEQUENCE: 109

Ala Leu Leu Phe Asp Ser Gly Glu Thr Ala
1               5                   10

<210> SEQ ID NO 110
<211> LENGTH: 9
<212> TYPE: PRT
<213> ORGANISM: Streptococcus pyogenes

<400> SEQUENCE: 110

Leu Leu Phe Asp Ser Gly Glu Thr Ala
1               5

<210> SEQ ID NO 111
<211> LENGTH: 10
<212> TYPE: PRT
<213> ORGANISM: Streptococcus pyogenes

<400> SEQUENCE: 111

Leu Leu Phe Asp Ser Gly Glu Thr Ala Glu
1               5                   10

<210> SEQ ID NO 112
<211> LENGTH: 9
<212> TYPE: PRT
<213> ORGANISM: Streptococcus pyogenes

<400> SEQUENCE: 112

Leu Phe Asp Ser Gly Glu Thr Ala Glu
1               5

<210> SEQ ID NO 113
<211> LENGTH: 10
<212> TYPE: PRT
<213> ORGANISM: Streptococcus pyogenes

<400> SEQUENCE: 113

Leu Phe Asp Ser Gly Glu Thr Ala Glu Ala
1               5                   10

<210> SEQ ID NO 114
```

```
<211> LENGTH: 9
<212> TYPE: PRT
<213> ORGANISM: Streptococcus pyogenes

<400> SEQUENCE: 114

Phe Asp Ser Gly Glu Thr Ala Glu Ala
1               5

<210> SEQ ID NO 115
<211> LENGTH: 10
<212> TYPE: PRT
<213> ORGANISM: Streptococcus pyogenes

<400> SEQUENCE: 115

Phe Asp Ser Gly Glu Thr Ala Glu Ala Thr
1               5                   10

<210> SEQ ID NO 116
<211> LENGTH: 9
<212> TYPE: PRT
<213> ORGANISM: Streptococcus pyogenes

<400> SEQUENCE: 116

Asp Ser Gly Glu Thr Ala Glu Ala Thr
1               5

<210> SEQ ID NO 117
<211> LENGTH: 10
<212> TYPE: PRT
<213> ORGANISM: Streptococcus pyogenes

<400> SEQUENCE: 117

Asp Ser Gly Glu Thr Ala Glu Ala Thr Arg
1               5                   10

<210> SEQ ID NO 118
<211> LENGTH: 9
<212> TYPE: PRT
<213> ORGANISM: Streptococcus pyogenes

<400> SEQUENCE: 118

Ser Gly Glu Thr Ala Glu Ala Thr Arg
1               5

<210> SEQ ID NO 119
<211> LENGTH: 10
<212> TYPE: PRT
<213> ORGANISM: Streptococcus pyogenes

<400> SEQUENCE: 119

Ser Gly Glu Thr Ala Glu Ala Thr Arg Leu
1               5                   10

<210> SEQ ID NO 120
<211> LENGTH: 9
<212> TYPE: PRT
<213> ORGANISM: Streptococcus pyogenes

<400> SEQUENCE: 120

Gly Glu Thr Ala Glu Ala Thr Arg Leu
1               5

<210> SEQ ID NO 121
<211> LENGTH: 10
<212> TYPE: PRT
```

<213> ORGANISM: Streptococcus pyogenes

<400> SEQUENCE: 121

Gly Glu Thr Ala Glu Ala Thr Arg Leu Lys
1               5                   10

<210> SEQ ID NO 122
<211> LENGTH: 9
<212> TYPE: PRT
<213> ORGANISM: Streptococcus pyogenes

<400> SEQUENCE: 122

Glu Thr Ala Glu Ala Thr Arg Leu Lys
1               5

<210> SEQ ID NO 123
<211> LENGTH: 10
<212> TYPE: PRT
<213> ORGANISM: Streptococcus pyogenes

<400> SEQUENCE: 123

Glu Thr Ala Glu Ala Thr Arg Leu Lys Arg
1               5                   10

<210> SEQ ID NO 124
<211> LENGTH: 9
<212> TYPE: PRT
<213> ORGANISM: Streptococcus pyogenes

<400> SEQUENCE: 124

Thr Ala Glu Ala Thr Arg Leu Lys Arg
1               5

<210> SEQ ID NO 125
<211> LENGTH: 10
<212> TYPE: PRT
<213> ORGANISM: Streptococcus pyogenes

<400> SEQUENCE: 125

Thr Ala Glu Ala Thr Arg Leu Lys Arg Thr
1               5                   10

<210> SEQ ID NO 126
<211> LENGTH: 9
<212> TYPE: PRT
<213> ORGANISM: Streptococcus pyogenes

<400> SEQUENCE: 126

Ala Glu Ala Thr Arg Leu Lys Arg Thr
1               5

<210> SEQ ID NO 127
<211> LENGTH: 10
<212> TYPE: PRT
<213> ORGANISM: Streptococcus pyogenes

<400> SEQUENCE: 127

Ala Glu Ala Thr Arg Leu Lys Arg Thr Ala
1               5                   10

<210> SEQ ID NO 128
<211> LENGTH: 9
<212> TYPE: PRT
<213> ORGANISM: Streptococcus pyogenes

```
<400> SEQUENCE: 128

Glu Ala Thr Arg Leu Lys Arg Thr Ala
1               5

<210> SEQ ID NO 129
<211> LENGTH: 10
<212> TYPE: PRT
<213> ORGANISM: Streptococcus pyogenes

<400> SEQUENCE: 129

Glu Ala Thr Arg Leu Lys Arg Thr Ala Arg
1               5                   10

<210> SEQ ID NO 130
<211> LENGTH: 9
<212> TYPE: PRT
<213> ORGANISM: Streptococcus pyogenes

<400> SEQUENCE: 130

Ala Thr Arg Leu Lys Arg Thr Ala Arg
1               5

<210> SEQ ID NO 131
<211> LENGTH: 10
<212> TYPE: PRT
<213> ORGANISM: Streptococcus pyogenes

<400> SEQUENCE: 131

Ala Thr Arg Leu Lys Arg Thr Ala Arg Arg
1               5                   10

<210> SEQ ID NO 132
<211> LENGTH: 9
<212> TYPE: PRT
<213> ORGANISM: Streptococcus pyogenes

<400> SEQUENCE: 132

Thr Arg Leu Lys Arg Thr Ala Arg Arg
1               5

<210> SEQ ID NO 133
<211> LENGTH: 10
<212> TYPE: PRT
<213> ORGANISM: Streptococcus pyogenes

<400> SEQUENCE: 133

Thr Arg Leu Lys Arg Thr Ala Arg Arg Arg
1               5                   10

<210> SEQ ID NO 134
<211> LENGTH: 9
<212> TYPE: PRT
<213> ORGANISM: Streptococcus pyogenes

<400> SEQUENCE: 134

Arg Leu Lys Arg Thr Ala Arg Arg Arg
1               5

<210> SEQ ID NO 135
<211> LENGTH: 10
<212> TYPE: PRT
<213> ORGANISM: Streptococcus pyogenes

<400> SEQUENCE: 135
```

Arg Leu Lys Arg Thr Ala Arg Arg Arg Tyr
1               5                   10

<210> SEQ ID NO 136
<211> LENGTH: 9
<212> TYPE: PRT
<213> ORGANISM: Streptococcus pyogenes

<400> SEQUENCE: 136

Leu Lys Arg Thr Ala Arg Arg Arg Tyr
1               5

<210> SEQ ID NO 137
<211> LENGTH: 10
<212> TYPE: PRT
<213> ORGANISM: Streptococcus pyogenes

<400> SEQUENCE: 137

Leu Lys Arg Thr Ala Arg Arg Arg Tyr Thr
1               5                   10

<210> SEQ ID NO 138
<211> LENGTH: 9
<212> TYPE: PRT
<213> ORGANISM: Streptococcus pyogenes

<400> SEQUENCE: 138

Lys Arg Thr Ala Arg Arg Arg Tyr Thr
1               5

<210> SEQ ID NO 139
<211> LENGTH: 10
<212> TYPE: PRT
<213> ORGANISM: Streptococcus pyogenes

<400> SEQUENCE: 139

Lys Arg Thr Ala Arg Arg Arg Tyr Thr Arg
1               5                   10

<210> SEQ ID NO 140
<211> LENGTH: 9
<212> TYPE: PRT
<213> ORGANISM: Streptococcus pyogenes

<400> SEQUENCE: 140

Arg Thr Ala Arg Arg Arg Tyr Thr Arg
1               5

<210> SEQ ID NO 141
<211> LENGTH: 10
<212> TYPE: PRT
<213> ORGANISM: Streptococcus pyogenes

<400> SEQUENCE: 141

Arg Thr Ala Arg Arg Arg Tyr Thr Arg Arg
1               5                   10

<210> SEQ ID NO 142
<211> LENGTH: 9
<212> TYPE: PRT
<213> ORGANISM: Streptococcus pyogenes

<400> SEQUENCE: 142

Thr Ala Arg Arg Arg Tyr Thr Arg Arg
1               5

<210> SEQ ID NO 143
<211> LENGTH: 10
<212> TYPE: PRT
<213> ORGANISM: Streptococcus pyogenes

<400> SEQUENCE: 143

Thr Ala Arg Arg Tyr Thr Arg Arg Lys
1               5                   10

<210> SEQ ID NO 144
<211> LENGTH: 9
<212> TYPE: PRT
<213> ORGANISM: Streptococcus pyogenes

<400> SEQUENCE: 144

Ala Arg Arg Arg Tyr Thr Arg Arg Lys
1               5

<210> SEQ ID NO 145
<211> LENGTH: 10
<212> TYPE: PRT
<213> ORGANISM: Streptococcus pyogenes

<400> SEQUENCE: 145

Ala Arg Arg Arg Tyr Thr Arg Arg Lys Asn
1               5                   10

<210> SEQ ID NO 146
<211> LENGTH: 9
<212> TYPE: PRT
<213> ORGANISM: Streptococcus pyogenes

<400> SEQUENCE: 146

Arg Arg Arg Tyr Thr Arg Arg Lys Asn
1               5

<210> SEQ ID NO 147
<211> LENGTH: 10
<212> TYPE: PRT
<213> ORGANISM: Streptococcus pyogenes

<400> SEQUENCE: 147

Arg Arg Arg Tyr Thr Arg Arg Lys Asn Arg
1               5                   10

<210> SEQ ID NO 148
<211> LENGTH: 9
<212> TYPE: PRT
<213> ORGANISM: Streptococcus pyogenes

<400> SEQUENCE: 148

Arg Arg Tyr Thr Arg Arg Lys Asn Arg
1               5

<210> SEQ ID NO 149
<211> LENGTH: 10
<212> TYPE: PRT
<213> ORGANISM: Streptococcus pyogenes

<400> SEQUENCE: 149

Arg Arg Tyr Thr Arg Arg Lys Asn Arg Ile
1               5                   10

-continued

```
<210> SEQ ID NO 150
<211> LENGTH: 9
<212> TYPE: PRT
<213> ORGANISM: Streptococcus pyogenes

<400> SEQUENCE: 150

Arg Tyr Thr Arg Arg Lys Asn Arg Ile
1               5

<210> SEQ ID NO 151
<211> LENGTH: 10
<212> TYPE: PRT
<213> ORGANISM: Streptococcus pyogenes

<400> SEQUENCE: 151

Arg Tyr Thr Arg Arg Lys Asn Arg Ile Cys
1               5                   10

<210> SEQ ID NO 152
<211> LENGTH: 9
<212> TYPE: PRT
<213> ORGANISM: Streptococcus pyogenes

<400> SEQUENCE: 152

Tyr Thr Arg Arg Lys Asn Arg Ile Cys
1               5

<210> SEQ ID NO 153
<211> LENGTH: 10
<212> TYPE: PRT
<213> ORGANISM: Streptococcus pyogenes

<400> SEQUENCE: 153

Tyr Thr Arg Arg Lys Asn Arg Ile Cys Tyr
1               5                   10

<210> SEQ ID NO 154
<211> LENGTH: 9
<212> TYPE: PRT
<213> ORGANISM: Streptococcus pyogenes

<400> SEQUENCE: 154

Thr Arg Arg Lys Asn Arg Ile Cys Tyr
1               5

<210> SEQ ID NO 155
<211> LENGTH: 10
<212> TYPE: PRT
<213> ORGANISM: Streptococcus pyogenes

<400> SEQUENCE: 155

Thr Arg Arg Lys Asn Arg Ile Cys Tyr Leu
1               5                   10

<210> SEQ ID NO 156
<211> LENGTH: 9
<212> TYPE: PRT
<213> ORGANISM: Streptococcus pyogenes

<400> SEQUENCE: 156

Arg Arg Lys Asn Arg Ile Cys Tyr Leu
1               5

<210> SEQ ID NO 157
<211> LENGTH: 10
```

<212> TYPE: PRT
<213> ORGANISM: Streptococcus pyogenes

<400> SEQUENCE: 157

Arg Arg Lys Asn Arg Ile Cys Tyr Leu Gln
1               5                   10

<210> SEQ ID NO 158
<211> LENGTH: 9
<212> TYPE: PRT
<213> ORGANISM: Streptococcus pyogenes

<400> SEQUENCE: 158

Arg Lys Asn Arg Ile Cys Tyr Leu Gln
1               5

<210> SEQ ID NO 159
<211> LENGTH: 10
<212> TYPE: PRT
<213> ORGANISM: Streptococcus pyogenes

<400> SEQUENCE: 159

Arg Lys Asn Arg Ile Cys Tyr Leu Gln Glu
1               5                   10

<210> SEQ ID NO 160
<211> LENGTH: 9
<212> TYPE: PRT
<213> ORGANISM: Streptococcus pyogenes

<400> SEQUENCE: 160

Lys Asn Arg Ile Cys Tyr Leu Gln Glu
1               5

<210> SEQ ID NO 161
<211> LENGTH: 10
<212> TYPE: PRT
<213> ORGANISM: Streptococcus pyogenes

<400> SEQUENCE: 161

Lys Asn Arg Ile Cys Tyr Leu Gln Glu Ile
1               5                   10

<210> SEQ ID NO 162
<211> LENGTH: 9
<212> TYPE: PRT
<213> ORGANISM: Streptococcus pyogenes

<400> SEQUENCE: 162

Asn Arg Ile Cys Tyr Leu Gln Glu Ile
1               5

<210> SEQ ID NO 163
<211> LENGTH: 10
<212> TYPE: PRT
<213> ORGANISM: Streptococcus pyogenes

<400> SEQUENCE: 163

Asn Arg Ile Cys Tyr Leu Gln Glu Ile Phe
1               5                   10

<210> SEQ ID NO 164
<211> LENGTH: 9
<212> TYPE: PRT
<213> ORGANISM: Streptococcus pyogenes

<400> SEQUENCE: 164

Arg Ile Cys Tyr Leu Gln Glu Ile Phe
1               5

<210> SEQ ID NO 165
<211> LENGTH: 10
<212> TYPE: PRT
<213> ORGANISM: Streptococcus pyogenes

<400> SEQUENCE: 165

Arg Ile Cys Tyr Leu Gln Glu Ile Phe Ser
1               5                   10

<210> SEQ ID NO 166
<211> LENGTH: 9
<212> TYPE: PRT
<213> ORGANISM: Streptococcus pyogenes

<400> SEQUENCE: 166

Ile Cys Tyr Leu Gln Glu Ile Phe Ser
1               5

<210> SEQ ID NO 167
<211> LENGTH: 10
<212> TYPE: PRT
<213> ORGANISM: Streptococcus pyogenes

<400> SEQUENCE: 167

Ile Cys Tyr Leu Gln Glu Ile Phe Ser Asn
1               5                   10

<210> SEQ ID NO 168
<211> LENGTH: 9
<212> TYPE: PRT
<213> ORGANISM: Streptococcus pyogenes

<400> SEQUENCE: 168

Cys Tyr Leu Gln Glu Ile Phe Ser Asn
1               5

<210> SEQ ID NO 169
<211> LENGTH: 10
<212> TYPE: PRT
<213> ORGANISM: Streptococcus pyogenes

<400> SEQUENCE: 169

Cys Tyr Leu Gln Glu Ile Phe Ser Asn Glu
1               5                   10

<210> SEQ ID NO 170
<211> LENGTH: 9
<212> TYPE: PRT
<213> ORGANISM: Streptococcus pyogenes

<400> SEQUENCE: 170

Tyr Leu Gln Glu Ile Phe Ser Asn Glu
1               5

<210> SEQ ID NO 171
<211> LENGTH: 10
<212> TYPE: PRT
<213> ORGANISM: Streptococcus pyogenes

<400> SEQUENCE: 171

```
Tyr Leu Gln Glu Ile Phe Ser Asn Glu Met
1               5                   10

<210> SEQ ID NO 172
<211> LENGTH: 9
<212> TYPE: PRT
<213> ORGANISM: Streptococcus pyogenes

<400> SEQUENCE: 172

Leu Gln Glu Ile Phe Ser Asn Glu Met
1               5

<210> SEQ ID NO 173
<211> LENGTH: 10
<212> TYPE: PRT
<213> ORGANISM: Streptococcus pyogenes

<400> SEQUENCE: 173

Leu Gln Glu Ile Phe Ser Asn Glu Met Ala
1               5                   10

<210> SEQ ID NO 174
<211> LENGTH: 9
<212> TYPE: PRT
<213> ORGANISM: Streptococcus pyogenes

<400> SEQUENCE: 174

Gln Glu Ile Phe Ser Asn Glu Met Ala
1               5

<210> SEQ ID NO 175
<211> LENGTH: 10
<212> TYPE: PRT
<213> ORGANISM: Streptococcus pyogenes

<400> SEQUENCE: 175

Gln Glu Ile Phe Ser Asn Glu Met Ala Lys
1               5                   10

<210> SEQ ID NO 176
<211> LENGTH: 9
<212> TYPE: PRT
<213> ORGANISM: Streptococcus pyogenes

<400> SEQUENCE: 176

Glu Ile Phe Ser Asn Glu Met Ala Lys
1               5

<210> SEQ ID NO 177
<211> LENGTH: 10
<212> TYPE: PRT
<213> ORGANISM: Streptococcus pyogenes

<400> SEQUENCE: 177

Glu Ile Phe Ser Asn Glu Met Ala Lys Val
1               5                   10

<210> SEQ ID NO 178
<211> LENGTH: 9
<212> TYPE: PRT
<213> ORGANISM: Streptococcus pyogenes

<400> SEQUENCE: 178

Ile Phe Ser Asn Glu Met Ala Lys Val
```

1               5

<210> SEQ ID NO 179
<211> LENGTH: 10
<212> TYPE: PRT
<213> ORGANISM: Streptococcus pyogenes

<400> SEQUENCE: 179

Ile Phe Ser Asn Glu Met Ala Lys Val Asp
1               5                   10

<210> SEQ ID NO 180
<211> LENGTH: 9
<212> TYPE: PRT
<213> ORGANISM: Streptococcus pyogenes

<400> SEQUENCE: 180

Phe Ser Asn Glu Met Ala Lys Val Asp
1               5

<210> SEQ ID NO 181
<211> LENGTH: 10
<212> TYPE: PRT
<213> ORGANISM: Streptococcus pyogenes

<400> SEQUENCE: 181

Phe Ser Asn Glu Met Ala Lys Val Asp Asp
1               5                   10

<210> SEQ ID NO 182
<211> LENGTH: 9
<212> TYPE: PRT
<213> ORGANISM: Streptococcus pyogenes

<400> SEQUENCE: 182

Ser Asn Glu Met Ala Lys Val Asp Asp
1               5

<210> SEQ ID NO 183
<211> LENGTH: 10
<212> TYPE: PRT
<213> ORGANISM: Streptococcus pyogenes

<400> SEQUENCE: 183

Ser Asn Glu Met Ala Lys Val Asp Asp Ser
1               5                   10

<210> SEQ ID NO 184
<211> LENGTH: 9
<212> TYPE: PRT
<213> ORGANISM: Streptococcus pyogenes

<400> SEQUENCE: 184

Asn Glu Met Ala Lys Val Asp Asp Ser
1               5

<210> SEQ ID NO 185
<211> LENGTH: 10
<212> TYPE: PRT
<213> ORGANISM: Streptococcus pyogenes

<400> SEQUENCE: 185

Asn Glu Met Ala Lys Val Asp Asp Ser Phe
1               5                   10

<210> SEQ ID NO 186
<211> LENGTH: 9
<212> TYPE: PRT
<213> ORGANISM: Streptococcus pyogenes

<400> SEQUENCE: 186

Glu Met Ala Lys Val Asp Asp Ser Phe
1               5

<210> SEQ ID NO 187
<211> LENGTH: 10
<212> TYPE: PRT
<213> ORGANISM: Streptococcus pyogenes

<400> SEQUENCE: 187

Glu Met Ala Lys Val Asp Asp Ser Phe Phe
1               5                   10

<210> SEQ ID NO 188
<211> LENGTH: 9
<212> TYPE: PRT
<213> ORGANISM: Streptococcus pyogenes

<400> SEQUENCE: 188

Met Ala Lys Val Asp Asp Ser Phe Phe
1               5

<210> SEQ ID NO 189
<211> LENGTH: 10
<212> TYPE: PRT
<213> ORGANISM: Streptococcus pyogenes

<400> SEQUENCE: 189

Met Ala Lys Val Asp Asp Ser Phe Phe His
1               5                   10

<210> SEQ ID NO 190
<211> LENGTH: 9
<212> TYPE: PRT
<213> ORGANISM: Streptococcus pyogenes

<400> SEQUENCE: 190

Ala Lys Val Asp Asp Ser Phe Phe His
1               5

<210> SEQ ID NO 191
<211> LENGTH: 10
<212> TYPE: PRT
<213> ORGANISM: Streptococcus pyogenes

<400> SEQUENCE: 191

Ala Lys Val Asp Asp Ser Phe Phe His Arg
1               5                   10

<210> SEQ ID NO 192
<211> LENGTH: 9
<212> TYPE: PRT
<213> ORGANISM: Streptococcus pyogenes

<400> SEQUENCE: 192

Lys Val Asp Asp Ser Phe Phe His Arg
1               5

<210> SEQ ID NO 193

```
<211> LENGTH: 10
<212> TYPE: PRT
<213> ORGANISM: Streptococcus pyogenes

<400> SEQUENCE: 193

Lys Val Asp Asp Ser Phe Phe His Arg Leu
1               5                   10

<210> SEQ ID NO 194
<211> LENGTH: 9
<212> TYPE: PRT
<213> ORGANISM: Streptococcus pyogenes

<400> SEQUENCE: 194

Val Asp Asp Ser Phe Phe His Arg Leu
1               5

<210> SEQ ID NO 195
<211> LENGTH: 10
<212> TYPE: PRT
<213> ORGANISM: Streptococcus pyogenes

<400> SEQUENCE: 195

Val Asp Asp Ser Phe Phe His Arg Leu Glu
1               5                   10

<210> SEQ ID NO 196
<211> LENGTH: 9
<212> TYPE: PRT
<213> ORGANISM: Streptococcus pyogenes

<400> SEQUENCE: 196

Asp Asp Ser Phe Phe His Arg Leu Glu
1               5

<210> SEQ ID NO 197
<211> LENGTH: 10
<212> TYPE: PRT
<213> ORGANISM: Streptococcus pyogenes

<400> SEQUENCE: 197

Asp Asp Ser Phe Phe His Arg Leu Glu Glu
1               5                   10

<210> SEQ ID NO 198
<211> LENGTH: 9
<212> TYPE: PRT
<213> ORGANISM: Streptococcus pyogenes

<400> SEQUENCE: 198

Asp Ser Phe Phe His Arg Leu Glu Glu
1               5

<210> SEQ ID NO 199
<211> LENGTH: 10
<212> TYPE: PRT
<213> ORGANISM: Streptococcus pyogenes

<400> SEQUENCE: 199

Asp Ser Phe Phe His Arg Leu Glu Glu Ser
1               5                   10

<210> SEQ ID NO 200
<211> LENGTH: 9
<212> TYPE: PRT
```

<213> ORGANISM: Streptococcus pyogenes

<400> SEQUENCE: 200

Ser Phe Phe His Arg Leu Glu Glu Ser
1               5

<210> SEQ ID NO 201
<211> LENGTH: 10
<212> TYPE: PRT
<213> ORGANISM: Streptococcus pyogenes

<400> SEQUENCE: 201

Ser Phe Phe His Arg Leu Glu Glu Ser Phe
1               5                   10

<210> SEQ ID NO 202
<211> LENGTH: 9
<212> TYPE: PRT
<213> ORGANISM: Streptococcus pyogenes

<400> SEQUENCE: 202

Phe Phe His Arg Leu Glu Glu Ser Phe
1               5

<210> SEQ ID NO 203
<211> LENGTH: 10
<212> TYPE: PRT
<213> ORGANISM: Streptococcus pyogenes

<400> SEQUENCE: 203

Phe Phe His Arg Leu Glu Glu Ser Phe Leu
1               5                   10

<210> SEQ ID NO 204
<211> LENGTH: 9
<212> TYPE: PRT
<213> ORGANISM: Streptococcus pyogenes

<400> SEQUENCE: 204

Phe His Arg Leu Glu Glu Ser Phe Leu
1               5

<210> SEQ ID NO 205
<211> LENGTH: 10
<212> TYPE: PRT
<213> ORGANISM: Streptococcus pyogenes

<400> SEQUENCE: 205

Phe His Arg Leu Glu Glu Ser Phe Leu Val
1               5                   10

<210> SEQ ID NO 206
<211> LENGTH: 9
<212> TYPE: PRT
<213> ORGANISM: Streptococcus pyogenes

<400> SEQUENCE: 206

His Arg Leu Glu Glu Ser Phe Leu Val
1               5

<210> SEQ ID NO 207
<211> LENGTH: 10
<212> TYPE: PRT
<213> ORGANISM: Streptococcus pyogenes -continued

```
<400> SEQUENCE: 207

His Arg Leu Glu Glu Ser Phe Leu Val Glu
1               5                   10

<210> SEQ ID NO 208
<211> LENGTH: 9
<212> TYPE: PRT
<213> ORGANISM: Streptococcus pyogenes

<400> SEQUENCE: 208

Arg Leu Glu Glu Ser Phe Leu Val Glu
1               5

<210> SEQ ID NO 209
<211> LENGTH: 10
<212> TYPE: PRT
<213> ORGANISM: Streptococcus pyogenes

<400> SEQUENCE: 209

Arg Leu Glu Glu Ser Phe Leu Val Glu Glu
1               5                   10

<210> SEQ ID NO 210
<211> LENGTH: 9
<212> TYPE: PRT
<213> ORGANISM: Streptococcus pyogenes

<400> SEQUENCE: 210

Leu Glu Glu Ser Phe Leu Val Glu Glu
1               5

<210> SEQ ID NO 211
<211> LENGTH: 10
<212> TYPE: PRT
<213> ORGANISM: Streptococcus pyogenes

<400> SEQUENCE: 211

Leu Glu Glu Ser Phe Leu Val Glu Glu Asp
1               5                   10

<210> SEQ ID NO 212
<211> LENGTH: 9
<212> TYPE: PRT
<213> ORGANISM: Streptococcus pyogenes

<400> SEQUENCE: 212

Glu Glu Ser Phe Leu Val Glu Glu Asp
1               5

<210> SEQ ID NO 213
<211> LENGTH: 10
<212> TYPE: PRT
<213> ORGANISM: Streptococcus pyogenes

<400> SEQUENCE: 213

Glu Glu Ser Phe Leu Val Glu Glu Asp Lys
1               5                   10

<210> SEQ ID NO 214
<211> LENGTH: 9
<212> TYPE: PRT
<213> ORGANISM: Streptococcus pyogenes

<400> SEQUENCE: 214
```

```
Glu Ser Phe Leu Val Glu Glu Asp Lys
1               5

<210> SEQ ID NO 215
<211> LENGTH: 10
<212> TYPE: PRT
<213> ORGANISM: Streptococcus pyogenes

<400> SEQUENCE: 215

Glu Ser Phe Leu Val Glu Glu Asp Lys Lys
1               5                   10

<210> SEQ ID NO 216
<211> LENGTH: 9
<212> TYPE: PRT
<213> ORGANISM: Streptococcus pyogenes

<400> SEQUENCE: 216

Ser Phe Leu Val Glu Glu Asp Lys Lys
1               5

<210> SEQ ID NO 217
<211> LENGTH: 10
<212> TYPE: PRT
<213> ORGANISM: Streptococcus pyogenes

<400> SEQUENCE: 217

Ser Phe Leu Val Glu Glu Asp Lys Lys His
1               5                   10

<210> SEQ ID NO 218
<211> LENGTH: 9
<212> TYPE: PRT
<213> ORGANISM: Streptococcus pyogenes

<400> SEQUENCE: 218

Phe Leu Val Glu Glu Asp Lys Lys His
1               5

<210> SEQ ID NO 219
<211> LENGTH: 10
<212> TYPE: PRT
<213> ORGANISM: Streptococcus pyogenes

<400> SEQUENCE: 219

Phe Leu Val Glu Glu Asp Lys Lys His Glu
1               5                   10

<210> SEQ ID NO 220
<211> LENGTH: 9
<212> TYPE: PRT
<213> ORGANISM: Streptococcus pyogenes

<400> SEQUENCE: 220

Leu Val Glu Glu Asp Lys Lys His Glu
1               5

<210> SEQ ID NO 221
<211> LENGTH: 10
<212> TYPE: PRT
<213> ORGANISM: Streptococcus pyogenes

<400> SEQUENCE: 221

Leu Val Glu Glu Asp Lys Lys His Glu Arg
1               5                   10
```

<210> SEQ ID NO 222
<211> LENGTH: 9
<212> TYPE: PRT
<213> ORGANISM: Streptococcus pyogenes

<400> SEQUENCE: 222

Val Glu Glu Asp Lys Lys His Glu Arg
1               5

<210> SEQ ID NO 223
<211> LENGTH: 10
<212> TYPE: PRT
<213> ORGANISM: Streptococcus pyogenes

<400> SEQUENCE: 223

Val Glu Glu Asp Lys Lys His Glu Arg His
1               5                   10

<210> SEQ ID NO 224
<211> LENGTH: 9
<212> TYPE: PRT
<213> ORGANISM: Streptococcus pyogenes

<400> SEQUENCE: 224

Glu Glu Asp Lys Lys His Glu Arg His
1               5

<210> SEQ ID NO 225
<211> LENGTH: 10
<212> TYPE: PRT
<213> ORGANISM: Streptococcus pyogenes

<400> SEQUENCE: 225

Glu Glu Asp Lys Lys His Glu Arg His Pro
1               5                   10

<210> SEQ ID NO 226
<211> LENGTH: 9
<212> TYPE: PRT
<213> ORGANISM: Streptococcus pyogenes

<400> SEQUENCE: 226

Glu Asp Lys Lys His Glu Arg His Pro
1               5

<210> SEQ ID NO 227
<211> LENGTH: 10
<212> TYPE: PRT
<213> ORGANISM: Streptococcus pyogenes

<400> SEQUENCE: 227

Glu Asp Lys Lys His Glu Arg His Pro Ile
1               5                   10

<210> SEQ ID NO 228
<211> LENGTH: 9
<212> TYPE: PRT
<213> ORGANISM: Streptococcus pyogenes

<400> SEQUENCE: 228

Asp Lys Lys His Glu Arg His Pro Ile
1               5

```
<210> SEQ ID NO 229
<211> LENGTH: 10
<212> TYPE: PRT
<213> ORGANISM: Streptococcus pyogenes

<400> SEQUENCE: 229

Asp Lys Lys His Glu Arg His Pro Ile Phe
1               5                   10

<210> SEQ ID NO 230
<211> LENGTH: 9
<212> TYPE: PRT
<213> ORGANISM: Streptococcus pyogenes

<400> SEQUENCE: 230

Lys Lys His Glu Arg His Pro Ile Phe
1               5

<210> SEQ ID NO 231
<211> LENGTH: 10
<212> TYPE: PRT
<213> ORGANISM: Streptococcus pyogenes

<400> SEQUENCE: 231

Lys Lys His Glu Arg His Pro Ile Phe Gly
1               5                   10

<210> SEQ ID NO 232
<211> LENGTH: 9
<212> TYPE: PRT
<213> ORGANISM: Streptococcus pyogenes

<400> SEQUENCE: 232

Lys His Glu Arg His Pro Ile Phe Gly
1               5

<210> SEQ ID NO 233
<211> LENGTH: 10
<212> TYPE: PRT
<213> ORGANISM: Streptococcus pyogenes

<400> SEQUENCE: 233

Lys His Glu Arg His Pro Ile Phe Gly Asn
1               5                   10

<210> SEQ ID NO 234
<211> LENGTH: 9
<212> TYPE: PRT
<213> ORGANISM: Streptococcus pyogenes

<400> SEQUENCE: 234

His Glu Arg His Pro Ile Phe Gly Asn
1               5

<210> SEQ ID NO 235
<211> LENGTH: 10
<212> TYPE: PRT
<213> ORGANISM: Streptococcus pyogenes

<400> SEQUENCE: 235

His Glu Arg His Pro Ile Phe Gly Asn Ile
1               5                   10

<210> SEQ ID NO 236
<211> LENGTH: 9
```

```
<212> TYPE: PRT
<213> ORGANISM: Streptococcus pyogenes

<400> SEQUENCE: 236

Glu Arg His Pro Ile Phe Gly Asn Ile
1               5

<210> SEQ ID NO 237
<211> LENGTH: 10
<212> TYPE: PRT
<213> ORGANISM: Streptococcus pyogenes

<400> SEQUENCE: 237

Glu Arg His Pro Ile Phe Gly Asn Ile Val
1               5                   10

<210> SEQ ID NO 238
<211> LENGTH: 9
<212> TYPE: PRT
<213> ORGANISM: Streptococcus pyogenes

<400> SEQUENCE: 238

Arg His Pro Ile Phe Gly Asn Ile Val
1               5

<210> SEQ ID NO 239
<211> LENGTH: 10
<212> TYPE: PRT
<213> ORGANISM: Streptococcus pyogenes

<400> SEQUENCE: 239

Arg His Pro Ile Phe Gly Asn Ile Val Asp
1               5                   10

<210> SEQ ID NO 240
<211> LENGTH: 9
<212> TYPE: PRT
<213> ORGANISM: Streptococcus pyogenes

<400> SEQUENCE: 240

His Pro Ile Phe Gly Asn Ile Val Asp
1               5

<210> SEQ ID NO 241
<211> LENGTH: 10
<212> TYPE: PRT
<213> ORGANISM: Streptococcus pyogenes

<400> SEQUENCE: 241

His Pro Ile Phe Gly Asn Ile Val Asp Glu
1               5                   10

<210> SEQ ID NO 242
<211> LENGTH: 9
<212> TYPE: PRT
<213> ORGANISM: Streptococcus pyogenes

<400> SEQUENCE: 242

Pro Ile Phe Gly Asn Ile Val Asp Glu
1               5

<210> SEQ ID NO 243
<211> LENGTH: 10
<212> TYPE: PRT
<213> ORGANISM: Streptococcus pyogenes
```

<400> SEQUENCE: 243

Pro Ile Phe Gly Asn Ile Val Asp Glu Val
1               5                   10

<210> SEQ ID NO 244
<211> LENGTH: 9
<212> TYPE: PRT
<213> ORGANISM: Streptococcus pyogenes

<400> SEQUENCE: 244

Ile Phe Gly Asn Ile Val Asp Glu Val
1               5

<210> SEQ ID NO 245
<211> LENGTH: 10
<212> TYPE: PRT
<213> ORGANISM: Streptococcus pyogenes

<400> SEQUENCE: 245

Ile Phe Gly Asn Ile Val Asp Glu Val Ala
1               5                   10

<210> SEQ ID NO 246
<211> LENGTH: 9
<212> TYPE: PRT
<213> ORGANISM: Streptococcus pyogenes

<400> SEQUENCE: 246

Phe Gly Asn Ile Val Asp Glu Val Ala
1               5

<210> SEQ ID NO 247
<211> LENGTH: 10
<212> TYPE: PRT
<213> ORGANISM: Streptococcus pyogenes

<400> SEQUENCE: 247

Phe Gly Asn Ile Val Asp Glu Val Ala Tyr
1               5                   10

<210> SEQ ID NO 248
<211> LENGTH: 9
<212> TYPE: PRT
<213> ORGANISM: Streptococcus pyogenes

<400> SEQUENCE: 248

Gly Asn Ile Val Asp Glu Val Ala Tyr
1               5

<210> SEQ ID NO 249
<211> LENGTH: 10
<212> TYPE: PRT
<213> ORGANISM: Streptococcus pyogenes

<400> SEQUENCE: 249

Gly Asn Ile Val Asp Glu Val Ala Tyr His
1               5                   10

<210> SEQ ID NO 250
<211> LENGTH: 9
<212> TYPE: PRT
<213> ORGANISM: Streptococcus pyogenes

<400> SEQUENCE: 250

```
Asn Ile Val Asp Glu Val Ala Tyr His
1               5
```

<210> SEQ ID NO 251
<211> LENGTH: 10
<212> TYPE: PRT
<213> ORGANISM: Streptococcus pyogenes

<400> SEQUENCE: 251

```
Asn Ile Val Asp Glu Val Ala Tyr His Glu
1               5                   10
```

<210> SEQ ID NO 252
<211> LENGTH: 9
<212> TYPE: PRT
<213> ORGANISM: Streptococcus pyogenes

<400> SEQUENCE: 252

```
Ile Val Asp Glu Val Ala Tyr His Glu
1               5
```

<210> SEQ ID NO 253
<211> LENGTH: 10
<212> TYPE: PRT
<213> ORGANISM: Streptococcus pyogenes

<400> SEQUENCE: 253

```
Ile Val Asp Glu Val Ala Tyr His Glu Lys
1               5                   10
```

<210> SEQ ID NO 254
<211> LENGTH: 9
<212> TYPE: PRT
<213> ORGANISM: Streptococcus pyogenes

<400> SEQUENCE: 254

```
Val Asp Glu Val Ala Tyr His Glu Lys
1               5
```

<210> SEQ ID NO 255
<211> LENGTH: 10
<212> TYPE: PRT
<213> ORGANISM: Streptococcus pyogenes

<400> SEQUENCE: 255

```
Val Asp Glu Val Ala Tyr His Glu Lys Tyr
1               5                   10
```

<210> SEQ ID NO 256
<211> LENGTH: 9
<212> TYPE: PRT
<213> ORGANISM: Streptococcus pyogenes

<400> SEQUENCE: 256

```
Asp Glu Val Ala Tyr His Glu Lys Tyr
1               5
```

<210> SEQ ID NO 257
<211> LENGTH: 10
<212> TYPE: PRT
<213> ORGANISM: Streptococcus pyogenes

<400> SEQUENCE: 257

```
Asp Glu Val Ala Tyr His Glu Lys Tyr Pro
```

-continued

```
<210> SEQ ID NO 258
<211> LENGTH: 9
<212> TYPE: PRT
<213> ORGANISM: Streptococcus pyogenes

<400> SEQUENCE: 258

Glu Val Ala Tyr His Glu Lys Tyr Pro
1               5

<210> SEQ ID NO 259
<211> LENGTH: 10
<212> TYPE: PRT
<213> ORGANISM: Streptococcus pyogenes

<400> SEQUENCE: 259

Glu Val Ala Tyr His Glu Lys Tyr Pro Thr
1               5                   10

<210> SEQ ID NO 260
<211> LENGTH: 9
<212> TYPE: PRT
<213> ORGANISM: Streptococcus pyogenes

<400> SEQUENCE: 260

Glu Gln Glu Ile Gly Lys Ala Thr Ala
1               5

<210> SEQ ID NO 261
<211> LENGTH: 10
<212> TYPE: PRT
<213> ORGANISM: Streptococcus pyogenes

<400> SEQUENCE: 261

Glu Gln Glu Ile Gly Lys Ala Thr Ala Lys
1               5                   10

<210> SEQ ID NO 262
<211> LENGTH: 9
<212> TYPE: PRT
<213> ORGANISM: Streptococcus pyogenes

<400> SEQUENCE: 262

Gln Glu Ile Gly Lys Ala Thr Ala Lys
1               5

<210> SEQ ID NO 263
<211> LENGTH: 10
<212> TYPE: PRT
<213> ORGANISM: Streptococcus pyogenes

<400> SEQUENCE: 263

Gln Glu Ile Gly Lys Ala Thr Ala Lys Tyr
1               5                   10

<210> SEQ ID NO 264
<211> LENGTH: 9
<212> TYPE: PRT
<213> ORGANISM: Streptococcus pyogenes

<400> SEQUENCE: 264

Glu Ile Gly Lys Ala Thr Ala Lys Tyr
1               5
```

<210> SEQ ID NO 265
<211> LENGTH: 10
<212> TYPE: PRT
<213> ORGANISM: Streptococcus pyogenes

<400> SEQUENCE: 265

Glu Ile Gly Lys Ala Thr Ala Lys Tyr Phe
1               5                   10

<210> SEQ ID NO 266
<211> LENGTH: 9
<212> TYPE: PRT
<213> ORGANISM: Streptococcus pyogenes

<400> SEQUENCE: 266

Ile Gly Lys Ala Thr Ala Lys Tyr Phe
1               5

<210> SEQ ID NO 267
<211> LENGTH: 10
<212> TYPE: PRT
<213> ORGANISM: Streptococcus pyogenes

<400> SEQUENCE: 267

Ile Gly Lys Ala Thr Ala Lys Tyr Phe Phe
1               5                   10

<210> SEQ ID NO 268
<211> LENGTH: 9
<212> TYPE: PRT
<213> ORGANISM: Streptococcus pyogenes

<400> SEQUENCE: 268

Gly Lys Ala Thr Ala Lys Tyr Phe Phe
1               5

<210> SEQ ID NO 269
<211> LENGTH: 10
<212> TYPE: PRT
<213> ORGANISM: Streptococcus pyogenes

<400> SEQUENCE: 269

Gly Lys Ala Thr Ala Lys Tyr Phe Phe Tyr
1               5                   10

<210> SEQ ID NO 270
<211> LENGTH: 9
<212> TYPE: PRT
<213> ORGANISM: Streptococcus pyogenes

<400> SEQUENCE: 270

Lys Ala Thr Ala Lys Tyr Phe Phe Tyr
1               5

<210> SEQ ID NO 271
<211> LENGTH: 10
<212> TYPE: PRT
<213> ORGANISM: Streptococcus pyogenes

<400> SEQUENCE: 271

Lys Ala Thr Ala Lys Tyr Phe Phe Tyr Ser
1               5                   10

<210> SEQ ID NO 272

```
<211> LENGTH: 9
<212> TYPE: PRT
<213> ORGANISM: Streptococcus pyogenes

<400> SEQUENCE: 272

Ala Thr Ala Lys Tyr Phe Phe Tyr Ser
1               5

<210> SEQ ID NO 273
<211> LENGTH: 10
<212> TYPE: PRT
<213> ORGANISM: Streptococcus pyogenes

<400> SEQUENCE: 273

Ala Thr Ala Lys Tyr Phe Phe Tyr Ser Asn
1               5                   10

<210> SEQ ID NO 274
<211> LENGTH: 9
<212> TYPE: PRT
<213> ORGANISM: Streptococcus pyogenes

<400> SEQUENCE: 274

Thr Ala Lys Tyr Phe Phe Tyr Ser Asn
1               5

<210> SEQ ID NO 275
<211> LENGTH: 10
<212> TYPE: PRT
<213> ORGANISM: Streptococcus pyogenes

<400> SEQUENCE: 275

Thr Ala Lys Tyr Phe Phe Tyr Ser Asn Ile
1               5                   10

<210> SEQ ID NO 276
<211> LENGTH: 9
<212> TYPE: PRT
<213> ORGANISM: Streptococcus pyogenes

<400> SEQUENCE: 276

Ala Lys Tyr Phe Phe Tyr Ser Asn Ile
1               5

<210> SEQ ID NO 277
<211> LENGTH: 10
<212> TYPE: PRT
<213> ORGANISM: Streptococcus pyogenes

<400> SEQUENCE: 277

Ala Lys Tyr Phe Phe Tyr Ser Asn Ile Met
1               5                   10

<210> SEQ ID NO 278
<211> LENGTH: 9
<212> TYPE: PRT
<213> ORGANISM: Streptococcus pyogenes

<400> SEQUENCE: 278

Lys Tyr Phe Phe Tyr Ser Asn Ile Met
1               5

<210> SEQ ID NO 279
<211> LENGTH: 10
<212> TYPE: PRT
```

<213> ORGANISM: Streptococcus pyogenes

<400> SEQUENCE: 279

Lys Tyr Phe Phe Tyr Ser Asn Ile Met Asn
1               5                   10

<210> SEQ ID NO 280
<211> LENGTH: 9
<212> TYPE: PRT
<213> ORGANISM: Streptococcus pyogenes

<400> SEQUENCE: 280

Tyr Phe Phe Tyr Ser Asn Ile Met Asn
1               5

<210> SEQ ID NO 281
<211> LENGTH: 10
<212> TYPE: PRT
<213> ORGANISM: Streptococcus pyogenes

<400> SEQUENCE: 281

Tyr Phe Phe Tyr Ser Asn Ile Met Asn Phe
1               5                   10

<210> SEQ ID NO 282
<211> LENGTH: 9
<212> TYPE: PRT
<213> ORGANISM: Streptococcus pyogenes

<400> SEQUENCE: 282

Phe Phe Tyr Ser Asn Ile Met Asn Phe
1               5

<210> SEQ ID NO 283
<211> LENGTH: 10
<212> TYPE: PRT
<213> ORGANISM: Streptococcus pyogenes

<400> SEQUENCE: 283

Phe Phe Tyr Ser Asn Ile Met Asn Phe Phe
1               5                   10

<210> SEQ ID NO 284
<211> LENGTH: 9
<212> TYPE: PRT
<213> ORGANISM: Streptococcus pyogenes

<400> SEQUENCE: 284

Phe Tyr Ser Asn Ile Met Asn Phe Phe
1               5

<210> SEQ ID NO 285
<211> LENGTH: 10
<212> TYPE: PRT
<213> ORGANISM: Streptococcus pyogenes

<400> SEQUENCE: 285

Phe Tyr Ser Asn Ile Met Asn Phe Phe Lys
1               5                   10

<210> SEQ ID NO 286
<211> LENGTH: 9
<212> TYPE: PRT
<213> ORGANISM: Streptococcus pyogenes

```
<400> SEQUENCE: 286

Tyr Ser Asn Ile Met Asn Phe Phe Lys
1               5

<210> SEQ ID NO 287
<211> LENGTH: 10
<212> TYPE: PRT
<213> ORGANISM: Streptococcus pyogenes

<400> SEQUENCE: 287

Tyr Ser Asn Ile Met Asn Phe Phe Lys Thr
1               5                   10

<210> SEQ ID NO 288
<211> LENGTH: 9
<212> TYPE: PRT
<213> ORGANISM: Streptococcus pyogenes

<400> SEQUENCE: 288

Ser Asn Ile Met Asn Phe Phe Lys Thr
1               5

<210> SEQ ID NO 289
<211> LENGTH: 10
<212> TYPE: PRT
<213> ORGANISM: Streptococcus pyogenes

<400> SEQUENCE: 289

Ser Asn Ile Met Asn Phe Phe Lys Thr Glu
1               5                   10

<210> SEQ ID NO 290
<211> LENGTH: 9
<212> TYPE: PRT
<213> ORGANISM: Streptococcus pyogenes

<400> SEQUENCE: 290

Asn Ile Met Asn Phe Phe Lys Thr Glu
1               5

<210> SEQ ID NO 291
<211> LENGTH: 10
<212> TYPE: PRT
<213> ORGANISM: Streptococcus pyogenes

<400> SEQUENCE: 291

Asn Ile Met Asn Phe Phe Lys Thr Glu Ile
1               5                   10

<210> SEQ ID NO 292
<211> LENGTH: 9
<212> TYPE: PRT
<213> ORGANISM: Streptococcus pyogenes

<400> SEQUENCE: 292

Ile Met Asn Phe Phe Lys Thr Glu Ile
1               5

<210> SEQ ID NO 293
<211> LENGTH: 10
<212> TYPE: PRT
<213> ORGANISM: Streptococcus pyogenes

<400> SEQUENCE: 293
```

```
Ile Met Asn Phe Phe Lys Thr Glu Ile Thr
1               5                   10
```

<210> SEQ ID NO 294
<211> LENGTH: 9
<212> TYPE: PRT
<213> ORGANISM: Streptococcus pyogenes

<400> SEQUENCE: 294

```
Met Asn Phe Phe Lys Thr Glu Ile Thr
1               5
```

<210> SEQ ID NO 295
<211> LENGTH: 10
<212> TYPE: PRT
<213> ORGANISM: Streptococcus pyogenes

<400> SEQUENCE: 295

```
Met Asn Phe Phe Lys Thr Glu Ile Thr Leu
1               5                   10
```

<210> SEQ ID NO 296
<211> LENGTH: 9
<212> TYPE: PRT
<213> ORGANISM: Streptococcus pyogenes

<400> SEQUENCE: 296

```
Asn Phe Phe Lys Thr Glu Ile Thr Leu
1               5
```

<210> SEQ ID NO 297
<211> LENGTH: 10
<212> TYPE: PRT
<213> ORGANISM: Streptococcus pyogenes

<400> SEQUENCE: 297

```
Asn Phe Phe Lys Thr Glu Ile Thr Leu Ala
1               5                   10
```

<210> SEQ ID NO 298
<211> LENGTH: 9
<212> TYPE: PRT
<213> ORGANISM: Streptococcus pyogenes

<400> SEQUENCE: 298

```
Phe Phe Lys Thr Glu Ile Thr Leu Ala
1               5
```

<210> SEQ ID NO 299
<211> LENGTH: 10
<212> TYPE: PRT
<213> ORGANISM: Streptococcus pyogenes

<400> SEQUENCE: 299

```
Phe Phe Lys Thr Glu Ile Thr Leu Ala Asn
1               5                   10
```

<210> SEQ ID NO 300
<211> LENGTH: 9
<212> TYPE: PRT
<213> ORGANISM: Streptococcus pyogenes

<400> SEQUENCE: 300

```
Phe Lys Thr Glu Ile Thr Leu Ala Asn
1               5
```

<210> SEQ ID NO 301
<211> LENGTH: 10
<212> TYPE: PRT
<213> ORGANISM: Streptococcus pyogenes

<400> SEQUENCE: 301

Phe Lys Thr Glu Ile Thr Leu Ala Asn Gly
1               5                   10

<210> SEQ ID NO 302
<211> LENGTH: 9
<212> TYPE: PRT
<213> ORGANISM: Streptococcus pyogenes

<400> SEQUENCE: 302

Lys Thr Glu Ile Thr Leu Ala Asn Gly
1               5

<210> SEQ ID NO 303
<211> LENGTH: 10
<212> TYPE: PRT
<213> ORGANISM: Streptococcus pyogenes

<400> SEQUENCE: 303

Lys Thr Glu Ile Thr Leu Ala Asn Gly Glu
1               5                   10

<210> SEQ ID NO 304
<211> LENGTH: 9
<212> TYPE: PRT
<213> ORGANISM: Streptococcus pyogenes

<400> SEQUENCE: 304

Thr Glu Ile Thr Leu Ala Asn Gly Glu
1               5

<210> SEQ ID NO 305
<211> LENGTH: 10
<212> TYPE: PRT
<213> ORGANISM: Streptococcus pyogenes

<400> SEQUENCE: 305

Thr Glu Ile Thr Leu Ala Asn Gly Glu Ile
1               5                   10

<210> SEQ ID NO 306
<211> LENGTH: 9
<212> TYPE: PRT
<213> ORGANISM: Streptococcus pyogenes

<400> SEQUENCE: 306

Glu Ile Thr Leu Ala Asn Gly Glu Ile
1               5

<210> SEQ ID NO 307
<211> LENGTH: 10
<212> TYPE: PRT
<213> ORGANISM: Streptococcus pyogenes

<400> SEQUENCE: 307

Glu Ile Thr Leu Ala Asn Gly Glu Ile Arg
1               5                   10

-continued

```
<210> SEQ ID NO 308
<211> LENGTH: 9
<212> TYPE: PRT
<213> ORGANISM: Streptococcus pyogenes

<400> SEQUENCE: 308

Ile Thr Leu Ala Asn Gly Glu Ile Arg
1               5

<210> SEQ ID NO 309
<211> LENGTH: 10
<212> TYPE: PRT
<213> ORGANISM: Streptococcus pyogenes

<400> SEQUENCE: 309

Ile Thr Leu Ala Asn Gly Glu Ile Arg Lys
1               5                   10

<210> SEQ ID NO 310
<211> LENGTH: 9
<212> TYPE: PRT
<213> ORGANISM: Streptococcus pyogenes

<400> SEQUENCE: 310

Thr Leu Ala Asn Gly Glu Ile Arg Lys
1               5

<210> SEQ ID NO 311
<211> LENGTH: 10
<212> TYPE: PRT
<213> ORGANISM: Streptococcus pyogenes

<400> SEQUENCE: 311

Thr Leu Ala Asn Gly Glu Ile Arg Lys Arg
1               5                   10

<210> SEQ ID NO 312
<211> LENGTH: 9
<212> TYPE: PRT
<213> ORGANISM: Streptococcus pyogenes

<400> SEQUENCE: 312

Leu Ala Asn Gly Glu Ile Arg Lys Arg
1               5

<210> SEQ ID NO 313
<211> LENGTH: 10
<212> TYPE: PRT
<213> ORGANISM: Streptococcus pyogenes

<400> SEQUENCE: 313

Leu Ala Asn Gly Glu Ile Arg Lys Arg Pro
1               5                   10

<210> SEQ ID NO 314
<211> LENGTH: 9
<212> TYPE: PRT
<213> ORGANISM: Streptococcus pyogenes

<400> SEQUENCE: 314

Ala Asn Gly Glu Ile Arg Lys Arg Pro
1               5

<210> SEQ ID NO 315
<211> LENGTH: 10
```

```
<212> TYPE: PRT
<213> ORGANISM: Streptococcus pyogenes

<400> SEQUENCE: 315

Ala Asn Gly Glu Ile Arg Lys Arg Pro Leu
1               5                   10

<210> SEQ ID NO 316
<211> LENGTH: 9
<212> TYPE: PRT
<213> ORGANISM: Streptococcus pyogenes

<400> SEQUENCE: 316

Asn Gly Glu Ile Arg Lys Arg Pro Leu
1               5

<210> SEQ ID NO 317
<211> LENGTH: 10
<212> TYPE: PRT
<213> ORGANISM: Streptococcus pyogenes

<400> SEQUENCE: 317

Asn Gly Glu Ile Arg Lys Arg Pro Leu Ile
1               5                   10

<210> SEQ ID NO 318
<211> LENGTH: 9
<212> TYPE: PRT
<213> ORGANISM: Streptococcus pyogenes

<400> SEQUENCE: 318

Gly Glu Ile Arg Lys Arg Pro Leu Ile
1               5

<210> SEQ ID NO 319
<211> LENGTH: 10
<212> TYPE: PRT
<213> ORGANISM: Streptococcus pyogenes

<400> SEQUENCE: 319

Gly Glu Ile Arg Lys Arg Pro Leu Ile Glu
1               5                   10

<210> SEQ ID NO 320
<211> LENGTH: 9
<212> TYPE: PRT
<213> ORGANISM: Streptococcus pyogenes

<400> SEQUENCE: 320

Glu Ile Arg Lys Arg Pro Leu Ile Glu
1               5

<210> SEQ ID NO 321
<211> LENGTH: 10
<212> TYPE: PRT
<213> ORGANISM: Streptococcus pyogenes

<400> SEQUENCE: 321

Glu Ile Arg Lys Arg Pro Leu Ile Glu Thr
1               5                   10

<210> SEQ ID NO 322
<211> LENGTH: 9
<212> TYPE: PRT
<213> ORGANISM: Streptococcus pyogenes
```

<400> SEQUENCE: 322

Ile Arg Lys Arg Pro Leu Ile Glu Thr
1               5

<210> SEQ ID NO 323
<211> LENGTH: 10
<212> TYPE: PRT
<213> ORGANISM: Streptococcus pyogenes

<400> SEQUENCE: 323

Ile Arg Lys Arg Pro Leu Ile Glu Thr Asn
1               5                   10

<210> SEQ ID NO 324
<211> LENGTH: 9
<212> TYPE: PRT
<213> ORGANISM: Streptococcus pyogenes

<400> SEQUENCE: 324

Arg Lys Arg Pro Leu Ile Glu Thr Asn
1               5

<210> SEQ ID NO 325
<211> LENGTH: 10
<212> TYPE: PRT
<213> ORGANISM: Streptococcus pyogenes

<400> SEQUENCE: 325

Arg Lys Arg Pro Leu Ile Glu Thr Asn Gly
1               5                   10

<210> SEQ ID NO 326
<211> LENGTH: 9
<212> TYPE: PRT
<213> ORGANISM: Streptococcus pyogenes

<400> SEQUENCE: 326

Lys Arg Pro Leu Ile Glu Thr Asn Gly
1               5

<210> SEQ ID NO 327
<211> LENGTH: 10
<212> TYPE: PRT
<213> ORGANISM: Streptococcus pyogenes

<400> SEQUENCE: 327

Lys Arg Pro Leu Ile Glu Thr Asn Gly Glu
1               5                   10

<210> SEQ ID NO 328
<211> LENGTH: 9
<212> TYPE: PRT
<213> ORGANISM: Streptococcus pyogenes

<400> SEQUENCE: 328

Arg Pro Leu Ile Glu Thr Asn Gly Glu
1               5

<210> SEQ ID NO 329
<211> LENGTH: 10
<212> TYPE: PRT
<213> ORGANISM: Streptococcus pyogenes

<400> SEQUENCE: 329

Arg Pro Leu Ile Glu Thr Asn Gly Glu Thr
1               5                   10

<210> SEQ ID NO 330
<211> LENGTH: 9
<212> TYPE: PRT
<213> ORGANISM: Streptococcus pyogenes

<400> SEQUENCE: 330

Pro Leu Ile Glu Thr Asn Gly Glu Thr
1               5

<210> SEQ ID NO 331
<211> LENGTH: 10
<212> TYPE: PRT
<213> ORGANISM: Streptococcus pyogenes

<400> SEQUENCE: 331

Pro Leu Ile Glu Thr Asn Gly Glu Thr Gly
1               5                   10

<210> SEQ ID NO 332
<211> LENGTH: 9
<212> TYPE: PRT
<213> ORGANISM: Streptococcus pyogenes

<400> SEQUENCE: 332

Leu Ile Glu Thr Asn Gly Glu Thr Gly
1               5

<210> SEQ ID NO 333
<211> LENGTH: 10
<212> TYPE: PRT
<213> ORGANISM: Streptococcus pyogenes

<400> SEQUENCE: 333

Leu Ile Glu Thr Asn Gly Glu Thr Gly Glu
1               5                   10

<210> SEQ ID NO 334
<211> LENGTH: 9
<212> TYPE: PRT
<213> ORGANISM: Streptococcus pyogenes

<400> SEQUENCE: 334

Ile Glu Thr Asn Gly Glu Thr Gly Glu
1               5

<210> SEQ ID NO 335
<211> LENGTH: 10
<212> TYPE: PRT
<213> ORGANISM: Streptococcus pyogenes

<400> SEQUENCE: 335

Ile Glu Thr Asn Gly Glu Thr Gly Glu Ile
1               5                   10

<210> SEQ ID NO 336
<211> LENGTH: 9
<212> TYPE: PRT
<213> ORGANISM: Streptococcus pyogenes

<400> SEQUENCE: 336

Glu Thr Asn Gly Glu Thr Gly Glu Ile

<210> SEQ ID NO 337
<211> LENGTH: 10
<212> TYPE: PRT
<213> ORGANISM: Streptococcus pyogenes

<400> SEQUENCE: 337

Glu Thr Asn Gly Glu Thr Gly Glu Ile Val
1               5                   10

<210> SEQ ID NO 338
<211> LENGTH: 9
<212> TYPE: PRT
<213> ORGANISM: Streptococcus pyogenes

<400> SEQUENCE: 338

Thr Asn Gly Glu Thr Gly Glu Ile Val
1               5

<210> SEQ ID NO 339
<211> LENGTH: 10
<212> TYPE: PRT
<213> ORGANISM: Streptococcus pyogenes

<400> SEQUENCE: 339

Thr Asn Gly Glu Thr Gly Glu Ile Val Trp
1               5                   10

<210> SEQ ID NO 340
<211> LENGTH: 9
<212> TYPE: PRT
<213> ORGANISM: Streptococcus pyogenes

<400> SEQUENCE: 340

Asn Gly Glu Thr Gly Glu Ile Val Trp
1               5

<210> SEQ ID NO 341
<211> LENGTH: 10
<212> TYPE: PRT
<213> ORGANISM: Streptococcus pyogenes

<400> SEQUENCE: 341

Asn Gly Glu Thr Gly Glu Ile Val Trp Asp
1               5                   10

<210> SEQ ID NO 342
<211> LENGTH: 9
<212> TYPE: PRT
<213> ORGANISM: Streptococcus pyogenes

<400> SEQUENCE: 342

Gly Glu Thr Gly Glu Ile Val Trp Asp
1               5

<210> SEQ ID NO 343
<211> LENGTH: 10
<212> TYPE: PRT
<213> ORGANISM: Streptococcus pyogenes

<400> SEQUENCE: 343

Gly Glu Thr Gly Glu Ile Val Trp Asp Lys
1               5                   10

<210> SEQ ID NO 344
<211> LENGTH: 9
<212> TYPE: PRT
<213> ORGANISM: Streptococcus pyogenes

<400> SEQUENCE: 344

Glu Thr Gly Glu Ile Val Trp Asp Lys
1               5

<210> SEQ ID NO 345
<211> LENGTH: 10
<212> TYPE: PRT
<213> ORGANISM: Streptococcus pyogenes

<400> SEQUENCE: 345

Glu Thr Gly Glu Ile Val Trp Asp Lys Gly
1               5                   10

<210> SEQ ID NO 346
<211> LENGTH: 9
<212> TYPE: PRT
<213> ORGANISM: Streptococcus pyogenes

<400> SEQUENCE: 346

Thr Gly Glu Ile Val Trp Asp Lys Gly
1               5

<210> SEQ ID NO 347
<211> LENGTH: 10
<212> TYPE: PRT
<213> ORGANISM: Streptococcus pyogenes

<400> SEQUENCE: 347

Thr Gly Glu Ile Val Trp Asp Lys Gly Arg
1               5                   10

<210> SEQ ID NO 348
<211> LENGTH: 9
<212> TYPE: PRT
<213> ORGANISM: Streptococcus pyogenes

<400> SEQUENCE: 348

Gly Glu Ile Val Trp Asp Lys Gly Arg
1               5

<210> SEQ ID NO 349
<211> LENGTH: 10
<212> TYPE: PRT
<213> ORGANISM: Streptococcus pyogenes

<400> SEQUENCE: 349

Gly Glu Ile Val Trp Asp Lys Gly Arg Asp
1               5                   10

<210> SEQ ID NO 350
<211> LENGTH: 9
<212> TYPE: PRT
<213> ORGANISM: Streptococcus pyogenes

<400> SEQUENCE: 350

Glu Ile Val Trp Asp Lys Gly Arg Asp
1               5

<210> SEQ ID NO 351

```
<211> LENGTH: 10
<212> TYPE: PRT
<213> ORGANISM: Streptococcus pyogenes

<400> SEQUENCE: 351

Glu Ile Val Trp Asp Lys Gly Arg Asp Phe
1               5                   10

<210> SEQ ID NO 352
<211> LENGTH: 9
<212> TYPE: PRT
<213> ORGANISM: Streptococcus pyogenes

<400> SEQUENCE: 352

Ile Val Trp Asp Lys Gly Arg Asp Phe
1               5

<210> SEQ ID NO 353
<211> LENGTH: 10
<212> TYPE: PRT
<213> ORGANISM: Streptococcus pyogenes

<400> SEQUENCE: 353

Ile Val Trp Asp Lys Gly Arg Asp Phe Ala
1               5                   10

<210> SEQ ID NO 354
<211> LENGTH: 9
<212> TYPE: PRT
<213> ORGANISM: Streptococcus pyogenes

<400> SEQUENCE: 354

Val Trp Asp Lys Gly Arg Asp Phe Ala
1               5

<210> SEQ ID NO 355
<211> LENGTH: 10
<212> TYPE: PRT
<213> ORGANISM: Streptococcus pyogenes

<400> SEQUENCE: 355

Val Trp Asp Lys Gly Arg Asp Phe Ala Thr
1               5                   10

<210> SEQ ID NO 356
<211> LENGTH: 9
<212> TYPE: PRT
<213> ORGANISM: Streptococcus pyogenes

<400> SEQUENCE: 356

Trp Asp Lys Gly Arg Asp Phe Ala Thr
1               5

<210> SEQ ID NO 357
<211> LENGTH: 10
<212> TYPE: PRT
<213> ORGANISM: Streptococcus pyogenes

<400> SEQUENCE: 357

Trp Asp Lys Gly Arg Asp Phe Ala Thr Val
1               5                   10

<210> SEQ ID NO 358
<211> LENGTH: 9
<212> TYPE: PRT
```

<213> ORGANISM: Streptococcus pyogenes

<400> SEQUENCE: 358

Asp Lys Gly Arg Asp Phe Ala Thr Val
1               5

<210> SEQ ID NO 359
<211> LENGTH: 10
<212> TYPE: PRT
<213> ORGANISM: Streptococcus pyogenes

<400> SEQUENCE: 359

Asp Lys Gly Arg Asp Phe Ala Thr Val Arg
1               5                   10

<210> SEQ ID NO 360
<211> LENGTH: 9
<212> TYPE: PRT
<213> ORGANISM: Streptococcus pyogenes

<400> SEQUENCE: 360

Lys Gly Arg Asp Phe Ala Thr Val Arg
1               5

<210> SEQ ID NO 361
<211> LENGTH: 10
<212> TYPE: PRT
<213> ORGANISM: Streptococcus pyogenes

<400> SEQUENCE: 361

Lys Gly Arg Asp Phe Ala Thr Val Arg Lys
1               5                   10

<210> SEQ ID NO 362
<211> LENGTH: 9
<212> TYPE: PRT
<213> ORGANISM: Streptococcus pyogenes

<400> SEQUENCE: 362

Gly Arg Asp Phe Ala Thr Val Arg Lys
1               5

<210> SEQ ID NO 363
<211> LENGTH: 10
<212> TYPE: PRT
<213> ORGANISM: Streptococcus pyogenes

<400> SEQUENCE: 363

Gly Arg Asp Phe Ala Thr Val Arg Lys Val
1               5                   10

<210> SEQ ID NO 364
<211> LENGTH: 9
<212> TYPE: PRT
<213> ORGANISM: Streptococcus pyogenes

<400> SEQUENCE: 364

Arg Asp Phe Ala Thr Val Arg Lys Val
1               5

<210> SEQ ID NO 365
<211> LENGTH: 10
<212> TYPE: PRT
<213> ORGANISM: Streptococcus pyogenes -continued

<400> SEQUENCE: 365

Arg Asp Phe Ala Thr Val Arg Lys Val Leu
1               5                   10

<210> SEQ ID NO 366
<211> LENGTH: 9
<212> TYPE: PRT
<213> ORGANISM: Streptococcus pyogenes

<400> SEQUENCE: 366

Asp Phe Ala Thr Val Arg Lys Val Leu
1               5

<210> SEQ ID NO 367
<211> LENGTH: 10
<212> TYPE: PRT
<213> ORGANISM: Streptococcus pyogenes

<400> SEQUENCE: 367

Asp Phe Ala Thr Val Arg Lys Val Leu Ser
1               5                   10

<210> SEQ ID NO 368
<211> LENGTH: 9
<212> TYPE: PRT
<213> ORGANISM: Streptococcus pyogenes

<400> SEQUENCE: 368

Phe Ala Thr Val Arg Lys Val Leu Ser
1               5

<210> SEQ ID NO 369
<211> LENGTH: 10
<212> TYPE: PRT
<213> ORGANISM: Streptococcus pyogenes

<400> SEQUENCE: 369

Phe Ala Thr Val Arg Lys Val Leu Ser Met
1               5                   10

<210> SEQ ID NO 370
<211> LENGTH: 9
<212> TYPE: PRT
<213> ORGANISM: Streptococcus pyogenes

<400> SEQUENCE: 370

Ala Thr Val Arg Lys Val Leu Ser Met
1               5

<210> SEQ ID NO 371
<211> LENGTH: 10
<212> TYPE: PRT
<213> ORGANISM: Streptococcus pyogenes

<400> SEQUENCE: 371

Ala Thr Val Arg Lys Val Leu Ser Met Pro
1               5                   10

<210> SEQ ID NO 372
<211> LENGTH: 9
<212> TYPE: PRT
<213> ORGANISM: Streptococcus pyogenes

<400> SEQUENCE: 372

```
Thr Val Arg Lys Val Leu Ser Met Pro
1               5
```

<210> SEQ ID NO 373
<211> LENGTH: 10
<212> TYPE: PRT
<213> ORGANISM: Streptococcus pyogenes

<400> SEQUENCE: 373

```
Thr Val Arg Lys Val Leu Ser Met Pro Gln
1               5                   10
```

<210> SEQ ID NO 374
<211> LENGTH: 9
<212> TYPE: PRT
<213> ORGANISM: Streptococcus pyogenes

<400> SEQUENCE: 374

```
Val Arg Lys Val Leu Ser Met Pro Gln
1               5
```

<210> SEQ ID NO 375
<211> LENGTH: 10
<212> TYPE: PRT
<213> ORGANISM: Streptococcus pyogenes

<400> SEQUENCE: 375

```
Val Arg Lys Val Leu Ser Met Pro Gln Val
1               5                   10
```

<210> SEQ ID NO 376
<211> LENGTH: 9
<212> TYPE: PRT
<213> ORGANISM: Streptococcus pyogenes

<400> SEQUENCE: 376

```
Arg Lys Val Leu Ser Met Pro Gln Val
1               5
```

<210> SEQ ID NO 377
<211> LENGTH: 10
<212> TYPE: PRT
<213> ORGANISM: Streptococcus pyogenes

<400> SEQUENCE: 377

```
Arg Lys Val Leu Ser Met Pro Gln Val Asn
1               5                   10
```

<210> SEQ ID NO 378
<211> LENGTH: 9
<212> TYPE: PRT
<213> ORGANISM: Streptococcus pyogenes

<400> SEQUENCE: 378

```
Lys Val Leu Ser Met Pro Gln Val Asn
1               5
```

<210> SEQ ID NO 379
<211> LENGTH: 10
<212> TYPE: PRT
<213> ORGANISM: Streptococcus pyogenes

<400> SEQUENCE: 379

```
Lys Val Leu Ser Met Pro Gln Val Asn Ile
1               5                   10
```

<210> SEQ ID NO 380
<211> LENGTH: 9
<212> TYPE: PRT
<213> ORGANISM: Streptococcus pyogenes

<400> SEQUENCE: 380

Val Leu Ser Met Pro Gln Val Asn Ile
1               5

<210> SEQ ID NO 381
<211> LENGTH: 10
<212> TYPE: PRT
<213> ORGANISM: Streptococcus pyogenes

<400> SEQUENCE: 381

Val Leu Ser Met Pro Gln Val Asn Ile Val
1               5                   10

<210> SEQ ID NO 382
<211> LENGTH: 9
<212> TYPE: PRT
<213> ORGANISM: Streptococcus pyogenes

<400> SEQUENCE: 382

Leu Ser Met Pro Gln Val Asn Ile Val
1               5

<210> SEQ ID NO 383
<211> LENGTH: 10
<212> TYPE: PRT
<213> ORGANISM: Streptococcus pyogenes

<400> SEQUENCE: 383

Leu Ser Met Pro Gln Val Asn Ile Val Lys
1               5                   10

<210> SEQ ID NO 384
<211> LENGTH: 9
<212> TYPE: PRT
<213> ORGANISM: Streptococcus pyogenes

<400> SEQUENCE: 384

Ser Met Pro Gln Val Asn Ile Val Lys
1               5

<210> SEQ ID NO 385
<211> LENGTH: 10
<212> TYPE: PRT
<213> ORGANISM: Streptococcus pyogenes

<400> SEQUENCE: 385

Ser Met Pro Gln Val Asn Ile Val Lys Lys
1               5                   10

<210> SEQ ID NO 386
<211> LENGTH: 9
<212> TYPE: PRT
<213> ORGANISM: Streptococcus pyogenes

<400> SEQUENCE: 386

Met Pro Gln Val Asn Ile Val Lys Lys
1               5

```
<210> SEQ ID NO 387
<211> LENGTH: 10
<212> TYPE: PRT
<213> ORGANISM: Streptococcus pyogenes

<400> SEQUENCE: 387

Met Pro Gln Val Asn Ile Val Lys Lys Thr
1               5                   10

<210> SEQ ID NO 388
<211> LENGTH: 9
<212> TYPE: PRT
<213> ORGANISM: Streptococcus pyogenes

<400> SEQUENCE: 388

Pro Gln Val Asn Ile Val Lys Lys Thr
1               5

<210> SEQ ID NO 389
<211> LENGTH: 10
<212> TYPE: PRT
<213> ORGANISM: Streptococcus pyogenes

<400> SEQUENCE: 389

Pro Gln Val Asn Ile Val Lys Lys Thr Glu
1               5                   10

<210> SEQ ID NO 390
<211> LENGTH: 9
<212> TYPE: PRT
<213> ORGANISM: Streptococcus pyogenes

<400> SEQUENCE: 390

Gln Val Asn Ile Val Lys Lys Thr Glu
1               5

<210> SEQ ID NO 391
<211> LENGTH: 10
<212> TYPE: PRT
<213> ORGANISM: Streptococcus pyogenes

<400> SEQUENCE: 391

Gln Val Asn Ile Val Lys Lys Thr Glu Val
1               5                   10

<210> SEQ ID NO 392
<211> LENGTH: 9
<212> TYPE: PRT
<213> ORGANISM: Streptococcus pyogenes

<400> SEQUENCE: 392

Val Asn Ile Val Lys Lys Thr Glu Val
1               5

<210> SEQ ID NO 393
<211> LENGTH: 10
<212> TYPE: PRT
<213> ORGANISM: Streptococcus pyogenes

<400> SEQUENCE: 393

Val Asn Ile Val Lys Lys Thr Glu Val Gln
1               5                   10

<210> SEQ ID NO 394
<211> LENGTH: 9
```

<212> TYPE: PRT
<213> ORGANISM: Streptococcus pyogenes

<400> SEQUENCE: 394

Asn Ile Val Lys Lys Thr Glu Val Gln
1               5

<210> SEQ ID NO 395
<211> LENGTH: 10
<212> TYPE: PRT
<213> ORGANISM: Streptococcus pyogenes

<400> SEQUENCE: 395

Asn Ile Val Lys Lys Thr Glu Val Gln Thr
1               5                   10

<210> SEQ ID NO 396
<211> LENGTH: 9
<212> TYPE: PRT
<213> ORGANISM: Streptococcus pyogenes

<400> SEQUENCE: 396

Ile Val Lys Lys Thr Glu Val Gln Thr
1               5

<210> SEQ ID NO 397
<211> LENGTH: 10
<212> TYPE: PRT
<213> ORGANISM: Streptococcus pyogenes

<400> SEQUENCE: 397

Ile Val Lys Lys Thr Glu Val Gln Thr Gly
1               5                   10

<210> SEQ ID NO 398
<211> LENGTH: 9
<212> TYPE: PRT
<213> ORGANISM: Streptococcus pyogenes

<400> SEQUENCE: 398

Val Lys Lys Thr Glu Val Gln Thr Gly
1               5

<210> SEQ ID NO 399
<211> LENGTH: 10
<212> TYPE: PRT
<213> ORGANISM: Streptococcus pyogenes

<400> SEQUENCE: 399

Val Lys Lys Thr Glu Val Gln Thr Gly Gly
1               5                   10

<210> SEQ ID NO 400
<211> LENGTH: 9
<212> TYPE: PRT
<213> ORGANISM: Streptococcus pyogenes

<400> SEQUENCE: 400

Lys Lys Thr Glu Val Gln Thr Gly Gly
1               5

<210> SEQ ID NO 401
<211> LENGTH: 10
<212> TYPE: PRT
<213> ORGANISM: Streptococcus pyogenes

<400> SEQUENCE: 401

Lys Lys Thr Glu Val Gln Thr Gly Gly Phe
1               5                   10

<210> SEQ ID NO 402
<211> LENGTH: 9
<212> TYPE: PRT
<213> ORGANISM: Streptococcus pyogenes

<400> SEQUENCE: 402

Lys Thr Glu Val Gln Thr Gly Gly Phe
1               5

<210> SEQ ID NO 403
<211> LENGTH: 10
<212> TYPE: PRT
<213> ORGANISM: Streptococcus pyogenes

<400> SEQUENCE: 403

Lys Thr Glu Val Gln Thr Gly Gly Phe Ser
1               5                   10

<210> SEQ ID NO 404
<211> LENGTH: 9
<212> TYPE: PRT
<213> ORGANISM: Streptococcus pyogenes

<400> SEQUENCE: 404

Thr Glu Val Gln Thr Gly Gly Phe Ser
1               5

<210> SEQ ID NO 405
<211> LENGTH: 10
<212> TYPE: PRT
<213> ORGANISM: Streptococcus pyogenes

<400> SEQUENCE: 405

Thr Glu Val Gln Thr Gly Gly Phe Ser Lys
1               5                   10

<210> SEQ ID NO 406
<211> LENGTH: 9
<212> TYPE: PRT
<213> ORGANISM: Streptococcus pyogenes

<400> SEQUENCE: 406

Glu Val Gln Thr Gly Gly Phe Ser Lys
1               5

<210> SEQ ID NO 407
<211> LENGTH: 10
<212> TYPE: PRT
<213> ORGANISM: Streptococcus pyogenes

<400> SEQUENCE: 407

Glu Val Gln Thr Gly Gly Phe Ser Lys Glu
1               5                   10

<210> SEQ ID NO 408
<211> LENGTH: 9
<212> TYPE: PRT
<213> ORGANISM: Streptococcus pyogenes

<400> SEQUENCE: 408

Val Gln Thr Gly Gly Phe Ser Lys Glu
1               5

<210> SEQ ID NO 409
<211> LENGTH: 10
<212> TYPE: PRT
<213> ORGANISM: Streptococcus pyogenes

<400> SEQUENCE: 409

Val Gln Thr Gly Gly Phe Ser Lys Glu Ser
1               5                   10

<210> SEQ ID NO 410
<211> LENGTH: 9
<212> TYPE: PRT
<213> ORGANISM: Streptococcus pyogenes

<400> SEQUENCE: 410

Gln Thr Gly Gly Phe Ser Lys Glu Ser
1               5

<210> SEQ ID NO 411
<211> LENGTH: 10
<212> TYPE: PRT
<213> ORGANISM: Streptococcus pyogenes

<400> SEQUENCE: 411

Gln Thr Gly Gly Phe Ser Lys Glu Ser Ile
1               5                   10

<210> SEQ ID NO 412
<211> LENGTH: 9
<212> TYPE: PRT
<213> ORGANISM: Streptococcus pyogenes

<400> SEQUENCE: 412

Thr Gly Gly Phe Ser Lys Glu Ser Ile
1               5

<210> SEQ ID NO 413
<211> LENGTH: 10
<212> TYPE: PRT
<213> ORGANISM: Streptococcus pyogenes

<400> SEQUENCE: 413

Thr Gly Gly Phe Ser Lys Glu Ser Ile Leu
1               5                   10

<210> SEQ ID NO 414
<211> LENGTH: 9
<212> TYPE: PRT
<213> ORGANISM: Streptococcus pyogenes

<400> SEQUENCE: 414

Gly Gly Phe Ser Lys Glu Ser Ile Leu
1               5

<210> SEQ ID NO 415
<211> LENGTH: 10
<212> TYPE: PRT
<213> ORGANISM: Streptococcus pyogenes

<400> SEQUENCE: 415

Gly Gly Phe Ser Lys Glu Ser Ile Leu Pro

<210> SEQ ID NO 416
<211> LENGTH: 9
<212> TYPE: PRT
<213> ORGANISM: Streptococcus pyogenes

<400> SEQUENCE: 416

Gly Phe Ser Lys Glu Ser Ile Leu Pro
1               5

<210> SEQ ID NO 417
<211> LENGTH: 10
<212> TYPE: PRT
<213> ORGANISM: Streptococcus pyogenes

<400> SEQUENCE: 417

Gly Phe Ser Lys Glu Ser Ile Leu Pro Lys
1               5                   10

<210> SEQ ID NO 418
<211> LENGTH: 9
<212> TYPE: PRT
<213> ORGANISM: Streptococcus pyogenes

<400> SEQUENCE: 418

Phe Ser Lys Glu Ser Ile Leu Pro Lys
1               5

<210> SEQ ID NO 419
<211> LENGTH: 10
<212> TYPE: PRT
<213> ORGANISM: Streptococcus pyogenes

<400> SEQUENCE: 419

Phe Ser Lys Glu Ser Ile Leu Pro Lys Arg
1               5                   10

<210> SEQ ID NO 420
<211> LENGTH: 9
<212> TYPE: PRT
<213> ORGANISM: Streptococcus pyogenes

<400> SEQUENCE: 420

Ser Lys Glu Ser Ile Leu Pro Lys Arg
1               5

<210> SEQ ID NO 421
<211> LENGTH: 10
<212> TYPE: PRT
<213> ORGANISM: Streptococcus pyogenes

<400> SEQUENCE: 421

Ser Lys Glu Ser Ile Leu Pro Lys Arg Asn
1               5                   10

<210> SEQ ID NO 422
<211> LENGTH: 9
<212> TYPE: PRT
<213> ORGANISM: Streptococcus pyogenes

<400> SEQUENCE: 422

Lys Glu Ser Ile Leu Pro Lys Arg Asn
1               5

<210> SEQ ID NO 423
<211> LENGTH: 10
<212> TYPE: PRT
<213> ORGANISM: Streptococcus pyogenes

<400> SEQUENCE: 423

Lys Glu Ser Ile Leu Pro Lys Arg Asn Ser
1               5                   10

<210> SEQ ID NO 424
<211> LENGTH: 9
<212> TYPE: PRT
<213> ORGANISM: Streptococcus pyogenes

<400> SEQUENCE: 424

Glu Ser Ile Leu Pro Lys Arg Asn Ser
1               5

<210> SEQ ID NO 425
<211> LENGTH: 10
<212> TYPE: PRT
<213> ORGANISM: Streptococcus pyogenes

<400> SEQUENCE: 425

Glu Ser Ile Leu Pro Lys Arg Asn Ser Asp
1               5                   10

<210> SEQ ID NO 426
<211> LENGTH: 9
<212> TYPE: PRT
<213> ORGANISM: Streptococcus pyogenes

<400> SEQUENCE: 426

Ser Ile Leu Pro Lys Arg Asn Ser Asp
1               5

<210> SEQ ID NO 427
<211> LENGTH: 10
<212> TYPE: PRT
<213> ORGANISM: Streptococcus pyogenes

<400> SEQUENCE: 427

Ser Ile Leu Pro Lys Arg Asn Ser Asp Lys
1               5                   10

<210> SEQ ID NO 428
<211> LENGTH: 9
<212> TYPE: PRT
<213> ORGANISM: Streptococcus pyogenes

<400> SEQUENCE: 428

Ile Leu Pro Lys Arg Asn Ser Asp Lys
1               5

<210> SEQ ID NO 429
<211> LENGTH: 10
<212> TYPE: PRT
<213> ORGANISM: Streptococcus pyogenes

<400> SEQUENCE: 429

Ile Leu Pro Lys Arg Asn Ser Asp Lys Leu
1               5                   10

<210> SEQ ID NO 430

```
<211> LENGTH: 9
<212> TYPE: PRT
<213> ORGANISM: Streptococcus pyogenes

<400> SEQUENCE: 430

Leu Pro Lys Arg Asn Ser Asp Lys Leu
1               5

<210> SEQ ID NO 431
<211> LENGTH: 10
<212> TYPE: PRT
<213> ORGANISM: Streptococcus pyogenes

<400> SEQUENCE: 431

Leu Pro Lys Arg Asn Ser Asp Lys Leu Ile
1               5                   10

<210> SEQ ID NO 432
<211> LENGTH: 9
<212> TYPE: PRT
<213> ORGANISM: Streptococcus pyogenes

<400> SEQUENCE: 432

Pro Lys Arg Asn Ser Asp Lys Leu Ile
1               5

<210> SEQ ID NO 433
<211> LENGTH: 10
<212> TYPE: PRT
<213> ORGANISM: Streptococcus pyogenes

<400> SEQUENCE: 433

Pro Lys Arg Asn Ser Asp Lys Leu Ile Ala
1               5                   10

<210> SEQ ID NO 434
<211> LENGTH: 9
<212> TYPE: PRT
<213> ORGANISM: Streptococcus pyogenes

<400> SEQUENCE: 434

Lys Arg Asn Ser Asp Lys Leu Ile Ala
1               5

<210> SEQ ID NO 435
<211> LENGTH: 10
<212> TYPE: PRT
<213> ORGANISM: Streptococcus pyogenes

<400> SEQUENCE: 435

Lys Arg Asn Ser Asp Lys Leu Ile Ala Arg
1               5                   10

<210> SEQ ID NO 436
<211> LENGTH: 9
<212> TYPE: PRT
<213> ORGANISM: Streptococcus pyogenes

<400> SEQUENCE: 436

Arg Asn Ser Asp Lys Leu Ile Ala Arg
1               5

<210> SEQ ID NO 437
<211> LENGTH: 10
<212> TYPE: PRT
```

<213> ORGANISM: Streptococcus pyogenes

<400> SEQUENCE: 437

Arg Asn Ser Asp Lys Leu Ile Ala Arg Lys
1               5                   10

<210> SEQ ID NO 438
<211> LENGTH: 9
<212> TYPE: PRT
<213> ORGANISM: Streptococcus pyogenes

<400> SEQUENCE: 438

Asn Ser Asp Lys Leu Ile Ala Arg Lys
1               5

<210> SEQ ID NO 439
<211> LENGTH: 10
<212> TYPE: PRT
<213> ORGANISM: Streptococcus pyogenes

<400> SEQUENCE: 439

Asn Ser Asp Lys Leu Ile Ala Arg Lys Lys
1               5                   10

<210> SEQ ID NO 440
<211> LENGTH: 9
<212> TYPE: PRT
<213> ORGANISM: Streptococcus pyogenes

<400> SEQUENCE: 440

Ser Asp Lys Leu Ile Ala Arg Lys Lys
1               5

<210> SEQ ID NO 441
<211> LENGTH: 10
<212> TYPE: PRT
<213> ORGANISM: Streptococcus pyogenes

<400> SEQUENCE: 441

Ser Asp Lys Leu Ile Ala Arg Lys Lys Asp
1               5                   10

<210> SEQ ID NO 442
<211> LENGTH: 9
<212> TYPE: PRT
<213> ORGANISM: Streptococcus pyogenes

<400> SEQUENCE: 442

Asp Lys Leu Ile Ala Arg Lys Lys Asp
1               5

<210> SEQ ID NO 443
<211> LENGTH: 10
<212> TYPE: PRT
<213> ORGANISM: Streptococcus pyogenes

<400> SEQUENCE: 443

Asp Lys Leu Ile Ala Arg Lys Lys Asp Trp
1               5                   10

<210> SEQ ID NO 444
<211> LENGTH: 9
<212> TYPE: PRT
<213> ORGANISM: Streptococcus pyogenes

```
<400> SEQUENCE: 444

Lys Leu Ile Ala Arg Lys Lys Asp Trp
1               5

<210> SEQ ID NO 445
<211> LENGTH: 10
<212> TYPE: PRT
<213> ORGANISM: Streptococcus pyogenes

<400> SEQUENCE: 445

Lys Leu Ile Ala Arg Lys Lys Asp Trp Asp
1               5                   10

<210> SEQ ID NO 446
<211> LENGTH: 9
<212> TYPE: PRT
<213> ORGANISM: Streptococcus pyogenes

<400> SEQUENCE: 446

Leu Ile Ala Arg Lys Lys Asp Trp Asp
1               5

<210> SEQ ID NO 447
<211> LENGTH: 10
<212> TYPE: PRT
<213> ORGANISM: Streptococcus pyogenes

<400> SEQUENCE: 447

Leu Ile Ala Arg Lys Lys Asp Trp Asp Pro
1               5                   10

<210> SEQ ID NO 448
<211> LENGTH: 9
<212> TYPE: PRT
<213> ORGANISM: Streptococcus pyogenes

<400> SEQUENCE: 448

Ile Ala Arg Lys Lys Asp Trp Asp Pro
1               5

<210> SEQ ID NO 449
<211> LENGTH: 10
<212> TYPE: PRT
<213> ORGANISM: Streptococcus pyogenes

<400> SEQUENCE: 449

Ile Ala Arg Lys Lys Asp Trp Asp Pro Lys
1               5                   10

<210> SEQ ID NO 450
<211> LENGTH: 9
<212> TYPE: PRT
<213> ORGANISM: Streptococcus pyogenes

<400> SEQUENCE: 450

Ala Arg Lys Lys Asp Trp Asp Pro Lys
1               5

<210> SEQ ID NO 451
<211> LENGTH: 10
<212> TYPE: PRT
<213> ORGANISM: Streptococcus pyogenes

<400> SEQUENCE: 451
```

Ala Arg Lys Lys Asp Trp Asp Pro Lys Lys
1               5                   10

<210> SEQ ID NO 452
<211> LENGTH: 9
<212> TYPE: PRT
<213> ORGANISM: Streptococcus pyogenes

<400> SEQUENCE: 452

Arg Lys Lys Asp Trp Asp Pro Lys Lys
1               5

<210> SEQ ID NO 453
<211> LENGTH: 10
<212> TYPE: PRT
<213> ORGANISM: Streptococcus pyogenes

<400> SEQUENCE: 453

Arg Lys Lys Asp Trp Asp Pro Lys Lys Tyr
1               5                   10

<210> SEQ ID NO 454
<211> LENGTH: 9
<212> TYPE: PRT
<213> ORGANISM: Streptococcus pyogenes

<400> SEQUENCE: 454

Lys Lys Asp Trp Asp Pro Lys Lys Tyr
1               5

<210> SEQ ID NO 455
<211> LENGTH: 10
<212> TYPE: PRT
<213> ORGANISM: Streptococcus pyogenes

<400> SEQUENCE: 455

Lys Lys Asp Trp Asp Pro Lys Lys Tyr Gly
1               5                   10

<210> SEQ ID NO 456
<211> LENGTH: 9
<212> TYPE: PRT
<213> ORGANISM: Streptococcus pyogenes

<400> SEQUENCE: 456

Lys Asp Trp Asp Pro Lys Lys Tyr Gly
1               5

<210> SEQ ID NO 457
<211> LENGTH: 10
<212> TYPE: PRT
<213> ORGANISM: Streptococcus pyogenes

<400> SEQUENCE: 457

Lys Asp Trp Asp Pro Lys Lys Tyr Gly Gly
1               5                   10

<210> SEQ ID NO 458
<211> LENGTH: 9
<212> TYPE: PRT
<213> ORGANISM: Streptococcus pyogenes

<400> SEQUENCE: 458

Asp Trp Asp Pro Lys Lys Tyr Gly Gly
1               5

<210> SEQ ID NO 459
<211> LENGTH: 10
<212> TYPE: PRT
<213> ORGANISM: Streptococcus pyogenes

<400> SEQUENCE: 459

Asp Trp Asp Pro Lys Lys Tyr Gly Gly Phe
1               5                   10

<210> SEQ ID NO 460
<211> LENGTH: 9
<212> TYPE: PRT
<213> ORGANISM: Streptococcus pyogenes

<400> SEQUENCE: 460

Trp Asp Pro Lys Lys Tyr Gly Gly Phe
1               5

<210> SEQ ID NO 461
<211> LENGTH: 10
<212> TYPE: PRT
<213> ORGANISM: Streptococcus pyogenes

<400> SEQUENCE: 461

Trp Asp Pro Lys Lys Tyr Gly Gly Phe Asp
1               5                   10

<210> SEQ ID NO 462
<211> LENGTH: 9
<212> TYPE: PRT
<213> ORGANISM: Streptococcus pyogenes

<400> SEQUENCE: 462

Asp Pro Lys Lys Tyr Gly Gly Phe Asp
1               5

<210> SEQ ID NO 463
<211> LENGTH: 10
<212> TYPE: PRT
<213> ORGANISM: Streptococcus pyogenes

<400> SEQUENCE: 463

Asp Pro Lys Lys Tyr Gly Gly Phe Asp Ser
1               5                   10

<210> SEQ ID NO 464
<211> LENGTH: 9
<212> TYPE: PRT
<213> ORGANISM: Streptococcus pyogenes

<400> SEQUENCE: 464

Pro Lys Lys Tyr Gly Gly Phe Asp Ser
1               5

<210> SEQ ID NO 465
<211> LENGTH: 10
<212> TYPE: PRT
<213> ORGANISM: Streptococcus pyogenes

<400> SEQUENCE: 465

Pro Lys Lys Tyr Gly Gly Phe Asp Ser Pro
1               5                   10

<210> SEQ ID NO 466
<211> LENGTH: 9
<212> TYPE: PRT
<213> ORGANISM: Streptococcus pyogenes

<400> SEQUENCE: 466

Lys Lys Tyr Gly Gly Phe Asp Ser Pro
1               5

<210> SEQ ID NO 467
<211> LENGTH: 10
<212> TYPE: PRT
<213> ORGANISM: Streptococcus pyogenes

<400> SEQUENCE: 467

Lys Lys Tyr Gly Gly Phe Asp Ser Pro Thr
1               5                   10

<210> SEQ ID NO 468
<211> LENGTH: 9
<212> TYPE: PRT
<213> ORGANISM: Streptococcus pyogenes

<400> SEQUENCE: 468

Lys Tyr Gly Gly Phe Asp Ser Pro Thr
1               5

<210> SEQ ID NO 469
<211> LENGTH: 10
<212> TYPE: PRT
<213> ORGANISM: Streptococcus pyogenes

<400> SEQUENCE: 469

Lys Tyr Gly Gly Phe Asp Ser Pro Thr Val
1               5                   10

<210> SEQ ID NO 470
<211> LENGTH: 9
<212> TYPE: PRT
<213> ORGANISM: Streptococcus pyogenes

<400> SEQUENCE: 470

Tyr Gly Gly Phe Asp Ser Pro Thr Val
1               5

<210> SEQ ID NO 471
<211> LENGTH: 10
<212> TYPE: PRT
<213> ORGANISM: Streptococcus pyogenes

<400> SEQUENCE: 471

Tyr Gly Gly Phe Asp Ser Pro Thr Val Ala
1               5                   10

<210> SEQ ID NO 472
<211> LENGTH: 9
<212> TYPE: PRT
<213> ORGANISM: Streptococcus pyogenes

<400> SEQUENCE: 472

Gly Gly Phe Asp Ser Pro Thr Val Ala
1               5

<210> SEQ ID NO 473
<211> LENGTH: 10

```
<212> TYPE: PRT
<213> ORGANISM: Streptococcus pyogenes

<400> SEQUENCE: 473

Gly Gly Phe Asp Ser Pro Thr Val Ala Tyr
1               5                   10

<210> SEQ ID NO 474
<211> LENGTH: 9
<212> TYPE: PRT
<213> ORGANISM: Streptococcus pyogenes

<400> SEQUENCE: 474

Gly Phe Asp Ser Pro Thr Val Ala Tyr
1               5

<210> SEQ ID NO 475
<211> LENGTH: 10
<212> TYPE: PRT
<213> ORGANISM: Streptococcus pyogenes

<400> SEQUENCE: 475

Gly Phe Asp Ser Pro Thr Val Ala Tyr Ser
1               5                   10

<210> SEQ ID NO 476
<211> LENGTH: 9
<212> TYPE: PRT
<213> ORGANISM: Streptococcus pyogenes

<400> SEQUENCE: 476

Phe Asp Ser Pro Thr Val Ala Tyr Ser
1               5

<210> SEQ ID NO 477
<211> LENGTH: 10
<212> TYPE: PRT
<213> ORGANISM: Streptococcus pyogenes

<400> SEQUENCE: 477

Phe Asp Ser Pro Thr Val Ala Tyr Ser Val
1               5                   10

<210> SEQ ID NO 478
<211> LENGTH: 9
<212> TYPE: PRT
<213> ORGANISM: Streptococcus pyogenes

<400> SEQUENCE: 478

Asp Ser Pro Thr Val Ala Tyr Ser Val
1               5

<210> SEQ ID NO 479
<211> LENGTH: 10
<212> TYPE: PRT
<213> ORGANISM: Streptococcus pyogenes

<400> SEQUENCE: 479

Asp Ser Pro Thr Val Ala Tyr Ser Val Leu
1               5                   10

<210> SEQ ID NO 480
<211> LENGTH: 9
<212> TYPE: PRT
<213> ORGANISM: Streptococcus pyogenes
```

<400> SEQUENCE: 480

Ser Pro Thr Val Ala Tyr Ser Val Leu
1               5

<210> SEQ ID NO 481
<211> LENGTH: 10
<212> TYPE: PRT
<213> ORGANISM: Streptococcus pyogenes

<400> SEQUENCE: 481

Ser Pro Thr Val Ala Tyr Ser Val Leu Val
1               5                   10

<210> SEQ ID NO 482
<211> LENGTH: 9
<212> TYPE: PRT
<213> ORGANISM: Streptococcus pyogenes

<400> SEQUENCE: 482

Pro Thr Val Ala Tyr Ser Val Leu Val
1               5

<210> SEQ ID NO 483
<211> LENGTH: 10
<212> TYPE: PRT
<213> ORGANISM: Streptococcus pyogenes

<400> SEQUENCE: 483

Pro Thr Val Ala Tyr Ser Val Leu Val Val
1               5                   10

<210> SEQ ID NO 484
<211> LENGTH: 9
<212> TYPE: PRT
<213> ORGANISM: Streptococcus pyogenes

<400> SEQUENCE: 484

Thr Val Ala Tyr Ser Val Leu Val Val
1               5

<210> SEQ ID NO 485
<211> LENGTH: 10
<212> TYPE: PRT
<213> ORGANISM: Streptococcus pyogenes

<400> SEQUENCE: 485

Thr Val Ala Tyr Ser Val Leu Val Val Ala
1               5                   10

<210> SEQ ID NO 486
<211> LENGTH: 9
<212> TYPE: PRT
<213> ORGANISM: Streptococcus pyogenes

<400> SEQUENCE: 486

Val Ala Tyr Ser Val Leu Val Val Ala
1               5

<210> SEQ ID NO 487
<211> LENGTH: 10
<212> TYPE: PRT
<213> ORGANISM: Streptococcus pyogenes

<400> SEQUENCE: 487

```
Val Ala Tyr Ser Val Leu Val Val Ala Lys
1               5                   10

<210> SEQ ID NO 488
<211> LENGTH: 9
<212> TYPE: PRT
<213> ORGANISM: Streptococcus pyogenes

<400> SEQUENCE: 488

Ala Tyr Ser Val Leu Val Val Ala Lys
1               5

<210> SEQ ID NO 489
<211> LENGTH: 10
<212> TYPE: PRT
<213> ORGANISM: Streptococcus pyogenes

<400> SEQUENCE: 489

Ala Tyr Ser Val Leu Val Val Ala Lys Val
1               5                   10

<210> SEQ ID NO 490
<211> LENGTH: 9
<212> TYPE: PRT
<213> ORGANISM: Streptococcus pyogenes

<400> SEQUENCE: 490

Tyr Ser Val Leu Val Val Ala Lys Val
1               5

<210> SEQ ID NO 491
<211> LENGTH: 10
<212> TYPE: PRT
<213> ORGANISM: Streptococcus pyogenes

<400> SEQUENCE: 491

Tyr Ser Val Leu Val Val Ala Lys Val Glu
1               5                   10

<210> SEQ ID NO 492
<211> LENGTH: 9
<212> TYPE: PRT
<213> ORGANISM: Streptococcus pyogenes

<400> SEQUENCE: 492

Ser Val Leu Val Val Ala Lys Val Glu
1               5

<210> SEQ ID NO 493
<211> LENGTH: 10
<212> TYPE: PRT
<213> ORGANISM: Streptococcus pyogenes

<400> SEQUENCE: 493

Ser Val Leu Val Val Ala Lys Val Glu Lys
1               5                   10

<210> SEQ ID NO 494
<211> LENGTH: 9
<212> TYPE: PRT
<213> ORGANISM: Streptococcus pyogenes

<400> SEQUENCE: 494

Val Leu Val Val Ala Lys Val Glu Lys
```

```
1               5
```

<210> SEQ ID NO 495
<211> LENGTH: 10
<212> TYPE: PRT
<213> ORGANISM: Streptococcus pyogenes

<400> SEQUENCE: 495

```
Val Leu Val Val Ala Lys Val Glu Lys Gly
1               5                   10
```

<210> SEQ ID NO 496
<211> LENGTH: 9
<212> TYPE: PRT
<213> ORGANISM: Streptococcus pyogenes

<400> SEQUENCE: 496

```
Leu Val Val Ala Lys Val Glu Lys Gly
1               5
```

<210> SEQ ID NO 497
<211> LENGTH: 10
<212> TYPE: PRT
<213> ORGANISM: Streptococcus pyogenes

<400> SEQUENCE: 497

```
Leu Val Val Ala Lys Val Glu Lys Gly Lys
1               5                   10
```

<210> SEQ ID NO 498
<211> LENGTH: 9
<212> TYPE: PRT
<213> ORGANISM: Streptococcus pyogenes

<400> SEQUENCE: 498

```
Val Val Ala Lys Val Glu Lys Gly Lys
1               5
```

<210> SEQ ID NO 499
<211> LENGTH: 10
<212> TYPE: PRT
<213> ORGANISM: Streptococcus pyogenes

<400> SEQUENCE: 499

```
Val Val Ala Lys Val Glu Lys Gly Lys Ser
1               5                   10
```

<210> SEQ ID NO 500
<211> LENGTH: 9
<212> TYPE: PRT
<213> ORGANISM: Streptococcus pyogenes

<400> SEQUENCE: 500

```
Val Ala Lys Val Glu Lys Gly Lys Ser
1               5
```

<210> SEQ ID NO 501
<211> LENGTH: 10
<212> TYPE: PRT
<213> ORGANISM: Streptococcus pyogenes

<400> SEQUENCE: 501

```
Val Ala Lys Val Glu Lys Gly Lys Ser Lys
1               5                   10
```

<210> SEQ ID NO 502
<211> LENGTH: 9
<212> TYPE: PRT
<213> ORGANISM: Streptococcus pyogenes

<400> SEQUENCE: 502

Ala Lys Val Glu Lys Gly Lys Ser Lys
1               5

<210> SEQ ID NO 503
<211> LENGTH: 10
<212> TYPE: PRT
<213> ORGANISM: Streptococcus pyogenes

<400> SEQUENCE: 503

Ala Lys Val Glu Lys Gly Lys Ser Lys Lys
1               5                   10

<210> SEQ ID NO 504
<211> LENGTH: 9
<212> TYPE: PRT
<213> ORGANISM: Streptococcus pyogenes

<400> SEQUENCE: 504

Lys Val Glu Lys Gly Lys Ser Lys Lys
1               5

<210> SEQ ID NO 505
<211> LENGTH: 10
<212> TYPE: PRT
<213> ORGANISM: Streptococcus pyogenes

<400> SEQUENCE: 505

Lys Val Glu Lys Gly Lys Ser Lys Lys Leu
1               5                   10

<210> SEQ ID NO 506
<211> LENGTH: 9
<212> TYPE: PRT
<213> ORGANISM: Streptococcus pyogenes

<400> SEQUENCE: 506

Val Glu Lys Gly Lys Ser Lys Lys Leu
1               5

<210> SEQ ID NO 507
<211> LENGTH: 10
<212> TYPE: PRT
<213> ORGANISM: Streptococcus pyogenes

<400> SEQUENCE: 507

Val Glu Lys Gly Lys Ser Lys Lys Leu Lys
1               5                   10

<210> SEQ ID NO 508
<211> LENGTH: 9
<212> TYPE: PRT
<213> ORGANISM: Streptococcus pyogenes

<400> SEQUENCE: 508

Glu Lys Gly Lys Ser Lys Lys Leu Lys
1               5

<210> SEQ ID NO 509

```
<211> LENGTH: 10
<212> TYPE: PRT
<213> ORGANISM: Streptococcus pyogenes

<400> SEQUENCE: 509

Glu Lys Gly Lys Ser Lys Lys Leu Lys Ser
1               5                   10

<210> SEQ ID NO 510
<211> LENGTH: 1379
<212> TYPE: PRT
<213> ORGANISM: Streptococcus pyogenes

<400> SEQUENCE: 510

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335
```

Ala Leu Val Arg Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
                450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
                690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
        755                 760                 765

Thr Thr Gln Lys Gly Lys Asn Ser Arg Gly Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser

-continued

```
            1160                1165                1170
Phe Glu Lys Asn Pro Ile Asp Phe Leu Glu Ala Lys Gly Tyr Lys
        1175                1180                1185
Glu Val Lys Lys Asp Leu Ile Ile Lys Leu Pro Lys Tyr Ser Leu
        1190                1195                1200
Phe Glu Leu Glu Asn Gly Arg Lys Arg Met Leu Ala Ser Ala Gly
        1205                1210                1215
Glu Leu Gln Lys Gly Asn Glu Leu Ala Leu Pro Ser Lys Tyr Val
        1220                1225                1230
Asn Phe Leu Tyr Leu Ala Ser His Tyr Glu Lys Leu Lys Gly Ser
        1235                1240                1245
Pro Glu Asp Asn Glu Gln Lys Gln Leu Phe Val Glu Gln His Lys
        1250                1255                1260
His Tyr Leu Asp Glu Ile Ile Glu Gln Ile Ser Glu Phe Ser Lys
        1265                1270                1275
Arg Val Ile Leu Ala Asp Ala Asn Leu Asp Lys Val Leu Ser Ala
        1280                1285                1290
Tyr Asn Lys His Arg Asp Lys Pro Ile Arg Glu Gln Ala Glu Asn
        1295                1300                1305
Ile Ile His Leu Phe Thr Leu Thr Asn Leu Gly Ala Pro Ala Ala
        1310                1315                1320
Phe Lys Tyr Phe Asp Thr Thr Ile Asp Arg Lys Arg Tyr Thr Ser
        1325                1330                1335
Thr Lys Glu Val Leu Asp Ala Thr Leu Ile His Gln Ser Ile Thr
        1340                1345                1350
Gly Leu Tyr Glu Thr Arg Ile Asp Leu Ser Gln Leu Gly Gly Asp
        1355                1360                1365
Ser Arg Ala Asp Pro Lys Lys Lys Arg Lys Val
        1370                1375
```